US010768179B2

(12) United States Patent
Kohno et al.

(10) Patent No.: US 10,768,179 B2
(45) Date of Patent: Sep. 8, 2020

(54) METHOD FOR PREDICTING RESPONSIVENESS TO CANCER TREATMENT USING P300-INHIBITING COMPOUND

(71) Applicants: National Cancer Center, Chuo-ku, Tokyo (JP); Daiichi Sankyo Company, Limited, Chuo-ku, Tokyo (JP)

(72) Inventors: Takashi Kohno, Chuo-ku (JP); Hideaki Ogiwara, Chuo-ku (JP); Yuichi Tominaga, Shinagawa-ku (JP); Saito Higuchi, Shinagawa-ku (JP)

(73) Assignees: National Cancer Center, Chuo-ku, Tokyo (JP); Daiichi Sankyo Company, Limited, Chuo-ku, Tokyo (JP)

( * ) Notice: Subject to any disclaimer, the term of this patent is extended or adjusted under 35 U.S.C. 154(b) by 0 days.

(21) Appl. No.: 15/121,001

(22) PCT Filed: Feb. 23, 2015

(86) PCT No.: PCT/JP2015/054991
§ 371 (c)(1),
(2) Date: Aug. 23, 2016

(87) PCT Pub. No.: WO2015/125956
PCT Pub. Date: Aug. 27, 2015

(65) Prior Publication Data
US 2017/0067899 A1 Mar. 9, 2017

(30) Foreign Application Priority Data
Feb. 24, 2014 (JP) ................................. 2014-032928

(51) Int. Cl.
| | |
|---|---|
| *A61K 31/4155* | (2006.01) |
| *G01N 33/574* | (2006.01) |
| *C12Q 1/6886* | (2018.01) |
| *G01N 33/50* | (2006.01) |
| *C12Q 1/68* | (2018.01) |
| *C12N 15/09* | (2006.01) |

(52) U.S. Cl.
CPC ... *G01N 33/57484* (2013.01); *A61K 31/4155* (2013.01); *C12N 15/09* (2013.01); *C12Q 1/68* (2013.01); *C12Q 1/6886* (2013.01); *G01N 33/50* (2013.01); *G01N 33/574* (2013.01); *C12Q 2600/106* (2013.01); *C12Q 2600/136* (2013.01); *C12Q 2600/158* (2013.01); *G01N 2333/47* (2013.01); *G01N 2333/91057* (2013.01); *G01N 2500/10* (2013.01); *G01N 2800/52* (2013.01)

(58) Field of Classification Search
CPC .................................................. A61K 31/4155
USPC ........................................................ 514/19.3
See application file for complete search history.

(56) References Cited

U.S. PATENT DOCUMENTS

2016/0130663 A1  5/2016  Kohno et al.

FOREIGN PATENT DOCUMENTS

| WO | 2008/157680 A2 | 12/2008 |
|---|---|---|
| WO | 2011/085039 A2 | 7/2011 |
| WO | 2015/005473 A1 | 1/2015 |

OTHER PUBLICATIONS

Gui et al (Nature Genetics, 2011, 43(9): 875-879).*
Ito et al (The EMBO Journal, 2001, 20(6): 1331-1340).*
Gao et al (Methods Mol Biol, 2013, 981: 229-238).*
International Preliminary Report on Patentability dated Aug. 30, 2016, issued in corresponding International Application No. PCT/JP2015/054991, filed Feb. 23, 2015, 8 pages.
Chan, D.A., and A. J. Giaccia, "Harnessing Synthetic Lethal Interactions in Anticancer Drug Discovery," Nature Reviews|Drug Discovery 10(5):351-364, May 2011.
International Search Report (with Written Opinion in Japanese) dated May 26, 2015, issued in corresponding International Application No. PCT/JP2015/054991, filed Feb. 23, 2015, 16 pages.
Kishimoto, M., et al., "Mutations and Deletions of the CBP Gene in Human Lung Cancer," Clinical Cancer Research 11:512-519, Jan. 2005.
Ogiwara, H., et al., "Histone Acetylation of CBP and p300 at Double-Strand Break Sites Facilitates SWI/SNF Chromatin Remodeling and the Recruitment of Non-Homologous End Joining Factors," Oncogene 30(18)2135-2146, May 2011.
Ogiwara, H., and T. Kohno, "CBP and p300 Histone Acetyltransferases Contribute to Homolog9ous Recombination by Transcriptionally Activating the BRCA1 and RAD51 Genes," Plos One 7(12):1-10, Dec. 2012.
Oike, T., et al., "Chromatin-Regulating Proteins as Targets for Cancer Therapy," Journal of Radiation Research 55:613-628, Feb. 2014.
Pao, W., and N. Girard, "New Drive Mutations in Non-Small-Cell Lung Cancer," The Lancet Oncology 12:175-180, Feb. 2011.
Shaw, A.T., et al., "Tyrosine Kinase Gene Rearrangements in Epithelial Malignancies," Nature Reviews Cancer 13(11):772-787, Nov. 2013.

(Continued)

*Primary Examiner* — Sean E Aeder
(74) *Attorney, Agent, or Firm* — Christensen O'Connor Johnson Kindness PLLC

(57) ABSTRACT

It has been found that CBP and p300 are in the relationship of synthetic lethality, and treatment inhibiting p300 is a promising approach for the treatment of CBP-mutated cancer. It has also been revealed that this therapeutic strategy achieves efficient treatment based on companion diagnostics because a p300 inhibitor can be administered to a cancer patient selected with functional suppression of CBP as an index.

12 Claims, 10 Drawing Sheets
Specification includes a Sequence Listing.

(56) References Cited

OTHER PUBLICATIONS

Kohno, T., "Gan no Kobetsuka Chiryo to Doyaku," Japanese Journal of Clinical Medicine 72 (Supplemental 2): 34-39, Feb. 2014.
Bowers, E.M., et al., "Virtual Ligand Screening of the p300/CBP Histone Acetyltransferase: Identification of a Selective Small Molecule Inhibitor," Chemical Biology 17(5):471-482, May 2010. (Author Manuscript provided, PMCID:PMC2884008, available in PMC May 28, 2011, 24 pages.).
Extended European Search Report dated Sep. 18, 2017, issued in corresponding European Application No. 15752232.7, filed Feb. 23, 2015, 12 pages.
Haery, L., et al., "Histone Acetyltransferase-Deficient p300 Mutants in Diffuse Large B Cell Lymphoma Have Altered Transcriptional Regulatory Activities and Are Required for Optimal Cell Growth," Molecular Cancer 13(1):29, Dec. 2014, 13 pages.
Iyer, N.G., et al., "p300/CBP and Cancer," Oncogene 23(24):4225-4231, May 2004.
Mullighan, C.G., et al., "CREBBP Mutations in Relapsed Acute Lymphoblastic Leukaemia," Nature 471(7337):235-239, Mar. 2011. (Author Manuscript provided, PMCID:PMC3076610, available in PMC Sep. 10, 2011, 13 pages.).
Pasqualucci, L., et al., "Inactivating Mutations of Acetyltransferase Genes in B-Cell Lymphoma," Nature 471(7337):189-195, Mar. 2011. (Author Manuscript provided, PMCID:PMC3271441, available in PMC Feb. 3, 2012, 19 pages.).
Yuan, Z.-M., et al., "Function for p300 and Not CBP in the Apoptotic Response to DNA Damage," Oncogene 18(41):5714-5717, Oct. 1999.
Notice of Reasons for Refusal dated Feb. 5, 2019, in Japanese Application No. 2016-504207, filed Feb. 23, 2015, 9 pages.
Yang., H., et al., "Small-Molecule Inhibitors of Acetyltransferase p300 Identified by High-Throughput Screening Are Potent Anticancer Agents," Molecular Cancer Therapeutics 12(5):610-620, May 2013 (Author Manuscript provided, PMCID: PMC3651759, available in PMC May 1, 2014, 19 pages).

* cited by examiner

SEQUENCE LISTING

<160> NUMBER OF SEQ ID NOS: 6

<210> SEQ ID NO 1
<211> LENGTH: 152199
<212> TYPE: DNA
<213> ORGANISM: Homo sapiens
<220> FEATURE:
<221> NAME/KEY: CDS
<222> LOCATION: (1)..(85)
<220> FEATURE:
<221> NAME/KEY: CDS
<222> LOCATION: (28908)..(29620)
<220> FEATURE:
<221> NAME/KEY: CDS
<222> LOCATION: (69138)..(69314)
<220> FEATURE:
<221> NAME/KEY: CDS
<222> LOCATION: (86291)..(86531)
<220> FEATURE:
<221> NAME/KEY: CDS
<222> LOCATION: (87823)..(87936)
<220> FEATURE:
<221> NAME/KEY: CDS
<222> LOCATION: (96991)..(97233)
<220> FEATURE:
<221> NAME/KEY: CDS
<222> LOCATION: (98611)..(98713)
<220> FEATURE:
<221> NAME/KEY: CDS
<222> LOCATION: (99039)..(99185)
<220> FEATURE:
<221> NAME/KEY: CDS
<222> LOCATION: (101100)..(101217)
<220> FEATURE:
<221> NAME/KEY: CDS
<222> LOCATION: (101735)..(101906)
<220> FEATURE:
<221> NAME/KEY: CDS
<222> LOCATION: (102260)..(102304)
<220> FEATURE:
<221> NAME/KEY: CDS
<222> LOCATION: (105224)..(105348)
<220> FEATURE:
<221> NAME/KEY: CDS
<222> LOCATION: (105987)..(106166)
<220> FEATURE:
<221> NAME/KEY: CDS
<222> LOCATION: (108931)..(109347)
<220> FEATURE:
<221> NAME/KEY: CDS
<222> LOCATION: (110564)..(110743)
<220> FEATURE:
<221> NAME/KEY: CDS
<222> LOCATION: (112008)..(112197)
<220> FEATURE:
<221> NAME/KEY: CDS
<222> LOCATION: (120945)..(121063)
<220> FEATURE:
<221> NAME/KEY: CDS
<222> LOCATION: (121869)..(122108)
<220> FEATURE:
<221> NAME/KEY: CDS
<222> LOCATION: (122541)..(122629)
<220> FEATURE:
<221> NAME/KEY: CDS
<222> LOCATION: (128111)..(128191)
<220> FEATURE:
<221> NAME/KEY: CDS
<222> LOCATION: (130234)..(130290)
<220> FEATURE:
<221> NAME/KEY: CDS
<222> LOCATION: (134563)..(134640)
<220> FEATURE:
<221> NAME/KEY: CDS
<222> LOCATION: (134956)..(135023)
<220> FEATURE:
<221> NAME/KEY: CDS
<222> LOCATION: (139368)..(139518)

```
<220> FEATURE:
<221> NAME/KEY: CDS
<222> LOCATION: (140193)..(140339)
<220> FEATURE:
<221> NAME/KEY: CDS
<222> LOCATION: (141245)..(141358)
<220> FEATURE:
<221> NAME/KEY: CDS
<222> LOCATION: (143102)..(143267)
<220> FEATURE:
<221> NAME/KEY: CDS
<222> LOCATION: (143714)..(143881)
<220> FEATURE:
<221> NAME/KEY: CDS
<222> LOCATION: (147980)..(148141)
<220> FEATURE:
<221> NAME/KEY: CDS
<222> LOCATION: (148444)..(148725)
<220> FEATURE:
<221> NAME/KEY: CDS
<222> LOCATION: (150043)..(152196)

<400> SEQUENCE: 1 atg gct gag aac ttg ctg gac gga ccg ccc aac ccc aaa aga gcc aaa      48
Met Ala Glu Asn Leu Leu Asp Gly Pro Pro Asn Pro Lys Arg Ala Lys
1               5                   10                  15 ctc agc tcg ccc ggt ttc tcg gcg aat gac agc aca g gtgaggaggg         95
Leu Ser Ser Pro Gly Phe Ser Ala Asn Asp Ser Thr
            20                  25 ggtccggggc ggcggggggcc cggggcgcgc tgtcaccccc acctgaaaga gagcgtccgg   155
gggtcgtggt cgcggatacc gatcgagccg ggagctcgga gcaggccccg cagcccgttc   215
ccctcgcccc gcgcgggagg gtggaagttc gtcgcaggac tgtcactggg cccgagttgg   275
tcagcacacg cccggtgcac tcggcctccc cgcacccgat cagccctcct cgcggggacc   335
ctagtggcac tccaggaggg aagaagtaaa gtgcagcgtg tgggtttgtt tggtaatgtc   395
ctacgcatcc atccgcggcc gtgtccacac gcgtggccgt ccagaggaat gacagcggag   455
ggtacctttg atgcttagag aaagcaagat gcgggccaaa ggtagggcag tgtgttttct   515
ggattggcga cacattgacc aggctgcatt cagaggacac tcacagcagc cgccagcttg   575
cgagttagaa ccgaagtttc ttggaatgag tgagttcctt ggaaagatgc ttagtgctta   635
ttttcaaaac tccttgtttt gtgtgtgtgt gtgtgtgtgt gtgtgtgcgc gcgtgtgtgt   695
ttttagtcaa ctagtcattc cattttcaa acccaaact tcgttagcaa gatgtcatga     755
aagttgctgt ggtgtgtttc atttccatgt ataacttcaa aagaaagtta aacagcaggt   815
ttaagttcat ttgggctgca atctccattt gagtttgtgt tgctttcaca gtgtagatgt   875
acaaagaatt aaggaatgta ggaattccaa tttttcaaaa aatggagca ggatactgaa     935 taaatcatct ttttgtttgt ttccttttcat taaacggctt ccctggaaac tttcttaagt   995
tatcatagct gcttaagaga agtatttagt tttctattaa ttcagtaatt ctgggtccca   1055
ctgcgctggt tcatggtaac atgaactagt tgtatttcct cttttagagc tctctccttt   1115
gccgcaaaaa cttgtgtgcc gctgcgaaca attccatctc cagcgcagct tgcatttctc   1175
cagtagtctt gcagtggtag catctgaaaa tcagtttcta atgaatgagt ccaaattgaa   1235
ttacatcgct gccttcagat ttgcactaga cacagctgtt caacttgtgg aaatagttct   1295
gtgaccgacc actagcatat taaaaaaaac tgctattgct gttgaaacaa aacctgaatt   1355
ttgtggctta agtttgaata caattcctgg aatcaagtta tgataagcga cgtttaatat   1415
taatgtagaa gtgaaaagcg atttttaaag atcaatcata aggagattct tatctagtta   1475
aaatttgtta aacagtgggg aggagtaaat gatgctcatg gtatataaaa atcactaatg   1535
```

```
cttttctttt tagctgataa aagttgagtt tgacgttaat cttataaaat gaacttattg    1595
aagtgagaaa tttggaaaca gtagtttaaa tgccgttgta ctgcaaaaca gatctccgtt    1655
gcttcattaa tcttgctgtg tttgagtagt cttcagttct gtgagacgta ggtcatacgt    1715
ggcgagttca gctttgaagc ttgtcttctg aaactggtaa cctggatggc tttgtagctt    1775
tgctgttgtt gaatgaattt gttgtagatt ttgtcttaaa aaggggggaca attagtaaca    1835 caagacttaa caaaaaggca tgtccttata tgtacatcca gctgtttcca agatggagcc    1895
caaaggttag cttttttccat agtagtgtcc attattggat gatcagatgc ttaataagtt    1955
gatcagaaag gattttccac acttaaccac cttttcccccc ttcctttaca attttgatcc    2015
ttgtaaggca caggggctct ttcgtgggac caaaagtcag ctttaaatgg ctccgattta    2075
atccaaagta gaaagtcaac atcatactta agttgggtca tgtgttacac attcatcacc    2135
atcacactat tgtgaaaggg tctgttagta tgggggacca aggaagggct cattatcaag    2195
cacattaaac aaggggctgc tgggcgccat ggctcatgcc tgtaatccca gcactttggg    2255
aggcggaggc tggtggatca acttcaggtc aggagttcaa gaccagcctg ccaacatgg    2315 ggaaacccca tctgtactca aaatacaaaa acatagccag gcatggtgac atgcacctgt    2375
aattccagct acttgagagg ctgaggcatg acaattgctt gaactcggga ggcagaggtt    2435
gcagtgagcc aagatcgcgc cactgcactc cagcctgggt aatggagtga gacgctgtct    2495
ccaaaagaaa cgagggacac tttgtctgtt gtaactgctc cactaagaaa ttgagtaatg    2555
agatggacag agatcttagg gatgtatttt aaacaaataa atggcttgag tttttacatt    2615
aaatacattc aaaaactgaa ggcatttggt taggtgggac agacctgaga ataacattct    2675
tgaggaactc aatcttattt tagtgacggg atgtgtctct gaggctccca ggggaaaatt    2735
gggcctagtg gagcagggtg tgtgcccggt gcatgtgatc aaatttgagg gagggaccct    2795
ctgtctagga gctgaggggt tgaaaggagg aggagcccct ggcagcctga gaaacaggat    2855
ctacttggac tgcagtgcat gtctgtagag actggcctgt ggggccacca gtgtcactta    2915
gatgtgtctg tgaaggggtgg cagtgagctg agagaaaaat gcacccgaca ttggggagct    2975
gctcagccag ggtgctgctc atctgggggc atggatgttg caaacagcac tcccgaaggt    3035
catgcagcac ctcagagtga tgaatgtcac tgccactgat gacaaacaag ttgccgaagc    3095
ctgggaagct tatgcagaga tgatgcagaa atacggaatg tgctgcgaat gagggtagca    3155
agagagaaac ggtacctttc accccactga agcagcagcc ctggagaggc acagaatttg    3215
atggcctcag atgttaaagt agcattttct tgtattatgt agaagccttt acactttctc    3275
atacatgagg tcttcccttta cttggcaccc ttacaataag tggggacttt atattaccgg    3335
tatatagtta gttgggtgtt ttggaaactt ctttatttaa tatgtccaag ttaaaatagc    3395
atattgtgtc tttcaacatc agagattcat gatttaacag tataagacaa atatccaggc    3455
aagcagtaga cttttgtttt ttgttttctg ggttgttttt ttttttttttt tttttttttt    3515 ttggtcagct ttattgcaaa atttgcacac aacagactgt ttataaagtt ttttgaaatt    3575
gcaggccagg gtggtggctc atgcctataa tcccagtgct tagggagact gagacaggag    3635
gattgcttga ggccagcagt tggagaccag cctggcaaca atagtgagac ccatctaaa    3695 caaaaaattt ttttaattag ttgggtgtaa tagtacaatc ctgtaatccc agctattcag    3755
gaggctgtgg caggaggatc gcttgagccc aggaggtcga ggctgcagtg agctgtgatc    3815
atgccactgc actctggcct gggtgacaga gtgagaccct gtctctgggg gaaaaggaa    3875
```

```
aagaaaaact acattctgaa gattgaacat agctgtgttt catcctgtgc tgtataagtg    3935
gctctaagca gttgtgatta cattttatga cgtgaatcct tttaaatgca atagggaagc    3995
ttatttaaag aaagctggtg gcgaatatgg ttgtcaacca aatggtctgt tatgtatgtc    4055
tggtacttta tgtatcagag tgcttttctc cacgtcacct cagtttgatc cttacagcgt    4115
cctgtgagga agggaagatg ctgttactgc tattttctag gtgaggaact ggacttgaga    4175
ggtgatacag ggtcaaaacc agatccaaac tagattgtta aagtccgtag ctctatatat    4235
ttattttcta agtctctatc tgtaaacaat gcatttactt gaatcgaccc aggaacctgc    4295
caagcttagt gagtttcagt agcggccttc ccgcacatga atgagatcac taagggggag    4355
gtttgtaacc acctgtggtg ggggcagcca ggagtgtatt cttcctcctg ggttagggcg    4415
tccccctttt ccctctggtt ctggtgttat cctcagcgtg acgtgtgtgg gctcgtgttc    4475
ctgtttacct cagggagaat gagaaacggt tatgttaccc catcagtgag ttctggctaa    4535
gtaggaataa aagttgtcat agagactttt aggactagga catttcatga ccgtgcttcg    4595
tttttgaata actgagaggg gtgagagcgg tggccccatt caaaggtcgt cagggatgaa    4655
ggtaggcaag gacaagtcat gtgcagggcg ccttagaggg ccttcagaag atggaaagtc    4715
gctcctggct gaacattcag atttgattct gtaaacagaa ttgaacataa cttacaaaga    4775
gactgagtcc tgcagttgga agttgatgct tagattagtc gcctgtgttt tcacagcttc    4835
taagtagtgt gttgtaattg tgtggcaaag tatgtgatta cctgggggt ccataattgc    4895
tgacttgtgt ttttacttga tgtatttgaa aacagttagg aaaatgattt tgccaaagtg    4955
tgtcttacct tagttaagat gaaatgtacc ttattgtgag tttctgaaga ttgcaaaagc    5015
ttgtcagttt agttttgggg gtcccattag tgagggcacc cctctttacc ttactcaaac    5075
cagctcttca catgtattcc aagaaactag agggcatgct aagaggtatt tctcaacaaa    5135
tggtttgtgc tcagatgctg ttgcttgtag ctgaggaatt tgactgcaga cttccccaga    5195
gccttggtgt cctgattggg cactgtgaga gaggggctac agttggacca ctctcaatcc    5255
tgtttgacgc tagaactctt tttagcctat tatgggtccg cagacttcct ctgcaaaggg    5315
ccagagagca cgcatttggc tttctgagcc atatggtctc ttgttgcaac tactcaaggc    5375
tgccatttca gcaagaaagt agccataggc gagtgggcct ggctgtgttc cagtaaaact    5435
ctagttgtaa agactggcat ctgaggactt cgcccatggg ctgcaatttg gtgactgata    5495
taacgtggga cttcattctc tgagcacccg ttggggagca ctggcctacc acggctgcac    5555
agacagcttt aaggaaaaca gcagcagggc aagttttctg agctgcatga tgtgagccc    5615
gggagagccc aggtgagcag caggctagct tgggtctcct gtcttggagc acttcagagc    5675
ttagcagggc cctctctctc tgtctttttt gttcctctgt aacagttata tggatgactt    5735
gatttaaaat cagacgaatt tatcagaaag cctggtgacc ggttgcattt ttctttgttc    5795
ttttgctttt tgttgacccc agtggcccac atggcatttc tcgtccgtct ttgtcatctc    5855
aggctctagg cttgctcccc ttcctgtgac accagaaggt gagcgtcagt aagaactcca    5915
gagcctttcc acggccctct tcccagcact tccctcccca ggggcagtgc ctgacacata    5975
gtaggccctc aggaaatatt tgagggaatt agtgaaagaa ttatatagta tttgtccctt    6035
aaagttctta tcattttctt gttaaggttt tactttcaag cagattgcca cctatcttct    6095
aattgggtct gttatttgct tccgagttcc gtacccatgg gctcccaccc ggccaccaaa    6155
ccagctggcc ttaggagtgc tgaggccaga gcatgtttgg ggcaagttac atcagctctc    6215
tgagctcaga gtttcctcat ctgtaacatg gagataataa caattcccat ctcagggtgg    6275
```

```
ttatgagggt agcctgagat gatgtgtgtc tggcatatcc gcccaatggg aactgacact    6335
agcgttaacc agggacgttg tcgtaccttg taagtcctag gacttactgg gagtgctagt    6395
ctgattggag caagacctgt ttctcagcag ttctggaaag gacagaagcc atgtgtgctc    6455
gtatccacag aaaccagtgt gcaggcacgc gtgtgatagt gtagcacctc agcagataca    6515
tagccgggaa ttctgtcatc tataccattg actctgtctc catttttat tgtattttta     6575 aaaataggaa cgtgatggcc atgaaagctt aaaattacga aaacttaaat ggtgtgtgtt    6635
ctgaattatt ttttctttta aatcaaatca ggatgtacac tgaaaattat tgataatttt    6695
gaagcatatt tcatggactg tttaagcagc agacaagtat gtgattctgt ttgtttactg    6755
tgtataattt atcttgaggt acctgttaag cattagcagt gtacacagga ttctgataga    6815
tgcctgtgag tacttagaac catcttgaga agatgaaacc tcgaggcaaa acttaaggaa    6875
agggtacaga aatgcagtca agtgcaaaaa ctctggaacc agaaagggtg atctgaataa    6935
ggcttcattt actccctccc ctgtttcctg agtgtccccg tgtgcagaag tccagggccg    6995
catgccccag tgggaggcag gccctgggat ggttgaggag ccttgggctc ctgtgacagc    7055
tcttctgctg agccagcaca gagccaggag ttggggaagc ctgcctgttt tccatgcatt    7115
cctggttgtt gggaaaagca ccctgaccat gacagtttgt ttcctggggt atcgttgtag    7175
gcccatggct tgctcacatc tgagtcctct tctggttgtc ccgtctctcc taggctctga    7235
agctcctggc cgtgccgtct gctttttagc acatgcgctc agcgttccct ttagtcctct    7295
ctgaggtctt ttccttgcag tgcatccctc cggatacact ccttgcttta actggaaaag    7355
gatgctgctc ttctcagtca ggctcaaact tggctttcgg caaaattctc ctattgcatg    7415
agtctttgat gcagaagtgt aagccttggg agcagtgcct gtgggggctt ttgcctgttc    7475
tcctttccct ggggccgtgc tctgctgaca ggggtgctac aataggccac gagcagagtc    7535
cccggggcgt cctggagtgg tcaggtcttt gccatttgag ctgtgacttg aagagatttg    7595
agcaagggca cacaaatcaa attgggcaag gctgtgtgaa aggcatggaa gtaaacaaaa    7655
gtggcccctc tctttttaaa gttttttta ttaagttcct agacaatata ggcggtgact     7715
gtggctgtat ttaaaatact gcctttaggg tgttttctgg ttctaaattt aggaagcaag    7775 gctattttg agctctgtct ctaaaagttg aattccttt aaaacttacc cttaagaaag       7835
atttggatat tatcccgtgt gacattttcc ccggtgtttc atttccatta atcaaaagac    7895
tgtttagttg aaccattgct aagaatagta aaatctaatg gggaaaataa ttctacatga    7955
ttaaatctga ctttactttc ccatttctag ttgtactgtc tgctattgtt tgaaaatgtc    8015
ttaatttgcc tttctaatat gcctgtacta tattgtatac agtaggtata ttttccagtt    8075
gcacctaatt caacctttcg aatttgcata atctgtggta aggagaaaaa gtagttgtgt    8135
agtggagttg tacaattctg ttgtaaagca aatctttta taattcacaa gctgcttctc      8195 ctcccctag tttggatttt tcttattaaa actgcaccac ctaaacatgt tttaacttta     8255
tggttaaaat aaccagtgaa atagaaaaat aagtcactgt tctgtatgat aacatgtaga    8315
gaaggcttgt acaacatttt aataaggaga tttgggtatt tgattacaaa ctgaatgagg    8375
acattcagga gctatagaaa tttatcaggt aattagggtt tgcttagaca attatagact    8435
ctacgagttt gacccagttg ctttggatta aaatattttg agtatttgtc acctgattaa    8495
aagtagaacc ttctaactgt gagtcacagt tgaaggaaat gtcagctttt tatacgggga    8555
ggcggtcagt gtggtgctga ggagggagcc ctggctcctg ctcagagtag actgtgagtc    8615
```

```
ccagctccca gctcggcagc gctgtgactt gggctggtga catcacattt gagttttgca    8675
gggtggggtg tgtgtgtgtg tgtgtgtgtg tgtgtgtgtg tgagtgagag agagagagag    8735
agagagatct ctaaaagggg cttttttaccc tgcagtattc catttgtttc ttttctttct    8795
cttctctctt ctttctttct tttttctttc tttcttctc ttttccttcc ttccttcctt     8855
cttttttttct ctttctttct tttccttcct tccccttccc cttcccctcc ccttctttac   8915
attacttttc ttctttccaa tggggtcttg cttgcccaag ctggtcttga actcccatcc    8975
ttcagcaatc ctgcctcggc ctcctgagta gctggaatta caggtgtgag atggagccac    9035
tgtgcctggc tctacttctg cttactttga ttatcttggt acatgggct actagggtgc     9095
ctggcatata gcaggttgag gcagctgttt ttattgttta attgtatggg aaaatattag    9155
ccatcaccta cttcttgggc cagtgaggac taagatgatg tagcctgacc cggaatcagg    9215
aggcttctca ctgaatacat gggaagcttc tgcccctgcc tgtttggctt tcagtgccag    9275
ctctagtgca gtttgggaac cagttttgtaa gaaaacgaac taagattcga gaatcttaca   9335
aaatgggtaa tcgtttgact cattttactc cgtctgtgtt tgcagttcaa ctgttttta     9395
ttggaaaatt gaactcttaa ttaaatggaa ctctgtttct agttattgct tcagaacaag    9455
ggcttgattt agattaggac ttagagaaaa gggaaaagta aatgcagaga aattataaat    9515
atagtatttt attgaaaaca gagttgggaa gaaaatggcc ttgggatcac tgtccagttt    9575
agtcaggttg gttgaaagga ataccagtga aactcaattg cctctcgggc tcagctacac    9635
agatcttgaa aggaacagat tcagctctgt gctgtactgt gtgacttttc tcctcctgca    9695
gattctatag taggaaattc ttttaatgga gattactgtt tttctgttct cctagatttg    9755
gtgtgatttt ttttttttat aagtaaaagt taccccgtgg tggacaaaat ttttccccga    9815
tttgtggata tctttactta aatctgattt acatattcag aacgtcacct ttattgaaaa    9875
taacaaaaag acataacata ttgataggtt ttctgtgtca ttgtggttgt tcctctacta    9935
ctgtgggaat cggttttgt ttgaagagca cacctgcccg tagttgaact tctgttgaga     9995
agtctctgag ggaatcattt gaatgatggc aagagaatca agtgtttgc tttcactgat    10055
ggctttctca gtcactgaaa ctttagggga gaacggattc tttcccagga ggaagagggt   10115
gaattgagat gttttccttgt ttggggatgc ctgtgttctc gggatgccct ccaagccagc   10175
gctgtccagt ggtcgttatt gggagggcgg ctctacgctg tgtctatatg acacagtact   10235
ggaaccacga gccacgtgtg gctgttgagt acttgaattg tgattagtgt gacttaggaa   10295
ctaaattta aatgttacct ggtttgagta aatgaagata gccacatgta gttagtcact    10355
acggtattgg acagcacaac tgtaagtaca tttacttatc ctctttgtct agagttttct   10415
ttaagatacg tatcacctag atatttatga caaagttcct ttaaaacgat catcttttaa   10475
agatgcaaga ctccaaatta aaaatgatga aagactcctt caaaaatatt cacggcttag   10535
gtcacactgt tcaggattat tcactaattt agaaaatatt tgttatgctg tgatgtaggc   10595
cctggcgatc cagtggggat gtgacaggcc ccatctctgc cctcatgggt ggtgatggat   10655
actggacagg taactgcagt caggtgtgac cttgaggggg acatactgtg cattgactga   10715
ggcaccagat ggggactgag cctgttttga agggtattgg aagtccccgg gggctgtgac   10775
gttagcactg acacctgagg gtgaatagga gatggcagat agtactgttc caggcagagg   10835
gaacagcact catagcaggg tggaggtctg gctcttgtga cagttttttgg gttatgttca   10895
ctgggctacc agaatttagg aggcctcatg gttttgcttc tgagatggtg gagactaaag   10955
gtgtggttct gccctgcggg ggttggtcgg cccgggatcc agtcttgact cctaccactt   11015
```

```
cattcttttta ttcagcaaat atttaagcac attttacgtg tggggcaccc tgctgggctg    11075
tggtgatgac agtagtggca gaagctgctt ctgtcctcat ggaactctga gttgtgtggt    11135
gtggtgggtg agcagtcccg tggtgcccac cgtggcctat agcatttcac actcagctcg    11195
atgtctgact ggaaggaagt ggatgcctca ggctgggtgg tcagggaggc ttgttggagg    11255
aaggacacca gagctcattg agggtgagta gagcatcagc ttgggcatct gaaggcgaga    11315
taacatcacc aagggccttg aatgtcagac ctaggagtcc aggttattat ttttttttag    11375
ggcttataaa acaaaattaa gctttaaaaa acccgtgtcc agagtgattg ggggagctcc    11435
tgtgatttat tttccagaag tctagattag cttttttcaag gtgtgttttt tcatccaagt    11495
tcaggtctgt agggagagta gacaatgctt tcccctcctg agcccgtttt tggcaggaa     11555 aagggcccca tgaaaagcag cttaagaact ggaactagtg ttcttattta agatgttagt    11615
aaatttttgt acaaacaatt ttcttttaaa agttttttta agttcttgtg agtagataat    11675
atattcatat ggttcagaat tccaaaaaag cagagtaatt ggtgaaaact cttcctcctg    11735
tctgtttctg gggtcactgg tcattcccct ccccataggc aaccagtgtt agctgtttct    11795
tacgtattct agagatggac tgtgcgtagc caggcaaata tggtctcttc ttactctttt    11855
tgccctaagt agcccatttt atgtaactct actatcagtg cctttcagac tgatacatat    11915
ctcagagctg ttggaaatgt tagtattaga aatgcaggct ttgttctatt tttttaaatt    11975 tattttatt tattttgaga cagggtctca ctctgtccgc caggctggtg tgcatttatt     12035
tgatcacagc tcactgcaat gtccaccttc tgggctcaag caatcccacc tcagcctccc    12095
aagtagctag gatgacaggt gcatgccact atgcctggct aattttttttt ttttttttt    12155 ttttagtaga gatacggggt cttcctatgt tgcctaggct ggtcttgagc tcctgggctc    12215
aagcagtcct tcaacctcag cctcccaaag tttagggatt acagatgtga gccactatgc    12275
tcggcccagg ctttctttta attaattaag tcttcttttt taacggtaaa atgttttggt    12335
gctgcattta gataaataac acaaaacaat tttaatgttt tctctatgtt atataaatag    12395
gaataattga agtttcttg ttttttgttt gagacggagt cttgctctgt cacttaagct     12455
gaagtgcagt ggtgagatta tagctcactc tagcctcaaa ctcctgggct caagccatcc    12515
tcccacttca gcctccgcag tagcttggac tacaggcacg caccaccatg cccagataat    12575
tttttattat ttttgtagag acagggtctt gctatgttgc ctaggcttaa agttttttta    12635
aaattaattc catgtcatct caaagaatat tagaggtttt gctactgtca tcaaaatgca    12695
tgtcatgcag ccagctcaca cagaagttgt gtttattgtt tctcaattcc tggaatagat    12755
tcttaaaact tctggttttt attacccacc ttaatagttg aaatagaaat atctgtaggt    12815
tagcaaccta cttcaacacc aagcagataa agtttcttga tgggtaggac ttctaagaac    12875 atttttcatta actccagacc ttttcgttaa tttagttaat taatgtagag attgtaaaac    12935
actgagtatg actcagaaat cctttagaaa agaaagggta aaatcagtga agttccttca    12995
gaagagtagc tgagttccct ggcattgcag atccagttga gggagagtga tgggtactta    13055
ggaggggaga aaagactgag aatcaataaa caaaggatgg agagcaaaaa tgataattag    13115
atctctttta ggggtagaaa gatatgctaa tggtgtatgt aggaaatttc tagaagggaa    13175
tctctagaaa ttgttttttcg gggttgagct agagatgttt tgggggctgt ttttcatttt    13235
atattctgag ggttttttt caacaaagc aaaaaaccat aaatgtattt actttcatag       13295
tgaaaaaaga aaaactagtt aaaaaaattc aaaacaaaac attttgggg tatatatgtt      13355
```

```
tttgtattgt tttatttta tatttgtgat taagagaatc tgttaaatgg tgagaagcaa    13415
agttttagtt aattcctgtt gcaaaacctt tagacctcta atgagaatta tttgaacaaa    13475
gtacaaatta cccctaagag gcgccatcca gagataggaa aatggattgt gttttagtgt    13535
ggcgtctgat catcacttgc tttgtcacaa gctccatttt taacatcatc tttatattag    13595
aggtttcttc attgatttgc tagaagccac aagacatgac agccaactaa ttttgagta    13655 ttttgaaata atgtcagatt tccctgtgtg agcgttgggt acaaaatgtt acatgtcgat    13715
tgtcacatcc ctttagaaaa aaatactttc gaaaagttct tctttaaagt gccctttct    13775 tttctagcct tttaagctta tttgtacact aaatatattt tgaactaata gtgaacccat    13835
ttcacatttt atcctcaaat cataaggacc ctaactggaa actggagcac tgggaaccat    13895
tccaggtgtt accacctggt gctgaagtta atcacctggg ccagtatatc cccagtgggg    13955
gtgccttaaa aaaaaatcag tttcttggcc gggcgcggtg ggctcacgcc tgtaatccct    14015
gcactttgga aggctgagtt gatggatcat gaggtcagga tatcgagacc gtcctggcca    14075
acatggtgaa accccgtctc tactaaaata caaaaattag ccgggtgtga tggcgtgcac    14135
ctgtagtccc agccactcag gaggctgagg caggagaatt gcttgaaccc agaaggtgga    14195
ggttgcagtg agctgaggtc gcgccactac attccagcct gggcgacaga tcaagactcc    14255
atctcaaaaa aaaaaaaaat tagttccttt aattacttaa actagtagtt cattcacatg    14315
gctcagaaaa ctcagaggac aaaacctgta gagagagcct ccctccacct agctcctccc    14375
aggtaaccac tggaagtagt gctgtcttcc agggtttatc tgtattcagg cagacgctgt    14435
tgactcttag ttctctcttc cccttcctag ccttttttctt cttaactgag gtagcatagt    14495
gtacacacag ctgcatacgt ttattgtctt cttacagttg tctaccattc cattatgtga    14555
cctgtgccat aattgcttta atcctctccc cactggtgga catttaggtt atttccagtc    14615
ttgtcttctc acaaacagtg ctttaatgaa tagccttgta aagttatgcg gacaggcaaa    14675
tctatggaac agattcatag aaatagaatt agtggttaaa aggcatatgc atttatagtt    14735
ttgatcatag caaattttcc ttcaagagcc tgtgtgttgg tagagtctta aaatgtgaaa    14795
ggcagcacat atattctcca ggtatacatt gctagatgtg ttgcagatat tctttttttt    14855
tttgagacag agtcttgctt tgtcgcccag gctggagtgc attggcacga tcttggctca    14915
ctgcagcctc cacctctcag attcaagtga ttctggtgcc tcagcctcct gggattacag    14975
gcatgcacta ccatgccccg ctaatttttg tattttagt aaaggagggg ttttgccatg    15035
ttggccaggc tggcctcgaa cgcctgacct caggtgacct gcctgccttg gcctcccaca    15095
gtgctgggat tacaggtgtg aaccaccatg cccagccacg gatattcttt atcagcatag    15155
tctatgatga gtaacactaa ggttgttctt cagcttgtga ttctccatca tgttgtgctt    15215
ctcagttgtt tctgaattct ctcatttat ggtgtacctt tttattatta ttttgagtca    15275
gggtctcact ctgtcaccca ggatggagtg cagtgacgtg atcttgactc actgtagcct    15335
ccatctcctg ggctcaagca gtcctcccac ctcagcctcc tgagcagcta ggactatggg    15395
catgtgccac catgcctggc taattttgt acttttttt gtagagaccg ggtttcgcta    15455
tgttgcccag gctggtcttg aactactgga cccaagcagt cccctgcct cggcttccca    15515 aagtgccagg attataggtg tgagccaaca tacctggtac tggcatactt tttggactta    15575
aggcattcat tttctgtttg tggctctcaa atagcccaca cgcctccacg cgttgtacat    15635
ggactggcac ttccaagtct gctttcacgt ctggaatatg ctctttcccc ctttcttgac    15695
ttcttgttgc cgcctgccag ctacatctca cagcatttgg ggcaaaggac ctggtctctg    15755
```

```
gatgtctgtt tgcttgttct tacaatatgg ctggggaatc tgaggtggct gggaatctgg   15815
ggtctggggc tgcttctgca aaggctagct cctagctcag cccccacatt cttcttcctc   15875
caggactgtt cttggctgga gaatcctctc cctgtaagca gggtggatag gcagctgact   15935
gtagcacctc tccggggtct ggtgcccctc tcagctgtgg tggtggtaaa caacccgttt   15995
ttgctcccct gtcccagatg attgggctaa cgtgcagggg ctgctgggtc attactgtgt   16055
tctggtggca gctggctgct atgacaggca ccttccattc cacccttgtc cccacccttc   16115
agggctgagg gaagcagcac gcaaaccatg ttgaggaaac taacgttgtc ttggctgtct   16175
gggaatggca cttccctgtg actgctaagt gcaccaaata aaaatagact tggctgcatt   16235
tccaggacag tttagggtcc caggtgacaa agaactttga ataaggactg tctagggttt   16295
tttgtttttg tttttgtttt gagacagaat cttgctctgt cacccaggct ggagtgcagt   16355
ggcgcgatct cggctcacgg tagcctctgc ctcccgagtt cagcaattct ccggtgtcac   16415
cctcctaggt agctaggatt acaggcaccc accaccacgc tcagctaatt tttgtatttt   16475
tagtagagat gaggtttcac catgttggcc agacgggtct tgatctcctg acctcaggtg   16535
atcttcctgc ctgggcttcc taaaatactg gaattacagg catgagctac tgtgcctggc   16595
cctgtcttgc ttgggttttt taaatggaag gtaaatagta atcattcagc gaagcaggat   16655
gttttttgat acctgataca gagtacagcc atcaagtgca tttgagaatg aataaaaaag   16715
ctaaaatttt ataatcaatt atgcaaaagt agattttacc ttttccaggt agcactcttg   16775
aatattgtat taagtgcatt ttgataaatc agtatttccc ttctgattca cattacagtt   16835
tctaaggttc tgtaattttt attgcagtta gtttaacctg ataccatagc ttgatttatt   16895
tccccttaat tcaaactttg aagttcatca tgtttccatg ttaaatgaac ttactaagca   16955
catttccgtg taaaagagtc ccctggatg gaccttctg tgacatgaag aatatttgtc   17015
ctgtaattta gctttcaaat aagaggcaaa ctctgagcag aacttcagag ggaaaggaca   17075
ctgagaaaag acagttccaa agaggcaggg acggaagaca gcaaggcagg caggcaaagc   17135
tggctgctct gccgtgggga gcttcaaggg aaaaacttca agatggcagg agcccctcgg   17195
taggtacgaa ttcgatacag tgggaagggc gtcactttgg taggtatgtg gatctgatac   17255
agtaggaaga accccactag aatgtcgtat atgaagaatg gacttcttgg ggaaggtcgt   17315
tgttaatgtc cacttaaata tcgttcatca tacaaaacac agcatatgac aggaaaacaa   17375
gaaaacccaa attctaagct ctagtataaa tgtaagtgct gtgttgaggg ttttaagaca   17435
attcggttta ttaaacccaa atttaataac ccgagattgt gtcactgcac tccagcctgg   17495
gcgacagagc aagcctgcct accgtagtga ggcccttccc accgtatgga acttgtacct   17555
accctggggc tcctgccatc ttggagcttt tccttgaag ttccccacag cagagcagcc   17615
atctctgcct gcctgtcttg ctgtcttctg tccctgcctc tttggagttg tcagtgtcct   17675
tttcctctaa acttctgctc agagcctctt atttgaagcc tttcctactt ttgttcactg   17735
ccttattcca cttggctgta aaatatgaca tacgtgttaa tttaagtttg tggcttggtg   17795
tccattggct gtcttcctca attagagtac agtcctctgg ggaggccgac ttctattcta   17855
tctcaaaccc agccggtcct gcaccgagtg agggcccctg agcagtgact cgcttccttc   17915
tcctggggag gagagggtgg gggctgccgg ccgagctctc tggctcttca gcagatcagt   17975
gattctgagg aggggcaaga cttactcaag ataagatcac tgttcagaat gaagtacaac   18035
ctcattgttc tgttctaatt agggattggt gtgtctgcat aaaagaagcc tgaattacgg   18095
```

```
aagattttag aaggaggttg ctttaattat ttcctaatag tcattgtaaa aaaaaaaaaa   18155
aaagttagat gtcttttggg aacttgttta aatgcctaga taaaaattac ttacgatggc   18215
ataaatatta ataaaacagc ttttctcttt cttttttttt ttttttttg gtatagagag    18275 ttgttccatt atatttattt gcataatccc caagaacttt caaagcaaag taacctttaa   18335
ttctactaga attgccacag atcagcaggg atgagtttat tagcaagtca ctaccattga   18395
taagtggcgg ctgttgagcg cctgctctgt accaaccctg gagtgccagg ttcttaaagg   18455
ctttggctgg ttcagccctc ataggtgcct tgggagatgg gattgggaca gtgatagtaa   18515
tgactaatat ttttgagtc cttactgcat gccaagctca gtgctaaatg ctgtatggtt    18575
taattctttc atcaacgatc ctgcgaagca ggtgctactg tcctttattt tattttattt   18635
atttattttt ttgggacaga gttttgccct tgttgcccag gctggagtgc aatggcgcga   18695
tctcggctca ctgcaacctc ccagtgattc tcctgcctca gcttcccgag tagctgggt    18755 tataggcacc tgccaccacg cccagctaat ttttgtaat tttcagtatt tttagtagag     18815
acagggtttc accatgttgg ctaggctggt ttcgaactcc tgaccatagg tgacccacct   18875
gtctgcctcc caaagtgctg ggattacagg catgagccac tgcacccagc tgtccttcca   18935
ttttagagct aaggaggggt acacagggag gcagtagctg tggtgacagc tgtgatctga   18995
accagggctt ggttgagtac tcttctcact acaccagact gcacttcctg tgtccgtagt   19055
gtctaattag taatagatca gtaaacacac cgagagcgta gtgtggcctc caggtcattt   19115
aacaataata ataacaacac tgtgaatcct tccaccactc tctagattcc tcatctctag   19175
gagtgaactt ttccaggatg ctttgcccct gctggatcaa gttttttgta tgtagttttt   19235
ttccttcaaa ttttgtttta attaacaaat aaaaattgta tgtatttatc atatacaaca   19295
tgatgttttg aaatatctat acattgtgga ttggctaaat tgagccaatt aacatgtgca   19355
ttacctcttc ctgtgtccgt taacttagaa attaaaaatt ctttttggag ccacagtggc   19415
acatgccagc agtcttggct acttgggagg ctgaggcagg aggattgctt gagtccagga   19475
gtttaggagt ttgaggctac agtgagccat gatcacactt gtgaatggcc actgcactcc   19535
agcctgggca acacagaccc catctcttaa aaaaaattcc ttttggaagt ttttcgaggg   19595
taggtaaata ggtgaataaa aatgtttagc ttttgaaaga tttaatagaa gcatttgagt   19655
agtcagggct atagtacaag tctgaggatg tagggaaaaa tcaggtttct cctatactcc   19715
tttattccta tactcagtgt caacagtcga cacagaacac ctctgggacc agatttgtgg   19775
agatgccccc agccacacac acacaccgag taggcactcg gtgctgcagc agacgccagc   19835
tgacaggcag atggtgtcag atcccacggt tgagggctca gtcctcaaga ctgcccccgc   19895
cccccaccat ttgcaagccc caagttgttt tacctgtgct tctgactggc tataaatggg   19955
gttcccacaa gccctcctt gggttcaatt aatttactag agcggttgac agagctcaag    20015
gaaacatgtt tactggtttt ttattgtaaa ggatattatg aaggatacca ctgaatatca   20075
ggtgataggg caaggcgtgt gagagggcca tgtagccttt ttgccccgtc caggtgtgcc   20135
actcttcagg aacctccatg tgttcagcta tctggaagct ctctgaaccc tgtacttgtg   20195 agttttatg gaggcttcat tacataggca tgattgatta aaccattggc cgttggtgat    20255
caacttaagc tttagtatct ctcccttccc tggaaattaa ggatgggctg aaagtcccag   20315
tcctctaatc agtcatgcct tggtcttcct ggtgaccagc tcctgtccga agctacctag   20375
gagctgccag ccatcagtca attcgtgagc atacgaaaag acattactgg ttgggtgtgg   20435
tggctcacac ctataatccc agcaatttgt gaggccgagg cggatggatc acctgaggtt   20495
```

```
gggagttcta gaccattctg gccaacatgg tgaaaccccg tctctgctga aaatacaaaa    20555
aattagccgg gtgtggtggt atgcgcctgt aatcccagct acttgggagg ctgaggcaga    20615
agaattgttt gaatccggga agtagaggct gcagtgagcc aagatcgtgc cactgcactc    20675
tagcctaggc gacagagcca aaaaaaaata aaaataaaaa aataaaaaat aaaaattcta    20735
ttttggagat tccaaggatt ttaggagttg tatgccagga gacagggtgg aagaccaaat    20795
acatagtcac agtattacaa aagtaatgca aagacaatc taaagaaacc atgaaaaaaa    20855
aatctaaaga aggagacct ttttcacagg aaatagggat gtgagagaga aattaggagt    20915
gggtgaggaa gagaaaatat gtgtgggagg gaaagcagag aagtatgaac acatcacaaa    20975
acagcatctg aactcttaca tgcttatttc ttacactact gttgctcatc ctacattatg    21035
ccatttaatc tgtgtatcaa ttctagggtt ggggttcatt gatgctgagt ttgtagccaa    21095
agagtgaaat atacttgggt ggtcccctaa aaggtaaaga gggcaatagg aaaaagtctt    21155
aaagagaaag atgacccagt gtaatatttc tagagaattc gttattgttt ctgttttcag    21215
aaagtagtag taaacattaa gattactgct ttatatcttt gactagacaa gcagcttgtt    21275
gatactgtgt atcctctata atgtgagcac tcattcagca cgtgggttta ttgagtgcct    21335
agtacatacg aagcatttta tgctaggcac tgagtagata agcaagacag gatccctgct    21395
ttcagggagc ttcagccccc acgcacgtta taacgtgaaa ttgttagcat aattttaacg    21455
cattgtgtct gtaggagcat aaaagagttc ttatttccag gagaaggtgt gatagaccag    21515
tcctgtcagt acaaataatc tggggctcca agtggaattc aaagaagaaa ataaggtatt    21575
atggaagagg aggctgtaga aaacctgaag aaaggtgtgt tttgtggata ctttggctga    21635
tggctttgaa attttttca gatgaggctg ttttcaaatg ttattggctg cacagattga    21695
tttagccacc cacctggtgt ttgattctag tagttcattc cttgcttaag gtgaaatgct    21755
gatttctgat catcattatt aagaatggat cctggaacag atgtaggtac catttgtctt    21815
tcagtgttta ggagtgatcc ccacctaaca gtctgcatgc agaccaccgg cttgggtttc    21875
ctagtataga agtgaatgtc ctctgtacct tgcttggtaa acagttgcct ttcctgaggc    21935
tggctgagtt tggctgtaac tttctccttc ctaagtccct actattttcc tcattcctca    21995
ctgggtcttc ccagcctcgt atgagtgtga tagaaatggg gaaatgtgta gcctctcttt    22055
tctctcattt cagcttaatg aaaggggtag cctcctggtt ggcagccagg aagctgcaaa    22115
agggaaaatt cctttcccta gctatggaag tatgacaggc agtgttcgct atttgatatc    22175
ggctggtgaa gtttccttga ggtgcaaatg ctctgggtgc agggtgccca cagtctcctt    22235
ttctttgcat tctcccgggc cccctggtaa cggtcagaga aagagggct tacctgggac    22295 tggatcgctg tcaatcgtga accttaggaa cttccgatga tacagattgc tcttgcttaa    22355
cccatgtgtt gggacacttt ggtgtgtaga aagcaaagct gtgttgtgtt gcaatatcct    22415
ggcctgcctc cttcactccc cttttgtcagt tttgctgaac tagggaatat ggaaatgtgg    22475
tgacagtggt aaacagaagg gtgatggtac gactacgtgt gcgccctatc ttgccttta    22535 aaaagccaca cctgtatatt tggttttaca catattcata tggtgaatta cagaagaaga    22595
atttgtctaa ctctgccttc acccaaacag ctggtatatg tatttggact gaaataggat    22655
gaaaaagtgg tcacggtggt cagagtgtag cagaccagtg aaaaacaaaa acactagccc    22715
aggacataag ccctgcttac aactttgaaa cttgcctgtg aatttgataa gaactagaat    22775
aaaccataaa tgaaaactga tagctctgag agtggcagga tgatgggtga agttttaac    22835
```

-continued

```
tctgggcgt tggtacccett gttttacagg tgagggtatg aagatgcaga gatgaagcag    22895
tttgcctaag gatgcaggat ttcaactcct gtgctcagct tccagctgtt ctgttcccat    22955
tgttctacac tgaggccagc cctgccctgg gtttcactaa gtactctctg agtttatctg    23015
ctcttctgtg gcctggcctc cctctcctag gaagagtgct tagggatgtt caaaatagcc    23075
agttaggtcg cctttttgcag attttttccaa acttaaatat aaaatatttg gcccttgttt    23135
gcttctgggt tacagtgctt gacacggtct cttcatcctc gccctggaca gaaaggaagg    23195
agagctgatc tctaatggta atggctccag ttcctggttt agatgaagtt tcattttcat    23255
gctcatcagt taaggaacac tgcatttttta aaagtagtta ttttgggctg cagtggctca    23315
tgcctgtaat cccagtgctt tgggagactg aagtaggagt atttcttgag gccaggagtt    23375
tgagaccagc ctgggcaaca tagcaagacc ccatctctac aaaaaaaaat ttttttaatt    23435
agctggcaag cctgggaaac atggcgaaac cctgtctctc caaaacagta caaaaatcag    23495
gtgggtgttt tggtgcaggg cggaagctgc attgagcctg caacttcact gcactccagc    23555
ctgggtgccg gagcaagacc ctgtcaaaat aattatttaa ttaattcatt aattaaaaat    23615
aaaataaaaa atgagctgtt tgtggtgggg cacacctgtg gtcccagcta tagggggctg    23675
aagcgggaga attggttgag tccaggagtt tgaggataca gtgagctgtg attgtgccat    23735
tgcacagagg tgacagagca agaccctatc tctaaaacat aaaataaaaa ataaaatgtt    23795
gttatttggg ggggtacata ttttcttttt tccttttatt tgtagttgac atgtgattgt    23855
atatattaag gggttacaga atattttgta acatgcatgc aatgcataat gagcaaatca    23915
tagtaattag gatatctacc acctcaaacg tttatcattt gggttggaca aaaatatta    23975 ttaaggagta ccgagtaaat ttgtgtgtgc aggtggacaa agcctggagg gcaacaaaca    24035
aaacagtagt tatgatagag aggacttttt aatacatatt taataaatat tgtacagttt    24095
gtgtctggac acctcagtga atctccaaat ttaggatagc aaaatagcgt aaaaactatg    24155
gattggaacc ctcagaagca tgttgagacc tatttcacca ggtacaggcc ctgtgccctc    24215
atggaactgt ctgctgtatc cgggatcaga ttcctttctc ttcaaaatga catgccctgt    24275
aaccatgagg aggtacccca aattgaagga ccttctacaa taacaactgg cctctattct    24335
tcaaaaatgt cagttatggc cgggtgcaat ggctcacgcc tgtaatccta gcactttggg    24395
aggcttaggc gggcggatca cctgaggtca gaagttcgaa accagcctgg ccaacgtggc    24455
gaaaccccgt ctctactaaa aatacaaacg ttagccgggt gcggtggtgc acgcctgtaa    24515
tcccagctat tctggctgag gttggagaat tgcttgaacc cgggaggcaa aggttgcagt    24575
gagcctggat cgtgccactg cactccatct agcgtgggca acagagcaag actctgtcta    24635
ataaacaaat aagaataaaa tgtcacttac gaaagacaaa ggccagggaa cctttgatcc    24695 ttttttcgatt aaacaaggtg acaaagacat gacaattaaa tgcaccatga tcctgaatta    24755
gatcttggat cttgtaatct catggctata ggacatgtca ttttgaagag acagatgtgt    24815
gataaagatc attattggga caaccagcaa aatttgagta agggcagtat attcagtatt    24875
gtatcagtgt tacatttcct gagttgcaca tgcatactgt gattatgtaa gaggatgttg    24935
ttaggagata cgtactgaag tacttaggag aacagtgtta tttcgtctgc aacttactct    24995
cagtctcggt ttttcttcaa aaactgttac atgcatgtac acactcctaa atcacatctc    25055
attccttaca gacaggtggg aagataacaa gtgtgtgtta gacgtggttt tctagactga    25115
caagagggac tggtctgttc tgcaggggca gcccaaagaa agtcttcata gttgctgtgt    25175
ttaatctgag tgggaactga ggtgagtttt agaatgagag attcaagaag aaagattccc    25235
```

```
aatgcctgtg ccagctctca gtgttgtggc tggaaagtag ggggcatctg gtgttgtcct   25295
gtaaaggaag gccaagaaga tagcctcacg tgccatgaga aggtgtttga acttcttcca   25355
tagacatgat gggtctgtta gggttagggt gaggttaaac tccagctaaa atggcttaag   25415
tgatagtaag tgtattttct cacataacat gaagtttgaa ggtggggaag tactagggtt   25475
gcatcactca gcagttcaga gatgatctcc ccaccccagg tgtttatgtt tttggctaca   25535
gccatcctta gcatgcaagt ggtgtctgct ctcctggcta cagggtgatt gtcacctgcc   25595
catgacgaga tctggtgaag aagaggaggg agatttcttt ctgagcatcc attgctgtga   25655
ggaaggaaca ccttttccac aatggtcctg gttcagtgta ccttcagatt cccttagctg   25715
agattgtgtc acttgcaaag gggaacgtga tcgtggtggt gggcttatct ggttactctc   25775
cctcctgtgg ccagggaacg ttcctcagag gaacctccca ggcagccact tcagatcatg   25835
tgggtgttgc cagcagcatg gggccagggg tattgggtga gcagacatta gggtctgcca   25895
ccatgcagaa aaaggtttt aattttcttt tcttttcgt gtgtgtgtgt gtgtgtgtgt   25955
ttgtttgttt gtttgtttgt ttttgagacg gagtttcgct cttgttgccc aggctggagt   26015
gcaatggcga tatctcagtt cactgcaact tccacctccc aggttcaagc gactctcctg   26075
cctcagcctc tcgagtagct gcaattacag gcgcctgcca ccacgcccag ctcattttg   26135 tgtttttagt agagataggg cttcgccata ttagccaggc tggtcttgaa ctcctgacct   26195
cagatcgtct gcctgccttg gcctcccaaa gtgctgggat tacaggcatg agctaccgtg   26255
cctggccgat gtatggtgtt ttttgtttgt ttgtttttt gagatggagt ctcactctgt   26315
ttcccaggct gtcatccagg ctggagtgca gtggcgcaat cttggctcac tgcaagctct   26375
gcctcctggg ttcacgccat tctcctgcct cagcctccag agtagctggg actacaggtg   26435
cctgccacca cacctggctg attttttata ttttagtag acagggtt tcaccgtgtt   26495 agccaggatg gtctcaatct cctgacctcg tgatccgcct accttggcct cccaaagtgc   26555
tgggattaca ggcgtgagcc accgcacccg gcctgatgtt ttaaagtatt atacagccgc   26615
ttattaaacc tcctgttatg gatagcagta ataataatag acagtactta gcatttacca   26675
cccataggca ctgtttgttc tcagtcgtgt tttacactta cttattcatt tggtcctcac   26735
aacagcgtta tgaggtgtag gggccattgt taccccctagt ttccagatga ggaaactgag   26795
gcaaagaaag gctgagtaac ctaccaaggt cacatcacta atgaataggg agctggaggc   26855
agagctggtg tccagtgtgg gcagcccag tatagagtct gtaaccacta ggaaaaactg   26915
cctctgggta ttttttgtgc tttttttttt ttttggatg ctacagataa tactaagatg   26975
aacatatttc tacatacttc ttccttgcac atacatgaat agcctggccg ttgtgggtta   27035
gagtgcgtgg gaaatgagag ggtagagatg acatgtgtag accacgcttc agagaaaagt   27095
tactttgaaa gggaccagaa aaagggttgt tttagttccc atttgtttcc ttatcaggaa   27155
agacggatta ttttgtttag tgttttattt cccttgggg tgaagacctg cttatgtctt   27215
ttgtccattt atagtcggga gtcactgtgc ttctcatctt cctgtatgat tgacatttac   27275 cccttttcata tactacaaat acttttaggc tcttatttt aactcttttgt agtttctgtg   27335 tatgtctttta ttatcatttg ctgcagcttc aacactttta agaaatcact gatttcattt   27395
tgcgttaaag ctagtttact tcttgtattt taactttttaa ataatgtaat cggccgggca   27455
cggtggctca cacctgtaat cccagcactt gggaggctg aggcctccca tggatcatga   27515
ggtcaggaga tcgagaccat cctggctaat acggtgaaac cccgtctcta ctaaaaatac   27575
```

```
aaaaaattag ccgggcatgg tggtgggcgc ctataatccc agctacttgg gaggctgagg    27635
caggacagtg gcgtgaaccc gggaggcgga ccttgcagtg agccgagatc acgccactgc    27695
actccatcca gcctgggccg cagagcgaga ctctgtctca aaaaaaaaaa aaaaaaaaaa    27755
aaaacaaatt taagattggc tttactgtcc tcaaattgct gttcatctaa gtcaatgccc    27815
agttactttg ttacacacat acattctttt tttttttttt tttttttttt tttttttttt    27875 tttttttgaga tggagtctcg ctgttgccca ggttggagtg cagtggcacg atctcagctc    27935
actgcaagct ccgcctccca ggttcacgcc attctcctgc ctaagcctcc tgagtagctg    27995
ggattacagg cgcccgccac catgcccggc taatgttttg tcttttttt ttttttttt    28055 tgagacggag tctcgctctg tcgcccaggt cggactgcgg actgcagtgg cgcaatctcg    28115
gctcactgca agctccgctt cccggttca cgccattctc ctgcctcagc ctcccgagta    28175
gctgggacta caggcgcccg ccaccgcgcc cggctaattt tttgtctttt tactagagac    28235
ggggtttcac cgtgttagcc aggatggtct cgctctcctg acctcgtgat ccgcctgcct    28295
cagcctccca aagtgctggg attacaggct tgagccacca tgcccggcca cacatacatt    28355
cttaaaagca ttttaaaatt ataattcagt gaatttggag tcttcccatt gttttctttt    28415
aatttgtata tctgagtttg ccctcaacac cacactattt aattattgtt ttagaatatg    28475
ataaatatag tagggctgtc cttctcatct ctgtttaact tttctgtctt cagaatttga    28535
agggtatttt ttcttttattt tcccaaacaa acttgtaaat cattttgaca ttactctttt    28595
tttttttttt tttttaattt tttttttttt tttgagacgg tgtttcggtc ttgttgccca    28655
ggctggagtg caatggcgtg atcttggctc accgcatcct ccacctcccg ggttcaagct    28715
attctcctgc cttagcctcc cgagtagctg ggattacagg catgcgctac cacacccagc    28775
taatgacatg actcttaaga catgctagtg ttcgtgctga atgccccatt aggttaagat    28835
catagaaacg tggcagttgg agagctgtaa aggttgctta gtttctcatt tccatttctg    28895
tttaattcct ag at  ttt gga tca ttg ttt gac ttg gaa aat gat ctt cct   28945
                  Asp Phe Gly Ser Leu Phe Asp Leu Glu Asn Asp Leu Pro
                  30                  35                  40 gat gag ctg ata ccc aat gga gga gaa tta ggc ctt tta aac agt ggg          28993
Asp Glu Leu Ile Pro Asn Gly Gly Glu Leu Gly Leu Leu Asn Ser Gly
        45                  50                  55 aac ctt gtt cca gat gct gct tcc aaa cat aaa caa ctg tcg gag ctt          29041
Asn Leu Val Pro Asp Ala Ala Ser Lys His Lys Gln Leu Ser Glu Leu
    60                  65                  70 cta cga gga ggc agc ggc tct agt atc aac cca gga ata gga aat gtg          29089
Leu Arg Gly Gly Ser Gly Ser Ser Ile Asn Pro Gly Ile Gly Asn Val
75                  80                  85 agc gcc agc agc ccc gtg cag cag ggc ctg ggt ggc cag gct caa ggg          29137
Ser Ala Ser Ser Pro Val Gln Gln Gly Leu Gly Gly Gln Ala Gln Gly
90                  95                 100                 105 cag ccg aac agt gct aac atg gcc agc ctc agt gcc atg ggc aag agc          29185
Gln Pro Asn Ser Ala Asn Met Ala Ser Leu Ser Ala Met Gly Lys Ser
            110                 115                 120 cct ctg agc cag gga gat tct tca gcc ccc agc ctg cct aaa cag gca          29233
Pro Leu Ser Gln Gly Asp Ser Ser Ala Pro Ser Leu Pro Lys Gln Ala
        125                 130                 135 gcc agc acc tct ggg ccc acc ccc gct gcc tcc caa gca ctg aat ccg          29281
Ala Ser Thr Ser Gly Pro Thr Pro Ala Ala Ser Gln Ala Leu Asn Pro
    140                 145                 150 caa gca caa aag caa gtg ggg ctg gcg act agc agc cct gcc acg tca          29329
Gln Ala Gln Lys Gln Val Gly Leu Ala Thr Ser Ser Pro Ala Thr Ser
155                 160                 165
```

| | |
|---|---|
| cag act gga cct ggt atc tgc atg aat gct aac ttt aac cag acc cac<br>Gln Thr Gly Pro Gly Ile Cys Met Asn Ala Asn Phe Asn Gln Thr His<br>170                 175                     180                     185 | 29377 |
| cca ggc ctc ctc aat agt aac tct ggc cat agc tta att aat cag gct<br>Pro Gly Leu Leu Asn Ser Asn Ser Gly His Ser Leu Ile Asn Gln Ala<br>                     190                           195                         200 | 29425 |
| tca caa ggg cag gcg caa gtc atg aat gga tct ctt ggg gct gct ggc<br>Ser Gln Gly Gln Ala Gln Val Met Asn Gly Ser Leu Gly Ala Ala Gly<br>205                 210                     215 | 29473 |
| aga gga agg gga gct gga atg ccg tac cct act cca gcc atg cag ggc<br>Arg Gly Arg Gly Ala Gly Met Pro Tyr Pro Thr Pro Ala Met Gln Gly<br>                     220                           225                         230 | 29521 |
| gcc tcg agc agc gtg ctg gct gag acc cta acg cag gtt tcc ccg caa<br>Ala Ser Ser Ser Val Leu Ala Glu Thr Leu Thr Gln Val Ser Pro Gln<br>235                 240                     245 | 29569 |
| atg act ggt cac gcg gga ctg aac acc gca cag gca gga ggc atg gcc<br>Met Thr Gly His Ala Gly Leu Asn Thr Ala Gln Ala Gly Gly Met Ala<br>250                 255                     260                     265 | 29617 |
| aag gtaagtgaac tgaagcactt tcaatacttc ctacctaacc gcgggctttc<br>Lys | 29670 |
| cctccgagta atgcgtaaaa tgggaccacg tggcccactc ctgttttcc tcttgggctc | 29730 |
| tccacgtgcc actcatgctt ggaagagaca gatttctttc taggataaag atctctgccc | 29790 |
| catttctgtc tttaaaatga gaattcttaa agaagtagga cagcttgcag gtcaggcagt | 29850 |
| tggaaagtac agggcctaat gtgtccgtga acctggtaga ggttgctttc tgcctgtgta | 29910 |
| ctgcccactg aggaggtgat cactggtctg tatgctcctc tgtggccatc cagtgaagta | 29970 |
| tctgttggca cagtatccat ttcactgaat gagaaagctg tgttccaggg ttgtcagctc | 30030 |
| actccctgct atgttaacaa ggaagaggtg gcagagccgg ggagaagcac aggcattcgg | 30090 |
| gtcccagagg aaacaccagt gcagtggttc ttcaagtggg gtccctgga ccagcagcag | 30150 |
| cagcagcatc ccctagaagc ttgttagaaa tgcagacttc tttattgact cagaagctcg | 30210 |
| gcgtggggcc tgggctttaa gaagcctcca gatgggtgct ggacacagtg actcacgcct | 30270 |
| gtgatcccag cactttggga ggccaaggtg ggtggatagc tcaactctag gagtttgaga | 30330 |
| ccagcctggg caatgtggcg aaaccctgtc tcttggaaaa aaaaaaaaa aaaaaaaaa | 30390 |
| agcagcagcc tccaggtggc tccaaggtca cgcacatcac acacacacac acacacacac | 30450 |
| acacacacac acacacacac acacacacac acacacacac acacacacac acacacacac | 30510 |
| acacacacac acacacacac acacacacg ccaagagctc tgctagggaa aggcctggac | 30570 |
| tgggatttgc agccaccagc cttgcagctg ccttctagag taggaactgg acttggagaa | 30630 |
| gggggaaggc agatgcctgg atagatgtga gacagctgga aaagcccagg actgacagga | 30690 |
| gcacagagaa ggaagggcag cctattccca ctgaagtgac aaacactgtg gatgctctgc | 30750 |
| ggccagaggc ttctcaacag cagccaccag gcacgtcttc aggcagtgga attcagcaca | 30810 |
| tcccagaaca gaaaatcagt ttgggctgtt ctttggattt gtttagtccc aagtaggggt | 30870 |
| gagggagaat aagagtagaa cacagtttcc ccagaaggtt gatgagagcg ttgggtgacg | 30930 |
| gatgcaaaac cctgtgaatg tcggaaacga gaggatttt ttttaactta agaaatgaag | 30990 |
| atgaagtaat gctcaatgtt taaattgcat ttgtcttttt tgaaatgtta gtagagagga | 31050 |
| acgtgaactt aagttttact tgtacctggc atttttaagaa gagtctgtat gagtgtgtca | 31110 |
| attgagaagg aatttctcat gggttatgg ttcctggaga gattgatcct tgttcctttt | 31170 |
| cccagttcat tcatcactct actccttact tttaaaactc tgtctattct ggagagttta | 31230 |

```
aatcatatga agtcgacata atagtataaa gcaatgattc ccaaactttt ttttaatctc    31290
aagactcctg aataatctta acaattactg aggaccccaa agagatttct ttaacatgtg    31350
cagtataccT ctcaatattt actatattaa atagtaaaac agaatattga aacacatttc    31410
atcatccgtc cagtgcagtg gaatcacaca tcacaaagta actagaaaac tagatctact    31470
gtgttcttgg gagagaatca gagggaaaag gcaaatcata tcttaggatt ttatggaaat    31530
agttttgaca tcatggtccc cctgaaaggt ctgggaccct ggactgcact tcaagagctt    31590
ttgataacat gtatgtagaa gttagacttt gtacacctaa acacaaagcc attatcacat    31650
gttaacagat ttaacagtaa cttcatgtca gccagtatcc acagaatagt cacgtttcca    31710
gtggtctcat atgttgtaat tttttttttt tttttctgag atggagtttc actgttgccc    31770
agtgtctgga gtgcagtggc accatctggg ctcactgcaa cctccgcctc ctgggttcaa    31830
gtgattgtcc tgcctcagcc tcctgagtag ctgggattac aggcgcgtgc cactgctccc    31890
ggctaacttt ttatatTTTT attagagacg gagtttcacc atgttggcca agctggtctc    31950
gaactcctga cctcaagcga gccacctgcc tctgcctccc aaaatgctgg gattacaggc    32010
gtgagccacc acgcccggcc tataagtagt ttttatagat ttttactcaa aatctacatt    32070
tcagttagtt gatatgcctc ttaagaatct gttctctgtt ggtctgtggg atccttacaa    32130
tttactgaag aaacatgttt tggttgttgt ctgctattta tcctggagag tgtcttccag    32190
aagttggact ttgctgatta cacctgtaac acttcatgct tctctgtcca cccaggcttt    32250
tcattccatc ctggggttcc tttatacaga gtggtctttc tttccaacag caactcgtgg    32310
atgtcactgg aaagtgagcc tcgttagcgt gctggggaca gttgtctctt gtttcctata    32370
ggtatctcaa agcagcccac tagaggtgga tagagtgcat ttttttaaag atgtgtcgtt    32430
gcctttgggt ggaatgaaag accaagtagt ggtgggcaga aagtaagagg gagagacaag    32490
tccattttaa accattccct ctctagaacc ttacgatagc agagccaact agattttaag    32550
atgcacaggg aaaaggcgct tttttttaaga taattttgtt ttaagaacga ttacacagga    32610
agtatatcct atgaaataat taaaatagta ggaaaagagc aacatcctcc ttacagataa    32670
agatttaaaa tacataatga aaccagacta cataagcacc ttactgtttt acttggcagt    32730
gtaccttaga tggcctctgt gacactgcac agagatttTT ttttcttact gatagcaaag    32790
tattccatta tatgatacat cataatttat tgatctcatc ctctgaggat gaacatttgg    32850
attgtttctg acttttttgct agtgcagcaa tgcctgtaca catgtgtcat ggattagatt    32910
ctgaaaagga gaattaatgg gtcacagact tgtttaaagt tgttttttag aaagtaaaca    32970
tgcacatggt ttaacgacaa acaaccataa aaatactctt aagagtaaga accagagagt    33030
taattcttaa ttcttgaatt ttggttctcc caaattctca ccaaaggcaa ctattatttc    33090
ttatctgtcc tgccagtgat gatgtatgcg tatagaggcg tagagagagg ggtgtgggta    33150
tgtgtgtgct atctccccag acataaagag tagcattaca cagcgttttc ttgtgagtgt    33210
agatgttccc ctccccaccc accacttaac aatacaagtt ggaaattctt ccatgctccg    33270
cgtagctgtc agtcattctt cataggtaca ataggaattc ctgatttggg tatatcgtaa    33330
tttaaggact tgtgccatgt aggctgagca tttaggttat tcccagtatt ttgctgtttt    33390
cacagttttg ctttgaacac attgtacata tatctttgta cagctgagtg accatatctg    33450
ctagataatt tattggacat gcaatttctg aattaaaaga tactgagatt ttaaatcagc    33510
atagataatc tcagatactc ttcagaaata ttgtgcaaat tacaccttca tcaagagtga    33570
```

```
ttgagcctct gtccaaatct tgaccaacac tgaatattac catccttttta cttacttgac    33630 attctgttaa gcaagttgtc ttctttgtta agtgtgtctt ttcataaggt cataggcagt    33690
tgtattttac tgattgttca taatctttgt ccatttgtct cttgaattgt ttgtcatttt    33750
ttctcattaa tttatattct taagtctctt aaaacatgtt tttcccttt gttatttgcc     33810 atagtctgtt tcaccaggaa tatggtcaca taggtttaca atatgttttt accaagtata    33870
tgttttcagt ttgtatagaa acacattttat ccatttattt cctttatggc ttttaggttt    33930
tatgtcacat tttagaagtg cttttcctat taaaaaatta agaaatattt tcctgtatttt   33990 ttctccttat tacatgactt tttttttttt ttttttttt gagataggggt ctcagtttgt    34050 tgcccaggct agagtgcagt agcatgatct cagctcactg caacctctgc ctcctggtct    34110
caggtgatcc gcctgcctca gcctccccag tagctgggac tacaggcgcg catcaccaca    34170
actgactaat ttttgtattt ttttgtggag acggggtttt gccatgttgc ccaggctggt    34230
cctgaactcc tgagctcaag cgatccaccc acctcagcct cccaaactgc tgggattgca    34290
ggcgtgagcc accgtgtctg gcctccttga atctttaact caatttattt tggcataagg    34350
agtgagacac agagatccag cagtatatat ttttcttgt tataatcatc ttagtaccat     34410
ttatttagta ttggtaatcc atctttctc ccactgatac gatatgctgt ttttggtata     34470
cactttattc tcttttcaaa catataggat ttgggtctaa tttctgaact ctttttcttt    34530
agttccattg acctttgctt gttcctgtgc cagaaaccta ttaacctagc tgtgtgatga    34590
cttttagtat atgacctcac tagttatttc tcacacaggt ggttctcaac tctgtctaca    34650
ctttatcaga tttatctgga gaattttaa aaatatgatg cctgaacccc actacagagc     34710
aattgagtta gaatctgggg gatatggtag aaacattcgt atagtgtgta gttcctcaga    34770
tgactttcat ggcagccagg gttgagaacc ccactgtgtt agataaattt aggacttttt    34830
ttcaaatttt aaaaacaaaa aatctttggg attttggatt tataagattc actacaactt    34890
tataagtcat tttaggaggg atgtgacatt ttaacagttt tgtgacttcc tgagtcttct    34950
tatacatata aattatcttt tctgggggtc ttatgttgct tggaagcata gtatggtttt    35010
ctttatctgt gtaataaatc tttcttacta agtttatttc tggaggtatt acgtggtttt    35070
tgttgctgtt ggtgatgagt tatatttcat tatctaactg gctattttaa tataggaaag    35130
atgttatgta tacgctactc tggtaatctg gctgctttat ggggttatct taattattct    35190
aatacgtttt caggagattc tcttgagttt tccaaggaga tagtcatctt ttgcattatt    35250
gatactttta ttttctcctt gccaatattt tttgccagtg tttatgctct taggcatccc    35310
tgtctcgtat cctacttaaa tggaagtgta tttagtgttc tgttattaag aataatgtga    35370
gctttggttt gtagtcagta gtatatttct tttaaaattg gggcataatc tgttcgtcat    35430
aaaataaatg ataatatcta aatgttaggt tttatcaaat ttctttttga tacctaccta    35490
tgttgattaa cctgtgatttt tcacttttcc atttatttat gtgacagatt atctgtgtag    35550
gttttataat atcaaattga accatctctg taattgtaaa atcaaaagtt aatgctgagt    35610
tttaattgct agtgcttcat ttagaatttt gtttctcatt tatcagtgat gaaattgatc    35670
catagctctt tttgtgcttt gtcaattttt atatcagtgt tacgttaact tggtcaaaaa    35730
gagtttgaaa gtctttttt ttttttttt tttttttg agacggagtc tcgctctgtc        35790
gcccaggctg gagtgcagtg gcgggatctc ggctcactgc aagctccgcc tcccgggttc    35850
acgccattct cctgcctcag cctcccaagt agctgggact acaggcgccc gccactacgc    35910
ccggctaatt ttttgtattt ttagtagaga cggggtttca ccgtttagc cgggatggtc      35970
```

```
tcgatctcct gacctcgtga tccgcccgcc tcggcctccc aaagtgctgg gattacaggc   36030
gtgagccacc gcgcccggcc gaaagtcttt catatttatt ctgtgaaaca gtttaaatcg   36090
atttggaatt atctattaca tgaagaattg agagacttca cccttacagt gatgtgggcc   36150
tgaagccttt ttttccctag gaagtgactg aagatctttg acaatagtgc cgggcgtggt   36210
ggctcacacc tgtaattcca acactttagg aggctgaggt gggaggattg cttgagccca   36270
ggagttcaag accagcctgt gaacataggg agaccctatc tttaaaaaaa atttaagaat   36330
tagctggtca tggtggcaca tgtctgtggt ctcagctact caggaggctg aagcaggtgg   36390
attgcttgag cccaggagtg caaagttgca gtgagccatg atcacaccac tacaatcaag   36450
cataccaaca gagtgagatt ctgactcaaa aaaaaaaaa aaatctttga caactttatt   36510
gctattttct ataaatattg gctcttttag gcttttagta gtctcttagg tcagtatcgt   36570
ttttatttag taaagtctaa atttgctttg attttgagaa aaactaaaag atacttaact   36630
tttaatcttt gttaaaaaa aggataggag gtaggcaagt cacatgttac agattaagaa   36690
gtggaggctg ccagtgagtg gcagaaccag gcttgcatcc acacggtctg ccagaggcc    36750 tgttaacact aatgcaatgc agcctgttct ttcgtaagtt ttacagtttc tgttttagta   36810
gaaaattctt ttcatctaat ctttaaaatt tgttaactta aagctgtgca aaaatgtgtg   36870
cagttctttg tcattttga tgtttgtgat tatttctctt ctcattccta atttttttt     36930 tttttttttt ttttttttg agatgggagt ttcgctcttt ttgcctaggc tggaatgcag    36990
tggcatgatc tcagctcact gcaacccctg cctcccaggt tcaagcgatt ctcctgcctc   37050
agcctcctga gtatctggga ttacaggcgc ccgccaccac gcccggctaa ttttttgtat   37110
ttttagtaga cacggggttt caccatgttg gccaggctgg ttttgaactc ctgacctcag   37170
gtgatctgcc cacctcagcc tcccaaagtg ctgaggttac aggcatgagc caccgtgcac   37230
tgccatctca tttctaattt tatgtgactc tgaaaatatt tacagtagga aaaacatgac   37290
ccttgttgac aacatggcaa tattaacaat acatgatatt actatttttt tcttttgttt   37350
acttttgtga tagaaggcat gataagagtt ttttaaagaa aaaacaattt ctttatttca   37410
acagtagcaa aacttaacat ttcgtcttat gaggggagca tgttcttgtt ttctactgaa   37470
aataactcat acacttgtcc tctagaaaga aagcaaaaaa gaccaattta ggtaggattt   37530
agaagccgta cagacactct ctttcctggc tacgggtgtt gagagatgtt gcttgacaca   37590
gagatgacag aaggaagcca gaagctggta gaaagaggaa ggtgtaattt cgggtcaagg   37650
ggtccggagg cattctgatt ttaaggttga taagaatttg ttttgtgac cttagaaatc     37710 ttttaagtac tttctttta ctaacaaatc tgaaacgtga ccaaaatagt ttgtatggta     37770
atccatcttc atagggggtc agattagggc ttattttttg aataaagttt ttggaatatt   37830 cgtcttttt agaaagtggt cagaaaaccc cggggttgat ttttgactgg aggtgttcct    37890
ggagtaaaag tttaaatta gatcagctcc cagtactcag tcagccatca ttttggtcag    37950
atactataaa gcagtgattc ccaaacttga atattcagca gagtcactgc aggcttgtca   38010
agacagattt ctgcctccaa cttaccaagt ttctgattca gcagattttg gttgggacct   38070
gagaatttac atttctaacc agctcaccgg tgaccgtaat tgtggtggtc agggaccaca   38130
ctctgagaat ctgtgctcta aggaatggaa ttagcagaat atagtcagta aagaattaat   38190
agaaccaagt tggctaagaa atgactaatc taccttctct attttgggta gattattgga   38250
aatctctaat attatttatt tattttgaga caaggcctca ctctgtcacc caggctagag   38310
```

```
tacagtggcg ttatcatggc tccctgcagc ctcgaactcc tgggctcaag cagtgctcca    38370
gtctcagcct cctaagtagc tggtactata ggtgtgcacc atcatgcctg gctaattttt    38430
ttgatttttt ttaaaaaatt gattctctta tatacacctt tatttgtact aaaaattgta    38490
aaaagagcac aaagtttcct cttattgcaa cccaaatttt tcttattatt acgctgtagc    38550
caaactaccc aatgctttct ttacccacaa gtgactttgc ttcaaattct cggtgttggg    38610
tttcatctca ctggctttgg gcttctaaaa cacatgggga tgcttatgtc ctcttggctt    38670
cgagtcaaat taagcagtag agctgaagta tactgaagtt attcagatac gttcaaacta    38730
cacagacccc ttatacatca ctagtatcat ggtagaaagg aaaagataca agaaaaatac    38790
atcctagaac tcattatcaa aatttttgat atatagtcta ttgtagcata aggtagcttt    38850
ctcaacctgc tacataaaat taccagcaag aaaaaaaagt acaagaataa gtttatggc    38910
tgaagtggct cagtgttgta attccctatt ctagcactct caaaagtacc ccatctgtta    38970
cacatgcaga aactgcagca gcatctgaaa tgtccactcc ttgattcatt ctgaactccc    39030
ttaagcccag tgtttgttag ttctcgttca agtctaggaa ctctgccgag taacaggtat    39090
ctcaattttg ccatccttc tttctgcata gacaggagtg ttcttaaatc ttctcctgta    39150
aagcaagtca tctctgattt ccctgaggat cattgctccc gtatactgtt gttggggtga    39210
gccttctggt agaggggaag agaatttggt actagggttg atagtcaagt tactaaggtt    39270
ctttatcaac atctcagagc agaagttttg agaggcccct gaatcgtcct gggaattttc    39330
ttcagtgagc attttttgaag actgggacca gggttggatt aaacttttgt gatgggtcca    39390
ttgtgtctca acacaacact gagcttctcc tggatctttg aaacccagca gaaactgttg    39450
ctggactctc aaattgccac aaggtagacc agaaagagcc tgaaaacccg aactccaacc    39510
atcttttttct ttccttttta atgcagacat ggtgttgcta tgttgcctgg gctggtcttg    39570
aactgaactc aagccgactg ccgtcttggc tgcccaaagt gctgggatta caagtgtgaa    39630
actatcatgc ctggctggaa tttctaatat ttaatagcaa gagaaataat actgtacatt    39690
tgtctgttgc tttcacttt ttcacgtgaa gtcatctgat tcttaacaca agaaataag    39750
ggaattttat attaagcata tcttaatttg gcctcttaaa agatcacaac aaaaatagtt    39810
tgtagaatga aactatgtag tgccatgaat taatacaggg taatgtggga tgtatataat    39870
tcctgtgggc acagctgttt agtagacatg ttaagtagcc taggactggc tcagggatct    39930
tattatgact ctaatgagag atgatcatag gtgtcctata gaatgtatga ttcaggatgt    39990
acctaccttc ccatgataat taatcatgaa tttcttttt ctttctttt cttttctctt    40050
tctttctctc actcttcctc tctctctttc cttctctttc tttctttcct ttctttcttt    40110
tccattcctt tcctttttcct tccttccttc ccttccttcc cttcctccc ttcctttcct    40170
tccctccctt ccctccccct cccctccc tcccttccc ttccttcctt tttctttctt    40230
tctttccca tagtttcact cttgttgtct aggtgggagt gcaatggcgt gatctcggct    40290
cactgcaacc tctgcctctt gggttccagc aattttcctg cctcagcctc ctgagtagct    40350
gggattacag gcatgcgcca gcatgcccag ctaattttt gtattttcag tagagacagg    40410
gtttcaccat gttggccagg ctagtgttga actcctgacc tcaggtgatc cgcctgcctc    40470
agcctcccaa agtgctggga ttacagacat gagccacctc acccagcctt atgaatttct    40530
tttttaaact ttttaattta atgagattgc atatgtatat taaatggatt gacacgcaca    40590
tagtagttag tgtacttact gcagcagcag tagtaatagc ggcagctcag actgccttct    40650
gcagatgtag tggctaattg ctttcaagcc tggcgtgggc tctggaataa gctgactcag    40710
```

```
ttcacatcca gggttcacta attattagct atgggaaact tatttaatct ctctgggttt    40770
tagttttttt ggcttttaaa tgaggataat agtagctgcc attgagaatt gttctatcaa    40830
ttaaaaatgg ataataatct ctatcttaca gaatcgcatg ccaattaaat gagatggtgt    40890
atgtaacatt cttagtatat gcataggttt actgaaaacc ttccagagaa tattgagtag    40950
tgaactagcg aggtgctgtg ccacataaaa tatttgagat agccacacaa catttgaagt    41010
gataatgaga ctgcttttct aatgttttcc gaaaacattt tttggtagtg aaagtagctg    41070
ttgagcttgg tggctcattc ttgtgatccc agctacttgg gaggcggagg tgggaggatt    41130
gctttaggcc aggaatttga caccagcccg ggcaacagat caaaatccta tatcaacttt    41190
taaaaagttg atgtttgtta tacaaaatta gcacagaaat gtctagaaaa gaaaatcttg    41250
cctgtaagcc tatcatccag tcatacttag cgctaaagaa aacatactcc tgatgttttc    41310
tctaccagtc ttttatctat aattatgtat cttttttaaa gtcaaagttg gagtagtatt    41370
tccagttaac ttttttggctg attattttct gtaacacaaa cggaatgaat gtttagcata    41430
ataacaacaa tgaagatttt catttgacat gtctcccagg ggaccatctt gaagagtaac    41490
ttaggcatgt gtcacttgat gggggtgaaa tgcatcatta agtgattatg ttatgctagg    41550
aacatcatag agtagttatg caaacctaga tggcatagcc tgttacacac ctaggctata    41610
tagtgtaccc tgttgctcct ggactataaa tctgtacatc atgttactgt aatgcatact    41670
tgggcagttg taacacggtg ccacaatgct aagtgtttat aaacctaaac atttctatac    41730
atagaaatgg tatagtagaa aatactgtat aaaagattta aaatagtaca cctgaccaga    41790
cactcagtcc catgcctgca atcccagcac tttaggaggg tgaggccgga ggatcacttg    41850
agcctgtgag ttggagaaca gcctgggcag catagatcct ggtgtgtgtg cagggggtgg    41910
gcgggtgtgt gtgtaaaaca cacctgtata aggcatttac tatgaatggt gtttgcagga    41970
ctggaagttg ctgtggatga gtgaatgagt ggtgagtgaa tgtgacagct gagaacgttg    42030
ctgtacactg ctatagactt tataaacact atatacttag gccatgctaa atttatttat    42090
ttttaaattt cagtaataaa ttagcttact gtaacttttc actttataaa cttcagtttt    42150
ttaaaaactt ttttattctt ttgtattaac acttagctta aaacactaaa cacattgtac    42210
aggtgtacaa acgtatttgt acttattcta taagcttttt ctattttaaa attttttatt    42270
atttatttat ttattattat tattatttt tttgagacag tcttgctgtg tatcccaggc    42330
tggagtgcag tggtgcaatc tctgctcact gcaacctccg cctcccgggt tcaagcaatt    42390
ctcctgcctc agcctcccga gtagctggga ctacaggtgc atgccgccac gcccacctga    42450
ttttctgtat ttcagtagag acgaggtttt accatgttgc ccaggctggt cgtaaactct    42510
tgagctcagg cagtctgccc gcctcggcct cccgaagtgc tgggattaca ggtgtgagcc    42570
accgcgcccg gccagttctt taattttta aacttttttg ttaaaagcta aaacataaat    42630
gtacacacat acacacagac acacacacac tagcctaagc ctgtacaggg tcaggatcat    42690
gaatatcact gttttttctcc tccacatctt gtcccactga aaggtcttca gaagcagtaa    42750
catgtatggg agactgtcat ctcctataat gacaatgctg ccttctggaa taccgcctga    42810
aggacctgcc ttgaggctgt tttacagtta acttaagaaa agtagaagg attatactct    42870
aataagtgta gtaaatacat aaaccagtaa catagtcatt tattatcatt atcggctatt    42930
atgtactata cataattgag ccatgctttt atacagctgg tagtgcattg atttgtttac    42990
accagcagca tcacagacac ctgagtaatg ccttatgcta tgacagtttc aacagctact    43050
```

```
acgtcactag gccattggaa ttttttcagtt ccatggtaat cttctgggac cactgtgtat    43110
gaggtctgta gtttactgaa atgttgttat gcaacacatg actgttcttg tacgaaaaac    43170
cattatcttc gttgctttat caactaaagg tagctattaa gatttggagt taaagaccta    43230
cctatatttt taaaatattt ttattatttt actttgatta ttttttggagt tgtaatttat    43290 atagcatgaa atgcacagat cttatatttg tcaaaccct ttacccatgt aacccacacc    43350
cctatcaaga ttcaggacat ttctcttagc ccagaaagtt cctttgtatg cctcccttt    43410 tctgtcccca ctcatccccc gacaattact gctaatttct tttttttctt tttttttcttt    43470 tttttttttt tttgagacac agtctcgctc tgtcacccag gctggagtgt actggcgcaa    43530
tctcggctca ctgcaacctc cacctcatgg gttcaagcga ttctcctacc tcagcctccc    43590
gagtagctgg gactacaggt gtgcaccacc atgcccagct ggcttttttc tttttggtag    43650
agatagggtt tcaccatgtt ggccaggctg gtctcaaact cctgacctag tgatccgccc    43710
acctcagcct cccaaagtgt tgggattaca ggtgtgagcc accgcgccca gctgctaatt    43770
tctgtaacca tgaattgctt tgcctgttct cagacctcac gtaatggaat catgtagtgt    43830
gatgacttat agtatgtgct ttttataag gcttcttttg ctcacaactt gttttctgag    43890
attcatccac gttgttggca tgaactagtt cttttttatt gctaaatggt attctgtttt    43950
gtgactagag cataatttgc ttgtccgttc tcccattaat ggacattggg gttgtttcca    44010
gtttgaagct attaagaata aatcttctgc cgggcgcggt ggctcacacc tgtaatccca    44070
gcactttggg aggccaaggc gggtggatca caaggtcagg agatcgagac catcctggct    44130
aacgtggtga accccccatc tctactaaaa atacaaaaaa tcagccaggt gtggtgccag    44190
gcgcctgtag tcccagctac tcgggaggct gaggcaggag aatggcgtga acctgggagg    44250
cggagcttgc agtgaccga gatcccacta ctgcactcca gcctaggcga cagagcaaga    44310
ctccgtctca aaaaaaaaa aaaaaaaaa gaagaaatct tctgtgagca tttttgtaca    44370 gcttttttg tgggcataga agttttcatt tctcttagat aaataactag caacgaaatt    44430
cactgtacaa ggaggtgtct gtttctggac tctgtagtct aagggcaaac tatagcccat    44490
gaaccacatc cagccccatg acctgttttt atatggcttg ccacgtaagg atgggttta    44550 tattttttaa ggattgttta aaaagaaaac aatctgggat ggaaaccgca ggtcatctgc    44610
aaagactaaa ttatttatta actggcccctt catagaaaaa aaaatccct gtacctttgt    44670 tctagtctgt tctattgatc tattttttcta ttcatttagt ttgttttta agaaaagctt    44730 ttttgtttgt ttgttttgtt ttgttttgga gaaggagtct cgctcttttg cccaggccgg    44790
agtgcagtgg cgtggtctcg gctcactgca acctccacct cccgggttca tgccattctc    44850
ctgcctcagc ctcccttagt agctggaact acaggcgcct gccaccatgc ccggccaatt    44910
ttttgtattt ttactagaga cggggtttca ccgtgttagc caggatggtc tcgatctcgt    44970
gacctcgtga tccgcccgcc tcggcctccc aaagtgctgg gattacaggc gtgagccact    45030
gcgcctggcc caagaaaagc ttttaaagat tttgggtttt tttagagtag tttgagcttc    45090
acaatgaaat gaaggtacag agattttcca tctattccct gttctcctag ttcatagtct    45150
cctccatttt caacatcctc cccaactccg ctgtctagaa tggtacagtt tgtcacaatc    45210
aataaaccta tattgataca tcataatccg aagtctgtag tttacactag ggttcactct    45270
tggtgttgta cattctgtgg acttggacaa atgtataatg atgtgcatca ttgtagtgtc    45330
atgcagagta ttttcactgc cctaaaagcc gtctgtgttt cacctcttca tccctctctc    45390
cttcccaaaa ccctggcaac cactgattgt ctccatagtt ttgcctttt gtaaagttac    45450
```

```
agtcacacag tgtgtagcct tttctcattg gcctcattca tttaataata tgtatttaag    45510
gttcctctgg gtcttttcat ggcaattatc cctttaccta ctgaaagact tcatggttgc    45570
ttccaagttt tggcaattat gaataaagct gccatataca tccatgtgca ggtttaagtt    45630
tttacctgtt ttgggtaaat accagtgagc acaattgctg gatcatatgg taagagtatg    45690
cttagttttg tgagaaactg caaaaatgtc ttccaaagtg tctatatcat tttacattcc    45750
caccagtgat gaatgagagt tcctgttgca ctacatcctc gccagcattt cgtgttgaca    45810
gtgttctgga tttggctgtt ctaataggca aatagtggta tcccattgtt gtcatttgca    45870
tttctgtgat aagatgtggg tcatcttttc atacgcttat ttgccatctg tgtgtcttct    45930
ttgatgaggt gtatgttaag gtctttggcc cattttttaa acaggttgtt attgttgagt    45990
tttgagagtt ctttatatat ttttgtaaat agatctttat cagatgtgtt tcttgcacat    46050
attttctccc agtctgtgga ttgtcttctc attctcttga cattatcttt gaaggggcag    46110
ttttaatttt aatgaagtca attttatcaa tcacaaaagt ttcatagatg aaactttcat    46170
agttgtactt tagctttaca gtaagtatta aagtcaggtt gcttagtttc tcgttttcat    46230
ttctgtttaa ttcctaggtt ttacaccatt atttgttgct agtatggaga agtataataa    46290
atgtttctgt attaatgttg tatcttgtaa ccctgctaaa ctcacttatt aattctataa    46350
gatgtcttag aattttctgg gacatgttgt ctgagaataa aaatagcttg cttcttcctt    46410
tttcatctgt atgcatttta ttcattttc tggctttaat gttctgccta ggacctctag    46470
tacaatgttt tgtttgtttg ttttgggttt cttttgagat ggactctcac tctgtagccc    46530
aagctgaagt gcagtggtgc tatctcgcct cactgcaacc tccacctctg gggctcaagc    46590
gattctcgtg cctcagcctc ctgagtaact gggactacag gcttgcgcca ccacacccag    46650
ctaattttgt attttagta gatacggggt ttcaccatgt tggtcaggct ggtctcgaac    46710
tcctcacctc aggtggtccg cccatctcag cctcccaaag tgctgggatt ataggtgtga    46770
gccaccgtgc ctggccagca caatgtttaa taaaaccaat gacagtgttc ttcccttgtc    46830
ttattcatga tctgtgggaa aaaagcattc agcctttcgt taagtataat gttagttgta    46890
ggctttaggt atcattcatt aggatgagga attctgtttc tagtttgctg agtcttttga    46950
tcataagcga ttactgaatt ttgccacatc ttttttcatt tattgagatg aatcataggg    47010
tgtttttttt ttcttttgaat gtgaattacg tctttctgag tgttgaacca gccttgcatt    47070
cctgtgagat aaccccactt gattgtggag tgttatcttt tttatatgtt actggatcag    47130
atttattaaa atattgttca ggattatgc ttccacagta atgtgctaca taacgaattt    47190
tggtcagcag cagactacat atacaacagt ggcccttaa gactataata tattttact    47250 gtgccttttc tatgtttaga tacacaaata cttacaattt tgttacagtt gcctccagta    47310
ttcagcacag taacaagctg tacaggtttg tagcctggaa gcagtgggct ataccataca    47370
gcctaggtgt gtagtaggct acaccatcta ggtttgttta agtacaccca aagtgtaagt    47430
tcccacagtg accagaatca cctaatgaca cttttctcag aagatgtcct tgtctttggg    47490
cgaagcatga ttggtatatt catgagtgat atgggtctat aactttctgt ttttttggag    47550
tgttcttatt tgttttgat aacaataata tactggcttc atgaagttac ctgggaattg    47610
ttccctttgt tctgaaagtt catttaagat tagtattatt tattcattaa atgtttgata    47670
aaattcacca gtgaagcgat ccaggtctgg agttttcctt gtgggaaggt tttaaaatta    47730
tgattcagtt actttaaatt tgaatagcta ataggtatta gctattcaaa ttttctgctt    47790
```

```
cttgtgctaa ttttggtaat ttgtattttt gagtaatata tccattttaa gttcttgaat   47850
tgatttggca tgaaggtgtt cataacattt ctctactctt ttcttttttt tctttctttt   47910
ttttttaact gagtcagagt ctcactccgt tgcccaggct ggagtacagt ggcatcatct   47970
cagttcactg cagcctccac gtcctgggtt caaacagttc tcccacgtca gcctcccaag   48030
tagctgtgct tacaggcgca caccaccatg cctggctaag tttcgtattt ttagtagagg   48090
aggggttttg ccatgttggc caggctggtg tcgaactcct gacctcaagt gatccgcctg   48150
cctcagcctc ccaaagtgct gggattatag gtgtgagcca ccatgcccgg cctctgtact   48210
cttttcttaa tttggataga atttataata atgtctggtg tgctctcttg ttttctctc    48270 attgatctag gttggggttt gtccattttt ttaatatttt caaacagcca gcttttgttg   48330
ttgtcagcct tttcttgttt gttttctatg tcatttattt ctgtctttat tttcttctgc   48390
ttatgttggc ttttctttgg ggtagaagtt tgtatcactg gttatttaga cttttccaat   48450
attaacattt gggcaataaa tttctcctta aaccctatgc atctttttta tttccccatt   48510
tctttgaatc ctttaaatcc ataaacataa aaaagtaccc caaatactgt tgttaattgc   48570
atctcaaatt ttaatacatt ttttaaatta gtttaaaata tgtttatatt ttacatgtga   48630
tttattcttt gacccatgga ttatgctgaa gtgtgtttag cttttaaata tttaggaatt   48690
ttgcagatat tttattgttg gtttttaact ccactgtgtt cagaaaacat gctttgtatg   48750
gtggttgtcc tttgaaattg aagacttgtc ttacggccca gcaaatggtt tttcttgaca   48810
aatattctat ctatacttga aaagaatgat caggcgcagt gtctcatgcc tgtaatccca   48870
gcactttggg aggccaaggc ggacagatca cttgagtttt agaccagcct ggccaacgtg   48930
gtgaaacctg tctctactaa aggtacaaaa aaaattaata gccaggcttg gtggtgcgct   48990
tctgtagttg cagctgcttg aggggctga gatacaaaaa tcgcttcacc ccaggaggta    49050
gaggttacag tgagctgaga tcgcgccact gcacttcagc ctgggtacgg agcaagactc   49110
tgtctcataa aaatagaatg tgtatcctac agttgtggga tgtgatgttt cataattgtc   49170
tattagaata agttggttga tggtgttcaa atccttatga ttttttttgtt ctattggtta   49230 ctaagagagg attattaaaa tctacaatta caatttttagg tttgtctggt ttttcattta  49290
gtcagaacaa aatgtaagta cttgtttcat gtgttttgaa actgttttat taggttaata   49350 tgtatttttgg attgtaatgc ctctggtaaa tttagccttt tatcattatg aaatatttgt  49410
ttttgttaat attctttgtc tttatctcct ttttctcata tttaatgtag actccttatg   49470
attagcattc acattttttt ttcactcttt ttgttttgtt ttgttttgat acaggatgtc   49530
actctcacct aagctgcagt ccagtggcgc agtctgggct ccctgcaacc tctgcccccc   49590
accccgggtg aggtgatcct cccacctcag cctcctgagt agctggaacc acaggcacac   49650
actaccacgt ctggctattt ttttgtattt ttagtagaga cagggtttca ccatgtttcc   49710
caggctggtc tcaaactcct gagctcaagc gatctgccca cctcgacctc ccaaagtgct   49770
gggattacag gcatgagtca ccacacccag cccactctta actttgtctc ttaagtatgt   49830
ctcttgtaag cagcgtagca ttagatctta tttaatttat tctgataacc ttagtctttt   49890
aattgtagtt tttagtttat ttatatttaa tgttgataat tgttgggttt aggtttctca   49950
tcttatttgt tttctgtttg ctgcttctgt gttttgttcc ttttttttctc ccttcctgct  50010 cttcttgtag aggcaaattc caacatctct gtcatctctg tatctgtttc atttacagtc   50070
ttgtttgttt aaatatagaa ttcctggtta tgggtcacat cttcctgctc cttggcatgt   50130
ccagtacttt tagactgtgt agtggaaatg gtggatgata atgttgttga atatgggttt   50190
```

-continued

```
tattgtcctt tattagtttg ttttgttctg gcaggctctt aattactcag atcagtttga   50250
ttctctcaaa gcttgttttt aaacttaact tagggcaggt cttgaagccc tgttccttag   50310
acatggcctt ggggtctcag tttaattcct gggatgttca gcaagatctt gaaactccga   50370
ctgatcagaa cttctatgtc tctagcactg tgccacctct ggaatctgtt caattcacaa   50430
ttccttcgta gtcctgcaca cttagttaca gctccagtaa gccctaggag gtgttggtga   50490
tgtgattgtt gtgtgtggtc gcactgggag atactctcca ttttaatggt gtgaacgtaa   50550
cattatgata tataatggtt gtcccgtagt gactgtgtat ttcacacttt aaacgttatc   50610
tctcatcttc tgaatcgtct gaggattaag ttcactgtag aaacttggga agtgccacat   50670
ctaacattct taatgtaaat gggtccaaat cataacttca aggaccaact tttccaaaat   50730
atttttgcta tattttaaaa agagttatat ttatacaaat taccatagac agtaatttgc   50790
tgtccatctg tcaccaagtt aaaatatcta agggttttta tgttgattac catgtaattt   50850 ttttttttt gcattttca aaattatgta tatgactata gcataaaatt tcagtgtgat   50910
ccaggtatga gcaaggataa caattactat atttattctt cctgaataac agtaagagga   50970
agagcagaaa aggacatgcc tattgtactg ggcactgtgc tgggtgcttt gcaaacatga   51030
tcttgctttt tctcattttt aataatcctg tgaggtgggt gccatatgtc ttttataaca   51090
aggagtaaaa tattctgaac cactttcctg cctatgcaga aaattattca agacgacaca   51150
tgtttgaaag tggtagaatt ttacttaaaa tccacctgtg attgactcca agcctgtatt   51210
tttttcgact gcatcatttt gtctgtaata cagctgtatt caaactatga tggtgaaata   51270
cataagacct tattttctgt gtgtgggtca ggttttcccc catgcacgaa atttatagaa   51330 caggtaaccct ggagagtgag tctaatttcc caggagtatt tttgtcaaat gaagaatttt   51390
actgcttatt ccttttaga aacatacct tgtatgctgt aagctttgcc tgtggtctga   51450
ttgggttatg gctcttaatc tgaaatacta attcagccaa gcaattttg taagacccat   51510 aaagaagtca gctttcgacg ggcatggtgg ctcacgcttg taatcccagt actttgggag   51570
gccgaggcgg gtggatcacc tgacgtcgtg agttcgagac cagcctgacc aacatggaga   51630
aacctcatct ctactcaaaa tacaaaatta gctgggcatg gtggcacatg cctgtaatct   51690
cagctactcg ggaggctgag gcaggagagt agcttgaacc caggaggcag aggttgcggt   51750
gagccgaggt tgcgccactg cactctagcc tgggtgacag agcgagagac tctgtctcaa   51810
aaacaaaaca aaaaaaaaag aagtcagctt ttctggctag aaaaatgtgc cttggcctat   51870
gtgcaagagg ccagcataat taattttctt aaacattatt ttttaaagtg atcttggcca   51930
ggtgcagtgg ttcacacctg caatcccaac actttgggag gttgaggcag gaggattgct   51990
tgagccaagg aggttgagac cagtgtgggc aacacagtga gactccatct ctacaaaaca   52050
ttttaaaaat tagctgggtg tggtggcacg tgcctatagt cccagctact caggaggctg   52110
aggtaggaag atcacttgag ctcaggaggc cgggctgta gtcagccatt gttgtatcac   52170
tgtactccag cttgggctac agagagaccc tgtctctaaa aaataaaaa gtaagtagcc   52230 aggcatggtg gcttatgcct gtaatcccag cactttggga ggctgaggtg ggtggatcac   52290
gaggtcagga gatcgagact atcctagcta actaggtgaa accccgtctc cactaaaaat   52350
ataaaaaatt agccgggcgt ggtggcgggc gcctgtagtc ccagctactc gggagtctga   52410
ggcagaagaa tctcgtgaac ctggaagggg gaggttgcag tgagccgaga ttgcgtcact   52470
gcactccagc ctgggcaaca gagtgagact ctgtctcagt caatcaatca ataaaataaa   52530
```

```
aagtaagcaa gatcactttt tgaaaaatat ttttcttaca ttatggtagc aaggaaaggt   52590
ttgattttta tgttctgagt tttttaaatt ttcaacacaa gaacaaagga tagtataacc   52650
aacatctgtg ttttcattag aattaatgcc tgttgatact tatcacatt  ccttcatagt   52710 tttttttttt ctttcattt  tttaagtaga cttaaatttt ttttagagag atagatcttg   52770
ctattatgtt gcccaagcag tggccgttca caggctcaat tatagtgtac tacagccttg   52830
aattcctggg tttaagcgat cctcaagcct caactttctc agtagatgaa actacaggcg   52890
gtgcaactga ctgagtagac tctatgttga gaacagtttt agatttacag aaaaattaaa   52950
agatagtaca acagggttct ttatctcctc cccaccatcc acgcacttcc tattgttagc   53010
ctcttacctt tcctgtgttg tgtttgtcat aagtaatgaa ccaatactga tacttgtgat   53070
taactgaagt ccatacttta atcaaatttc ctttaatttt ccctaatgtc cttctgttgt   53130
ggaataccat ccatgatacc ccattacttt taatcgtcct gtctccttag gcgcctcttg   53190
attgtgacgt tttctcagcc tttccttggt ttttaatgac cttgacagtt ttgaggagaa   53250
cgagtcaggt gtattatagg atgccctct  gtacagattt gtctgatgtt tttctcatgg   53310
taagactggg cttatgggct tttgaaagga agatctcagc agccaagggc cattttacc    53370 acgtcacttt gagggtgcgt tgtgtcatgg tgactttacc actatggttg atgctgccca   53430
cagccacctg gttgaggtcg tgcctctcag gtttctccac tgtaatgctc cgcttccctc   53490
ctccatgcca tcctctttgg aaggactcac tatgttaag  gataggggt  ttatattcta   53550 ccttctttag gcaaagtgtc tacataattt atttagactt cttcagtgtg ggagatctgt   53610
ctcttcatag ttttttacta aatgaaatca attttaacag gataaatgaa agtgtctttt   53670
acatgatatg tattcatctt gctccccgcc cgccgagact gggtctggct ctgtcaccca   53730
ggctggagtg cagtgatgtt atcttggctc actgcagcct ttgcctctgg ggcacaagca   53790
gtcctcctac cccagcctcc tgaggagctg ggactacagg ctcatgccac tgcacccggc   53850
tgttttttgt agagatggag atttgccatg tggcctaggc cagtctcaaa ctcctgagct   53910
caagcaatcc acctgcctca ggctcccaaa gtgctgggat tacaggcatg agccaccatg   53970
cctggcctca tcttgctttt ttaagaacag tattaaaatt catacataaa gatttgattc   54030
atttattcta acctgttcat atgattatga attcttcctt gtatttttt  ccgttacagt   54090 tttctctatg ctttttgaaga tacacaatga cattttaatg aaaactttgt ctcttataag   54150
aggttcaaat ggtgtggctg aatctcagaa acaagagatt ttgtcttagt aattttttaaa  54210 ataaaggcaa agttactcac aaattaggtt tccccccagc atctttaatc atctttgatt   54270
acttgataaa aaatgccttc taactgtgat gtagatctca ttttcttttt ttttttgtcag  54330 aagaggactg aacccctttt ctgagtgctc tactgaggca aagtgtccag agccctccac   54390
ttagagctgg gaactgaatg tcagtgacat tttcttgcca gcaagtataa atgcttatca   54450
actaattgca attccaaggc catacttcca tagatataca tctgtgtaat tattacatat   54510
ttttggataa gaatgtggca ctgtggtttg tggctttcaa aaaatggcgc atggtctgaa   54570
gtagtgtgat tgcagggatt gcatttttat ttactaagta aaaacttaat gcccttagca   54630
gtgagtcata ttattcattt catgtttttc taccaagtaa tgaagaatga actggaaaac   54690
aagccacctg aaactcttcc tagaacaaag caagagatag ataatactga gaaatgccaa   54750
ctttagacat tgtcttgcag ttattgactt taaattattg tagtaaggat gcatgcctgt   54810
tttaagtact gtagaaagtc tgttcatttt atagaatcct gtctcatgtt agagattttc   54870
tgtgctctat ttttgcaaag agatcttaga gccacctcaa gattgcacag tgctttgtag   54930
```

```
ttttcagagc attttcccat gtgctatccc atttaaacca gaaaccacaa gttagagcgg    54990
ccctgcgtga atggcaaaca ggagtgtata tatcagcgat gagtgggcac actgttgagg    55050
cacagggagt gattgaggcg tagagattgg ggacagtgca aggaggggac tgagtgtgtt    55110 ttctcccta aaaacctggc acattttgct tagagagtta cagtagaacg ggaagcaccg     55170
gcctgcttgg cagttgtagt ctccaagttg accgggtatg gttcagccta ggcgtgctgc    55230
tgccgccgcg tgtgggctcg gtgaggcaaa ggcgtgtggg gatgggagtg gccagaggtg    55290
ggaggccatc actcttgact tgagtccatc aggatttgaa tgcagagatc agagcagcgt    55350
ttgttcctgt ctgtcgatgt tatgagtgat gctcttctga gacagtgctt gccttctgtg    55410
actaaccatc agtatgaata accagctctc tcctgagctt tccagtttcc gtgttcattt    55470
taattaacac tttagctctg tcagttaacc cccagccagg tggctgcaca tcctaccact    55530
tttttgtgga catttagatt atttgattag agatagactt tgaaactgca agattcatgg    55590
ctatccaggc ccatcccaga ggtgtttttc cccattcctg tttatgatga ggttgcagag    55650
gcgtagcctc ggtcaactgt gtctgttacc atttagctcg cctttgcagg cccagctctt    55710
gacccccttg tttgcctccc agtcaggacc cctctccctt ttgaaactcc atttagcagt    55770
cgatgttggt ggcacctgtt aaccgcacat gtctgatttc cttgtggctt gtgtctctta    55830
cctttggctt gggagaacgt ggccctgtgt gtgtcaccac tgcacagtac ctccctcctg    55890
aaagacttta acacacttca tgttcctaga tgagtgtgtg tgtgtgtgtg tgtgtgtgtg    55950
tgtgtgtgtt gccacagcct tttcaacttc cagtgtccta aagataagag catcactgct    56010
gaagagagct aggggcgggt ggcaacgtga tagctgccta gtggtctcct tgctgggaag    56070
gtctgctgct cgataggaac tgtctgacta gaagtgtgcc ttgccatgga aacttgggaa    56130
ctaaatgcat tcaggtccat ccctcatgct ccagtctctt gcttgctgct ccctgaagct    56190
caggccagat agatcaggat gaaggggcat cccttgctgc ctaaactttg aaccagagtt    56250
caaacagcag ggatcattgt acctttgtgg taccaagagc caaacgtggg atgtctgagg    56310
agaaaaagca gaagctgtta gagccacgcc tggcttttg tgtcctgagt aggtgtcgac     56370
cttgtttgtt tctatttct ttcctcccgc cctccctgca gagagtggtg ggcctgtgct     56430
gaggctcctt gaaatgtctt ctagccacag gtataaggca ttcgagcaaa gcttgacagg    56490
ttacgcggcc acgttgtgac cagggcaaat ttgatttcag ttaccactca gcggcaatct    56550
ctgtcaccaa cagtttgatc tacctagttt tattcagtgt ttaatgacag tttaatgttt    56610
taagtagagt tgtgcagcct aacagggtcg tcttgccatt ttgggcactc agaatgtttg    56670
agtagagaac gactttaaga aacaactttt cctccttaaa ataatgcttt gtatagagaa    56730
tatgagtcat aatagaaagt attaagaaag aacatttgct tacaagccat ccagagaaat    56790
cactatgaaa tattttggtg ttctgtcctc cttgctgtgt ataggtgtgt gttttatggg    56850
gattatacat ttgtgtcctt tttttctttt taattttgta acttagaagg aacgttttct    56910
ctgtcagtaa tcagagtcac ctttgtggta ccagcggttc cttatgttga cctcacccct    56970 ctccctttc taggcgcttc ctgtgtattc tctcgaaaca aggcacagag actgcagcgg     57030
actgagccag ctcctggctc cctcagcacc cttccctgtt ttgtctcctc gctgacatca    57090
ccagtcagga gggacgactg tatttaagag cactttactt tgctaattat gttttgtta     57150 ggactctgta caccctcagct tttgttaaga ggtagagcca catatttttg ataacaatat    57210
atctttgagt gtgctttaca cttttagatt tatggcattt aataagctgg gcaagatctt    57270
```

```
ctttggctgc tgcagtcctc ctcttgccac tgaggtccag gagattcgcc atgaggagat    57330
gacacagaac cctcaggcag cctcacgtca cctcccaggg ctcatcccac gagctgttct    57390
tcctgctccc acagtagagc tgacggcctg cccagttcaa gaattagttc tgttttcctg    57450
ccccaaagta gaggaggaac acagtcctct gaaatgtcat cttctttct cctttaaatt     57510 ttactagaaa tagtcagtgg ctgtctgtct taaagccttg tgagttctgt ccgatcttta    57570
tttctccttt tctctgaacc gttgcgttac ctatacacat tcacgcctc ctttattgcc     57630 gcctcctta ctgtgcgttc ttgacgtccc tttttatgag tgagtggagt gtagatccgt     57690 ggaaaaggt gcttctctgc cttgcatgag cgctctatgt ggaagtctg gggaaaacat      57750 cgggtggctt tgtcaggtga cttattgagg ccctctgtcc cgctgggcca tagttggatt    57810
gcagtgtaaa ttaatttcgt ctttacaaag attcactctt ttgtgtgtgt gtgtgacaga    57870
gtcttgctgt gttacccagg ctggagtgca gtggtgcaat cttggctcac tgcaacctcc    57930
tactcccagg gttcaagtga ttctcctgcc taagcctctc cttaagcgat tctcctgcct    57990
aaacctgtag ctgggctac aggtgtgtgc caccatgcct ggctaatttt tgtatttta     58050 gtagagacag ggtttcacca tattggccag gcgggtctcc aactcctgac ctcaggtgat    58110
ccacccgcct tggcctttca aagtgctggg attacaggcg tgagccacca cgcccagcca    58170
agattcagtc tttatagaat aaaatttttc tcacattttt tatcaccttt tcttcttttt    58230
tcctcttttt ccattgcccg tgtgaagttg gcttggattg gcatgaaagg ggcacttaat    58290
cctgaagaga gtctactctt ctacctaaaa aaaaatatta ggacttaaaa gaattaggag    58350
aaacagtgcc ttcaaatttt atctcccttt tcttggatca ttttgcctca gattagctgt    58410
tctttgtgta aaatactctg ggaagtggtg tccagggtgc ggggctatgg aatcccagtc    58470
actgggcagt ggggatggaa gaccttgctc cacgaactcc ccagtctcct ggaaaggctg    58530
ctggccatcc actctgggcc ccacagggag gattgccatg gtgagggcct cccagtccag    58590
gggttgacag ttaagtctgc agactcagaa ccctcagttg tcactcactg cgagtagcaa    58650
catctcccag gagtgtagcc tttatgtgaa tcaagcactg atggtttgaa ataaaaaatg    58710
tcatcagatt tttagaatca gaaagaactt taaagatcac ctaatgataa tctaaatgct    58770
tcctatttta tagataagga aaactgaggg accaagaggt ttgtcccagt tacatggctg    58830
atgaggggca gaaacaggat tagaaatagt ttctccagtg accttgaccc gtcgttttg     58890 cttatgcatt aatgcagact gcaccttggg gaaccagcgt ctctaactgt agggacctgc    58950
caaggtgtac caatagtatt agggtgccgg tttcactgct agaagtttct ggagcagttg    59010
ggtgactaac agtgaggata caggcctgca tttccactct tcttctaagt cacattctgg    59070
tcgtggctgt gtgtgtgtgt acacagtggc tcaattatgg atcactacat cctcaacctc    59130
ttgggttcga gcagtcctcc cacctcagcc tccgaaatag ctgggactac aagcacacgc    59190
cgtcacacct ggctaattat ttttgtaga gaaggggtt ttgctacgtt gcccaggttg     59250
gtctcaaact cctggcctca gcaatcctc gtgcctggga ggatcttaac ccaagaagac     59310
aaggaatgct tcttgaaaga cattatccaa atgaaataca gtgagagttg ctaaatactt    59370
tgttactagt cttccagtta ggacttatcc ttccagggca aatgttcaga cctggggcc     59430 gcacattttc ctgaatgcat tccaggttgg cagcacataa gacttcaatt gagggggaag    59490
gtgggctgtt cacctgccca ggtgctttag cccaactctc ctgccccagg tgcaccctgg    59550
acagccaagt gctgtctgtg gcactgtaat cagtggcgta tttctcctta ctctatattt    59610
accaagttga tatactggaa ggattccaag agcaagcgag tgatagcaga caactgaatg    59670
```

```
cagtcatgtc tttccatgaa aactgctttt cttggctttc ttccaacaat ggtaggttgc   59730
caagagaaaa tgcttttggc tttacaaatg atctggccgt agtctggggt ggttctggtt   59790
ctttatgtca ttgaaaatga taaatatttc tggctattca attatttagc aaacttttgc   59850
tcttgatgta ctgaactgtg ttgttttttt acaccttata tgaatttgtg gttttacatg   59910
tataccaact tgtggagaaa gatgctaaaa aaactccagc ttgaaaaata tgtcaggtta   59970
ggctgaagcc acatcaaatg gaagtttgtt gctgtgtcgt ggctggctta tgagtggtag   60030
ttgcatccat ttcttttttc gtgggagtgt tctttcatgt tcagttcttc tatgttttgg   60090
tttaaatttt aacccaagaa tgttaggcta gggtatttta atcatatgtc attattgctt   60150
atgatttaag tttgaaataa acaccctgag tttattgttc ttaaagctaa aaacaatgt    60210 agaatgaaaa ctggaaacgc ttatgattta ccaggacaat tagaaaataa tggccttttc   60270
agagtatttc tacaaatagc aaatgcacaa gattgttgtt gtcacagtgt ttttctgaaa   60330
atgtcccata atccaaatgc cagtaatccc agccggcctc tccctatcgt cctacatgtt   60390
ggaaccactc tccaccatta cacgttctct gtaaagcatt cctttatttc attactgttt   60450
aagcatggtc aggaaagaaa tcatatgtag tgtagaatga ttgctcccaa agctgtctct   60510
cacctcctca cccctagtac tcactgtcgc agctgctcat cttagtgctt cgcatatagg   60570
aacttgttta gttctcacgc aacccttaga ggaggtgctg tgatctccat tttacagatg   60630
ataaaaccaa ggtgcagaga ggtttaagta aatccctagc aagtggtgga gtcgccattc   60690
agatatcccc agagcccaca tagttgaccg caatggcatg ttgcctctat ggatgaaatt   60750
gtatttgtgg ctgtgttcca ataagaaaaa tttggttttt tcagaaagag gcattgggct   60810
gcctttggcc cacaggccgc actttgccac cctgttttca tagacagatc ctgtctctgt   60870
cccggctact ggcgtgaggc cggtgaactt gaaggagaca gagttgcgtt aagcggggag   60930
gtgatgagcc cccgtgcaag ggtgaagcct ctagtggggg ctgtggggag cgtctgctga   60990
gttctcaggc tgatttagtg tgtccctgcc cttttcgggg ggccccttcc tcacctataa   61050
agtggtaggt tttagctagt cttatttctc cacttgtctt tgcaaagctt attactgaac   61110
atcatatttt ggttccttt tgtgtgtttt tgaccagcat cagtgacacc ccccaaagcc   61170
cacttcctct gagtggtctg ctgtgtattg tggcttgagg cgtgtcttga ggtgtgagga   61230
aaactgctga agtagtcagc tgctgcaaaa atggacttag tgggctcctc ggaaccacct   61290
taaggccagg tgcggtggct cacgcctgta atcccagccc tttgggaggc caaggcaggc   61350
ggatcacttg aggttaggag tttgagacca gcctggccaa cgtggtcttt agtaaagatg   61410
gggaaacccc atctctacta aaaatacaaa aattagccag gcgtggtggc acgcgcctgt   61470
agtcccagct actcaggagg ctgagacggg agaatcgctt gaaccaggga ggcagaggtt   61530
gcagtgagct gggacggtgc cactacactc cagcctgggc aacaagagtg agactccatc   61590
tcaaaaaaaa aaaaaaaaa aaagaaaaga aaacctaaac atcaaactcg gcacttgttg    61650
cactgagagt ttctgatggc ctggccgact ctaggtcaag ttctgcgtcg cagtgccatt   61710
tctggccgtc ctcctccccg gcccccatt ggtcacatgg tggcccctc aggtgcatac     61770 tcataagtgg ttatgtcaa cccttcttg tgagtgtgca cttcaaaatg acgtttggag     61830
atgaaaactg ggggagtttg tttgtcggag tggttgttct tatgagtggt tgatgtctct   61890
ggaagtggac tatttgcaaa ggctcccata catggctcag ggttgtgtga gatgaggaac   61950
cagcttgccc ttccctgaaa atgaggggca tggaggaagt ttccttcctc caaggacagg   62010
```

```
tattcttaat ctttaggaga tcttagagtg accctcagaa atgaacatca cacaaaattg    62070
tgaactggtg cccacccaaa tgctccctcc cctgccccca tggactgcct ggcccattgc    62130 ctcccccag tggagtttgg cctgcaaaga acgtgtttct ctgacctttt cgacagaaga    62190
gccagaaaat ggatgcttgg cttgctacta ttgtagaaac ctgttctggg gaaatacttc    62250
tattttgatg atttcttcta taaccttca gtctaaaccc cttttcaata tcaggagttt    62310
ttctgatgat attgaaggac ttgacttgac ttttctctct ccttaaaccc ttaattagtt    62370
tttggatttc catttactaa cttttttacg agactagatc tcacttgaga aagggggag    62430 ttaggtgagt agtagagaga ttctcctggt tagtgagtgg agagaatctt tctggtcttt    62490
ctgagcctgg agcttgtttt cttactaatg ttttgatagc tgtcatatca ttacaagtag    62550
aaaatgatag tatttgtccc acacactgag gtaaacagag gaggctgttg gcagccagaa    62610
gtgaccatgg aggctgatgg gtcagtaatt ctgtgtgcaa gtggaaagct ctgggtaagg    62670
gcatgagtgg ggccttgtac caaagtcagg gttttcctgg cccaaagatg tagcacagag    62730
gacccatttt atagccagac tggacttgtg tatctgctgt gatcacacac acccgtttca    62790
ccattctgaa aaccaactcc gaaggcctgt tctcgttctg cccgacttt cagcatggga    62850 aagtagctgt ccactcctgt ccactccaac tggtagctga gatccttgtt tggaagtttt    62910
gaagatagaa agggcactgt tcctgctgcc tcttccgatg ccccctccag ccattgctga    62970 ccctcttgt gccttgactt tggtcacttg ttcgtggttc tttgaccacc tccttcctgg    63030
ctctattcct aggggctgcg tggcatggtg gtgctttggc gtgttcattc atttgggtcc    63090
ttccgctgca tccctggtat gttgcagggg atgcagagaa tgttccagga aggtgagaag    63150
ttttatccta gttttgtgac caaaacaggt tcaggataga ttattacaaa catttatgtg    63210
acagataatc ctctagagcc gtgtggtact ttgtactttc cgtggtaccc atgtctgctg    63270
gagtagatgg acagtcacag tctgcctttt ccctcctctt tgttgatcat ggtcactcac    63330
ctacttgcca gacagttcag acccgcagcc acaggattta atggatgggc taggctcagc    63390
accaggattt gctgcaggtg cctctttgta ttgttcttgg gttttgagct gaacttaaag    63450
aggaatttcc tcatcagagc tcacactgca gtcatgttaa ggctaatcca gtttcacccc    63510
cattctttct tgggggcagt ggttggagtt ggggaaacct caggatctgg cttcaatatt    63570
tttcttatca tacacaggga ctatgcatta catattttta ctctctgagt gaagtgatag    63630
aaaacagaag taggttctca aacagttaat tgattgatac gcttggtcac aatgcttttt    63690
aatgggaaac ctgggagagc tgtgaggcat tgtttaattt agtttcatta tggaagctct    63750
tgttcttttt ttgggtactt actatagtta acttttccta ttttctgaga ttaaacttga    63810
attaaatgct taaaggagtt ctgttaggaa gaacagagta aaagaaactt ctaatatgta    63870
tgggctgttg ttgaatgagg cagaatataa atactttatg ggttttaatt tgttaatata    63930 taaatttac tattaactga acagttgcct attctctgtt ctgcttttt aattttattt    63990 aaaagagtgt atggaataca aaaaaaaaga atgaataaga ctttgtattt gctagcacaa    64050
cagggtgact attcaaaaat aatttaattc tacatttta aataactgaa agactgtaat    64110
tggattgttt ataacacaaa ggataaatgc ttgaggtgac ggacacccca tttaacctgg    64170
gtgtgattat tacacagtgc atgcctgtaa aaaaaactca tgtaacccat aaatatatat    64230
acctactatg tacctcccaa aattaaaaat gaaaaaactt tttaaaagat tatatagagg    64290
ttctctagca gcattaaacc aaatcctgat gaacctccat tgaaaataaa gccagcttta    64350
caaaaaaaaa aaaaattttt ttttttttt tttttgaga tggagtctcc cctctgtcat    64410
```

```
ccaggctgga gtgcagtggc aagatctcag ctcactgcat tttctgcctc ccgggttcaa    64470
gcagtttatt ctggctcatc gtgggattat acgcacgcac caccatgcct agctaatttt    64530
tgtattttta gtagagatgg agtttcacca tgttggccag gctggtctcg aactgctgac    64590
cttaagtgat ccgcctgcct tagcctccca aagtgctgga attacaggca tgagcaccca    64650
gcctaccaaa ctattatcaa gtacctgttg ggacgtttaa agaaatgtag atttctcatta   64710 attagcgtta gacatcttga ttttagtatt tcattttggg cattggtcct aagaagtata    64770
tgttagccta gggtggggga ccacagtgct cagtttgatt aatggagaat agatatatac    64830
taggaattca gaaatctaga atctctagaa gcaaatggtt tttattcata actgcaggct    64890
aggaccagtg catggctctt gagttctgcc aggaggtggt ttggcaccag gaggtagcct    64950
tgcctgggca atgagcagtg atacctgtg agagagctga cctctttagc ctggttatta     65010
actttctctg ataaggagag gctggggctg gccctggtgc cagagatttg aaccctaacc    65070
tcctgcatgt agcctgggtt ttgttttat cataggctaa agacgggaat ttttttcccct    65130 attttgaga attgtgtaga tccctatgag ctggacgttc cttacatacc gttcatgatc     65190
tttgacttgc catcttttttt accttgtgag aatcaaggta aaaacttgtt gagactgttt    65250
ccttcactct cttatctgat ggccaagaag aaaaggtaca aacacgtttt tgatgaaatc    65310
tgtcagagcg cttccaaaca ctgggttacc ctttgaaatt gaccagttat ggccaggcgt    65370
ggtggcttat acctgtaatc ccaacacctg ggaggcttg aggtgtatgg atcacttgag     65430
gccaggagtt tgaggccagc gtggccaaca tggtaaaacc ctgtctctac taaaaaatac    65490
aaaaatttgc tgggtgtggt ggtgcatgcc tgtgaactca actacttggg aggctgagac    65550
acgagaattg cttgaatctg ggaggcggag gttgcaggga gctgaaatca tgccactgca    65610
ttccagccta ggcaacagaa cgagactctg tctcaaacac acacacacac acacacacac    65670
acacacacac acacacacac acacacacac agaacgagac tctgtctcaa acacacacac    65730
acacacacac acacacacac actaaacaac attgaccagt tagaaaaggg ccccaggcca    65790
ggcaagtatt acccatctga tcacacactc atactcaccc tggcagggct atcttaggaa    65850
aattgtcaaa atatctggga agttttggaa ataaactttc tgaagcaagt caggtgaact    65910
ttgaggtcca cagagcacac tggcctcttg gtacttaggt cccctcttct ctggagccag    65970
ggtgcctggg catttggtgt ggaaggaaga tggttacctg ttcccttccc cacccttca    66030 gctgtcaccc actttggttt gtcaatgctg ggcctaatta attagaaact tccaaaagac    66090
gttgattttt tgtttgtttg tttgtcaaat tggttgacat aaggtgtgag ctccgtgaca    66150
agtgggaaat gcatctacgc agcctcagaa ctgggcttgg ctcataccag gcacttggtg    66210
aataccagtt gacttcgagg atgaattgat cgagggaaaa tgagtgtggg tgttctgtca    66270
tattttgtcc gaagtcagaa atttaggaac tggggaaaa aaaactatat ttttgttgt      66330 tgttcgtgtt gttgtattca aattctaggc ttctaagaac aatgtttcag cggtttggtt    66390
atatgtaata agacaaattc tgagagtagt aagtgttcca tggaattaat ttagtatagt    66450
ggtttctgaa aatataaatt cctgcttcaa ttaagtttca gatgacagtt gaaggaagct    66510
tcttgcaaat cagaaatgtg cttaatattt atcgagctac catcttgcct agattaagtc    66570
atttgaactc gaaattgagt ctggtttgtg gacttgcaga agaattagtg tctcagttca    66630
cttaagtaga gcaccctagtg gtgacaagaa tgtgattgct ttccaaaagg tgagaaatgt   66690
cacctaggag gactacatgg ggaaggaaat cacctgcgta tgaaatgcac agagctagaa    66750
```

```
ctttctggtt atactccttt ggttttatt tgtgtttctg tacaggcatt tcagcagaaa   66810
gggccagttg tgttgagtgt tgatttgttt gtagcctaga cttttagagc tgaaagaaat   66870
aatacgatcc atcttgttca agacactcat cttacaggcg aggagtttga agtccataga   66930
aggaatgtta agttacccag agtggacatg ctggcgtggc agtcaccagg tgaggctgat   66990
ggagagaact gagctatgat ttcttaactg gaaactcacc cctgggaggt tttccctatg   67050
cggggacctt cccagtccat caaactgacc actactccag aaatacagaa cacacaatag   67110
acagaaggtg gaatattaga gctttgcaaa aaagcaaaga caggcagccc aagcatccag   67170
tttcttaatt agtcgttgtt tctccacagg gagaaagata agcactggga tattgccatg   67230
gcaattcctg aattgacctg tggaggctgg agctgggggt catcagggaa cttggcccac   67290
atctgttgat ggaaggaatt ccagttggtt gcaggccctc acggaagcat agctgagggt   67350
tcctcttcc cattcctgcc tttatctagt atatatttga tttcagtgca ctttaatttt   67410
ataaaaact ttattatgga aaattttagg ccgggcgcag tggctcacac ctgtaatccc   67470
agtacattgg gaggccaagg tgggcggatc acctgaggtc aggagttcaa gaccagcttg   67530
gccaacatga tgaaactttg tctctactaa aaatacaaaa attagctggg tgtgatggca   67590
cgagcccata atcccagcta ctcaggaggc tgaggcagga gaattgcttg aacctgggag   67650
agggaggttt cagtgagccg agatcacgcc actgcactcc agcctgggtg acagagtgac   67710
acactctcaa aaaatataaa taaatacata aattttacac ctgtacagtg gtagagagga   67770
tactataacc tctctgtacc catcgcctac tgcttggtta gtgattatca gtaccttacc   67830
aggctctctc catctatgcc cttttcctgc cacctcctcc tgcccagtgg attagaggtg   67890
acccttaagc aactcagggg ttaagggtgc tgaccctgcc agtcgaaaat ctgcttgtaa   67950
ccttttgact ccataaaagt ttaactacta ctaatcccct gctgttgatc agaagcctta   68010
ccaatagcat acacatttgc ttaacacaaa tttcatgttt tatgtgttat atactgtatc   68070
tttacagtga agtaagctag agaaaagaaa acgttattag gaaaaccgta aggggccggg   68130
cacggtggct catgcctgta atcccagcac tttgggaggc caaggtggat ggatcacctg   68190
aggtcaggag tttgagaaca gcctggccag catgatgaaa ccgtgtctct actaaaaata   68250
caaaaaatt agccggacct ggtggcacgt gcctgtagta ccagctactc aggaggctga   68310
ggcaagagaa tcgcttgaac ccaggcggta gaggttggca gtgagccgag acagctccac   68370
tgcactccag cctaggcgac agagcaagat gctgtctcta ttaaaataaa taaataaaac   68430
cataaggaaa agaaaatata tgtaccattc attaagtgaa agtgggtcat catcaaggtc   68490
ttcatcctca ttgtcttcac gttgaggagg atgaggaggt gctggtcttg atctcttggt   68550
tggcagaggc tgaggagttt gaagaggagc aggagagatt gaaaaatatt tccatatatg   68610
tagacccatg cagttcaaac ccatgttggt catgggtcag gtgtatttta aaggagatcc   68670
caggtgttgt atcatttcat tgcaatattt ccactgtgtg ttttgaacta atggaaactt   68730
agttcaaatc tgatggggaa cctaacagaa actagatacc tatagagtaa ttaaggatta   68790
aactgaaaga attccccttg ggtagcagct ttggaaggtt ttgttttcca aatgactttc   68850
ttcgggtgtt ggtgccattg ttggggcagg agggattgag tgaggagagt ggctgagggt   68910
gggggaaac agctcgtcta cttgcgggat ggggtttagg gtgaggagag agtggctgct   68970
aggagctgct tcatgagcct tctgcttgga gcatgtgaac ctgataatga accttgaatt   69030
tatcattgca atgagtattt cataggaaac tgtgtgagca tttcccaggc ccttcctttt   69090
atattgactg cgtcaccaca gctgatgtta cctctttttt gtttcag atg gga ata   69146
```

|  |  |  |  |  |  |  |  |  |  |  |  |  |  |  |  |
|---|---|---|---|---|---|---|---|---|---|---|---|---|---|---|---|
|  |  |  |  |  |  |  |  |  |  |  |  | Met | Gly | Ile |  |
| act | ggg | aac | aca | agt | cca | ttt | gga | cag | ccc | ttt | agt | caa | gct | gga | ggg | 69194 |
| Thr | Gly | Asn | Thr | Ser | Pro | Phe | Gly | Gln | Pro | Phe | Ser | Gln | Ala | Gly | Gly |  |
| 270 |  |  |  | 275 |  |  |  |  | 280 |  |  |  |  | 285 |  |  |
| cag | cca | atg | gga | gcc | act | gga | gtg | aac | ccc | cag | tta | gcc | agc | aaa | cag | 69242 |
| Gln | Pro | Met | Gly | Ala | Thr | Gly | Val | Asn | Pro | Gln | Leu | Ala | Ser | Lys | Gln |  |
|  |  |  | 290 |  |  |  |  | 295 |  |  |  |  | 300 |  |  |  |
| agc | atg | gtc | aac | agt | ttg | ccc | acc | ttc | cct | aca | gat | atc | aag | aat | act | 69290 |
| Ser | Met | Val | Asn | Ser | Leu | Pro | Thr | Phe | Pro | Thr | Asp | Ile | Lys | Asn | Thr |  |
| 305 |  |  |  |  | 310 |  |  |  |  | 315 |  |  |  |  |  |  |
| tca | gtc | acc | aac | gtg | cca | aat | atg | gtaagttacc cttggccctc agtgttatgg | 69344 |
| Ser | Val | Thr | Asn | Val | Pro | Asn | Met |  |
| 320 |  |  |  |  | 325 |  |  |  |

| | |
|---|---|
| ctctccggtg ggtgctgtgg tctgtggatt tttaccattc tcacagtgaa agtctataac | 69404 |
| taaaagtgtg tcagtaggtg ataggaagag aacccagatt tctcatgagt agctctctaa | 69464 |
| atgagtttaa cattttctgt gatgagctag caacaggaga gataggtgag gatgattcag | 69524 |
| ccgctcttcc caggctcctt tgttgatgg agagaattca cgtgcacgaa tcactttacc | 69584 |
| tttctctcca gaatcatgag aaccagagac actggctttt cttacacttc ctgtttgtta | 69644 |
| gtggcttgat gatgtcagta gaagcccatt gatttgtatt accgtcagat gatggacatt | 69704 |
| tatcttccaa agacaatact ctgttgatga gatgcatatt acgtccaaca caatagatga | 69764 |
| ttccacgtgt cttcatcctc cctgaggttt gaagggattt tatagatggg aaatctataa | 69824 |
| aatgggaatt atccttatca cttctcaacc tgatgaatca agatattaat gggaaaatat | 69884 |
| ctccttttgc accaccaaat aatagaatct cttttatttc aaaacactga ggggtagtgc | 69944 |
| gttcttttgt ccagcctctc ttgttcaccc ccagtgctgc atgtctggtg tgctcttggt | 70004 |
| ggtgggtgag gaccacaagc agccatctct ccccactgtg cttgttgctg agagcctgac | 70064 |
| cttcccagct gccatagtga tttgggaaga tcacaagaaa gtgagaggat tatgttcaga | 70124 |
| aaaagttgct ttttgtcttt cggttttta tgcttttat tttgaagtat ttgttgtaaa | 70184 |
| gatagcacag agaattccta tatatctttc acctcatcca gcttcctctg atgcatctta | 70244 |
| cataaccttg gtcttttctc aaaactaagt aattaacatt gcttacagtg cttagaagtt | 70304 |
| ttgaggttgc tgggaagcag agagagccag atctctttat ttacttgttt gataaaatca | 70364 |
| ggaaatggga ataatgaggt gtcctgtcag gtgctggctc cctgctgtat ggtacctcca | 70424 |
| tttaaaaagg tggttgaggc cgggcgtggt ggctcacacc tgtaatgcca gcactttggg | 70484 |
| aggctgaggc gggtggatca ctaggtcagg agttcgaggc caggctggcc aagatgatga | 70544 |
| aaccccgtct ctgctaaaaa tacaaaaatt agccgggcat ggtggcgggc acctgtaatt | 70604 |
| ccagctactc aggaggctga ggcaagagaa tcgcttgaac ctgggaggtg gaggttgcag | 70664 |
| tgagcggaga tcgcgccact gcactctagc ctgggtggca gagcaagact ctgtctcaaa | 70724 |
| aaaaaaaaag gtggttgggt atgtacaagt aacaaaactt gctctcaaaa ctgtgaaaac | 70784 |
| aacctaaagt tcttaggact tctttatttc ttctgataat cccettgtaa ctttccttga | 70844 |
| tatgcttctt tctttccaat aacttttgt tgccaggatt gtcctgttcc tgatagtgca | 70904 |
| ggtccagaac ctgaaacaga gcccagagga ccctaggtca gccccctcaag ttcagggaac | 70964 |
| ggtactgacc tgcataatgc tgggctctgg caccacacag atcccgttct ctcctgtgct | 71024 |
| tccttttcca gtcctcaccg aaaggacagt agtgtggact ctggggttag ctgtcatcga | 71084 |
| ttatgcctgc tcagtaacca ggagcacatt ttggcttcat agtgaaagca tttgctttt | 71144 |
| ccaagacttc ttgtgtttta cagtcaggga aaccctgacc taacatttg ctccctttc | 71204 |

```
tcttttaaaa tattctccag ccccacttcc ccatcccctc tcctttatct acaacttagt    71264
gacagaatct gtgctccggg cccctctgct gcctccactg ctgctccaga gggctgaact    71324
tggcagatgt ggtatgcttg tcaagggcag tttctgcccg ggactgcaaa gaggctgctc    71384
attcccttca cctgcagcag ggctggagcc gtttggtctg gggcaggctc ccctctgcct    71444
ctgcactgat ggcagttctc tgctgtgagc cggttgtgcc ccagaggatg ttgggcagca    71504
tccctggccc tacccactgg gtgcttacag ccttctcctc taagccatga taatcaaaaa    71564
tggctcaagg caccaacata tgttctccag ggcatagtcg cccctagtta aaaactcctg    71624
ctctggagaa ctggagagta attaggagaa gcagtagcaa cagcatctca tccttttgct    71684
tgtcttccag acatctgaca aaagtagaac cacttctttt cctctctgcc tctctctctc    71744
ccccgctgcc ccccccttct ttcatccctc cctctcccct tctctcccca cccctctct    71804 ttctctctcc ctctcttcct gtttcttggt ctgtctctga tcttctcagg gtaaactgag    71864
aaagcatttt tgtccatggg aactgcattg gttgcctggt ggccactgtc tcacaagaac    71924
ccctgtggac tttgagacag atccacaaat gcctgttggg ggtaaactga atgacaccac    71984
tgaccctgga gggcacagat cagatggggc tgtgcccacg tgtgcctttg tgaggcagcc    72044
tgacccagga acagccttca gtgctccaca tagtggtagg aaccagaggg gctggtggga    72104
aagtggggta ccagcacaca tggtctcccc aacatctttc taggtaattt ttaacatatt    72164
cctgcaatag cctcttgaga gacatcattc caggtcccat tttacagctg agcaagttga    72224
gactctgagg agtttgggtt gttcaaagct atgtagcttc ctgtttgcaa agcctgaaac    72284
tcttcagtta tgttctgagg tcatgttttt gcagccctga gcctgccggg aatgcttcac    72344
cagcccgtgc ttacacagtt tgtctgcagt tcctcagatg tgttttgtag tcttttgaa     72404 ttttgaaaat tatatctggc ctcaaaaccc acagactttt gcatactgag ggcaaacact    72464 tacaagaaa tctaggtcta tttactgaaa aaatgaggtg tcaaacatat ttgcatttat     72524
tgtcatgctt tagggggtac ccaactaaat ttggtgtccc aaacaatccc agtcaggact    72584
ccagtgccaa atcacctggt gccctctgca gctctttcct ggagtgattt agccacgtgg    72644
tcttgggcca gggagctctt gttcctctcc cctcctagtt tctataggag tccaacactg    72704
ggtagcattg aggaagggaa ggatatgatc attcaattaa tttgtcacat gtgttgaaag    72764
ccttttgtgg gctcaggtgc tggagtcggc tccccagaag gcaactggga gtgacacaga    72824
gctcactcca cttttgtgaa atggaaggtg tagtggccac ggaaaacaaa tcgttacaaa    72884
ctgctccaag aggtctgcgt agcactcagc ggttcagatt gtcataggga cctctttaga    72944
tggagccatc agagaaggcc acattgagga aggagattta aaggcaagat tggaaagttg    73004
agaagaagcc acagagaccc cagggtattg ggacagcact ggcttgcgta ggaactggta    73064
gaagtccaga aaggccacca tgagggaagg gagcagggcg tgagtggaag ttgggggttg    73124
agcaggaacc atttcagggg gccttggagg gaagatgggc catcggctta cagggtgggg    73184
tgtgatgcag gaagttgaag ccactttagc tgagtgagga ggagaagttc aagggcgatc    73244
cttctggaag tggaacccac ctgattcttg gtgacgtctt gcttaagctt tggattgggc    73304
tttctgacat tttcacaaaa tgccgtgtag aagtgggata cgtcttagac tgagaacatt    73364
cagtgaccag aggggcctca tcttcaggtt ctcccacgtg gtctcctgca agagttattt    73424
ctaatgtgga gttcgtaggt gtgatttttt ttttttttta agaactgcgt tatgagact     73484 tcaccattaa agttgagatg caggagattc atcagtagtg ctgcttattt aaaattgctc    73544
```

```
atgagtgatg ttacgatttg ttgtgactga gtttcagaat tttggagtgg aggttgtgga    73604
cagggcccac ggcagctgct gatctacgtc tctgaatgga agggtggtgt ggctggaaga    73664
ctgtgtagac gggaggatgg gagagtggtc ttctgtgtcc tgccagaata tcacagctgc    73724
ggcagtgaca ctggtagcac ctgagcggca agccatgtgc taggatgccc tccagggccc    73784
cctgtgtcca ggggttcatt ccattgctgt gtctcagcac ctgtccatgg ccccacctgc    73844
atccgagtga ctggcagttc ctgggcctca cccagtcctc ccgattcaca atctcttagg    73904
acgaaggtgc agaatctgtg tcttgtagtc actcttaact tgtgaaactt cagcttttt    73964 ctttctcaat ttcccaattc cacctaattc cctctaatta taactcagat aattcttaaa    74024
tacatgggct tgcggttctt tgtgttctgc tggaactcgt ggttttacat gagctggtct    74084
agtgattctg atgtggaata aagatcatga aagccactgt ccactgacac catgagccat    74144
tggcattgtg accagctgtc ccactgtgga gtggacttac tttgttggtc ttcatgtcca    74204
ctttagtact tcagaaggct tcactaatct tcccccactc cccaaccttg tttgtcatat    74264
tttcataatt ttctgtcccc tgtctagatt gtgatcattg agggagcaag acttaaactg    74324
gctgcatagg gttaagcttc gtgaacgcca ggatctctct ctgttgtcgt ctttgatgag    74384
ctcctcttag ttttggtttc cttgcacaaa tgcctgtgtt ccctaacatt atacacaagc    74444
tcctttcact gcacaagtag aaattgtaaa atcactgctt gtctaatacc tccctctatc    74504
ctaggactaa agagagtcct tacagagttc tgtggagacg gcaggtgaat agtcatgtca    74564
tctctttacc ataacagtgt ctatagaaaa attacactat gattatgaat tgtgtctcac    74624
taattgaact ggaaaacgtg gggaaggttt ggaagtaagc ccttgtctat aattattagt    74684
gatttaagtg tttgtgtatt cttaagagtt tacatctatt gactccatct gtatcttgaa    74744
gatcactgag aaaacatgta tgcagggcct tcaaatgccg ctaagtataa atcttctatt    74804
caaacttatc cccgttggtt ttggcaataa gtatcagctg ggaaacataa tttaagcaca    74864
aaataatgat acgtgatgtg ttgcaaatga gaagaaacta taaattgaga gaaagtagcg    74924
agtcctttgg tattaggggt agccccacat attacaaggc ctcagtcaag gtcatttaac    74984
ttactttcca gtatgggttt cccattaacc agcagtatct tttctagagt ctgattagta    75044
taatcctttc ttcagcaaaa cctcctaggt ggaagcataa atcatctcaa agatactcat    75104
gtaaagtgga ggcctagcca gaaggttttt tttgttttgt tttttgtcta cacaagatgt    75164
gctgcatact tactaacagc cagcattgca gcctctgcct gcctgctgga agtgtataat    75224
gaggatagca ggcatttctg agaaatgaag tgacttttag aagaaccgag taaatacacc    75284
gcagtagtcc tgcaagaagc aacaactcag taaacagcac aggtcatggg tctgggtgag    75344
gtcagtcgta gctagcagta atgcgaatat aatacttcac ttcctctgga gcggtgtgag    75404
ctacatcagt ctctgcacag cccaaatcac cctaacttcc ttttacctt tccacaaccc    75464 tttgagatgg ccctgaggtt cacgtcacca aaaagacagt ctgtccagta actaatttgc    75524
caagttatca aaaattgtg taaattttg tttatgttcc ttttttttccc tctaatcctt    75584 agaacctgta aatgtcgtaa gtattcttga agaatacata tgtatatatc aacagtattc    75644
aagaagagta ttctaaaaac tttaagtttt tagtaaattg gtaattctct tgaacttggt    75704
cattcgactc ctggtctggt ccagcagtca ctttgaccgt aggaatagat ctggtgcctt    75764
ctatcttcta tcttgcaggt tgtctttttt gttgttctt tggttggttg gtcgggtgat    75824
tttttttttt taagctgggg tctcactgtc accccatttg gagtgcagtg gtgtagtctt    75884
cagctcactg catcctcttc ctcccaggct caagcgatcc tcccacttca gccccgagt    75944
```

```
agcttggacc acaggcacgt gccaccatgc acagcaaatt ttttgtattt tttttggtag   76004
agacaggttt cgccatgttg ctgaggctgg tctcaaactc ctgagctcag gagatccacc   76064
cacctgggcc tcccaaagtg ctagcatcac aggtgtgagc cacctctccc ggccacctta   76124
taggttttct ttgtgctgta acaagtaact cccacccctt ctaggtagaa tgctgggttc   76184
tgaaggctgt ggctgtgggt ccaggaagag agtggggagg gagtggcaag tccctcgccc   76244
ttggccacat ttcttaccct gagccttggc cttgggctca ggctttcctg ctccccttag   76304
ccatttgctt tctactttaa atcacagctt taagattact tataaatcat tctggattat   76364
ttccctattg aatttagatg ttttgttttt tttgttgttg ttgttgttga gagagagtct   76424
cgatctgtcg cccaggctag agtgcagtgg cgcgatcttg gctcactgcc acctctgcct   76484
cccaggttca agctattctc ctgcctcagc cttccgagta gttgggatta caggcgcccg   76544
ccaccgcacc tggctaattt ttgtattttt agtggagaca gggtttcggc atgttggcca   76604
ggctggtctt gaactcctga cctcgtgatc cacccccccc ccccccctcc ccgccgtcag   76664
cctcccaaag tgctgggatt acaggcgtga gccaccttgc ccggcctgaa tttagatctt   76724
aaattttaag ataatcttat tttttaaaa aaatcaata aacacaaagc aaaaagaaga     76784
aaacacaaga aacatttcct ctatgaaaat agctatgttg tgtttcttac cagtttatca   76844
cctctgaggt gattatcgct tcttcccagg ttggcagctg tgtacattta atgagcattt   76904
tctttgtttt atggcgccac agctttgcat acccagctgt tgtaggtcct tatgagggaa   76964
cctgagcaag tggttattgc agagccagcc cttgttctgc ctgatgttcg ctttggtatc   77024
gttttctgat tctaggtgga ggttgtggag gagtcaggtt tccaggtggg tgggggagta   77084
tccgaggagc ataggtttgg accctgttgc gatgtggaag gttgaggacg agcagcaaga   77144
atcccagcct ggtgtggatc cggggcattg gctgcacaga ggggtgacac tgtccttcct   77204
tgttctttct tggtcagtct cttgctgttt ggaacacagg gtcctttgaa gacatgataa   77264
cctactcttg gacacacagt aaaaaatgac ttatttttt gtgaggaatg tgaggataag    77324
cgttattatc cacattctgt atgcacatct ctgttatgtc cttagcatag aatacaggca   77384
ctataggaaa aatggcattg gggctaaatt acccaaaacc tatgtagcaa taacagtcct   77444
aataaaaatg catgttagat tcttttaaaa tttaaggaat aggctgggcg cggtggctca   77504
ctcctgtaat cccagcactt tgggaggcca aggcgggtgg atcacttgaa gtcaggagtt   77564
tgagaccagt ctggctaaca cggtaaagcc ccgtctctac taaaaataca aaaattagtc   77624
aggtgtggtg gcacacgtct gtaagtccag ctacttggga gggtgagaca ggagaattgc   77684
ttgaatctgg gaggcagagg ttgcagtgag ccgagatcat gctattgcac tccagcctgg   77744
gtgacagagc gagactctgt cacaaaaaaa aaaaaaaaa aaaaaaaaaa aaaaaaatt     77804
aaggaatacc agagtaaata taaagagttt gcttttaaag gtagtttgac agtggagtat   77864
acacagtggt tgaggctgcc aattatgtaa taagcaacac atgcaaagag cctgtggcta   77924
aaccgagtga agatgatggg tggggtgagt gggctcagtg agctttgtgt taacctccct   77984
ttactcagtg gctcaaaata gtaacaggca ggggagacta aggtttaaac cagtatggct   78044
ctcacaccat actcacctcc tccttccaca ttacaaattg catgtgaaat gatcctcgct   78104
ccagaaacac atattgcata tattttaagg cttctgacag ataccattat agtgctttcc   78164
atcaaaagcc atgtacccga ttaccagcat cacaccatct tcccaaggct agggactgtt   78224
accccgttct tctgtttttt tttagacaga atgttgctct tgttgcacaa gctggagtgc   78284
```

```
agtggcgcaa tctctgctca ctgacgcctc cacttcctgg gttcaagcga ttcttttgcc    78344
tcagcctccc gagtagctgg gattacaggt gtgcgccacc acacccagct aatttttat     78404 attttttagta gaaatggggt ttcaccatgt tagttaggct ggtctcaaac tgctgacctc   78464
aagtgatctg cccacctcgg cctcccaaag ggctggatta caggtgtgag ctgctgcacc   78524
cagcccaccc tgtcctttaa taggagaaaa tgatgtcatc ttactttgat gagcatttct   78584
ctcatgagta agatttaaag tgcttatgtt tagagacata ggcatttatt tgagttgctt   78644
tggtcctgtt gttcaccagt tttcctgtca gattctctta gaacacttta taatgcaagg   78704
tggtcagccc tctgtggagg aggggcacag agagctgcag gattgggct ttgctgctag    78764 ttggttggct catcacccag gcaaggccct ttccttgggg cctcagttac ttcacctgtc   78824
gtgtgtggct agtccccaga gtactcttcc ctcggggatg tgtgtgtctt caatgaactg   78884
ctgtaccttg gaccctgaac acagagcctg gcacagagtg aggaataaag atggactggg   78944
aggagaaaaa ataatagctc catcatgatt tgttttgtct tgtgtctttc agatttaatt   79004
tttcctagtt cataaatggc ccttacactt gttcctagtg attttagtca tagaaagaat   79064
gccagtcttt atgtaatcta gcctctcaca cctatttaat tgtacagtct tctcctgcat   79124
tggagtcgcc catgggcttt ttgttctttt ttctcttttc tcaatgtttt tgattttgtt   79184
tttgtctttt tttagcaaca gggtcttgct atgttgccca ggctgggta cagtggcaat    79244 tcacaagcac agtcgtggga gactatagca ttgatctcct gggctccagc agttctccca   79304
cctttgcctc ctgagtagct gggactacag gtgtaccacc actcctggct tcttaaatgt   79364
ctttattctc attgtaaagg cacatatatg ttaattttgg aaaaattggg aaagtctaa    79424 attaaaaaaa caaagcaggc tcgtctctta ggggaaaaat gagaggatct gtattttaag   79484 aattttact ggaaggccgg gtgcaatggc tcatagctat aatcccagca ctttgggagg    79544
ccaaggcgag ataattgctt ctgcccagga gttcaagacc agctcgaaca acatggcaag   79604
actctgtctc tacaaaaaat tttaaaactt agctgggcgt cgtgatgcac acttgtcatc   79664
tcagctactc aggaagctga ggtgagagga tcgcttgagc ccaggagggt gagactgtgt   79724
gagccatgat tgcactactt cacttcagcc tgggtagcag tgagaccctg tctccaaaaa   79784 taaaagaat ttttactggt aatagtgagg aacactgctt tatgttctgt gactaaagcc    79844
tttactgcct ttacgtaaca aagtacccac cttaattacc ttcccatact tttacaattt   79904
aattttttat atttagttcc tcatcatttt cttactgatt cgtctgattt tgttttctcg   79964
ggaatttccc cccaaaatgg aatgcttttt ggtattaaaa tagtagtcac ttaaacagct   80024
ttttgttaaa gcataaaggt ctgccttatt gttgttagta attcgttgcc ttaaataaca   80084
gtcattggat gttttctccc acaaattcag acagggcttg gctggcccat tcccctgctc   80144
cacatggctt tgacagggt tatttgaggt ctgccttatt tttcatgggt gcctcttgtt    80204
tcattataag tctgtagcca taggatgttt aattagtcca cctttaatag acatttagaa   80264 tttttttccag ttttcaatat ttaatcagaa tgtgatgcat tatctttgca cacatatttt  80324
aacatacttg tccaattact tccttaacaa tgaatcatga aagtggagt tactgtcaaa    80384 agaaatgcat gttttttcttt ttgatacatg ttgctttcca aaattacacc gaattgccag  80444
agtacttgag aattgccatt tctttatatc ctcatcaata ccaattagca ttttttaaat   80504
cttggccata tagatagatt aaacatgcct cattgtttta tttctattcc tttagtgatt   80564
agtaagaact ttttaaaaac agcttttaa gatataattc atgtaccata tagtcccttgc   80624 ttcaagtgta cagttgagtg gtatttagta tattgtgtaa ccatcaccac agtcaattct   80684
```

```
gaaacatttt caccactcca aagagaaacc tagtaccatt agcagttatt ccccatttcc   80744
cctgaacccc catctccagc caaccgctag tctttctacc cccatggatg tatctattct   80804
gggcatttcc tagaaattga atcacagaat atgtggtctt tgtgactgg cttcttttac    80864 gaagcatgtt ttcggagttc atgttgtagt atgtgtggt acttcccttt ttacggttga    80924
ataatattcc gttttggtta tacaccgtgt tttgttttc ccttcatcac ttgatgggca    80984
tttgaattgt atccactttt tggctatttg taaaaggctg ttgtgaacat tttttacagt   81044
tttcgtgtga acgtgcattt tcagttcttt tggttgtata cctaaaatag gaattgcaga   81104
ggtcatgtgg taattttatg tttgaccttt tgaggaattg ccagactgtt ttccagagtg   81164
gctgctgcct tctacattcc cacaccaatg tatgaggatt ccaggttctc cacgtcctgg   81224
ccaccctgtt gctattggtt agcatttgac tttttattat agccatgtgg tgggtgtgaa   81284
gtggtatctc actgtggtct taacttgcat ttccctaatg gctaataagg ttcaacatct   81344
tttcatgtgc ttattggcca ttcgtgtatc ttctttgcat aaataactgt tcagagcttt   81404
cacttatttt ttaattgggc tattagtctt tttattactg agttgtaaga gttttttaaaa  81464 tatgttctag atgcaagtgc tttatcagac ctatgatttg caaatatttt ctctttcact   81524
ttccactttc acagttcatt attttgtaat ggtatccttt gaagcataaa agtttaattt   81584
tttatgaaat cagtttattt ttcttttatc acttgcactt ttggtgacgt agtaagaaac   81644
tgcctaatcc aaggtcgtga agatttattc tcggttttct tctgtgaatg gtacgattgt   81704
cactcttacg ttgaagtgtt tgctccacct tgagttcatt tttgagtggg aggtagagag   81764
gaggctgcct gcatccttct gcctgggctg tccagtgcct gtgctcctcc tcattgtcat   81824
tgagaaacga tccctccctc ccttgtgttg cctcagcacc aaggtgtaga acattttgt    81884 atttgtcgtt tctttgtgtt ttgtgaggtg tctgcatttt ctttgcccaa ttttttagtg   81944
ggatagtatc ctttctttcc tgagagcatt tgcataaaag atcaaccaat ttgctcgcag   82004 ttttttcactt tttaaactcc attatgtgtt tatgttaaga aggctttctc atcctcatgt   82064
cctaaaagtt tttaaatttt tttctccatt ttaagccatt tttattcact ttagttcatg   82124 tgaattttt ttttttttaaa taaaagggaa gataaggatc aaagatgcct caccactctt    82184
gaatgtaaag caccaccttt aggagacaat cgtcctctct tatctggggt ttcactttct   82244
ggggtttcac ttaccagcaa tcacaaaata agtgagtgca gtacaataag gtgtttagag   82304
agagagagag agagaccaca ttcatgtagc ttttattaca gtgtattgtt agtaatggtt   82364
ctatttcatt attagttaat gttaatctct tactatacct aatttataaa ttaaacttta   82424
tcataggtgt gtgtataggga aataatacag tatatatagg attcagtact atctgaagtt  82484
tcaggcatcc actgggagtt ggaacctgaa ctctgaggat aaggggggac ttctatatgc   82544
taatttgata tacacctatg tctgtttctg gacttaagta aagaaattag ctttatagta   82604
tgtttcagta tctggcaata tagattgccc ctttattttt actgttttc aaaattttct    82664 tggctcttag aaaaacaaaa tcacacaaaa cgtagattac ttttggggca gcttccacca   82724
cgatggcttt gttctgtgct ttaaagggag gttccgaagt actctccctc catcctcagt   82784
gcctgcctgc cagtgggaac tgggcaggga ggttgggaaa gtctgaagga tgcttctgac   82844
agatttgggg gccacctgca gttcacatct aactctcatg gctcattgaa caccagcctg   82904
ggagaggagg aaattaagtg tgcccctgta tttgtaagta ctttgcaaaa ctaagctagt   82964
cccagacaaa tatacagaat tccatgggga aagacagaga cagggacata agacattttc   83024
```

```
cattccactg ttgattcacc ctcagaatgg cttttgagat gcatgttgta aacaatatgt   83084
agagctcatt aaactgtgca tttgtcctcc atccagaggt agacaaataa cagaacaaat   83144
tttaaatttg ccatatagtt tccaaccatc ctgttttgac atatggtcag gtgtagtgca   83204
aaagacacta ttaaaaatac atgccaggct gggcgtggtg gctcatgcct gtaatctcag   83264
cactttggga ggctgaggtg tgccggtctc tttaggtcag gagttcaaga ccagcttggc   83324
caacatggtg aaaccccatc tctactaaaa atacaaaaag tagccaggcg tggtggtggg   83384
catctgtaat cccagctact tgggaggctg aggcaggaga atcgcttgaa cccaggaggc   83444
agaggttgca gtaagctgag gtggcgccac tgcactccag cttaggcgat agagtgagac   83504
tcccgtctca aaaaaaaaa aaaaagtaca agccagttag gtggcaccac acatctgtga   83564
tcccagctac atgggaggct gaggtgggaa gatcagttga gcccaggagg ccagcctggg   83624
caacatagca agaccttgtc tctgaaattt taaaaaaaga atattttttaa gtcccaaatg   83684 aaatcagtgt gttaattgtt ggtgaattaa gaacagtctg gttataattt acttgtagag   83744
ctaaattttt tgcctaattt ttatataatt tttttggtat gtgatatttc tgtactttaa   83804
gacacagtga gaggacaact gtgtggtctc ttcaacaagg tagtgtcagg agtaaaaaaa   83864
gggaagatac aatagattaa gaaccttaaa aacaaccaaa tacaggatgt gggccttctt   83924
ggggtcctga tttgtgaaca ccagctctaa aagacatgtt ttggacaacc agagaaattg   83984
ggatatgact cagtattagc tgatgcccaa gaaggatggt tcttttttctt aggtgtaagg   84044 atgatatcct ttccttttcca ttttttctgta tgtttgaaat tttcataaac gtaaagaaa   84104 gagtcctaaa tgaggctcat tttgtgtttc tcccattcct ccatatctcc attcctgttg   84164
atttctcgat ggaccttcca atccacaggg ataagccagt tgagcagtgg acttaacacc   84224
agtactgcat gcttgcaggg gcagctcaag gcctgttttgc ttactgaagc tttattaca   84284 gttataaaaa ataaggagg ggccagggat tccagtttat gccccataac aagaactagt   84344
taaatgagta taaagttaaa agagtaacat gctgttcatt acaagtcatt ccagcccact   84404
atctgagaca gtttagtggt atggggcaga acatggaaaa aacactaagc aaaacatgtg   84464
tgttgcaggg gagatacgag gctctattga ttatggttca tacgtaaaca tttatataga   84524
aaaaagaagg gaaaaaaacc tatcaacgct ttagtagtgg actcctggat aatgggattt   84584
taattgttgt taattatttc tgtagtagtt ctctagcttt ccaaatttcc tgcagtgtat   84644
atatatactt ttataatcag gaaaaaataa acataagagg ctattttctc ttaggagttg   84704
agccctgcat tcatggtgtt ctgcttctca gctaggatgc tgattttgct ttgggtcctt   84764
ctcagaattg ctttgggtcc ttctcagact tccaagagtt ttgctcccaa gcccagccac   84824
ccagcttttc tacgtactta ttttctagtt ctcataaagg taaaatcaaa acagaaaact   84884
ctataaactt ttaaaagtga gctttgattc attaaaaatt atttgtatag ttttctctcc   84944
tctttgtgaa tatacagttt tgattcatac atttttaaaa aatccgagtg gcgtactta   85004 ggggaggtaa tgagggtcgt ggaagcaagc tggaaatatc agagtactag agaaaattgg   85064
aaatcccgga actgtggatg atactgttgc acattaggaa cacttctctt actgcctaag   85124 tcttttttcag taagttttatc tgaagaatgc ttatagtttg taaagaagaa gactctatgg   85184 gtccccttttt ccatttgcct tgctgttaaa aggtttgttt ggtctggctt gttatttcag   85244
gcaactgaaa gcaaaccctt tctgtatttt tagcagatca ccaaatcttt aaaaattgtc   85304
agctgtctga gtggaaattg taatgaaaaa caaagcatag gacaagaatg catttcccat   85364
tgcactgggt ggttgtatta aggctaactg tcattattct tttaggagag gtaatggttg   85424
```

```
ctgtgaaatc aagctgcacg cattgtcctt ctagtcatgt gataatgaaa tccaaaaggt    85484
ggctctgatt cttttgcta catcaaatgt ttgtagtaca ttgcaattgg tcaggccttg    85544
gcaaatcttt tttttttttt tttttttttt tttttttttt tgagacggag tctcgatctg    85604
tcgcccaggc tggagtgcgg tggcgccatc tcagctcact gcaagctccg cctcccgggt    85664
tcacaccatt ctcctgcctc agcctcccga gtaggtggga ctacaggcac cgccaccac    85724
gcctatagtc ctaattttt ctgttttta gtagagatga ggtctcatcg tgttagccag    85784
ggtggtcccg atctcctgac ctcgtgatcc gcctgcctcg gcctcccaga gtgctgagat    85844
tacaggcgtg agccaacgcg ctcggccagg ccttggcaat ctttttaatt aggttgtacc    85904
ctatgaaatt gccagtgttt ggccatttgg gacctacaga aacagcagtt tcatatggtc    85964
cagctggtat agtacacagc ttttcctgta gttgtgtata ttgtagagtg agttggattt    86024
tggttgctac agtgaagagc cagccattgt cttgcttgga tgataattgt atacaagtga    86084
acttgaatca gccttgctgc tgagttgggt tgatttctgt gctgctggat cttcttaaag    86144
tcatcagtgg gttagagaac tacaccagcc ttctctctgt ggtcggtatt atccatcagc    86204
ttttgctttt gtttgagaaa taattaatga atatgacttg gaactctgag aggttaaagt    86264
atttttatta ttttgctttta ttttag tct cag atg caa aca tca gtg gga att    86317
                              Ser Gln Met Gln Thr Ser Val Gly Ile
                                                  330
gta ccc aca caa gca att gca aca ggc ccc act gca gat cct gaa aaa       86365
Val Pro Thr Gln Ala Ile Ala Thr Gly Pro Thr Ala Asp Pro Glu Lys
335                 340                 345                 350
cgc aaa ctg ata cag cag cag ctg gtt cta ctg ctt cat gct cat aag       86413
Arg Lys Leu Ile Gln Gln Gln Leu Val Leu Leu Leu His Ala His Lys
                355                 360                 365
tgt cag aga cga gag caa gca aac gga gag gtt cgg gcc tgc tcg ctc       86461
Cys Gln Arg Arg Glu Gln Ala Asn Gly Glu Val Arg Ala Cys Ser Leu
            370                 375                 380
ccg cat tgt cga acc atg aaa aac gtt ttg aat cac atg acg cat tgt       86509
Pro His Cys Arg Thr Met Lys Asn Val Leu Asn His Met Thr His Cys
        385                 390                 395
cag gct ggg aaa gcc tgc caa g gtaagtgctg tttttggaac tcctagtggt        86561
Gln Ala Gly Lys Ala Cys Gln
    400                 405
agaggtcagg aagaatttgc ctttattgtt cttacagcag ctctctggtt cataaggctc    86621
cggcagcctg agtgctgcct tccattgggt gtggcaagac atgttgcgct cacgttcccc    86681
acgcgacgac agtcaggtgc tccaggaagt cttatctgct gaagagaaag gcgatttggt    86741
tttctgatac tctgtgaact tctgctgctt gaagctgtgc cccgtatttg ttcttttcct    86801
ccttcctctg tcacggaaga cattggtcac ttcttgagca ctgtctttgt tgtgaatgtc    86861
tagattgtgg ttttctttg gggcaatgaa catagcacag gcacgtgcag gcacacgccc    86921
ttcctgcatc ccaacatctg tcttggtggc ctgcggcctt gctcctctgt cctgtgtctt    86981
gaggcaagtg cggatgacag cgaagttgtc ctgggtgact ggcagtgaca tgggaaacta    87041
tgcactgtat catcccaggg ggggtggtga actaggcact tcacgtgccc tctgtctccc    87101
cttttaccgc agacacctca tttctaccga aggaagtgtt tcttattaac agctgtactt    87161
tcctttaatc tttattctct ttccttctct gcttatgctc ataaacttag gggaatctcc    87221
ccctggtctc cccgtctccc gttgtgacat ttgtgagtcc ccagagtaac cctgttgtaa    87281
cagagaagca gagaagggta aggttagacc tttagaagat gaagacggaa taaccagggt    87341
```

```
cagttagcct ctcgagtact tcttcaccaa gtgcccagag tccctttcag aatctctaca   87401
gacttctcat ttgcttctct atctgtattt cttcactgta gtatttaggt ggtttcatct   87461
tgaaacataa ttgaacattt ttattttaaa tagtgacatc acagaactat tatttgttct   87521
acctttcatt gcagttgttc gctattccag gttgaatagt ttttgttttg ttttgtgggc   87581 tgcccttat cacccatcct tcataacatt gcttctaggg gaagttttgt ttggatttct   87641
caacagtcaa cttacaaact ttttggaaaa cagcctgttt gtaagttgag gactgcctat   87701
actgtgttat ggttacactt gttaccattt tcttatggaa tctggcatta taatttaggt   87761
ataattgaaa gtgtgacgat ttggatagaa aaataacatc tcgttgtttt tctggtcata   87821 g tt  gcc cat tgt gca tct tca cga caa atc atc tct cat tgg aag aac   87869
  Val Ala His Cys Ala Ser Ser Arg Gln Ile Ile Ser His Trp Lys Asn
              410                 415                 420 tgc aca cga cat gac tgt cct gtt tgc ctc cct ttg aaa aat gcc agt      87917
Cys Thr Arg His Asp Cys Pro Val Cys Leu Pro Leu Lys Asn Ala Ser
            425                 430                 435 gac aag cga aac caa caa a gtaagtgagc acggggggcag agaagcttgg          87966
Asp Lys Arg Asn Gln Gln
            440 agatgagaat agaagttgtt tctaaagaaa attcagagag taggtaggga gtgggcaggg   88026 gttatgagcc atggagtgca gggtgaggta gggcggacag cagcccaagg tacagccaag   88086 ctcagagggc aggcgggctc tccgtgtcag gaacggctgt gataatgttg gaccctgact   88146 cactcactgc ctctccctct ccctgccccc tgcatacatg cacttgaagc agcatggaac   88206 agcagagtca ctttgttcac tgagccaaca cgaagacatg gtatttcctg acagttactc   88266 catacgtgag aatttaaatt ccatgtcgct ataatggcag tgacgtctta gggagggga   88326 tagagggat acttcttttg gaattggaaa gcccttatcc tgaagtaaat tttgaaggct    88386 ctgtcagtca gtctgggtca gtataaaatc ccacacagac atttatgaag gtttccctct   88446 acgtggagct atggtcccca gaactctttg tataactaaa cgttcactct gcttcacagt   88506 gagagcctct gccctagggc tgctgcatcc tgatcacccc agtcgttttg ccgttgtcta   88566 ggttgtctgt agccctcggc acggctggtt acgcagcgat ccctgcttgt tgggaggtcc   88626 gcctggggct ctgggctcc ctgccatttg taggcttcag gcagtaagaa ggatgaacct    88686 ccctcccgtt tttcaaccat cttcctgtca ttttagaggt aaaactgtgg tctttgggtg   88746 tgtcattcag tttcggacag ctaggaagtg cccttcagtc tcctgtcccc tctggctgga   88806 gctgtaccct tagcgaccct tccagcacag cacagtcttc ctcatcttcc tccatctcgt   88866 ctgtgccatc ttgccaccct cccctgtttt gtgtattacg tgttcattcc tctcattctt   88926 cttgatcatc cttcctcaag accccgcagc tgcctggaga acatgtgctg ctttctttc   88986 tggttgtttc tgagtggccc agggaaagat ggaaaaagtg ctttgttcct aagagtactg   89046 tggagtggcg tgccagtgac agccccgtg gttttccttt tactgagtcc agcccacctc    89106 cctctggcgg cgagggagta ggcagcgagc tgacgctgac cctgcttcct ttaaagcagg   89166 gtgtccctgt catagagaag agaaatgcca gggtaatggg gcctgttatc tgcctcccta   89226 cagaagaacc acaacgagtt tccttttaaaa gccagtttcc tggccaggcg caatggctca   89286 cgcctgtaat cccaacactt tgggaggccg aggcgggcag atcacctgag gttgggagtt   89346 ggagaccagt ctctactaaa aacacaaaat tagccgggcg tggtggcgca tgcctgtaat   89406 tccagctact tgggaggctg aggcaggaga atcacttaaa cctgggaggt ggaggttgcg   89466 gtgagccgag atcacgccag tgcactccag cctgggcaac aagggcgaaa ctccgtctca   89526
```

```
aaaaaaaaaa aaaaaaaaaa aaaagccagt ttcctaaaag tcagttaaat tattctttga    89586
ttgactaaaa tttgaattaa taaacaattt ccctggacat ttcttatata aagtgacatt    89646
ctggaatcct gggtcttcta gaaccagata tttgggacag tagttctaat ggaatacagt    89706 ctgttttttcc tcccacatta ctgtaaaagt tttttctttta gtatattgtg atggctaaat    89766
ttcttgtgtt ttagggcaca tttcagtaat aggctcttta agtgccaaaa tattcattgt    89826
caagtttgta gttatacaat attctatgaa taatgagcta gaattttatt cttaacttta    89886 atttggggt gtggcttttt gaggatcttt tgttttagt acatactacc atgacagttg    89946
taaactttgg tgatttctct ttttaagaaa cacttatgtg gttttgttt taaaagaaaa    90006 aagaagcgta tgtggttttt ttttttaaa ccatccttat aacggcctga gtgttgtgaa    90066
aattgattct gtgcatgctc tctcaagtgg taaaccacag gttttctact agtcagaatg    90126
taagatatta ccaggatgat tttataaagt cacaaggaag atttagatta acttgctgca    90186
aggttttggt agtttttttt tacaaaagta tgattgacaa ggtttcagca atatccttt    90246 tgtaaatttt attgttttt ctcttctccc aaagcaaatt atgcttatcg tgtgtgaact    90306
cttgagttag gaacccagag aggaaaatgt gaatctgacc ctacgttggc ttaaggttgg    90366
gttttgaaga caatatatat gttaaaaata acgtaagggt gacctccctc aaaggaccga    90426
ggtagagaca agtcagtgca atcagcattc ttttcgagga gaattggagc gcacctgact    90486
actttgtaga gaaaggtggg acttggtgga gcccagtgca aacagaataa caaaggaaga    90546
acatttcaga cagtggggac agtgtctgca cagtgcacag cttgtgaggg catgcatttg    90606
actggactgg ggttcctgtg caaacgaggt gaacagaaag gtggactgtg atgagctcct    90666
ggaagcctca gggactctgc cgagacccac ctgtgctcgc tctgtggaga ctgccttagg    90726
ggccccggga ctctgctttt taggcagtgt ttcccacagg ccagcgctgg tcttacctga    90786
tgcacacttc cttggtcagc acatgctcca ctctcttaac ttctgtgatt aatgtctcta    90846
ctgagagaac cttccagaat cacctgtggc gctaatctga ggttctttga aatgaagccc    90906
agaccattga ttacctttt ggcctgtgtt gagttttgtt tggttggttg gtttgttttg    90966
agacggagtc ttgctctgtc acccagactg gcatgcagtg gcatagccaa gtctcactgc    91026
agcctcaacc tctcgggctc aagcagtcat tccacttcag cctcctgagt acctgggact    91086
gcaggcatct gccaccatac ctggctaatt tttgtatttt ttgtagagat ggggtttcac    91146
catgttgctc aggcttgtct cgaactcctg agctcaagtg atcttcccac cttgacctcc    91206
caaaagtcct gggattagag gcgtgagcca ccgcgcctgg cctcattcga ttttttccttg    91266 aattgttttt taaagattct gtaatcactg atctcgagtt aaccatccct tatagcaata    91326
ttcaattttt tttgaataat taggacttgc caagataagt atcttatgtc agtcctggca    91386
tctgacctcc agtaaattca gtgcacagag tggcatggtt gactgggctt tgggacccgt    91446
gagcaggttc ccctcttggg gcttatgctg cctcacttgt gaagttcttg ctgctcaaag    91506
tgtaggcctc agggaagcca tagaggtgct cccaggttgt aagcaataaa gaaattgggc    91566
ccccatttga gacctcttat attaaaacct gcattttat aaaaatcctg ggtgattagt    91626
gtgcacatta aaatctgaga tgcactgctc tggatgcctt ggaagaccag gtatctgggc    91686
cagtgctggt gagagggttt gagtcattct ctgagagaga gaccaggggt tttccaacct    91746
agagtccccc agggactgtt gaagcaagtg tgcagggtcg gccccagagc cagcctaatg    91806
cacgcactgt cccggctgcg tcagccatgg ccccagctgc tgcccggcat ctccatgagt    91866
```

```
gtagctccca ctgcttcacc tggcaacatg ttccatctgt aggtgcctca gattgtttaa    91926
aacacctcct tttggccgga cgcagtggct aacgtctgta atccttgcac tttgggaggc    91986
tgagtgagac aggcgggttg cctgagctca tgttcaacac cagcctgagc aacacagtga    92046
aaccccgtct ctactaaaat acaaataatt agctgggcat ggcagcatgc gcctgtagtc    92106
ccagctactc ggtatcctga ggtgggaggc tgaggcagga gaatgacttg atgaacccgg    92166
gaggcagagg ttgcagtgag ccaagatcgc accactgcac tccagcctgg gcgacagagc    92226
aagactacgt ctcaaacaaa acaaaacaaa acaaaaaacc aaaacaaaac aaaaaaaaaa    92286
acctcctttt tttatatgga gtcaagatct ccgtcctttg aactgccact catcgaatag    92346
cccatcaggt gcccagtgag tgtgtgtgga gcaggcccct tgttcacttg agggcccttc    92406
agagattttc acctcttttg acagactgta gtgggatggg ggacagcaag gagcagaatc    92466
tgaaggctgt agagagaatg gtgggcttga ttgaccctga cttaagcacc aaagggtcgt    92526
gggtgatgtg tttcatctga acagcttttc tccttgctag caaggagcag tgtcactgcg    92586
ccagtgtcac ttggcttctg aagaaagcct tttgcttgag ggcttgtggc cgtgcctgat    92646
aggaggctga gtctccagcc tggcagtgcc tgggttcccc tcagtgcttc tcttcactgt    92706
ggtgccccac gcagtgcata ggaaggtgcc aggtaggaag taggtcctgg cccacacaat    92766
gcccgcaagg tacggtggtg ccaccagcaa ctttgtagag atggctgcag gtctgaataa    92826 attcttttt tttttttttt gagacgaagt ctcactctgt cgcccaggct agagtgcagt    92886
ggcgcgatct tagttcaccg caacctccgt ctccctagtt caagtgattc ctgcctcagc    92946
ctcccgagta gctgggatta caggcacatg ccaccatgcc tggctacttt atgtattttt    93006
agcagagatg gggtttcacc atgttgtcca ggctggtctt gaactcctga cctcaggtga    93066
tctccccacc ctcatactcc caaagtgctg ggattacagg cgtgagccac ctgaataaat    93126
tctagcattg ctttttagt agaaatctaa gtgtcttggt atccttggga atttggttcc    93186
aggacacccc aggtatacca aaaccaggtg gactcaagcc ctacagctgg ccttccccat    93246
acacaagttt cgcctcccgc aagcactgtg tttctggcct gcgttgggtg accccgtggc    93306
tcactctcgt gctggtgaag catcagctgt agcaactact gctctgcttc atggtctgtc    93366
tccccctacc ctcacaaagt ttggagattt gattcatgtc cgttttcact gaatttccaa    93426
atggagttca gttttattga ggatgattag gggcttaagt tgtctgagta actgagttct    93486
ttgcatcagc aacatagact gtacagaaaa cctcttagtg gaacattcct ttttttcttt    93546
gttttttgag acagagtctc tctgttgccc aggctggagt gtagtggcgc gatctcagct    93606
cactgcaact tctacctcct aggttcaagc ggttctcctg cctcagcctc ccaagtagct    93666
gagatgacag gcacgcacca ccacactcag ctaattttg tattttaat agagatgggg    93726 tttcaccatg ttattagcca ggctggtctc gaactcctga cctcaagtga tccacctgcc    93786
tcggcctccc aaagtgctgg gattacaggc atgagccact gcaccagtt acacttggcc    93846 gtacccggcc tcttagtgga acattgtttg tgcatgaaga gtggcaggtg agtccgagaa    93906
agagcctgct ataaaacttg gccttttgtt cataggtcat aggctccttc ttcagcaaca    93966
tcagaagggg tggtgagact aggggatgtt ggggagcttt aaagaggtaa atatcccgga    94026
caggagtgtt gcctgatggg cccagaagaa cccagccact gtgttagtgc attgcaggtg    94086
tgttgtgact tcctaaaagt tagagcttta tgctctagcg aggaaaaaag atgtaaaaat    94146
ggccaaatga gcacacggcc ttgacattgg aagaagttaa gtggcaataa tacagaaagg    94206
ataaatagag aaacttcatc cttagggatg ccaggtagat ggaccaatct ccgtgcattt    94266
```

```
ctgttcagtt ccaagacact ccatgggctg cgctgcgagg gcccacgatg tgctggccgc    94326
tgcgctatag ctggcacgtc ccctggactc tgcacagcag gttacgtggc ccatgtggca    94386
ggtggtgaag agcaaaaccg aatttgacat taatcccacc tttcagggat gcacagggaa    94446
cgtgacatga gcctgatttt ccctgtccca gggttccaag gtgcagtttg ggtgcattag    94506
gtgattatta gataatctgt tgtccctagg ctcagggaat gcagagattg tgcccacacc    94566
atgtctggga gcctggcaga gtgtactcac tgagtctgtc acgtgagtga gtgaatacac    94626
gaagggtcag tgtctaaaga caagcgggta caggagtcac tgtgggattt cagagaggga    94686
ttgggaatac caccatggag cacttggagc accttgaggt tgcagtacag ttgatggtgg    94746
cttatacata gtgactcccc tttcagtcag ccatcaccct gcagtgaatg cctgagcacc    94806
cttacccttc agtatttgtg tcatttcatg taatagcatc atttggactt caaattcagc    94866
catgcttaaa tggcagagac cttctttatt tgttcataat taatttcctt tgcttctgaa    94926
ttttagaaat gatgagttcc aaatgcttct cataggtata ttttctttta aaataaaaat    94986
ataataatgt ttacgtttag aaaatgaatg cctctaacac aaaatgcagt gaccgtgtca    95046
gcagcttccg tgggaggcct atgtgagtat gaggcgttgg ctgccctgta agtgctgtga    95106
gcttaggagt ggcattcact gtaaggtggg gcattttagt taagtagatg gcacttgggg    95166
aggtgtggat aaaagagaaa tgtagtagga agaagtcaat aaagggttta cgggaaatgg    95226
aaggctccat actttgtttc ttttaagttc ttctccacag tccatcacca tgtgtgttaa    95286
atatagtgta gccctgttct tccttacagc gcaaggttgt agaaaaataa actatcctac    95346
cactgttaac tttgatttct ataccatagt gcttcttaaa aatgtaggat gtcggtttca    95406
gaagtatggt ggacacatgt ttaaagtttt ggggagtagt aagtattaga atactttttaa    95466 aggtattgtg cgtgacttac ttcagctaca cacttgtcat aaagtgcacc ttgggagttg    95526
cttttcattt atgttaatga gtgcttggtg tatgtagttg tgtctgatga gtgttaatga    95586
gttgatctga atatcattat tagaaaagtt aatagtatgg aaagtataat taccaggaat    95646 ttttttttcac acattttagt ttaattaagt tgctctggta ggtattgggt ttattatagg    95706
tgtgctgatg gttgaatgtg agaatattac tgttacacat agtggttggg atttgaaaga    95766
aaggctttgt ggtcgtgttt tatgtatcaa aaatggtgtg ttatagcaac aacactataa    95826
gatgctattt ttaacatgac tctaaaattt gtggaagtta gaaaggaact caaaaatagg    95886
aataaatggt atcatataga acttctgcca tatgataaat tttcacacaa cagcatttgg    95946
gttgttgcga cagatgaggg ggcaggcaaa caggtaacag gtgggtaggt aggtgggtag    96006
atgaattgac cttgaaatgt ccaagttgat gcaagtttgg agttgtctct ccattacctt    96066
ggaagccctt tgggatggag ctccttatgt tgacaccagt ttttccttta gtctcctggg    96126
gttagctagc tggatggggc agcttccctg ccagccagca gtgggcctca gtagcagaag    96186
ctgactttgg ccacgtgagg cagagccacc tcctgaatat cagaggtgct gaggtagccc    96246
ctggataata agaccatgc agaattgcga agcctcactc caaccttaat ttcaaacagc    96306
tcagtcagtc aatcaatcaa gtacagtatt tcttgaacag cttcatgtag ccggagagct    96366
cagcatggtg ctctgctgca taggaatccc atcagaagga tatgtccatg ctgtcattgt    96426
ttgtgtatgt ttcaaggact tgcaattatg tgatttggaa gagcacatta tagatttatt    96486
aatcaaaact gaccgaccag gtatcatctc tgctccttct cttaagccct ctgtacctgt    96546
gcaggtgagc agtgaaggac agggttgggg tcaacaggag ggggctcctc tgttcatctc    96606
```

| | |
|---|---|
| agaggtgtct gctggtcccc agagaatcag acgtttccct tgtcatacat ttgccactcc | 96666 |
| ctggaactga cttcttgagg agtctctagg ttttaagaca taataatttt tttcaagtgt | 96726 |
| tatctgtgag attttatggt ctgttgcatg ctaagataga aacttgactt ttctttaact | 96786 |
| ttttgttcct cacttactgc taggcagaat aaatgagtcc ttcagcacag ttcctttctc | 96846 |
| cctaggcttg tttactgctt tatgatattc atgtgtagta ttttgatgaa atgtatttgc | 96906 |
| ttctcaatag ttttaaatc attcgtgggc ttctcccttt tacttacctc tcgttttgt | 96966 |

| | | |
|---|---|---|
| ctgtctgtct gtttgtcgtt atag cc atc ctg ggg tct cca gct agt gga<br>                                       Thr Ile Leu Gly Ser Pro Ala Ser Gly<br>                                            445                       450 | 97016 |
| att caa aac aca att ggt tct gtt ggc aca ggg caa cag aat gcc act<br>Ile Gln Asn Thr Ile Gly Ser Val Gly Thr Gly Gln Gln Asn Ala Thr<br>             455                       460                      465 | 97064 |
| tct tta agt aac cca aat ccc ata gac ccc agc tcc atg cag cga gcc<br>Ser Leu Ser Asn Pro Asn Pro Ile Asp Pro Ser Ser Met Gln Arg Ala<br>       470                       475                      480 | 97112 |
| tat gct gct ctc gga ctc ccc tac atg aac cag ccc cag acg cag ctg<br>Tyr Ala Ala Leu Gly Leu Pro Tyr Met Asn Gln Pro Gln Thr Gln Leu<br>485                     490                       495                      500 | 97160 |
| cag cct cag gtt cct ggc cag caa cca gca cag cct caa acc cac cag<br>Gln Pro Gln Val Pro Gly Gln Gln Pro Ala Gln Pro Gln Thr His Gln<br>             505                       510                      515 | 97208 |
| cag atg agg act ctc aac ccc ctg g gtaggtgaag gaactctcaa<br>Gln Met Arg Thr Leu Asn Pro Leu<br>             520 | 97253 |

| | |
|---|---|
| cttcgttctt acttgtccac atgcagcaaa gggaatggag tgatggaacc caaggcagtt | 97313 |
| ttcagtttgt tttgtgtttt ttactacggt ggttgaaata aaaatctcc caggaaaaag | 97373 |
| ctgaagtatc tgatgcaagg aaaatgttac atgcttataa aaagagcagc atttgcaaat | 97433 |
| gaagcaatgt ttttgttgct tgctgtgcca cttctgtctg gacggttttc ataaagaatg | 97493 |
| tgccatgtgc ctcagaatgc agatctcaca agtcaggatg ctgactggac gcctcatgct | 97553 |
| gactgttgtc atttatttgt tggagtactt gtgtttgcca gtttctcaca catcttggtt | 97613 |
| agggtctacc cctcagttgg aagtgaccag cctggacttc agcaggttaa tgacaatgac | 97673 |
| aggagtcctg gaaactcttg gctcaggctg ctggacatgt catggtttct tttgtcaccc | 97733 |
| cagcccatta tttgccagcc tttgatcgtt tgctcacaca tcgccatgat tttgccattt | 97793 |
| ctgcatatgg tttccttaat attttcttt aagtggacac agtcccttta catttaggct | 97853 |
| taagctaagc agtgatgtct gtgaagtcaa gactggctga ctagttgtgc tagttttgtt | 97913 |
| cttttccctaa tagagtaact attttacact taaaaattac tccttaaaat atgcccagct | 97973 |
| aaagtcatct tacttgttgc tttctggaaa acaactgccc taatgaatgt ctaactaata | 98033 |
| ctggccagga gactgagtta gaatcctgag acccaagtgt taatctaact cctctcctgt | 98093 |
| tgatggtata atttgggact agcttaacct tttttagtct cagctttcgt ttcctttaat | 98153 |
| aggaagattg tagacaaatt gacctctata ttttttttcct gagcttaatt tctatgattt | 98213 |
| tattttctga tattgggggt ggagacacag aggtgtgtgt cagtgcagct gagtcactca | 98273 |
| ggagcgatac taatgaagca gaatgaaagt aagaggctgc atgtgggtca tttataactt | 98333 |
| tttcacttag atagcagcta acctccataa acacacctta ctttggttac aaagtagagt | 98393 |
| ggggagggtg tctactgatt atttgtgcac gttgattacc attattgaaa atatgacact | 98453 |
| cagagttcct gccgcagtgc ttactataac tggccagaat cacttattta aataaccacc | 98513 |
| aattgtttat atggtggcat gttggttatc tgtcatcaaa actttgaagt atatattaaa | 98573 |

```
                                                          -continued atttaactgt tgattgattt cttttctgtc tttaaag ga  aat aat cca atg aac      98627
                                            Gly Asn Asn Pro Met Asn
                                            525             530 att cca gca gga gga ata aca aca gat cag cag ccc cca aac ttg att       98675
Ile Pro Ala Gly Gly Ile Thr Thr Asp Gln Gln Pro Pro Asn Leu Ile
            535                 540                 545 tca gaa tca gct ctt ccg act tcc ctg ggg gcc aca aa gtaagaccct         98723
Ser Glu Ser Ala Leu Pro Thr Ser Leu Gly Ala Thr Asn
            550                 555 gtttcagatc tgagtgacag tccaacagga gcatggactg agaaccacac aaaactgatt     98783 cttttctaaat gtgtggcaga gaaaatagtt taaatgggt ggtgaggggt gaatgctgtt     98843 ttccttttt tctttaatta taaatgtaga gcagataata gattaaaaca tagtttaagt      98903
tttatttatt tacatcactt ggctctcctg acttaaactt ttaaaagtca catgtggtgg     98963
cagaagaacc ttactagaca aagtgtgttt gagtcacttc agtagatgga tgaagtgtct    99023
ttatttcctc cttag c cca ctg atg aac gat ggc tcc aac tct ggt aac       99072
                  Pro Leu Met Asn Asp Gly Ser Asn Ser Gly Asn
                  560                 565                 570 att gga acc ctc agc act ata cca aca gca gct cct cct tct agc acc     99120
Ile Gly Thr Leu Ser Thr Ile Pro Thr Ala Ala Pro Pro Ser Ser Thr
            575                 580                 585 ggt gta agg aaa ggc tgg cac gaa cat gtc act cag gac ctg cgg agc     99168
Gly Val Arg Lys Gly Trp His Glu His Val Thr Gln Asp Leu Arg Ser
            590                 595                 600 cat cta gtg cat aaa ct gtacgtaaca gttttgcagt ttcatagatg              99215
His Leu Val His Lys Leu
            605 tttgattta ttcctgtgtt gcccattggc taccagatga cagtaccctag ggagcctata   99275 caagtcacgt gcttatttag ggagccactc tcactgctgg tagagttctg gcagccctag   99335
gcaggccaga gattcccaca ctctatgtcc tcggtgagcg ggggtgacaa agagagcatt   99395
ggtggctctg tactgccgag gggcactgac ttgcagcccc tatcaccgag gcaaagaccc   99455
tcagtgcagc ccggccttaa tgtgcttctg cactttaggc tgcgtgaggg gctgggggtt   99515
agctcaagag cctaccctta ttttgtagtt ccagattcta gttgtggaga ccctcagaa    99575 ttggaaaagt ttagagtata gatggcatgt cattatcacc ttacagttag ttaacataac   99635
ggaaagttaa cagttaactt ttttttttt ttttttttt gagacagagt ctcgctctgt    99695
tgcttagact ggagtgcagt ggcacagtct tagctcactg caacctccgc ctcccaggtt   99755
caagtgattc tcctgcctca gcctcccgag tacctgggat tacaagcacg tgccaccacc   99815
cccagctact ttttgtgttt ttggtagaga cagggtttca ccacgctggc caggctggtc   99875
tcaaactcct gacctcaagt gatccgtcca cctcagcctc ccgaagtgct ggggttatga   99935
gccaccgcac ccggccttt tgttgttgtt gttgttgaga gagagagacg gagtcttgcc   99995
aggttaccca agctggtctc aaactcctgg cctcaagtaa tcctcttgcc ttggcctccc  100055
aaagtgctgg gtggcatgag ccaccacacc aagcctaacg ttgttgagct agttatttta  100115
aatgagctag acttacattc cctttgagtt ttttcccttc cttatttga tcaaattttt   100175 tttagtaata agtagtttaa aaattaggga tttgaaaatc gtgttattct ggaaatgacc  100235
cagcacatac ttgttaatag caaaatattg atgtgtttga tgtgtagata agttgatagg  100295
tcaggattgt ctccagggag ttaacttcat tcatgtattg acatgcgagg caagagaggc  100355
ttggcatttc tctccacact gtattgccac cagagataca tgatcctgat tttgtagtgc  100415
```

```
ttatttgatg gcattggaag tagcttcagg ccaggtgcag tggcccccac gtgtaattcc      100475
agtgctttgg gaggctgagg tgggaggatt atgtgagccc aggagttcag gccagccggg      100535
gcaacataat aaaactccat ctctacagaa aatttaaaaa ttagccaggc atggtggtgt      100595
gcacctgtac ttcccagctt actttagagg ctgaggtggg aagatcattg agcccaggag      100655
ttcaaagttg cagtgagcta tgatcatgcc actgtactcc agcctgggcg atagagcaag      100715
accctgtgtc tttttttttt ttttcttctt ttttttggtat ggagtctgac tctgtcgccc     100775
aggctggagt gcaatggcac gatctcagct cactgcaacc tctgcctccc gggttcaagc      100835
aattctcttg cctcagcctc ccgagtagct gggattacag gcatccacca ccatgcccag      100895
ctaatttttg tatttttagt agagacggga tttcaccacg ttggccaggc agatctcaaa      100955
ctgctgacct caggtgattc tcccgcctca gcctcccaaa gtgctgggat tacaagcgtg      101015
agccaccgcg cctggacgaa accccatgtc tttaaaaaaa agaagaaaaa aaaaagtagt      101075
ttgatagatg tgttatcctt tcag c gtc caa gcc atc ttc cca aca cct gat        101127
                              Val Gln Ala Ile Phe Pro Thr Pro Asp
                              610                 615 ccc gca gct cta aag gat cgc cgc atg gaa aac ctg gta gcc tat gct          101175
Pro Ala Ala Leu Lys Asp Arg Arg Met Glu Asn Leu Val Ala Tyr Ala
    620                 625                 630 aag aaa gtg gaa ggg gac atg tac gag tct gcc aac agc agg                  101217
Lys Lys Val Glu Gly Asp Met Tyr Glu Ser Ala Asn Ser Arg
    635                 640                 645 gtaggttgct gtttaccgtg ctctggcctc tacagcatct gtagtagaca gcactacatt      101277
tgtctgcttt gttatctgga aatagtggaa tctatgtagt tgggacagac tcctcccctt      101337
gaggccactg accaaggaga cttcccagat aagacacaaa tctcctgcag aactctcttg      101397
attagctaca ttggtgcatg gagtatataa atttacatta tatccatggg atatattttt      101457
catagtaggt ggtgttgtaa tattgttagc atcagtgaat attcaagaag ttcatttgaa      101517
tgaaatggaa catgtattaa gtacctacta tttgatatgt cctataaagt cattgggaat      101577
tcagcaagaa tgtgggcttc tggtgtatca ggtatttgca tactactttt gccagtgtac      101637
tcaatgagga agttcattag ttagaaccta caacacagat cattcagttg ctttttacag      101697
ttttaactgt tcatattga atattattgc tttttag gat gaa tat tat cac tta         101752
                                           Asp Glu Tyr Tyr His Leu
                                                               650 tta gca gag aaa atc tac aag ata caa aaa gaa cta gaa gaa aaa cgg         101800
Leu Ala Glu Lys Ile Tyr Lys Ile Gln Lys Glu Leu Glu Glu Lys Arg
    655                 660                 665 agg tcg cgt tta cat aaa caa ggc atc ttg ggg aac cag cca gcc tta         101848
Arg Ser Arg Leu His Lys Gln Gly Ile Leu Gly Asn Gln Pro Ala Leu
670                 675                 680                 685 cca gcc ccg ggg gct cag ccc cct gtg att cca cag gca caa cct gtg         101896
Pro Ala Pro Gly Ala Gln Pro Pro Val Ile Pro Gln Ala Gln Pro Val
            690                 695                 700 aga cct cca a gtaaggattt tatttcctac tgccatccct tagcctgttt              101946
Arg Pro Pro ccttggtttt ccttcgtgtt tggggtgtat ttctaagaac agagaattag aatatctgat      102006
gcatgccctg cagaagctgt tgatgtggca gtggccctga ccacctgcct caggctgtgt      102066
tgggacactg agtttctctc ttgggaaggc cctttacagg gtgcgctggc attggaacac      102126
acgtgctttt ggacctattg gctgttttcc cttttaagtt tgaagtccta ataagaaatt      102186
tcctattcct gaatcaagga ttatattaaa taactagggt ggttttgttt ttgttttgt       102246
```

```
tttgccacca tag at  gga ccc ctg tcc ctg cca gtg aat cgc atg caa   102294
           Asn Gly Pro Leu Ser Leu Pro Val Asn Arg Met Gln
           705             710             715 gtt tct caa g gtattgaact gtttgtggtg aatcatattt tagttttaca       102344
Val Ser Gln ttcaacagcc ataactttca ctgttttttc ctctccccct gtatatttct ttctaaccct 102404
ttcttctttc cattccttt tgctgataag cagaattcag ttctacaggt agtatggata 102464
tgtttatagt atgaagtttg agattatag gaaagatctt ccaagagata agaagcagta 102524
tttagctatt tatttattta tttatttcta ttttatttta ttttattttt attttttga 102584
gatggagtct cgctctgtcg cccaggctgg agtgcagtgg ctccatcttg gtcactgca 102644
agctccgcct cctgggttca ccattctc ctgcctcagc tcctgagta gctgggacta 102704
caggcgccca ccaccacgcg tggctaattt tttgtatttt taatagagac ggggtttcac 102764
cgtgttagcc aggatggtct tgatctccgt gatccgtcca cctcagcctc ccaaagtgct 102824
gggattacag gagtgagcca ctgcacccgg ccttagcttt ttattttact ttattttctt 102884
ttcttttatt ttttgagac agagccttac tttgttgccc aggctggagt gcagtggcac 102944
gatctgggct cactgcaagc tccgcctccc gggttcatgc cattctcctg cctcagcctc 103004
catagtagct gagactacag gcacctgcca ccacgcccag ctaattttt gtatcttttt 103064
ttttagtaga gatggggttt caccatgtta gccaggatgg tctcaatcgc gtgaacttgt 103124
gatctgccca ccttggcctt ccaaagtgct gggattacag gcatgagcca ctgcacccgg 103184
ccagcttttt atttttttaa tggatggtga aggggtgtg gtacgttact cttaggaaga 103244
gtccgagaaa gaagcaccct agatgtgggg agggagtgct tctgaatgct gagaaggaga 103304
agcatgcaag acagtcctag actgctgagc acttgcagag gctgaaatgg ggacggcacg 103364
ggctgctctt ggcccaggg gttaagccca gctggctgga tgtcaacttc tggagagagt 103424
gtacacacag gtcctgtgcc aggttggggt gtcagcagct gtctcaacaa ccttgaaagg 103484
ttcttaagta gagagcctct ggtttttggt tggttgaagc agtgattttt attttgggc 103544
agggagcatt tgaaaaccct gtagctcttg accattgaga cccaagcagg aggacatttt 103604
tccaggttgt gaaacaaggt ggtgacatta tccagaagac tctaaggaaa gaggctttgc 103664
tcaggctttg attttgaaa gaaatcaagg agtcaggctg gcacagtgg ctcacacctg 103724
taatcccagc actttgggag gccgaagcag gaggatcact tgaggtcagg agtttgagac 103784
cagcctagcc aacatggtga aacccccgtc tctattaaaa atacaaaatt tagccaggca 103844
tggtggtgca cacctgtaat cccagctacg cgggaggctg aggcaggaga attgcttgaa 103904
cccaggaggc ggaggctgca gtgagttgag atcacaccac tgcactccag cctgggcaac 103964
aagagcgaaa tctcatctca aaaaaaaaa agaaagaaat caaggagtca gagaaattga 104024
gccttgggaa agtggctgga tgctgtgttg gggattggtc caggacttca gcctggatag 104084
gaagatgctg ctggtgtggg gtatgatgcc cctgctgttt accagcagaa tattggaata 104144
gatgttttct agttatgcac ttagcaacct ccctaccagc acatctgggt aaatacagat 104204
ttctttaagt gctgttcctt agtaattgtt tttcattttg tttaaaaaaa ttctcaagga 104264
gtggggaagc ttacattata gactccctgg aaagtcttcc tggtctgcat cggcactccg 104324
ttatttgagg gtaccatttc taggtagcca ttgaaggtag tgctccgtga gtcatccttt 104384
gagccttctc atgactacag cagcgctaag gcagcacctt ccagaaattc tctaaagggt 104444
tctgtcagat tctagtgttg gtcctaagac taatttgaac tggtgcttct ttagaactca 104504
```

-continued

```
gagtttacag agtattattg gaaattggaa ggaactagac accgcagtct ggagacactt    104564
actggctgtg aagtgtcttt cagtgatgtg gtgttcctgt aaactacagg aggctaaggt    104624
tgaggacggc tgacccttgg gcacttctta atgcttaagg tgcttgcaaa attaaaagaa    104684
catttggaga cttagcacag attctaacaa tgaatgtaaa cccagcaagg agctgggaat    104744
cctcggatga tgggcgtcag ctgctccaga ggcattaggt atgggtgtgc acagaagctt    104804
gccctggtct ctggaaacat ctcttctgta gcttgtgagg gtgctgtcct ttcagggcac    104864
ctcctcaccc tctttgttgc tatgacactt tggtactgtg ccctctggct cagctctacc    104924
acagcctcgt ttaatgtctc acttgttcct gtcttaccca accttatgcc ttcatgtcct    104984
cgtccttccc tggtacccct caccatgcca ccgtcaccac ccccacattg atgccgtttt    105044
ctctggatat ggagaagtct gttccttcat catcttcatt gattaattgg gtgatttctt    105104
ttcagttttc tgttgcctgt gcgttccatc ttatttttact aagagtttta tttagcaagt    105164
tgtaattctg ttttcctgtg ggtgcttttc ctaatgaacc gttgtgggta catttacag     105223
```

| | | | | | | | | | | | | | | | | |
|---|---|---|---|---|---|---|---|---|---|---|---|---|---|---|---|---|
|gg | atg | aat | tca | ttt | aac | ccc | atg | tcc | ttg | ggg | aac | gtc | cag | ttg | cca | 105270 |
| | Met | Asn | Ser | Phe | Asn | Pro | Met | Ser | Leu | Gly | Asn | Val | Gln | Leu | Pro | |
| Gly | | | | | | | | | | | | | | | | |
| 720 | | | 725 | | | | 730 | | | | | 735 | | | | |

```
caa gca ccc atg gga cct cgt gca gcc tcc cca atg aac cac tct gtc     105318
Gln Ala Pro Met Gly Pro Arg Ala Ala Ser Pro Met Asn His Ser Val
        740                 745                 750 cag atg aac agc atg ggc tca gtg cca ggg gtaagtgttc tctttcgctg       105368
Gln Met Asn Ser Met Gly Ser Val Pro Gly
        755             760 tgctgcagat agccctccct ctcacatgga acattatcta agcagcagaa ttcatgtcac    105428
ttgagaatcc tgtggttctt gttcctttga atttgggtta tgctttattt ctttcatctc    105488
tcattttaaa aaaattatta ctacacagaa ttatttgact gttagttatt ttattggaat    105548
aacaaattca taggaatgtg tggctttgtg agaatgtggg agttccaagg ctggagaagg    105608
cagcctcaga tatgtggcca gcagggaatt gtcagcatct gttgactgag agctcgctgt    105668
tccgaggctg ctttctaaac actttagaga actcataggc atgtcttaaa ctttaaatta    105728
tagcctgcta ttgatttcta ttcagaggac atttttgaagc tggctcattt gagagattgc    105788
ctgagaaagt gtgtaaggtg cccaggagcg cgggagttct tagcaagtgg tggtctcttc    105848
ccatgaggaa gggcaggatg tgagccctgt gcttgccatc ctctggggtt gtgaagcctt    105908
ggatcattct ggctcacctt gaaaactctg gccgtcagct tccgaactac agctctggtg    105968
```

| | | | | | | | | | | | | | |
|---|---|---|---|---|---|---|---|---|---|---|---|---|---|
| gtgcttgttg | tctcgtag | atg | gcc | att | tct | cct | tcc | cga | atg | cct | cag | cct | 106019 |
| | | Met | Ala | Ile | Ser | Pro | Ser | Arg | Met | Pro | Gln | Pro | |
| | | | | | 765 | | | | | 770 | | | |

```
ccg aac atg atg ggt gca cac acc aac aac atg atg gcc cag gcg ccc     106067
Pro Asn Met Met Gly Ala His Thr Asn Asn Met Met Ala Gln Ala Pro
        775                 780                 785 gct cag agc cag ttt ctg cca cag aac cag ttc ccg tca tcc agc ggg     106115
Ala Gln Ser Gln Phe Leu Pro Gln Asn Gln Phe Pro Ser Ser Ser Gly
        790                 795                 800 gcg atg agt gtg ggc atg ggg cag ccg cca gcc caa aca ggc gtg tca     106163
Ala Met Ser Val Gly Met Gly Gln Pro Pro Ala Gln Thr Gly Val Ser
805                 810                 815                 820 cag gtactgtgcc ccactgggac cgtggctccc taggaaataa aattcttgtg          106216
Gln ttaagttttg gttttttttt tctgtcttcc ttcgtggaaa ttaaaattcc agaatgcaca    106276
tttcatgtct ttgtatcagc ttctctttgt tttctccacc tttgtcctgt agtccttaac    106336
```

```
tcgtttggaa tttctcttat cctttctggg ttaactatat gcaaaagtgg gaatggatttt   106396
agaattttg gtttgtatgc ttttgtgttt tgatctttga gttttgttt tcttattttt     106456
tgtttgtgta ttttaaattc taactttaac gtgaccctga gaggcattag gattttaaaa   106516
agcgagtgag aaggacccat gaattcactc ttgatgattt ggcttttgtt tcttttgacc   106576
tgtctccact gccaggtgaa atcaagctaa cagaatcatt tcaatagttc ccttcttgtt   106636
aaatgttttt aatttctcaa tctagagctg aagaaattga ttttccattt attccttcct   106696
ttttcctct tttgttagtt gtagtgcgta tcattgctac tgtatacaaa atatacatgt     106756
atttaaaaca caccaaatcc tccctaaaag ataaaattct tgttttaagt ttttttttgt   106816
ttgtttgtct gttttaagac agggtctcgt tttgttgccc agactggagt gcagtggtac   106876
aatctcggct ctgcaacctc cgcctcccgg gttcaagcga ttctcctgcc taagcctgcc   106936
aagtacctgg ggttacagat gcccgccacc acacccagct aatttttttt tttttttttt   106996
tttttgtatt tttagtagag acgggatttc accatgttgg ccaggctgat ctcgatctcc   107056
tgacctcagg tgatccaccc acctcggcct cccaaagtgc tgggattaca ggagtaagct   107116
accgtaccca gccttgtttt gagtttttaa tgtgaaataa tgctgcataa gtcattatta   107176
tatattagat ttcctcacta aatgattatt cttaactttc cataacattt catttctcta   107236
gaacaaggat tagcaaactt cgtgtaaagg gccagatact aaatattttc agctttgcag   107296
gccattcaat cttggttttc atcacttctg ttcttgtagt gcagaagctg ctgtggtaca   107356
taaatgaggt ggctgtgtgc caataaagct ttatttacag aaacaagcag ctcagtgtgt   107416
ttgccctggg agattgccaa cccctgctct agaacagtga ttcagaatca tttttaaaat   107476
gttcacaaat aattctgaag tgtatcccca gtatagaacc actgcactga aacagttctc   107536
tttcagtaac taacgtgtgt gtgtgtgtgt gtgtgtgtgt gtgtgtgtgt gtttgtgttt   107596
cagagagaat ttttttttta aattttaat tgttaagggt acttatggat gtatatattt     107656
atggtcaata acttttattc ttattttat ttatttattt tatagtcccc agggaagaag     107716
caacttaaaa aaaaaatacc ttttctaag ctaagcttag aaaatgttaa agaacattgg     107776
gtacatgtta tagaacatga agcttatagg ctgggtcaat gtacagtagc tcccccaatc   107836
tgtcatttca ctttctgagg tttcagttac ctggggtcaa ctgtggtcca aaaatattaa   107896
atgggaaatt ctgggaataa acaattcata aattttaaat taattagcta ggcatggtat   107956
tgcacgcctg taatcccagc tactgaggag gctgaggcag gagaatcact ggaacccggg   108016
agatggaggt tgcagtgagc caagatcatg ccattgcact ccagactggg tgacagagcg   108076
agactctgtc ttttttttt taaaaaaaa aaaaaaagt tttaaattga gtgccattcc      108136
aagttgcatg atgaattctg tcaccatccc actctgtgcc cccagggatg tgaatcattt   108196
atttgtccag catttccaca ctgtagacac tacccacctc ttagtcactg agtgtccacc   108256
ttggttgtca gatccaaaaa tcttggtaaa tattgggttc agtactatcc gcagtttcag   108316
gcgttccaag actggggtc ttggaatgta tccgagtgga tatgagggga ctgctgtaga    108376
tgtgtgtgtt taagccataa gtttcaatgg ttgttttaat tatataaatc agactataag   108436
aaacgtgtgt agtttaccg ttattgagga gtgcccatta caagtgtata gctcgatgaa    108496
ttttcacaag cagaacactc ccaagaaaat gtgattaaat tcccatacat ttggctgggc   108556
gcggtggctc acgcctgtaa tcccagcact ttggaaggcc gaggcgggag gatcacttga   108616
ggtcaggagt ttgagaccag cctggacaac atggcaaaac ccgatctcta ctaaaaacag   108676
aaaaattagc tgggcgtggt gacgggcacc tgtaatccct gctactcgag aagctgagac   108736
```

```
aggagaattg cttgaaccca ggaggcggag gctgcagtga gccgagatcg caccattgca  108796
ttgcagcctg ggcgacaaga gtgaaactgt ctcaaaaaaa aaaatttttt tttcatacat  108856
ttaatttttc aaatgtttca tcacattttc aaacggggga ataatttta ccatactctg  108916 tccatttctg gtag gga cag gtg cct ggt gct gct ctt cct aac cct ctc   108966
              Gly Gln Val Pro Gly Ala Ala Leu Pro Asn Pro Leu
                          825                 830 aac atg ctg ggg cct cag gcc agc cag cta cct tgc cct cca gtg aca   109014
Asn Met Leu Gly Pro Gln Ala Ser Gln Leu Pro Cys Pro Pro Val Thr
    835                 840                 845 cag tca cca ctg cac cca aca ccg cct cct gct tcc acg gct gct ggc   109062
Gln Ser Pro Leu His Pro Thr Pro Pro Pro Ala Ser Thr Ala Ala Gly
850                 855                 860                 865 atg cca tct ctc cag cac acg aca cca cct ggg atg act cct ccc cag   109110
Met Pro Ser Leu Gln His Thr Thr Pro Pro Gly Met Thr Pro Pro Gln
                870                 875                 880 cca gca gct ccc act cag cca tca act cct gtg tcg tct tcc ggg cag   109158
Pro Ala Ala Pro Thr Gln Pro Ser Thr Pro Val Ser Ser Ser Gly Gln
            885                 890                 895 act ccc acc ccg act cct ggc tca gtg ccc agt gct acc caa acc cag   109206
Thr Pro Thr Pro Thr Pro Gly Ser Val Pro Ser Ala Thr Gln Thr Gln
        900                 905                 910 agc acc cct aca gtc cag gca gca gcc cag gcc cag gtg acc ccg cag   109254
Ser Thr Pro Thr Val Gln Ala Ala Ala Gln Ala Gln Val Thr Pro Gln
    915                 920                 925 cct caa acc cca gtt cag ccc ccg tct gtg gct acc cct cag tca tcg   109302
Pro Gln Thr Pro Val Gln Pro Pro Ser Val Ala Thr Pro Gln Ser Ser
930                 935                 940                 945 cag caa cag ccg acg cct gtg cac gcc cag cct cct ggc aca ccg       109347
Gln Gln Gln Pro Thr Pro Val His Ala Gln Pro Pro Gly Thr Pro
                950                 955                 960 gtaagcctct ctgtctctgc tgttttgggg ccaagactct tagaagataa ttttcccata  109407
aaaattgtgt gtcaggccag gcgcggtggt tcacacctat aatttcagca ccttgggagg  109467
ccaaggtggg agaatcactt gagcccatga gttcaagacc atcctgggca acatagtgag  109527
acctcgtctc cagcaaaaaa aaatttttt taaccagaca agcatggtgg tgtgtgcctg  109587
tagtcctgta gtcccagcca ctcagaaggc ttaggtggga agatcacttg agcctaggag  109647
gtacaggtta cagtgagcca agatcacgcc actgtactcc agcctgggca acagagcgag  109707
acattgtcat cttttgtttg tttacttaaa actccattga ggctgggcgc ggtggttcac  109767
gcctgtaatc ccactacttt gggaggctga ggcaggcgga tcaccggagc tcaggagttc  109827
gagaccagcc tggccaaagt tgtgaaacct tgtctctaca aaaatataaa aattagccgg  109887
gcatgatggc tggtgcctgt attcccagct actcggagg ctgaggcggg agaatcgctt  109947
gagcctggga ggcagaaatt gtatcgagcc gagattgcgc cattgtactc cagcctaggt  110007
gacagagtga gactccgtct caaaaaaaaa aaaattccat tgagtaagaa tttgcaaatt  110067
aggaattctt ttagtggttc cttcgtgtaa tgttcattta ctccaccagc accgtgttc   110127 ctaccgttca cacaggctgg gtaacactgt ctttgggtag gcacttgatt tccctccctt  110187
cagatgtgct taggcattca taattcagcc ttttaccata cacattaacc accatattga  110247
agggaattaa tttcaaaata tgagatttca tgatttagct agaaaacttc gagaaaataa  110307
atttatgtca aagtttgaaa agctctgctg ttttcctctgc ctttgtgcca agacctgagt  110367
tgtacctctg gctgctgtta cctccctcta gaactcattc ctactttaac ccctgttctt  110427
```

```
cggtttcaca gaagggcacc tgctggatca gtattgagaa atgttaatgg gaaattgtag   110487
gttgcatgag cagcatagtt gaagatcatt tatgttacct tgcttactga agtcagtgct   110547
ttcggttttt tcacag ctt tcc cag gca gca gcc agc att gat aac aga gtc   110599
               Leu Ser Gln Ala Ala Ala Ser Ile Asp Asn Arg Val
                                965                 970 cct acc ccc tcc tcg gtg gcc agc gca gaa acc aat tcc cag cag cca    110647
Pro Thr Pro Ser Ser Val Ala Ser Ala Glu Thr Asn Ser Gln Gln Pro
        975                 980                 985 gga cct gac gta cct gtg ctg gaa atg aag acg gag  acc caa gca gag   110695
Gly Pro Asp Val Pro Val Leu Glu Met Lys Thr Glu  Thr Gln Ala Glu
        990                 995                  1000 gac  act gag ccc gat cct  ggt gaa tcc aaa ggg   gag ccc agg tct    110740
Asp  Thr Glu Pro Asp Pro  Gly Glu Ser Lys Gly   Glu Pro Arg Ser
1005      1010                  1015 gag  gtgggtgccg ctccctagga atgcattgac tgcgtatcgc aactttaccc         110793
Glu
1020 aggtgtcctc gggcgaggct tggagcctgc catgggtatc cctgacttta gttaaaatat   110853 tctgtttgaa tgtgggttcg gggtttggtg tataggaaat tgattgaaaa cagcttggtt   110913 tttcattttt aaatatgagg ggtgggttta ttttgcccga aatgaagaat actggctttat 110973 atttgaaata cttgaatcat ccaacagcct tttattttat gttctccatt catttctagt   111033 tctgcagagg tagactacag aagggtggt ggattcattt actaattaac ctatggcaga    111093 agctgaaagc tggcagaccg tgggctggat ccagcctcta aatgtgtttg gcccacacaa   111153 taccttaaaa atcaggaaat tgcaaataaa actctagatt tctggctttt cttgaaaaat   111213 gagatgcttt cagcattgtg cctgcatccc tgtgtgacag cagtctggtt gtgagcacca   111273 actgtagtgg gctctccaat tagccacagt ccccactgct ccttcctgtc tcataccaca   111333 cctgcctctg agaaggactt ttggtccctg ccccaacttt caaggagatt tttattccaa   111393 attagaaata tctgtagtga aaatctgag tatgtgcaat ttttaaagca gttttacatt    111453 taaaaacttt taaattaggc tgggagctgt ggctcacacc tgtaatccca gcactttggg   111513 aggccgaggc aggtggatca cttgaggtca ggagttcgag accagcctcg ccaacatgat   111573 gaaaccccat atctaccaag aatataaaaa attagccgag tgtggtggca cacgtgta     111633 atcccagcta ctcgggaggc tgaggcagga gaattgctag acccaggag ggggaggttg    111693 cagtgagcca agatcttgcc attgcactcc agcctgggtg ttagactctg tctcaaaaaa   111753 aaaaaaaaaa aaaaaaaaaa aaaaaaacac ttttaaattt aggaccataa ttgcactgac   111813 tctgtgctga agcgacttaa tgaacaccaa gtactttatt tcttcttccg gaagagaaga   111873 ggaatcataa atgcaactct gactagagga aggttttaac aaacctgttt taggcttgta   111933 agagtcttcc cgtgaggttg cggtaacata aaggtgtttg atattcatat gttatctgta   111993 atgtttttct caag atg atg gag gag gat ttg caa gga gct tcc  caa gtt   112043
              Met Met Glu Glu Asp Leu Gln Gly Ala Ser  Gln Val
                                1025                 1030 aaa gaa gaa aca gac ata gca gag cag aaa tca gaa cca  atg gaa        112088
Lys Glu Glu Thr Asp Ile Ala Glu Gln Lys Ser Glu Pro  Met Glu
        1035                1040                 1045 gtg gat gaa aag aaa cct gaa gtg aaa gta gaa gtt aaa  gag gaa        112133
Val Asp Glu Lys Lys Pro Glu Val Lys Val Glu Val Lys  Glu Glu
        1050                1055                 1060 gaa gag agt agc agt aac ggc aca gcc tct cag tca aca tct cct         112178
Glu Glu Ser Ser Ser Asn Gly Thr Ala Ser Gln Ser Thr Ser Pro
        1065                1070                 1075
```

```
tcg cag ccg  cgc aaa aaa a gtaggccatt tattcattac cttattaaag      112227
Ser Gln Pro  Arg Lys Lys
         1080 catgctgctt ttccacggtg ttaggattcc atgtggagga ttaaaagcta aagtagaaac 112287
ataattctat ctgccctttt acctttcttg cctgccattc cccagactt ccctgcaga 112347
aacactcagg ctgagcagga cccctgccct gtgcctgtgg ggctcatggc aggagtgaga 112407
gatgagctgc tgctccgagg gcacccaggc tgcagagctg tcttctgatg gtgctggcag 112467
gggccgagtt gaaatgtgtc tgggtccttg agcaggttaa ggagcttggc tttactcata 112527
aaagtataaa gaaccagtga tgtatgtgag taggagaata accaaaaaag ccataattta 112587
aggaagatgg tcattatgac agcacagggt gacttggagg cagaaggttt ctgcaggtgc 112647
agtgaggaag ctgagcatgc agagtgaggg gcagggtggc gcctagggac cctgtgtagt 112707
gagacatggg ggaggggtag gttaggcatc tttggggtct gagatgtgtg aggtaagccc 112767
gcctcacagt ggaagttgga tggaatccat ttgagatgta tccacagtaa agagataaca 112827
gggtatcaga aaattgtcaa gtgaacctta gaaatgggag acaggactca gaaagtccaa 112887
ggctgcagat gacactttg ggaaagattg cagagaaatg ttagagactg agaccatgtt 112947
actctgcagc tggaagggac cctggagagt gtggagtaca gtgaatctca gggctcttta 113007
tactcttaga aattgagggc cccagagagt tgttgtgtgg attatctatc attgcttact 113067
ctactggaaa ctaaagttga gaaatttgag tacagtggct tacacctgta atcccagcac 113127
tttgggaggc tgagatggga ggcttgcttg atgctgggag ttcaaaacca gcctgagcaa 113187
catagcaagg ctccatctct acaaaactaa ataaaacta gctaagtgtg gtggtgcacg 113247
cctataattc tagctgctcg agaagcgaa gcggcaggat tgcctgagcc taggagtttg 113307
aggctgcagt gagcccagat cacatcactg cactctagcc tgggagacaa aagtgagatt 113367
gttgtctgaa aaaaaaaag agaaaaattt ttaaatattt agttcattta aaatagtctg 113427
ttacatggca cccatagaaa acatttatat gaaaaacaat ttttccaaaa caaaaataag 113487
taagaatagt ggcgttatta agggtatctg cctctgcatt tactgtgttg tgattggtta 113547
ttttggttga agtgtatgaa gaaaatcctg tagttggtaa agggagaagt attttcgtag 113607
cccttcagc tgattgtgga tattctttga tactatacca aaattcagcc agtgaaggtt 113667
tcttaaaggt tagttgcgac attgaaccag aatctatagc actggatttt tcatagtctg 113727
tgacattaga atccattgat ccatcttgta cttggaatgg atcttttgtg cttgcatgat 113787
ttttttttca attgacactt aagttctgca gattttccat atgttgacat atttcactat 113847
acagtgtcaa aaaaaaatca acatttgtta ataccaccat cagtctcttc aaacaagtct 113907
taccaactta gaaaagcagg gcgtgcatgg tggctcacac ccgtaatctc agcattttgg 113967
gaggctgagg gggaaggatt gcttgagccc aggaattcag ggtctatgat tgcaccactg 114027
cactctagcc tggagctcag gagttcgaga gcagcctagg caacatgcg aaacctaatc 114087
tctattaaaa aaaaattagc tgggtatggt agtgcatgcc tgtagctgca gctactcgag 114147
aggttgaggt gggagaatca cctgagcctg ggaggtcaaa gatgcactga gccttgatca 114207
tgtcactgta ctccagccta agtgacagag tgaggccctg tctcaaaaaa taatactaat 114267
aataaatttt gagaagctgt gaagcccatg tacaagtttt ccaaagcatt tgatttttt 114327
atgaaagccc aaattttagc attggcaaca aatactgtca gttgtccttg aagtaactgg 114387
ccctctttgt tcatttctga gaaaatgtct gacatataac cagagcttag taactatagc 114447
```

```
ttatctctca gtcattcctg aaagtttaa tgtgctccac gagggcaagc agctacttca    114507
gctgtaaatt ccaacacttg cccaagtact gcctcctgat gtggccactg tgcctatgca    114567
gcgcacatct tttattctgt gtgaggagat aggcagaatg tttcatcaca cagaataaaa    114627
gacatgtacc aggcggccag acgcggtgcc tcacacctgt aatccccgca ctttcggagg    114687
ccaaggcagg cagatcacga ggtcagcaga tcaggaccat cctggctaat acggtgaaac    114747
cccgtctcta ctaaacaaaa tacaaaaaat tatgcgggcg tggtggcggg cgcctgtagt    114807
cccagctgct cgggaggctg aggcaggaga atggtgtgaa cccaggaggc agagcttgta    114867
gtgagccgag atactgcact ccagcctggg agacagagcg agacgccgtc tcaaaaaaca    114927
aaaacaaaaa caaaaacaaa acaaaaaaaa aaaccacaca catgtaccaa acgcttaaga    114987
tttaatacaa ggaatacttt ttactatctc atcaagaata tttttcagc caggtgtggt    115047
ggctcacatc tgtaatctca gcactttgga aggccaaagt gggaggatca cttgaagcca    115107
ggagttcaag actagcctgg gcaacatagt aagaccctgt ctctacaaaa aattaaaaat    115167
cagccaagtg tggtggtgca tgcctgtagt cctggctact caggaggctg aggcagcagg    115227
atcacttgag ctcaggggtc caaggctgca gcaagctgtg atgccactgt tggactccag    115287
cctggacaac agagcaaggc cctatctcaa aaataaatta attaattaag aaatgagtgg    115347
acacagtggc tcccacctat aatcccagca ctttgggagg cgaacacagg aggattactt    115407
atggccaggt gttcaagacc agcctgggca acgtagtgag accctgtctc tacaaaacag    115467
tttaaaaatt agccaggtgt ggtggtgcac ctgtagtccc aatggctcag gaggctgagg    115527
tgggaagatt gcttgagccc aggaggttga ggctgtagtg aaccatgatt gtgccagtgc    115587
gttctagcct ggatgagaga gtgagaccct gtcttaaaaa taaagaatat tttttcttgg    115647
ctgggagcag tggctcatgc ctataatcca aggactttgg gaggctaagg caggaggaat    115707
acttgaggcc aggagttcaa gccagcctgg gcaacatagc aagaacccat ctctacccaa    115767
aaaaagaag aaaaatttta aacaaatttt cttaagcatg gctggtattt tttttcttgt    115827
gactgtacag cagcagcagt gtgtgtgata acagtagagt ttggtgatgt tggctttctt    115887
ttcctttgtt tttgcttttt agctgggtgt ggcagcatgc gcctgtagtc ccagctactc    115947
ggaaggctga ggcaggagaa tcacttgaac ccaggaggtg gaggctgcag tgagccgaga    116007
ttatgccact gcactccagc ctgggcaaca gagtgagact ccttctcaaa aaaaaaaaa    116067
aaaaagattg cttttttccc atctgtgcag atgtccaaca tagtgcaaaa ggcaaatgat    116127
aatttagtgt tataaaaatt gtttcaggcc gggcgcagtg gctcacacct gtaatcccaa    116187
cactttggga agctgaggcg ggtggatcac ctgaggtcag gagttccaga ccagcctggc    116247
caacatggcg aaaccccgtc tctactaaaa atacaaaaat tagtcgggcc tggtggcgca    116307
tgcctgtaat cccaactact caggaggctg aggcagaaga tcacttgaa cccaggaggc    116367
ggcagaggtt gcagtgagct gagatcgtgc cattgcactc cagcctgggc aacaagagag    116427
aaacttcgtc tcaaaacaaa attgtttcag gctgggcttt ggggttcaca cctgcaactc    116487
cagcactttt ggaggctgag gtgggaagat cacttgaggc ccagagttca agaccagcct    116547
gggcaacatg gtgagaccct gtctctgtag aaaaaaataa gaaatagct ggttatggtg    116607
gtgcatgctt atagtccctc atgctactca tgaggctgaa ttaggagggt tgcttgagcc    116667
taggaggtca agtttgcatg cagtgggctg tgattacgct actgcactcc agaagacctc    116727
gtctcaaaaa aaaaaaaaa attggtttca gttttggtga aatagttttc atcttacagc    116787
acatagaagg gcctagggca gtgctataac ttgagcacct aaaatgtgac cagggtggcc    116847
```

```
gggcgtggtg gctcacccct ataatcacag cactttggga ggccgaggcg ggcggatcac   116907
gaggtcggga gatcgagacc atcctggcta atacagtgaa accctgtctc tactaaaagt   116967
acaaaaaatt agccggccat ggtgacaggc gcctgtagtc ccagcgactc gggaggctga   117027
ggcaggagaa tggcatgaac ctgggaggcg gagcttgcag tgagccgaga tcgcgccact   117087
gcactccagc ctgggcgaca gagcaagact ccgtctcaaa aaataaaaa tgtgaccagg    117147 gtgaccgagg aactgagttt tttattttt gtaatattat tcgtttggta aatttcagt    117207 agtcacaggg gctggggact gcgatatgag acagcagcct ccaagggctc gagagccgcg   117267
tttttgggag atgctggtgc gctgcaacag ccctgccgcg tggagcaggt cctcgggcca   117327
gaggagggga gcggcgcagt tcacatacac tcctgacttc acttctgcac atatgggatc   117387
ttcttacaga aaggtgctgg tgaagacagg agtctgaaaa tgctctcctc ggccaggcac   117447
cgtggctcac gcctgtaatc ccagcacttt gggggccgag attgcaccac tgcactccag   117507
cctgggtgac agcgcgagac tccatctcaa aaaaaaaaaa aaaaaaaagg aaagaaaatg   117567
ctctcctcag cacggaattt gaatagttat ttaatgaatg aataaatgat caaccaaagt   117627
gacacttgtt tcaggccctg tcactcccga ttaccactgg ggcggtgaca gggtctgcag   117687
gccttctccg tgcagaggcc cagtgatcca cgctgtgggc tttgtcgtc ctgaggcctc    117747 tgttaccact cctcagtgct gccactgtgg cacggaggca gctacagatc ctatataaac   117807
gaatgagcac agctatgtgc caataaagct gtattttgg agactaacac ttgaattttg    117867
tgtgattttc acatgtcatg aaatagtatt cttttctttt tcttctgcca aacattaaac   117927
aatgtgaaat ccattgttag ctcttgggcc atacagaaaa gcaagcagct ggccacattt   117987
ggcctcttgg tcataatttg ccaacccctc attcagagaa atcaaaaggc tatttgttac   118047
ataattgttt tctcataaaa agttattcaa agactagcaa atgctgcttc gtctgtgcat   118107
aaaacagaag aaaggagtta gtaggaagca aggctgtgtg tttccgacgc ttcccactgt   118167
gaagggcacg tctgcaccct ggaccaggcc tttgcacctt caagtgctgg ggaccgtgtg   118227
cgtggggagt gctgcgtcgg ggttttacc tggttgcccg gacctcaggc tgctgtcaga    118287
ggtctgaagc agccacgtgc cctggagagg aggcggtgtc tgcggaggtt ggtcaagagt   118347
ctgtatcctg ggctttgatg gaaatgagcc ctgaggcatg ttcttggtgc gcctgttttc   118407
atctctaaag tgagcctgtt aaacacatgg gttttttcctt ccaacttttta acttttgctt   118467 tcaccagtta ggaatcagat gacgctttcc agaatttgtc aagttagacc atccccaccc   118527
cacacagaat tgatggcagg tccatgtacc tgatgcttgc cgcttcccaa ctggaacttt   118587
aaatgtttac catattttaa tctgatttt aaattacagt ttaccactta cctgttgtaa    118647
gaaatctttt cagccgggca tggtggctca cacctgtaat cccagcactt tgggaggctg   118707
aggcaagcag atcacatcac ctgaggtcag gagttcgaga ccagcctgac caacatggag   118767
aaacccagtc tctactaaaa atacaaaatt agctgggtgt ggtggtgcat gcctgtaatc   118827
ccaactactc ggaaggctga ggcaggagaa tcgcttgaac ccgggaggcg gagattgcag   118887
tgagccaaga tcacgccatt gcactccagc ctagacaaca agagtgaaac tccgtctcaa   118947
aaaaaacaaa tcttttcaag atacaaaaaa cagaccaggc ccagtggctc acacctataa   119007
tgttattgct ttgagaggct gaggcaggag aatcacttga ggccgagagt tcaataccag   119067
cctgggcaac atagtgatat gacaagatca cttgagccca ggagtttgca gctacagtgg   119127
ctatgatggc gccactacat tgccctccag cctgggcgtt ggagcaagac tctgtctcta   119187
```

```
aaaatataaa atgagatggg catgatggct gggtacagtg gctcatgcct gtaatcccag    119247
cactttggaa ggccagggcg ggtagatcat ttgagatcaa gagtttgaga ccaacctggc    119307
caacatgatg aaacccatct tctactaaaa attacaaaaa tcagctgggc gtggtggtgg    119367
gcacctgtaa tcccagctac tcgggaggct gaggcaggag aatcacttga attcaggagg    119427
ctgaggttgc tgtgagccga gatcgtacca ctgcactcca gcctgggtga cagagcaaga    119487
ctctgtctca aaaaaaaaaa aaaaaaaaaa aaaaaaaacc tgggcatgat agcttagtgc    119547
ccgtaatctc agcactttgg aaggctgagg caggggagc gcttgagctc aggagttcga     119607
gaccagcttg gacaacatag tgagacctca tctccataaa aaatttaaaa atgagtcagg    119667
catggtagca cacacctgta gtcccagtta ctcctgaggc tgaggcagga ggatggcttg    119727
agcctgggag gttgaagctg cagtgagctg agatgatgcc attgtccccc aacctgggca    119787
acagagtgcg accttgtctc aaaaataata atttaattaa aaattaaaga acaccaagaa    119847
aaaatacatc acttataagc taaggcatca gaatgcctga gacatctttg cctccagttt    119907
cttctctgtg tgagtgaaca tgagccaggt ggggtcgtga cacgctgact gctgactggc    119967
cggcctccca caccgaacag cttccctggc acctgttccc atacttgttg agggtttgta    120027
tgaatgtacc atcttgaatg tatttggcag ccagtatttt atgtttgtat tagtgaaaac    120087
agagagtgta gtaggcagta aggtgtctga ggggttggag aaattggcat tagtaaatgt    120147
gggagtaagc aatatggaac tttttataaa aatgctttat tttgtagctc tattactgtt    120207
tacatttatg agattcaaaa ccgtttgtct ccagtggcct gaatttaatt tagccaagga    120267
taaaaaactt tactcagagg atcttttaag gtcccttcca atgaaatggt cttttttttt    120327
tggagacaga gttttgctct tgttgtccag gctggagtgc agtggcgcaa tctcggctca    120387
ctgcaacctc cgtctcctgg gttcaagcaa ttttcctttc tcaccctctc gagtagcggg    120447
gcttatagga accccgaca cacaccaggc taaatttgtg tttagtagag acgaggtttc      120507
actacgttgg tcaggctggt cttgaactcc tgacctcagg tgatccgccc tcctcagtct    120567
cccaaagtgc tgggattaca tgtgtgagcc accatgccca gcctgaaatg gctttatttg    120627
ccacccagtt tgatgaatga gacagatttg ggagttagct ttactttctt tttcagccaa    120687
gtttttaatg ttggaaacct ttcatggaag aagcaaactt cccagtgttg tattttgcct    120747
cacaagctga acacagttct gacactagtg tgttttcaga agcttagtc cttaacggtg      120807
atggacgaga gcccctcgag tgccttagga gcatcgtggc tgggatgtca cagcagccag    120867
gattccgttt taaatgtgag gtaggaggga tctgagcacc ttttacaaag tgtctttct     120927
tgatgttttc tctgcag tc  ttt aaa cca gag gag tta  cgc cag gcc ctc       120976
                    Ile Phe Lys Pro Glu Glu Leu  Arg Gln Ala Leu
                                1085               1090
atg cca acc cta gaa gca ctg tat cga cag gac cca gag tca tta           121021
Met Pro Thr Leu Glu Ala Leu Tyr Arg Gln Asp Pro Glu Ser Leu
1095               1100                1105
cct ttc cgg cag cct gta gat ccc cag ctc ctc gga att cca                121063
Pro Phe Arg Gln Pro Val Asp Pro Gln Leu Leu Gly Ile Pro
1110               1115                1120
gtaagttaat tcataaaaat agattataac tttgctggtg tgacttctga gtgtccattg    121123
ttttatctct tgaaattaga taaaataatc ccctgccctt gaagattgtt ctcctaatat    121183
aaaaaactgt tgtctgttaa cagttatcag tgaaagtgtt tattttgttt gatttcacct    121243
gttcatgaag ccctggtcct tggaggaggg gtgcactgaa gcaagggaag cacatgcccc    121303
tgagacttca ctttatattt ggggccttgt gtcactttttg tctgaaagaa tttgtgaaca   121363
```

```
tgaactgtaa aaaaatattt gggcttctct cttttatatt cctggatagc cttgcaaagg    121423
ccatggggac ccagccgatt ctatgtagca gtcattacta gctttgtgtt tatatttgtc    121483
ttgtaatttc attttgcttg ctaggatcaa gagtgaatat ctagaaatac acactgtttg    121543
ataaacttgt tcactatttt aattcagtgg attaaagatc tatttttaaa attttttgtt    121603
agaagtatct tttaacaatt tttctttact tttgcctttg gagtattata atgtgatcat    121663
acctgaaaat actaattaca cttttagtga gtaaaatcag ttgcgtcaga ggttattttc    121723
ttttcatttc ctatttctta ctgttgggaa tggaagttat tttggtgctt tctgtttcta    121783
ttatttaaaa acaaagctgc cagatgagac tggcatttgg atattggggg attccctata    121843
ctgagaccat ttttttttt ttaag gac tat  ttt gac atc gta aag  aat ccc    121895
                           Asp Tyr  Phe Asp Ile Val Lys  Asn Pro
                               1125              1130 atg gac ctc tcc acc atc aag cgg  aag ctg gac aca ggg  caa tac        121940
Met Asp Leu Ser Thr Ile Lys Arg  Lys Leu Asp Thr Gly  Gln Tyr
            1135             1140              1145 caa gag ccc tgg cag tac gtg gac  gac gtc tgg ctc atg  ttc aac        121985
Gln Glu Pro Trp Gln Tyr Val Asp  Asp Val Trp Leu Met  Phe Asn
        1150              1155              1160 aat gcc tgg ctc tat aat cgc aag  aca tcc cga gtc tat  aag ttt        122030
Asn Ala Trp Leu Tyr Asn Arg Lys  Thr Ser Arg Val Tyr  Lys Phe
        1165              1170              1175 tgc agt aag ctt gca gag gtc ttt  gag cag gaa att gac  cct gtc        122075
Cys Ser Lys Leu Ala Glu Val Phe  Glu Gln Glu Ile Asp  Pro Val
        1180              1185              1190 atg cag tcc ctt gga tat tgc tgt  gga cgc aag gtacagtttt              122118
Met Gln Ser Leu Gly Tyr Cys Cys  Gly Arg Lys
        1195              1200 aagtttttcc ggaaagtgaa ttttcctggt taatccagcc agagggtgt tatactaata    122178 tgagaccacg cctgtatact gggagtgcat atgtgcaatc tgctgtctgg tgacacagtt    122238
gatgcctgaa gcgatgtgat gggtgatcag agctgggtgt acaggcgctt actgagggag    122298
gccatgggga gcgtttctg gctgcccctc tctgcctgtg gtacctgtct gtagtgaatg    122358
tctcttagag ccagttctat cacatgctat cccaaaatgt cttttaaagct actaaaattg    122418 ttagaaaact gtctaatata ctaacagaaa taatttacta gtctctatag tagactagaa    122478
cattataaga cagtaaatgg aatgtatttt tatataaaag tatttctcct ttattttgc    122538 ag tat gag  ttt tcc cca cag act  ttg tgc tgc tat ggg  aag cag ctg   122585
   Tyr Glu  Phe Ser Pro Gln Thr  Leu Cys Cys Tyr Gly  Lys Gln Leu
       1205              1210              1215 tgt acc att cct cgc gat gct  gcc tac tac agc tat  cag aat ag        122629
Cys Thr Ile Pro Arg Asp Ala  Ala Tyr Tyr Ser Tyr  Gln Asn Arg
        1220             1225              1230 gtaagcgtca agcagcatcc tgcattatgt cttagggcaa ggcacgttca tctggttata    122689
gtctgtgtac attattctct tcctgaagtt ccaataaaaa gtgcccaat ttcaggccga    122749 gtgtggtggc tcacgcctgt aatcccagca ctttgggagg ctgaggtggg agaatcactt    122809
gagcccagga gttatgttat cagccttggc gacatagaga aaccccatc tctatttgaa    122869 aagaaaaaaa aagagaaaaa gtggctcggt tcagtgtct tgttagtcac ttaggccat    122929 ggcctcttag ttagttataa agcgtacttt tacagtgtaa aaactgtaac ctcagagcca    122989
agtcttgccg tactacttgg attaggtacg ttatttcttc agcctgccc gttctaaaac    123049 gcagccctag aagcaagcgt ctgaagttga gagtaactct gataaaggtt gacatgcctt    123109
```

```
tttcaagatg ttcatagagt agaaaatgtg gattttacta ttctacctgc aaatatttgc    123169
ctggtaattt ggcctgatca gtctcatgga aagacttgca tgagtgctgc ttcctataag    123229
gcagaggaaa agggtccatg atctttatt ttaaattta cactagcagc acgatacaaa    123289
atgagatctg gtgttttaat tgagttcaag aatgtgattc tgttgcctcc tattataaga    123349
tggccatttc agggttttgt gagtggtgga tctgcttaag aaatacttgc cattcttttg    123409
gaatatgaag atggctaaag aatagatctc ctgtcttaaa ataggtagag agtgagaata    123469
gtattttttg ttgtggtttc ccacaaaata cagcttgcgt agttttggag ttgtttgaga    123529
agtcagctta tctgtaccgc agcgtgtaag tgtccatgtg ccgctgcagt gtgagcgcac    123589
catgcgtgga ggcacaggtc aggaatcttg ctcaaactgt gacgttgcct ctattttatg    123649
agccagcagc tggattctct gtggccaaga tagaggtttg tgcctgttct ttgtctttag    123709
gttcaaataa taagcgtcaa cagtgggtt tggcgttttt tattatttta ctctcatttg    123769
gtcagagtaa ttatgtccta tacttcaaag aagacagaag gcttttgtt atttgttcac    123829 aggcctgaaa attttggagt tttatggtta tgtgtttta ttcttctatg tttttttaa    123889 aaatccatat tcaagataag taataactcc catcaaaatc ctattttta aaaaaatcct    123949 tttgacacaa aaatgtctca aaaaaggttc ctaagccttt tctattagga ataagcctgg    124009
cctgcttatt cctaatactg ttcagtgtag tgaaacactg gtgcaagggg aaggacaga    124069 ccctaaactg catccctgct agaagtgcag cgtgtgcaat tgtcctgctg aaaatagttt    124129
aacattcaga gtctgatttc catctcaact tccccttat caatagaaac attttatgac    124189
caagtttaaa atgataccat agccccttcc taatgggatc tctcccatag tgacttgctg    124249
ctctttggga agttctggcc actccttta tgcttttagc cccatgacct tcagcagacc    124309
ccatgatgta ttaatgtatt aagcttagcc ttgtctgtga tacagacaat agcgtcttcc    124369
ctcgcagcct cattttgtca ggtcctcaat gatgaaataa tgaataggaa tgcactttaa    124429
aaaccatttg tgccaagcaa aataaagtta atgatatctt cagagaaagg ttaatattaa    124489
ctacacccag aaaaatgcca cccctgctac gttgcccaac acagttttgg tctagaagga    124549
aggtagattt tttaccactg tctctaaagt gttgtggggc ctgttcctgg gtccgttggt    124609
accctgcctt tgctgatttg cacagatttt ggtcttttac attgagagca attaaagtta    124669
aatggaattg gtaggaccaa agagtcattg atggcatatg aagtcattga tggcatataa    124729
agtcattgat ggcatgaaag ttctgaaacg tctaatttta tttctgtata gaacttcatt    124789
tttactaaac aaaagtaatg tatttttaag agtggaaatg caaataaagg agttccattt    124849
tattagtgat aatttttaaa gcgtaggcgt agcgttcctc agacgatcac aggcatgctc    124909
tctagaacag tgtatctgac tgagtaggtt agcatattat catcctgaga aagcagtggc    124969
ctgattctgt aacaaatact ttaactgctt atgttttat tttcaacttt gactatttat    125029
gaacactgca gtgttcttat gaataattgt cttggcactt gtagtcctaa actgggcact    125089
tagaacaata aaaaatccta cagatcattt aaacaagtga aaccctaata tataagtgag    125149
cgtatgatta cattttcact tgttttcata ctttgcaaat ttgaaagtaa ctcatgttgg    125209
aaaaactgtt ctttagcttt cccagttagt atctgtagat aatataagta ttatctatag    125269
atatcccagt gatatgtact gatatggtac ttaaaacaat ctgcatttga aaacttagtc    125329
catatattaa attaccctta cagataaact atgcagttcc atggtactat agcaaccctg    125389
aaatgcatca tcactggatt atgtgaagta tttctccttt gcaattccat attcatcaag    125449
ctgcttcctt cacaccaggc aaaatgtcat ctaggcgctt aagttgaaaa gtgaatttct    125509
```

```
aaatctttat gtgtttccag ggagaataaa gtgtggacta ggtaagaagg tagggggcagt   125569
ctggcaataa catctatcac tcatagactg ccagggttgc tttagctgat tttactagtt   125629
gggggtgact gttcccttt ctgtgtgctg tcttcctctc tcagaacagt aataaagtga    125689
agccacgggc ccctcttcct ccccttctta aacacgaaca ggctaaattg tccatttctc   125749
cagcagtttt gaggcagaca aggagtctgt tgataatgct ttgcctcccc ggttctgatc   125809
ctgggatttt ccagggtggg agtcagtcat acaggaagag cctcagtttc ccagccactg   125869
catgggctgc cattccacca ccagtgcctc cctcagtgtc actttcctcg gtggggaagg   125929
atgggtttat ggttcttgtt tcctggatgt tgctgggctt gctgtcctta aataaaagca   125989
aaggatttct ccaggatttt aaaccatttt agactcacct gtgattacgg tgggagtttc   126049
atttcagaat gtcttgaacg gtcccttcta gttggccata gttctgcgtg tttgattgta   126109
tcatgaatgg ggcactcaat taggagtttt acttataaaa gggaagtatt ggggattgag   126169
ggaatgtctt ttttgtgtat tgttttggtt gccactgaat tggtttatag tttctgtact   126229
ttaattcctt cttgccagtg atgaccatac cctcctgcac acggaagttc ttcttcatac   126289
cggatttag gatatttaca aaatagtgaa tggccagaat attgctatag ttcattcagg    126349
gaaaaaaaaa atacatattt aaagaaaaac attaatctgc ctcttgcctg tcagagtgtt   126409
aaatcctgac ataatttatt aattgagtta gtgccaaata aattagtccc agcaagaaac   126469
cttcattaat ctagtgaatc tgtcatgttc ctcatcaacc aaacacaaaa aattggctca   126529
tcttgagatg tgcatgcact gaagttgtat gctttaaaat ttgctgtatg tgtgtggtta   126589
gtgaaataca acagacaaaa tgctcaatgt attgaattaa gattagattt gggacttgtg   126649
ggggacctgt cctagtggta gtgaactggc cacacggtgg cccacgcctc agtcttctgt   126709
agccgtgtga gtgcgcaagt gagtgagact gcagctgccg cgtcccattc tgcacttggt   126769
ggttcagcct ggcgctcgag tcctgtcgca ctgttttaa tactaatcct tcctggcatc    126829
ttgtagacat agttttgagc actaaaccgc attcgtgctg ccgtcgctac ctgacactca   126889
ttcttctcgc ttgtgtgatc cacctccacc cgcttgttta ttcttacggt attcttgtgt   126949
actcatcttg ttttatgcag catcagcctg catttctgtt gatttctcat ttatgtcctt   127009
tccaaacatt tagtagtttt tattttaatt gtttgtattt gatagcttga gcccaggctc   127069
tatattgtct tacaagaaat tggggtgatg gataatttct caaatgcaga ttgttcttta   127129
aagattaact ctaaattcac ttaacttgga ttgcccccaa gtcagaacag tcattcgcta   127189
agtctttcag attgatgaat gattggtccc agtaccaaaa atgtcaaatc aaagcttaga   127249
attgaatttt caaagattgt tcatggattt acatatattg tatttcttat acaatatatc   127309
acatttctta ctctgtatat tcatattgat aaatgggtgg aaagtctttg accctgactg   127369
catttatgtt aaatgtttgt ctagaatatg gatttggttt catttgtatt gtaacacaat   127429
taactgaatg attaacatga aaaaaaaaaa aacaggaaaa aattaaaatc agttctgggt   127489
gctcagcatt ttcatacatt taaagatctg gcttaatacc ggaaataaaa tctctgaatt   127549
gctgtcaagc ataaattttc cattttgaaa aataaagcta tttcagttta aattgctttt   127609
ttaaggcctt ttgtcagact gttttgttca agtaaatttt tccatctcaa accctggagt   127669
tatatttgac tttctctgag taagaacaaa attcagattc ctaaatttgg gctccatgca   127729
attctagtat taacaactcc ttgaaaacat ttgcctcttg gagccggacc gagcctgtcg   127789
ttgttagtga tgatggcctg tgatgtgtgc aatgagaccg aatgctaatc aatgctttgc   127849
```

```
cttggctttc tgctctgtgt tgtcttggtg tctgcgtctt acctctgtgt ctgtgctatt    127909
tgttcccttc cctgttctct aatcctgcct ttccccacct gccccctgtt cctttcattg    127969
tcctcactga cccatcaatc aaccaacaac gccccccctt cgtcgtggtg ctctgccctg    128029
ctctgattgg tggcttcgtt gcttgggtgg ctgtgtgtta tgatggacca gttcacccaa    128089
gtatggcctt cttgctgaca g  g   tat cat ttc tgt gag aag tgt  ttc aca    128138
                            Tyr His Phe Cys Glu Lys Cys  Phe Thr
                                    1235                1240 gag atc cag ggc gag aat gtg acc ctg ggt gac gac cct tca cag           128183
Glu Ile Gln Gly Glu Asn Val Thr Leu Gly Asp Asp Pro Ser Gln
        1245                1250                1255 ccc cag ac  gtaagtaccg tcctgtcatt ttctctgggg tgagggaggg               128231
Pro Gln Thr
        1260 tgaccttaaa ttgttttttc ctcttaccaa tgactataag gaaggtaccg gtgccatttt    128291 gacttccttg caatgttttt tggttttttg tttttgagac aggttctcat tctgtcacct    128351 gggtggtgtg cagtggcact atctcgactc actgcagcct tgaccacttg ggttcaagcg    128411 atcctccttt ctcagcctct caagtagctg ggattacagg tgcacgccac catacccagc    128471 taatttttt  gtattttttg tagagacgag gtctcgccat gttgcccagg ctagtctcaa    128531 actcctagac tgaagcacaa tccacctgcc tgggccttcc aaagtgctgg gattacagtc    128591 tgttgtgttg tggggtttgt ttcatattaa ctatgatcac atttaatttg aatatgtgta    128651 tacgtataca tttacactga aaaatgtgtt ttggctgaac cacagcgcca cctctgcctt    128711 tatcattcaa ggcggtggta ctgtggccta ccactggaga ccactggtct ctcttgacct    128771 tggtctgtct ttttttctaa ataattgct  ttttcctagt ggttccattt tggggaatta    128831 gaaattttct ttatttaat  tttttttttg aaatggggtc tcactgttgt tacccaggct    128891 ggtcttgaac tcttgcctca agcagtcctc ctgccttggc cttccaaagt gctggggcca    128951 ccatgcccga ccatgtaaat tttcagttat acctgagaaa ccaggtatcc ccatttgcag    129011 aactggcagt agcaaaaaat gagtttggtg tacatgccct gccctttaca tttagtttat    129071 ctccacttaa acctccatcc tttcagttac tgaagtctaa tccagattaa tggattccag    129131 tgttctccaa ccccattttt tggcctaaag tctaaatgtg tttccttcct tcactagtgc    129191 tttacctgtt gttaccagc  tccaaagtgg acagctatga ctttgttagt tcactcctgc    129251 acagggttaa acttgtattt ccagtgttta ttatccggca gagttacctt cgagtgttag    129311 aatggccact gtgtggcaag aaaaagcaaa tgcacaaatt gtgttatcaa ctcatttcta    129371 tacttaagta actaaaaacc tgccagccac ccaccacatc tgcccaggtc tgccgttccc    129431 tcttttcgtc agactgagtt ccccagtctt ccatgattcc taccacccta ccacagtgtg    129491 acttccccaa cagaaaggaa gggtttgcca caggagcttc ttccagcagt gtaggcactt    129551 acgctctacc attttctttg ttcaaatgca gaaaaacct  aacttgtaag acaaacaaac    129611 caaagtgact gaaattctac attttcaatt tatttccctt gtcatcctaa ttctctttag    129671 tctagttgtg tgattaataa ttggattgtt gcctgagcaa catagtgaga ccccatctct    129731 acaaaaaatt aaaaaaactt aacagggcgt ggtggtttgt acctgtagtc ccagctactc    129791 agaaccgggg tgagtttgag ttcagccttg caacataat  gagaccctca tctccacaaa    129851 aaatcaaaaa attagccagt cctggtggtg catgcctata gtcccagcta cccaggagga    129911 tcacttgagc ctaggaggtt aaggctgcag tgagccatgg tcacgccact gcactccagc    129971 ctgggcaaca gagcaagacc ttgtctctga aaaaacagaa ggaaaagaaa tgatagtgga    130031
```

```
atatgtagaa aaagacattg tagtgttcta cgaaattaaa ttttctgttc attccgttat    130091
tacatgtact tgagatttta aggggccatc atgtcttttt gtttgaagaa ctagttacaa    130151
aataacattc cagagaccct atagtttata ctcaacagat aaattttagt taataaaaca    130211
tgttttctta ttttaaaaca ag g aca att tca aag gat  cag ttt gaa aag     130261
              Thr Ile Ser Lys Asp  Gln Phe Glu Lys
                                 1265 aag aaa aat gat acc tta gac ccc gaa cc gtaagtatat agctatttct         130310
Lys Lys Asn Asp Thr Leu Asp Pro Glu Pro
1270                1275 tttttacttt cagttttggt ttgaaatcgg taaagttact ccttatggag tggggtgtgg    130370
gtaaaaacat tggaaatatg ttgccgtaag tggaatttct ggtgtgaggt tatcttttag    130430
atatagattt cttttaaact taaacaaaat atgtatgtct ctgtaacatg tactctagtt    130490
actggatttt aacaatgata agattaaatg gatgttttag ttctatgaga acctctctaa    130550
taatttggtc atgggtgtct ttaagaagcc atttagcatg aatctttaga gaccaaaggt    130610
taggagtatt tggtggggta gtactagtag tatcgtttaa agggaaatac cagaaagaaa    130670
acctcttgga aactgctttc tcaaataatg taaagcttgg cacattttct tgccattgtt    130730
aagcactttt tttgttgttg tttttgtttt gttttgtttt ttgagacagt ctcgctctgt    130790
ccccgaggct ggagtgcagt ggcacgatct cggctcactg caggctccgc ctcccgggtt    130850
cacgccattc tcctgcctca gcctcccgag tagctgggac tacaggcgcc caccaccacg    130910
cctggctaat ttttgtatt tttagtagag acggggtttc actgtgttag ccaggatggt    130970
ctcgatctcc tgacctcagg tgatgtgcct gtctcggcct cccaaagtgc tgggattcca    131030
ggcgtgagcc accgcgcccg gccctgttaa gcactttcct acagtgatga gtgagagtgc    131090
tgcatttgct aaccttgctt cataacagcc cctaaagaga cttcagattt ttttcagtgt    131150
ggtagcctct tcccaggtcc ccaatgtaaa gttctgaggg cgctccaaat tggcatggcg    131210
atactggcta ttttttgtcc ccagggtgag cacaggctcc aggagcgttg gctacttggg    131270
aagtgtgggc tgtgactcag ccaaggcaag aaacagaccc tgctctccct atcctgaccc    131330
tctccaggga agccagtggc tagagtggca agcacagatt tctacccagg ccacctctgg    131390
aaacctagct tgacttttgg caggttactt catctctacc agcacatggt acacagacag    131450
gacgatgatg tgaaatccta gagctgtagt cttggcgaga tgccagggca gagcgcccac    131510
ccctctcatg accatcggat tgttttttcct gactttccac cttttctttc acattgtgtc    131570
tttctctcct tggctttata gtttcattat tatttatatc tacttttctt tccttttttt    131630
ttttccccct gagacaagtc ttgctctgtc cccaggctg gagtgcagtg gcgcgatctc     131690
ggctcactgc agcctccgcc tcccagattc aagcaattct ctgccttggc ctcccaagtg    131750
gctgggatta caggtgcccg ccaccacgcc cagctaactt atgtatgtat gtatgtatgt    131810
atttattttt attttgaga tggagtttca ctcttgttgc ccaggctgga gtgcaatggc     131870
acaatctcag ctcaccgcaa cctccgtctc ccgggttcaa gcgattctcc tgcctcagcc    131930
tcccgagtag ctgggattac aggcatgtgc caccacacct ggctaatttt tttgtatttt    131990
tagtagagac ggggtttcac catgttagcc aggatggtct cgatctcctg acctcgtggt    132050
ccacccgcct cggcctctca aggtgctggg attacaggtg tgagccaccg cacccagcct    132110 gtattttag tagagacgag gtttcaccat cttgaccagg ctggtcttga actcctgacc     132170
tcgtgatcca cccacctcgg cctcccaaag tgctgggatt acaggcgtga gccaccgtgc    132230
```

```
ccggccaatt tatatctact tttcaacttc aaaatatatt acattcaagt agtaggtgcc    132290
aggcagaggg aacacatgga tgagtgaagg ggtctccttc ctgctggttg tagtctagag    132350
agacagctgg gtaatggcac agcctgcagc aggagacagt acaagtgagt cccagacaga    132410
agggaccctg cttgggcaga gcggcatcac cacagttgcg cctggtttcc tggacaagat    132470
gacatttaca ttgaagctgc agagcattct agaaacaaag gcatgaaaga acacaggttg    132530
ctcaataaaa ctacaaggcc cctagagtgg gtggttggta ggcagaggtt aacttcatga    132590
agggccatta cactgtctct tgacgtttag actttatcct ataatgtgct gaggaggttt    132650
tgaagaatag cactggttct agtgtaagag ggtcatcttt ggtctatgag gtgaactgaa    132710
cagaagagga gaagacattg ttctgtagta gagaagttag ttaagagaca caaagcagga    132770
gaaggcaaga aactgaaaca ccaattaaag caagagcttt tggagccagg cagggggct    132830 tgctggggga ctgagggaag gggagacatc tagttggccc ataataattg ggagtgggag    132890 aaaggggaa attcaaaatg gatgtcatgg ggtctagaat atgcagtgtg ttttgtttgt    132950
ttggattttg tttgttgttt ttgaaacagg gtcttgctgt gtcacccagg ctggagtgca    133010
gtggtgcagt catagctcac tgcagccaca acctcccaga cccaagcagt cctcccagct    133070
cagccttcta agtaactggg actacaggca cacaccacca tgcccagcta attttaaat    133130 tttttgtaga aatggggtct ccctattta cccaggctgg tctcaaactc ccagtaaagc    133190
aatccttcca ccccagcctc tccacatgct aggattacag gtgtgagcca ctgcacctgt    133250
ccccagtgta gttttggggg acactccttt cccctgacat gggagggaag agttgagagc    133310
aggggaccct tggagacggc acaggaattg aggaagttct tggccccaac ctttgaaatt    133370
cttagcgttg gggatgagct cagtggctga gttgtcaaag acagagcttg tggaggataa    133430
gcactggagg aaaggagtgc agattcagag cagctgccac gtggaaggga gaggtagcca    133490
gacagagccg ggctgtcaga gagtgccata ggaccatgaa cgggtgccgc catttgtgtg    133550
tgtgtgtttt tttttcaca gatctgtgtg tgtgtctttt cttcctcc agcagactgg    133610 gcagagaagc cagatgaggg tagacccatg gctgagggct tgcatagcac gtgcaatgga    133670
cagattaagg ggacgagggc aggggcacac tttagaggag ctgtagctca aagctcagga    133730
gcacacaggg aatcacatta ctcaccagtc ccttcagcct atcctcggag gtatgcattg    133790
tggtggcagc aagggaggga gctgacaaaa acccaaggtc ttgacctcaa aatgtcatct    133850
tggcatttaa gattcctggg ttgaggcggt tcctggaggt gacggagccc tggtgggccg    133910
tggttgtggg ctgccgtaga acagtgtgga ggattcgtgg ggaatgggtg gtccattctc    133970
tcgcttcacc agtgtttact tgaataaacc cttgtcaact tgccagtagg cctgacacat    134030
tccacctttt gtaactgact cagaactggt gtttttgtgc ctcgcgccta gcgtggctgc    134090
tctgaactgg ccgtgtttcc cattagtatc ctcaacaatt ttagacttaa gagcacatgt    134150
ttagaactca aagtattgtt ctctattttt taagtcagtt ttggcatgtg aaatcaccta    134210
gagaaggcat tgttcttgca aatgtgtagc agtgtcagaa ataccggcct gtgaaatatg    134270
tatttgtcgc agcaattttt aaaaagtaaa gtttccttc tggttgcaaa gggagattgg    134330
gagaaaagag gaatgaagcg cttgtacaaa caaaagaaga aagctttttc ctgtagaaga    134390
tatcatacgg atgcattgta aaatatagct gaatcagcca acacacgcat taatgtcagc    134450
actactcaaa gtaacccaga gaacaaggtg tggacgcaca cacagacttc tacaagtgac    134510
tctggtcttg tggttccgtg tgctttaaca gtgcgccttc tttgcctcct ag t ttc      134566
                                                           Phe
                                                           1280
```

| | | |
|---|---|---|
| gtt gat tgc aag gag tgt ggc cgg aag atg cat cag att tgc gtt<br>Val Asp Cys Lys Glu Cys Gly Arg Lys Met His Gln Ile Cys Val<br>                1285                          1290                          1295 | 134611 |

```
gtt gat tgc aag gag tgt ggc cgg aag atg cat cag att tgc gtt    134611
Val Asp Cys Lys Glu Cys Gly Arg Lys Met His Gln Ile Cys Val
            1285                1290                1295 ctg cac tat gac atc att tgg cct tca gg gtgagttgtt tccctggcc    134660
Leu His Tyr Asp Ile Ile Trp Pro Ser Gly
            1300                1305 tggagggcag ttctgcacag agccagtggc ggggcagttg cagtggctac tgcatctcat 134720
tcattgttgt cagcaagaat tcagcgatta agagagatgg cagttggttc taaatttaag 134780
ttctaagcgt ttgtccgctt taggaattgt ggaatcaaag cagtctgcct cttcactctt 134840
taattttata ataatgtgat ttaaactgcc aacaaactat ctgaatgctg cattttgttg 134900
gtttgacaat ttacatcatt atatacagtc tcatcatacc actattattt tgcag t    134956 ttt gtg tgc gac aac tgc ttg aag aaa act ggc aga cct cga aaa    135001
Phe Val Cys Asp Asn Cys Leu Lys Lys Thr Gly Arg Pro Arg Lys
            1310                1315                1320 gaa aac aaa ttc agt gct aag a gtaagtttcg ggaagctttc tgtttcctgg 135053
Glu Asn Lys Phe Ser Ala Lys
            1325 actgcacatt ttagaaactt gtagaaattg tccccattgt tctttggttc ctctcaacac 135113
atggttctga ggttcggttg tcaaagattt tcgttagttt ttttccccagt actttgtatt 135173
tttcttgtct catccttaag gagagccagg ccagtcatga gggtaagaat gcagaatgtg 135233
tcttcagggg cttcactgag aataggcagc acagctgtga gtccctgaag tctgtgcttc 135293
tcagaatggt catctcagcc acggggctgc tgagcacaga gctcagagca ggactcgcag 135353
ccttgggctg tggatcttca tcaagtgtaa aacatctcag tccacccctta aagggaatat 135413
ttggcctgat tgttatatga aagtcagcat ttatgatcag cgcatgtttt agatgaaagg 135473
ttagatgtgc agtaaacttt gtaaattctg agaaaattta tcaacagatt attctcaagt 135533
ggtttagacc taagacccct caccctcgt gcgtgcatgt gtggtgtaat gttggccagc 135593
actctctaac cctgggccct atgtgggctg ccgtgggtct gtcccgtggg tgctggcttc 135653
tgctacagtg gggtatgagc catggcctct gggaaccagc caccacccca ggagcggtag 135713
gagcctggcc tgcatgtgga cttggctgga catgttactg cagctggtgg tgcctgtgca 135773
gaaatagaag gaacaacctg ttactgctag aagtaacttt gcatgagtag actttctttt 135833
ttttttaatt tgagacattc tcgctctgtc gccaggctgg agtgcagtgg tgcaatctca 135893
gctcactgca acctccacct cctgggttca gcgattctc ctgcctcagc ctcccgagta 135953
gctgggacta caggcgcccg ccaccttgcc cagctaattt ttgtatttttt agtagagacg 136013
ggtttcacca tgttggccag gacggtctca atctcttgac cttgtgatcc gcccgcctcg 136073
gcctcccaaa gtgctgggat tacagccatt agccaccgcg cccggctgac tttttttttt 136133
aagaccacat tgcattgtta tcaaaagttt atggttattt aatctttata gagtcaattc 136193
tcaagtcttg ggatgccctt ctgcagcttg acgcgcagg ctggcctttt gccgagtaa 136253
ccagcaaacc cacacaagaa cggcaactgc agcagtgttc taacattgac ttgccagctg 136313
ctccctacag ctgtcacctt tctctggcag gacaggtgac tagcatgttg ctcaggagat 136373
ccccaataga accagggtca tttggggagc tcagagtaga agagagatgg aaatgctagg 136433
atggaccatg cactggggga aggggaggag gaagccaccc tgtagacttg agactgagtc 136493
ttaattcaag ttcaaactct gttgttaacc aacatccaaa gttatgcaat agcttacact 136553
gcctctgtta aaaacttgtg aaatatcact cattgataaa ctattgtaat acttttcctt 136613
```

```
agctcggttt ctcaactgag gcactgttga catttcaggc caggtaaccc tctgttttag   136673
gggctgtcct gcgcattaca ggattttagc agcatgcctg gcctctgccc actcagtgcc   136733
agtaacacct tcctcagcaa ttcattacgt ctgtcagaaa tgtctccaga cattgccaga   136793
tgtcccctgg aggggcacag ttgcctccat ttgagaggcc ctgcttcaga ggattcactc   136853
tgagtgagtt cgctaatgca tttgagcaaa ttggaagttc ttccctgggc cagaggctca   136913
gtagccaaaa cagaattacc cagagaacta ggcctccgta gaacagtcat tgcctgaaag   136973
gggcaggagg tgactgggcg gaatggcaca agtggcccca gagcaggtcc agccccctcc   137033
caccgcagca tccagaaaga cccgtgggca ttcggtagat gagcccaaga tctagaaatg   137093
gaacattact ggagaaaagg gcctaggaga ctagaggtag ctctactctc agtgtgagcg   137153
tgtgtcagca caggcgttgt ggtgtctgat cacagagtaa aggtatgctt ccttaatctt   137213
gcattgaaaa ccatctcctt cgcatacacc atatgcaaaa ccaaattcag gtagattaaa   137273
aagcgagaaa agtaaacaaa actgcagatg cattcaggat aaaagtaaga taataatttt   137333
attgtgttga gttatgaaaa gccttcctta aaaagataca gcccagagat gagaaaggaa   137393
aaggcacaaa aggcccctgt catgcgccat ggatgaagat acaagttgaa tgccagaaag   137453
cgagggcac aatttaaagt gttcattttt agatttagca agtctacttt cacacatgta   137513
tcctataaaa atatttgcac atatgcataa cggcacatac aaggacataa ctgcagcaat   137573
ggcaaggagt gatgaaaaag taggaacagt ggccaaatcg agtgataaca gaaaggagg   137633
cagcactgtg aggaaggttg cgcagagtgc accgcagtga gcacggcctg cgcctagacc   137693
cctgtgctgt ctgagaccac ctctggagta tgcagccatg tgtggatcac aggtgtcaaa   137753
tagcgaagtt actctggaag agtttttttt gtttgttttt ttggggggtt tttttgtttt   137813
ttttttgttt tgttttgttt gtgcagacag agtctcgctc tgtcgcccac actggagtgc   137873
agtcacgtga tgtcggctca ctgcaagctc ttgcctcccg ggttcacgcc attcgcctgc   137933
ctcagcctcc cgagtagctg ggactacagg cgcccgccac catgcctgta gtcctaattt   137993
tttctgtttt ttagtagaga tggggtttca ccgtgttagc caggatggtc ccgatcgcct   138053
gacctcgtga tccgcctgcc tcggcctccc aaaatgctgg aattacaggc atgagccatc   138113
gctcccgact taattttgca ttcttagtgg agacggggt ttcaccatgt tggccaggct   138173
ggtctcgaac tcctgacctc aggtgatcca ctcgcctcag cctcccaaag agctgggatt   138233
acaggtgtga gtcactgcgc tcagcttaat tttgtatttt tagtagagat ggggtttctc   138293
cgttttggtc aggctggtct tgaactcctg acctcaggtg atccacctgc ctcggcctcc   138353
caaagtgctg ggattacagg catgagccat tgtgcccggc cacatttttc ttttaaatc   138413
atttttattc aggtacaact tatccaaaaa tcagcaccac tggtttgttt attgcagaaa   138473
aatgaaattt agaagtttgg tctaaatttt ctagctcgct aaggaatctt cgaaaattcc   138533
caattttcct atttctcact aatgtaggaa atatttaaaa gccagcaaag aagaaaacat   138593
cttttaaaat ctcattgtct atacgtaatc actaagaacc ttttgcaact ttcccttata   138653
gttttttaac ctgtatatga ggcgttctct gtcctgaagt aatgtcctgc ctctggctag   138713
ctcctgtgac ggtagccctc ccggggctgg ccctgggtga ggaggggtgg cggcggggag   138773
gtgagcccag gaaaggctgc cctcgccaag gctcggaaac ttcattcgtg caccgcacga   138833
ggcgatggct cagggcaggc ttggacacca atactttgcc agctcctgag gcaccggaca   138893
ggctctggcc agagcttaat tggttagccc tagaacgttc cacgttcacg tcagactcca   138953
tagtagggac tttctcctca gagctgggca ggaggagccc actgagggtg tgccatctct   139013
```

```
gccctccagg gaaagcggga agcaacaggg aaacatccat ctgctccgcc ctagagcccc  139073
tgtcaatttt ggacccaccg ctataggtct tctgccccat actgttagaa aaagatgcag  139133
gttacctggg cacgtaaacg gttttcagga gtggagtgcc tgagatccca gagtccacct  139193
ttcctttata taacactcgt gtcacaggac agattagatt tcttccgtgt ttggagaaca  139253
ttagtccttt aaaatatcag cctgtgctgc aaagtggggt ggattctcta gtctcagtca  139313
ctgtctcagc agtgctgttg aagccctctc acctgctcct tctggacttc ctag gg     139369
                                                                  Arg
ctg cag acc aca aga ctg gga aac cac ttg gaa gac cga gtg aac         139414
Leu Gln Thr Thr Arg Leu Gly Asn His Leu Glu Asp Arg Val Asn
    1330            1335                1340 aaa ttt ttg cgg cgc cag aat cac cct gaa gcc ggg gag gtt ttt         139459
Lys Phe Leu Arg Arg Gln Asn His Pro Glu Ala Gly Glu Val Phe
1345            1350                1355 gtc cga gtg gtg gcc agc tca gac aag acg gtg gag gtc aag ccc         139504
Val Arg Val Val Ala Ser Ser Asp Lys Thr Val Glu Val Lys Pro
    1360            1365                1370 ggg atg aag tca cg gtcagtgtgc tgctctcta cagtgctctg cgagcagtcc       139558
Gly Met Lys Ser Arg
             1375 ccacgcccgc ttgccagagc ctgctctctg caaagctctt gagtttgagg tcatccttcc  139618 aagactttgc agcagcgaat gcgtgcagta gcccccctcag ctgcggttgt cctgtctggg  139678 gttttagtta cccctatacag tgcagtaagc tattttgaga gagagaccac ataccatatt  139738 atagtatact gtttataatt ttcttatttt attattactt attcttgtta atctcttgct  139798 gtgcctaatt tataaattaa aattttgtga ccagtacagg tgtataagaa aaaacgcata  139858 gaggttgata ctgtccatgg tttccagcat ccactgctgg tcttggaaca tacaccccgt  139918 ggataagggg gactgctgta tagccagtcc tcctcagaat cccgtatttc attcacagag  139978 gtgcagttcc ctagtgaggg aaactggtca gaaagcaagt gctccctgct ccggggctga  140038 ctggcccata gggaggactc caggccacgg tctgaggagg tggccatgcc tccgctcatc  140098 tgcagtggcc agagttagag gagcaggcct ggtgtgcaga agcacttgt cagcaacagc    140158 ctttgtaaat gtccggctct ggcttttgtt tcag g ttt gtg gat tct ggg gaa     140211
                                        Phe Val Asp Ser Gly Glu
                                                          1380
atg tct gaa tct ttc cca tat cga acc aaa gct ctg ttt gct ttt         140256
Met Ser Glu Ser Phe Pro Tyr Arg Thr Lys Ala Leu Phe Ala Phe
1385            1390                1395 gag gaa att gac ggc gtg gat gtc tgc ttt ttt gga atg cac gtc         140301
Glu Glu Ile Asp Gly Val Asp Val Cys Phe Phe Gly Met His Val
1400            1405                1410 caa gaa tac ggc tct gat tgc ccc cct cca aac acg ag gtagttttcc       140349
Gln Glu Tyr Gly Ser Asp Cys Pro Pro Pro Asn Thr Arg
1415            1420                1425 agctccttcc agggcgtgtc attcagtgag ccgtgttagg atagaccagg gctcttaagt  140409
gtcccagagg agcctgtgag ccttcatagg ggattaaagt aaatgaaacc acaattaact  140469
aaccaaagta gttagttttg ttttccatta aactagcggg aaatgaactg ttgagatgac  140529
tgcagtgagc gtgttttgtg tggcgagtct gtgtgggacc cgctcttacc taacgcaggt  140589
aaacctgggg agttgggatg ggacagcctg gcacctgaac agaggaagta gctctgccac  140649
gagggcttca tgtgcagtca ggaatctggg caagaaggaa ctaaaagtgg cttttctcag  140709
tttgccttaa ctgtggctct ctgtgccgag tggtgccatt catccttttg ttcagtgacg  140769
```

```
aaaactgaat tccatttaac tgattggcag cagggttggt gactggttgg ttttgggtt    140829
ttggtttgtt tgtttgttta tcacatcctg tttggtggcc agtgtaaata ccatcaaaag   140889
aaaaactggc caatcacagc actgtgggag gccgaggtgg gaggataact ggaccacagg   140949
agtctgagac aagtctgaac aacaaagtga gaccctagct ctacaaaaaa taaattatct   141009
gggcatgatg gtacatgcct tgtcatccta actatgtggg agtctgaggc aggaggattg   141069
cttgagccca tgaggttgag gttgcagtga gctgtgaccg cgtcaccgca ttgcagcctg   141129
aatgacagag caagaccctg tctaaaaagt aaacttccag ggtgttgttt gttgcttgtg   141189
tttgatttca gatttgaggg ataccctgag ttaaacatgt gcctccttcc cacag g     141245 cgt gtg tac att tct tat ctg gat   agt att cat ttc ttc cgg cca      141290
Arg Val Tyr Ile Ser Tyr Leu Asp   Ser Ile His Phe Phe Arg Pro
        1430            1435                    1440 cgt tgc ctc cgc aca gcc gtt tac   cat gag atc ctt att gga tat      141335
Arg Cys Leu Arg Thr Ala Val Tyr   His Glu Ile Leu Ile Gly Tyr
        1445            1450                    1455 tta gag tat gtg aag aaa tta gg    gtgagtttgg attaaattat ttggaactag 141388
Leu Glu Tyr Val Lys Lys Leu Gly
        1460            1465 taagaaccct ttatttttta ctgtatgttt attccgtgaa ataatgggta ttttaagttt   141448
tatgcgtttt tattttttcca tcctaagatc aattcagaat ctccaaagct cctctttcca  141508
ggtgctcccc gagcctcaca ggtctggctc ctgggcacgt agcaagctct ttccctacct   141568
ttacttcctt ttcattccct ttttttttt ttttaacttt attgaggcaa agtttacata    141628
tcatagaatt cccctttttt ggatatatga ttcagtggtt tttagtaact ttacccatta   141688
gtgcaactat cacaagtcag tttcagaaca ttgttattga cctataagat ccctcctgct   141748
gcggtggatc acctgaagtc aggagttcaa gaccagcctg accaacatgg tgaaacccca   141808
tctctactaa aaattaaaaa aaaggccggg cgcggtggct cacacctgta atctcagcac   141868
tttgggaggc cgaggcgggc ggatcacaag gtcaggagtt tgagaccagc ctgaccaaca   141928
tggtgaaacc ctgtctctac taaaaataca aaagttagcc gggcatagta gcatgagcct   141988
gtaatcccag ctactcaaga ggctgaggca ggagaattcc ttgaatccag gaggcggggg   142048
gttgcagtga gctgagattg tgccactgca ctccagcctg ggcgacagag caagactcca   142108
tctcaaaaaa agaaaaaaga aagaaaagaa aaaagaaaaa atacaaaaaa aaattggctc   142168
acctagtctg taatcctagt actttgggag gccaaggcag gtggatcacc tgagatcagg   142228
agttcaagac cagcctgacc aacatggtga accctgtctg tactaaaaaa tacaaaaaat   142288
gagccaggcg tggtggcggg tgcctagcgt aatcccagct cctcaggagg tggggcagg    142348
agagccactc gaaccaggga gacagaggat gcgctgagtc gagatcatgc cattgcactc   142408
caccctgggc aacaacaatg aaactctgcc ccccgcccgc aaaaaaaaaa aagaaaaaa    142468
gaaaaaaaat gttcctcctg cccttgctg ttaaaccttc cctgcccag gcgaccacta     142528
atctactttg tctctctgaa tttgtctttt gtgaatcctg tgtgtaaacg gaaccctgca   142588
gcgtatgctg tcttgggtct ggcttccttc tctagccctt ggtttctgta ctctagacct   142648
gccccattcc cttctgaaac ttgaaaagga tagggcatt tgatcaaagt gtcttgaaca    142708
gaatgaatga ggtttatgtt gacattgacc cttggagaaa aatagtcaac cgaactgcct   142768
ttacagtgca caggaggaag gggatggcat tgccttgatg agccatcata ttccctggtt   142828
ctttaatgag gcctcaggtt tcttttgcag cctcggccct gccctgtgtg tgcacccca    142888
gggagaagtg ttgcagggct aatttgcagg cttgcatttg ctcaggataa agttcgagcc   142948
```

```
ttgcccccac cacacccagc tttgtgggca ttcattctct ctctctggtt acttctgtcc  143008
tggctttagt ccttgctcct ctgctataac tccttaaagg cagggccgat ttcactggca  143068
cgttcatctg acgtgtgtgc gtgggtcctg cag g tat gtg aca ggg cac atc    143120
                                      Tyr Val Thr Gly His Ile
                                                          1470 tgg gcc tgt cct cca agt gaa gga gat gat tac atc ttc cat tgc       143165
Trp Ala Cys Pro Pro Ser Glu Gly Asp Asp Tyr Ile Phe His Cys
        1475            1480                1485 cac cca cct gat caa aaa ata ccc aag cca aaa cga ctg cag gag       143210
His Pro Pro Asp Gln Lys Ile Pro Lys Pro Lys Arg Leu Gln Glu
        1490            1495                1500 tgg tac aaa aag atg ctg gac aag gcg ttt gca gag cgg atc atc       143255
Trp Tyr Lys Lys Met Leu Asp Lys Ala Phe Ala Glu Arg Ile Ile
        1505            1510                1515 cat gac tac aag  gtacccggcg ctgaaggaag gtggtggctt tgtcacaac       143307
His Asp Tyr Lys
        1520 tgagggagg atatttgtgt gccttttct tgcattcgca tacttgttaa ttaccttcac   143367
ttatgaggat tagaaagcag aaaaataaaa gcctaaagtg agaacttaga agcatttctc  143427
tcagctgatt gaggctttcc cctggccgtc tgagagcagc acagttggag ctgtttccat  143487
cagtgggcat tggggcctgt gcatcactgt tgcacacata ggggctccag cactgtggtg  143547
gggggtgcac atgtgtgggg gtctgctgca ctgtggtggg ggggcacaca tgcatgggac  143607
tctgccacac catggtgagg ggcacgcttg cgtgggggtc tgtcgcacca tggtgggggg  143667
cacgcgtgca tggccctcat ctcactgttg tgctttgccc actcag gat att ttc   143722
                                                  Asp Ile Phe aaa caa gca act gaa gac agg ctc acc agt gcc aag gaa ctg ccc      143767
Lys Gln Ala Thr Glu Asp Arg Leu Thr Ser Ala Lys Glu Leu Pro
       1525            1530                1535 tat ttt gaa ggt gat ttc tgg ccc aat gtg tta gaa gag agc att      143812
Tyr Phe Glu Gly Asp Phe Trp Pro Asn Val Leu Glu Glu Ser Ile
       1540            1545                1550 aag gaa cta gaa caa gaa gaa gag gag agg aaa aag gaa gag agc      143857
Lys Glu Leu Glu Gln Glu Glu Glu Glu Arg Lys Lys Glu Glu Ser
       1555            1560                1565 act gca gcc agt gaa acc act gag  gtacagaccc ttctctgagc           143901
Thr Ala Ala Ser Glu Thr Thr Glu
       1570            1575 tccattgccc acgtgtcccg ctggagctgc agggtggcag ctgggaggc gcgtgtcgac  143961 tgttaggtcc ttcctgtggt ggtgtctccg ttcacacatg cacgtcgaca ccacctgcag  144021
cacagggcgt tggtgggcag cagtgtgggc tctgcactct ctgcacagtg gatgctctgg  144081
ggagctgggg gtccacttag actcggagag ggaagagagg aagacagaaa atgggacatg  144141
gggcagtcag gacacaaccc gctgatgtaa aaagtgagtc gaggaggcac agggttgcca  144201
ggccttattc cgtgtttggt ggccactctg cacatgatgc tcatgccctg ctgccctctc  144261
tccttggcgc tgcccctgag tgccaggcag tgcagactga gccaaacaaa accccatccc  144321
tggccaggcg cggtggctca cctgtaacc cccgcacttt gggaggccga ggcaggcgga   144381
tcacaaggtc aggaaaggga gaccagcctg gctaacacag tgaaacccca tctctactaa  144441
aaatacaaaa atttagccgg ttgtgggagg gggcacctgt aatcccagct acgagggagg  144501
ttgaggcagg agaatcgctt gaacccggga ggcggaggtt gcagtgagcc tagattgcgc  144561
cgttgcactc cagcccagga gacagtgcga gactccgttt cagaacaaac aaaacccat  144621
```

```
ctccgccccc aagggagtgg ctgtgtcctg gtaggatgtg aaacaaaaag aacccagacc   144681
caagcatggt gtgctctgag cgtggcagag ctctgaaggg gaaggagcct tggggaggtg   144741
gcgtgtgggc cagacccgcc caccacagga aggtgctgga agaggacccg ccaggcggtg   144801
ggaggaggcg cgctgtgtgc gggtttgtgc ggctgtctgg ggaagagatg atggtggcgt   144861
gggtgtgggc tgtagctgta ggtgcaggga gagcgatgac gaacgttgaa ggctgcagcc   144921
ccagaacttg ggacaggcga ttgtgaccag tgaggaaaag cggtgaatgg aggtggctct   144981
tgcgtgggct gctgccatgg gtgaggcagc cgggagccgg ctggggacat actgccactc   145041
tggtgcctgt cccatatgag agcacgtctg tgaggtgggt gccggatggg ctgtaggcgg   145101
agcgtggggc ctgggccgct tccgccacac acactcgtgc tcactgcaca ggtggttgag   145161
aggcagccac ctgctggacg cgcccccaga gtgtcattcg caggacagag gaggcgcggg   145221
caggggtgg cgtgggttta cgccctaggt ggctcctaag cagagctcct ggcctgttgt    145281
cttcggactt gctcccgctg gagtgtagct ggtctcactg gtgtctggtg agttaatgct   145341
tgagttccat ctcctaaggg tgacacggga ggttaccgcg tccgagacag gctttgcgca   145401
gctgagttcc accccaggag ggggcacctg cctgtggcat ggcagcagtg gggttgtcca   145461
gaagacaggc tgatagggg ctcctgctgg ggcagccttc cctgtgcacc ggggacatgc    145521
atgtgttagg aggcgggatg ctgaggtgtc ggcatgtaga cctgctgtcc cttgtgtgtt   145581
tggttcatgg acaacaatgg gcagggacat gccttcgtca gcaacacccc aggagctcgc   145641
tctggggggtc agccttagtg agggctggtg cgtggggtgg agcactgctt tgctattagc   145701
tctgctctgc atcatgctgt caattctggg aaatggggaa aggctcgcga tagtgtcagg   145761
tggggcgaga aacggaacca gctccctgtg tgcagtccca gcttcgtgag gaatgtcgca   145821
aacacggaga caaatgtgcc cagggaaagc tccagaacac agaacactgc tgctcgggaa   145881
gaccagaaaa acaaaacttt ttaaaattac ttgtctatat tttcttaatt tcatgaacat   145941
atttatttta taatttttgta aaaatagact tccaggccgg gcgtggtggc tcacgcctgt   146001
aatcccagca ctttgagagg ccaaggcagg tggatcactt gaggtcagga gtttgagacc   146061
agcttggcca acatggtgaa accccgtctc tactaaaaat acaaaaatta gccaggtgtg   146121
gtggcgcacg cctgtagtcc cagctacttg ggaggctgag gcaggagaat cacttgaacc   146181
cgggaggcac agattgcagt gagccaagat tgtgccactg cactccagcc tggtgacaga   146241
gcgagactcc atctcaaaaa aaataggctt cctttgtttt aaggctgaca caaaaattga   146301
gcacagagtt ccagtatatt gcagcacgca gtttctcctg ttactaatgt cttaccttag   146361
tgtggcacat ttgctgccac ggtgagccat ttgttgatgt tgatgcatta ttgttaagtc   146421
tacacttcgt tccaatttcc tcagttttcc cctgacgtcc ctttctgtc tctgaatcct    146481
gcggaggacc cacgtgatat ttgggctcct cgggctgctt gtcggtgggg tgggaatttt   146541
tttttttttt ttttgagatg gagtctcgct ctgtcgccca ggctgagtg cagtggcgcc    146601
atctcagctc actgcaagct ccgcctcccg ggttcacacc attctcctgc ctcagcctcc   146661
cgagtaggtg ggactgcagg cacccgccac cacgcctggc taattttttg tgttttagt    146721
agagacggag tttcaccgtg ttagccaggt tggtcttgat ttcctgacct cgagatccgc   146781
ctgccttggc cttccaaagt gctgggatta caggtgtgag ccaccccgcc cggctggatt   146841
gttgaattct ctctggactg accccctctct ttgaacacca agagtctctc tcatcttgtt   146901
aaaaatgaaa ctctctggct gggcacggtg gctcatgcct gtaatctcag cactttggga   146961
ggctcaggcg ggcggatcac cgaggtccg gagttcaagg ccagcctgac caacatggtg    147021
```

-continued

```
aaacccatc tctactaaaa atacaaaaat tagctgggtg tggtggcagc acctataatc  147081
tcagctacta gggaggttca ggcaggagaa tcgcttgaac cttggaggca gaggttgcag  147141
tgagccgaga tcgcgttatt gcacttcagc ttgggtgaca agagcgagac tctgtctcaa  147201
aaaaaatgat aggtagccgg gcatggtggc gggtgcctat aatcccagct acccaggagg  147261
ctgaggcagg agaatcactt gaacccaaga tgacaccact gcactccagc ctggcaacaa  147321
gagcaaaact ccgtctctca aaaaaaataa agctctctgt taaagtgtaa gtgagtggta  147381
atcctgcgtt ctttccagag gaggagcctg tgggctgaga gcaagcccac cttcagccag  147441
tcaggcgcag cactgatggc cccagcaggg agccagcctg ctctccgtgg gccttgagtg  147501
gaccccgcag gggcctcaga gtccctgctc ttgatggggc agctgctttt cccatcagca  147561
gctttcctgt ctcctggaag ctctcatgct ttctcgggtg tgtagagcct tcctcaaggc  147621
agacagctgc tgaccacagt tgtgacgtgg aatcttccgc atctggttgt ggcacagtgg  147681
aaacagcccc cactgccctc atttgttaat ttctgaactc gcactctggg tctcttttcc  147741
cctttagagg cagcgtggca taaagctgat aatgacacca gcctggccga ggacaggccc  147801
tgctctgtcc cgaaggctgc agcacctaca gccacctgta gccgttcacg tatgggtct   147861 gcctggtggt gacctacttt ggcctgagct tcctgatgcc cacggcctgg gagctgggcg  147921
tccgtgccaa gtgtggaggg gcacttgcct ggtctcacag ccttgcgtgt tgttgcag    147979
```

| | | | | | | | | | | |
|---|---|---|---|---|---|---|---|---|---|---|
| ggc | agt | cag | ggc | gac | agc | aag | aat | gcc | aag aag aag aac aac aag | 148024 |
| Gly | Ser | Gln | Gly | Asp | Ser | Lys | Asn | Ala | Lys Lys Lys Asn Asn Lys | |
| | | | 1580 | | | | 1585 | | 1590 | |

| | | | | | | | | | | |
|---|---|---|---|---|---|---|---|---|---|---|
| aaa | acc | aac | aag | aac | aaa | agc | agc | atc | agc cgc gcc aac aag aag | 148069 |
| Lys | Thr | Asn | Lys | Asn | Lys | Ser | Ser | Ile | Ser Arg Ala Asn Lys Lys | |
| | | | 1595 | | | | 1600 | | 1605 | |

| | | | | | | | | | | |
|---|---|---|---|---|---|---|---|---|---|---|
| aag | ccc | agc | atg | ccc | aac | gtg | tcc | aat | gac ctg tcc cag aag ctg | 148114 |
| Lys | Pro | Ser | Met | Pro | Asn | Val | Ser | Asn | Asp Leu Ser Gln Lys Leu | |
| | | | 1610 | | | | 1615 | | 1620 | |

| | | | | | | | |
|---|---|---|---|---|---|---|---|
| tat | gcc | acc | atg | gag | aag | cac | aag | gag gtaggcgtgg gctgcggtgc | 148161 |
| Tyr | Ala | Thr | Met | Glu | Lys | His | Lys | Glu | |
| | | | 1625 | | | | 1630 | | |

```
tgcagccgtg cctctggccg ggaggaggga aagactcgca gctggcgggc gtgggcccgt  148221
gtgcaggtct gtggtgggag ggaagtggcc cccaggaaac caagtggacc agttgggtga  148281
catcatgcaa cgtgtcacca attttgttcc atcccaaggc atcagggcca tcaggctcag  148341
ccacctgcct attctgcagg ctgggtggct gcgcctgccc tgagctcacc actggaggtg  148401
ccatgtccct tgtgtgggac taaagcccct cctctcctgc ag gtc ttc ttc gtg    148455
```
| | | | | | |
|---|---|---|---|---|---|
| | | | | | Val Phe Phe Val |

| | | | | | | | | | | |
|---|---|---|---|---|---|---|---|---|---|---|
| atc | cac | ctg | cac | gct | ggg | cct | gtc | atc | aac acc ctg ccc ccc atc | 148500 |
| Ile | His | Leu | His | Ala | Gly | Pro | Val | Ile | Asn Thr Leu Pro Pro Ile | |
| 1635 | | | | 1640 | | | | 1645 | | |

| | | | | | | | | | | |
|---|---|---|---|---|---|---|---|---|---|---|
| gtc | gac | ccc | gac | ccc | ctg | ctc | agc | tgt | gac ctc atg gat ggg cgc | 148545 |
| Val | Asp | Pro | Asp | Pro | Leu | Leu | Ser | Cys | Asp Leu Met Asp Gly Arg | |
| 1650 | | | | 1655 | | | | 1660 | | |

| | | | | | | | | | | |
|---|---|---|---|---|---|---|---|---|---|---|
| gac | gcc | ttc | ctc | acc | ctc | gcc | aga | gac | aag cac tgg gag ttc tcc | 148590 |
| Asp | Ala | Phe | Leu | Thr | Leu | Ala | Arg | Asp | Lys His Trp Glu Phe Ser | |
| 1665 | | | | 1670 | | | | 1675 | | |

| | | | | | | | | | | |
|---|---|---|---|---|---|---|---|---|---|---|
| tcc | ttg | cgc | cgc | tcc | aag | tgg | tcc | acg | ctc tgc atg ctg gtg gag | 148635 |
| Ser | Leu | Arg | Arg | Ser | Lys | Trp | Ser | Thr | Leu Cys Met Leu Val Glu | |
| 1680 | | | | 1685 | | | | 1690 | | |

| | | | | | | | | | | |
|---|---|---|---|---|---|---|---|---|---|---|
| ctg | cac | acc | cag | ggc | cag | gac | cgc | ttt | gtc tac acc tgc aac gag | 148680 |
| Leu | His | Thr | Gln | Gly | Gln | Asp | Arg | Phe | Val Tyr Thr Cys Asn Glu | |
| 1695 | | | | 1700 | | | | 1705 | | |

```
tgc  aag  cac  cac  gtg  gag  acg  cgc  tgg  cac  tgc  act  gtg  tgc  gag    148725
Cys  Lys  His  His  Val  Glu  Thr  Arg  Trp  His  Cys  Thr  Val  Cys  Glu
1710                1715                     1720 gtaggccctg cccccacccc cacccccaca gccggcctgg ggtctgacga agcatcctgt            148785
cccctttgcat gggtgcccgg gttggtgtct gtacctgatg gtggctgcac tgactcctcc           148845
agaactagga cagcgtcaca aggcagaagg cgttgctgtg tgtgtgtttc ctaaacctgc            148905
tctgtgtagc cacagccaca ggcctgaccc tggggacggc cagagggagg ctctgctggg            148965
aagtctggcc tgtctgtgcc cagttctagt cttgctaaat ggctggaaac cccgctgtc             149025
ctgttggcag cttgggcccc tctggccact tgttcctgaa ggaccccccg gtcatgctcc            149085
ctcactcccc tctaggaatt ttgaccccccc tgtgaaatga cgtgggtgtc ccttgcatgg           149145
gccgagtcag gctgtgcagg gcaggcaggt gacagatccc accatccccc tcccaggaca           149205
gtcaccatca cctgccaacc cggagcctcc tcacttgctg tggtgtctgt agcggggcag            149265
agcgggtcct cagcagagcg agggcctttc ttccctcccc accttcacac acttcttccg            149325
cttctccacct ttctccagtc tcctttgtcc tctttctagt ttctgaatgc ggcagttttc           149385
atatcttttt gtgaacacag tcatggtacc tggtcctagg gctccatcag gttgccaggt            149445
gcgagcagtt ttcagtaact tgggcttgcg cgttgggaa gtcccactgg tgcactgcgg             149505
atagctcagg cctcccaga ggcacttcac ggcagctgtc ggcgctttgg gagggaccgg             149565
cctccctcag cctttcactg tctggcttca tagtttgagt acaggagttg gacaggctgt            149625
ggcaagggct gatgtgactc ccaggtcaga ggaagtcgga aggaaggggg ctggtgtcta            149685
ctgtccgtga gcttacaggc caggggttct tggggcatgg gtcaggttat ctttgagcct           149745
tcagggctgt tgccaggagt gaaggtcctt gggagcaaca cataggcagt ccatgccccc            149805
gtcctgtcca tgatcccatg ttgtccatga tcccatcccg tccatgatcc catcttgtcc            149865
gtgctcccgc cctgtccggg tctcccacct gtccgtgctc gcatcctgtc tgggtctcct            149925
atcctgcctg ggtctcctgg cacagaccca gacttagcgg tggagggaag cagccaggat            149985
gcctggtggt actgggtccc atgctgacac cggcctgtcc cctttccttg cttgcag              150042 gac  tac  gac  ctc  tgc  atc  aac  tgc  tat  aac  acg  aag  agc  cat  gcc    150087
Asp  Tyr  Asp  Leu  Cys  Ile  Asn  Cys  Tyr  Asn  Thr  Lys  Ser  His  Ala
1725                1730                     1735 cat  aag  atg  gtg  aag  tgg  ggg  ctg  ggc  ctg  gat  gac  gag  ggc  agc    150132
His  Lys  Met  Val  Lys  Trp  Gly  Leu  Gly  Leu  Asp  Asp  Glu  Gly  Ser
1740                1745                     1750 agc  cag  ggc  gag  cca  cag  tca  aag  agc  ccc  cag  gag  tca  cgc  cgg    150177
Ser  Gln  Gly  Glu  Pro  Gln  Ser  Lys  Ser  Pro  Gln  Glu  Ser  Arg  Arg
1755                1760                     1765 ctg  agc  atc  cag  cgc  tgc  atc  cag  tcg  ctg  gtg  cac  gcg  tgc  cag    150222
Leu  Ser  Ile  Gln  Arg  Cys  Ile  Gln  Ser  Leu  Val  His  Ala  Cys  Gln
1770                1775                     1780 tgc  cgc  aac  gcc  aac  tgc  tcg  ctg  cca  tcc  tgc  cag  aag  atg  aag    150267
Cys  Arg  Asn  Ala  Asn  Cys  Ser  Leu  Pro  Ser  Cys  Gln  Lys  Met  Lys
1785                1790                     1795 cgg  gtg  gtg  cag  cac  acc  aag  ggc  tgc  aaa  cgc  aag  acc  aac  ggg    150312
Arg  Val  Val  Gln  His  Thr  Lys  Gly  Cys  Lys  Arg  Lys  Thr  Asn  Gly
1800                1805                     1810 ggc  tgc  ccg  gtg  tgc  aag  cag  ctc  atc  gcc  ctc  tgc  tgc  tac  cac    150357
Gly  Cys  Pro  Val  Cys  Lys  Gln  Leu  Ile  Ala  Leu  Cys  Cys  Tyr  His
1815                1820                     1825 gcc  aag  cac  tgc  caa  gaa  aac  aaa  tgc  ccc  gtg  ccc  ttc  tgc  ctc    150402
Ala  Lys  His  Cys  Gln  Glu  Asn  Lys  Cys  Pro  Val  Pro  Phe  Cys  Leu
```

|     |     |     |     |     |     |     |     |     |     |     |     |     |     |     |       |
| --- | --- | --- | --- | --- | --- | --- | --- | --- | --- | --- | --- | --- | --- | --- | ----- |
| aac | atc | aaa | cac | aag | ctc | cgc | cag | cag | cag | atc | cag | cac | cgc | ctg | 150447 |
| Asn | Ile | Lys | His | Lys | Leu | Arg | Gln | Gln | Gln | Ile | Gln | His | Arg | Leu |       |
| 1845 |   |   |   |   | 1850 |   |   |   |   | 1855 |   |   |   |   |       |
| cag | cag | gcc | cag | ctc | atg | cgc | cgg | cgg | atg | gcc | acc | atg | aac | acc | 150492 |
| Gln | Gln | Ala | Gln | Leu | Met | Arg | Arg | Arg | Met | Ala | Thr | Met | Asn | Thr |       |
| 1860 |   |   |   |   | 1865 |   |   |   |   | 1870 |   |   |   |   |       |
| cgc | aac | gtg | cct | cag | cag | agt | ctg | cct | tct | cct | acc | tca | gca | ccg | 150537 |
| Arg | Asn | Val | Pro | Gln | Gln | Ser | Leu | Pro | Ser | Pro | Thr | Ser | Ala | Pro |       |
| 1875 |   |   |   |   | 1880 |   |   |   |   | 1885 |   |   |   |   |       |
| ccc | ggg | acc | ccc | aca | cag | cag | ccc | agc | aca | ccc | cag | acg | ccg | cag | 150582 |
| Pro | Gly | Thr | Pro | Thr | Gln | Gln | Pro | Ser | Thr | Pro | Gln | Thr | Pro | Gln |       |
| 1890 |   |   |   |   | 1895 |   |   |   |   | 1900 |   |   |   |   |       |
| ccc | cct | gcc | cag | ccc | caa | ccc | tca | ccc | gtg | agc | atg | tca | cca | gct | 150627 |
| Pro | Pro | Ala | Gln | Pro | Gln | Pro | Ser | Pro | Val | Ser | Met | Ser | Pro | Ala |       |
| 1905 |   |   |   |   | 1910 |   |   |   |   | 1915 |   |   |   |   |       |
| ggc | ttc | ccc | agc | gtg | gcc | cgg | act | cag | ccc | ccc | acc | acg | gtg | tcc | 150672 |
| Gly | Phe | Pro | Ser | Val | Ala | Arg | Thr | Gln | Pro | Pro | Thr | Thr | Val | Ser |       |
| 1920 |   |   |   |   | 1925 |   |   |   |   | 1930 |   |   |   |   |       |
| aca | ggg | aag | cct | acc | agc | cag | gtg | ccg | gcc | ccc | cca | ccc | ccg | gcc | 150717 |
| Thr | Gly | Lys | Pro | Thr | Ser | Gln | Val | Pro | Ala | Pro | Pro | Pro | Pro | Ala |       |
| 1935 |   |   |   |   | 1940 |   |   |   |   | 1945 |   |   |   |   |       |
| cag | ccc | cct | cct | gca | gcg | gtg | gaa | gcg | gct | cgg | cag | atc | gag | cgt | 150762 |
| Gln | Pro | Pro | Pro | Ala | Ala | Val | Glu | Ala | Ala | Arg | Gln | Ile | Glu | Arg |       |
| 1950 |   |   |   |   | 1955 |   |   |   |   | 1960 |   |   |   |   |       |
| gag | gcc | cag | cag | cag | cag | cac | ctg | tac | cgg | gtg | aac | atc | aac | aac | 150807 |
| Glu | Ala | Gln | Gln | Gln | Gln | His | Leu | Tyr | Arg | Val | Asn | Ile | Asn | Asn |       |
| 1965 |   |   |   |   | 1970 |   |   |   |   | 1975 |   |   |   |   |       |
| agc | atg | ccc | cca | gga | cgc | acg | ggc | atg | ggg | acc | ccg | ggg | agc | cag | 150852 |
| Ser | Met | Pro | Pro | Gly | Arg | Thr | Gly | Met | Gly | Thr | Pro | Gly | Ser | Gln |       |
| 1980 |   |   |   |   | 1985 |   |   |   |   | 1990 |   |   |   |   |       |
| atg | gcc | ccc | gtg | agc | ctg | aat | gtg | ccc | cga | ccc | aac | cag | gtg | agc | 150897 |
| Met | Ala | Pro | Val | Ser | Leu | Asn | Val | Pro | Arg | Pro | Asn | Gln | Val | Ser |       |
| 1995 |   |   |   |   | 2000 |   |   |   |   | 2005 |   |   |   |   |       |
| ggg | ccc | gtc | atg | ccc | agc | atg | cct | ccc | ggg | cag | tgg | cag | cag | gcg | 150942 |
| Gly | Pro | Val | Met | Pro | Ser | Met | Pro | Pro | Gly | Gln | Trp | Gln | Gln | Ala |       |
| 2010 |   |   |   |   | 2015 |   |   |   |   | 2020 |   |   |   |   |       |
| ccc | ctt | ccc | cag | cag | cag | ccc | atg | cca | ggc | ttg | ccc | agg | cct | gtg | 150987 |
| Pro | Leu | Pro | Gln | Gln | Gln | Pro | Met | Pro | Gly | Leu | Pro | Arg | Pro | Val |       |
| 2025 |   |   |   |   | 2030 |   |   |   |   | 2035 |   |   |   |   |       |
| ata | tcc | atg | cag | gcc | cag | gcg | gcc | gtg | gct | ggg | ccc | cgg | atg | ccc | 151032 |
| Ile | Ser | Met | Gln | Ala | Gln | Ala | Ala | Val | Ala | Gly | Pro | Arg | Met | Pro |       |
| 2040 |   |   |   |   | 2045 |   |   |   |   | 2050 |   |   |   |   |       |
| agc | gtg | cag | cca | ccc | agg | agc | atc | tca | ccc | agc | gct | ctg | caa | gac | 151077 |
| Ser | Val | Gln | Pro | Pro | Arg | Ser | Ile | Ser | Pro | Ser | Ala | Leu | Gln | Asp |       |
| 2055 |   |   |   |   | 2060 |   |   |   |   | 2065 |   |   |   |   |       |
| ctg | ctg | cgg | acc | ctg | aag | tcg | ccc | agc | tcc | cct | cag | cag | caa | cag | 151122 |
| Leu | Leu | Arg | Thr | Leu | Lys | Ser | Pro | Ser | Ser | Pro | Gln | Gln | Gln | Gln |       |
| 2070 |   |   |   |   | 2075 |   |   |   |   | 2080 |   |   |   |   |       |
| cag | gtg | ctg | aac | att | ctc | aaa | tca | aac | ccg | cag | cta | atg | gca | gct | 151167 |
| Gln | Val | Leu | Asn | Ile | Leu | Lys | Ser | Asn | Pro | Gln | Leu | Met | Ala | Ala |       |
| 2085 |   |   |   |   | 2090 |   |   |   |   | 2095 |   |   |   |   |       |
| ttc | atc | aaa | cag | cgc | aca | gcc | aag | tac | gtg | gcc | aat | cag | ccc | ggc | 151212 |
| Phe | Ile | Lys | Gln | Arg | Thr | Ala | Lys | Tyr | Val | Ala | Asn | Gln | Pro | Gly |       |
| 2100 |   |   |   |   | 2105 |   |   |   |   | 2110 |   |   |   |   |       |
| atg | cag | ccc | cag | cct | ggc | ctc | cag | tcc | cag | ccc | ggc | atg | caa | ccc | 151257 |
| Met | Gln | Pro | Gln | Pro | Gly | Leu | Gln | Ser | Gln | Pro | Gly | Met | Gln | Pro |       |
| 2115 |   |   |   |   | 2120 |   |   |   |   | 2125 |   |   |   |   |       |
| cag | cct | ggc | atg | cac | cag | cag | ccc | agc | ctg | cag | aac | ctg | aat | gcc | 151302 |

```
Gln  Pro  Gly  Met  His  Gln  Gln  Pro  Ser  Leu  Gln  Asn  Leu  Asn  Ala
2130                2135                          2140 atg  cag  gct  ggc  gtg  ccg  cgg  ccc  ggt  gtg  cct  cca  cag  cag  cag      151347
Met  Gln  Ala  Gly  Val  Pro  Arg  Pro  Gly  Val  Pro  Pro  Gln  Gln  Gln
2145                2150                          2155 gcg  atg  gga  ggc  ctg  aac  ccc  cag  ggc  cag  gcc  ttg  aac  atc  atg      151392
Ala  Met  Gly  Gly  Leu  Asn  Pro  Gln  Gly  Gln  Ala  Leu  Asn  Ile  Met
2160                2165                          2170 aac  cca  gga  cac  aac  ccc  aac  atg  gcg  agt  atg  aat  cca  cag  tac      151437
Asn  Pro  Gly  His  Asn  Pro  Asn  Met  Ala  Ser  Met  Asn  Pro  Gln  Tyr
2175                2180                          2185 cga  gaa  atg  tta  cgg  agg  cag  ctg  ctg  cag  cag  cag  caa  cag          151482
Arg  Glu  Met  Leu  Arg  Arg  Gln  Leu  Leu  Gln  Gln  Gln  Gln  Gln
2190                2195                          2200 cag  cag  caa  caa  cag  cag  caa  cag  cag  cag  caa  ggg  agt  gcc          151527
Gln  Gln  Gln  Gln  Gln  Gln  Gln  Gln  Gln  Gln  Gln  Gly  Ser  Ala
2205                2210                          2215 ggc  atg  gct  ggg  ggc  atg  gcg  ggg  cac  ggc  cag  ttc  cag  cag  cct      151572
Gly  Met  Ala  Gly  Gly  Met  Ala  Gly  His  Gly  Gln  Phe  Gln  Gln  Pro
2220                2225                          2230 caa  gga  ccc  gga  ggc  tac  cca  ccg  gcc  atg  cag  cag  cag  cag  cgc      151617
Gln  Gly  Pro  Gly  Gly  Tyr  Pro  Pro  Ala  Met  Gln  Gln  Gln  Gln  Arg
2235                2240                          2245 atg  cag  cag  cat  ctc  ccc  ctc  cag  ggc  agc  tcc  atg  ggc  cag  atg      151662
Met  Gln  Gln  His  Leu  Pro  Leu  Gln  Gly  Ser  Ser  Met  Gly  Gln  Met
2250                2255                          2260 gcg  gct  cag  atg  gga  cag  ctt  ggc  cag  atg  ggg  cag  ccg  ggg  ctg      151707
Ala  Ala  Gln  Met  Gly  Gln  Leu  Gly  Gln  Met  Gly  Gln  Pro  Gly  Leu
2265                2270                          2275 ggg  gca  gac  agc  acc  ccc  aac  atc  cag  caa  gcc  ctg  cag  cag  cgg      151752
Gly  Ala  Asp  Ser  Thr  Pro  Asn  Ile  Gln  Gln  Ala  Leu  Gln  Gln  Arg
2280                2285                          2290 att  ctg  cag  caa  cag  cag  atg  aag  cag  cag  att  ggg  tcc  cca  ggc      151797
Ile  Leu  Gln  Gln  Gln  Gln  Met  Lys  Gln  Gln  Ile  Gly  Ser  Pro  Gly
2295                2300                          2305 cag  ccg  aac  ccc  atg  agc  ccc  cag  caa  cac  atg  ctc  tca  gga  cag      151842
Gln  Pro  Asn  Pro  Met  Ser  Pro  Gln  Gln  His  Met  Leu  Ser  Gly  Gln
2310                2315                          2320 cca  cag  gcc  tcg  cat  ctc  cct  ggc  cag  cag  atc  gcc  acg  tcc  ctt      151887
Pro  Gln  Ala  Ser  His  Leu  Pro  Gly  Gln  Gln  Ile  Ala  Thr  Ser  Leu
2325                2330                          2335 agt  aac  cag  gtg  cgg  tct  cca  gcc  cct  gtc  cag  tct  cca  cgg  ccc      151932
Ser  Asn  Gln  Val  Arg  Ser  Pro  Ala  Pro  Val  Gln  Ser  Pro  Arg  Pro
2340                2345                          2350 cag  tcc  cag  cct  cca  cat  tcc  agc  ccg  tca  cca  cgg  ata  cag  ccc      151977
Gln  Ser  Gln  Pro  Pro  His  Ser  Ser  Pro  Ser  Pro  Arg  Ile  Gln  Pro
2355                2360                          2365 cag  cct  tcg  cca  cac  cac  gtc  tca  ccc  cag  act  ggt  tcc  ccc  cac      152022
Gln  Pro  Ser  Pro  His  His  Val  Ser  Pro  Gln  Thr  Gly  Ser  Pro  His
2370                2375                          2380 ccc  gga  ctc  gca  gtc  acc  atg  gcc  agc  tcc  ata  gat  cag  gga  cac      152067
Pro  Gly  Leu  Ala  Val  Thr  Met  Ala  Ser  Ser  Ile  Asp  Gln  Gly  His
2385                2390                          2395 ttg  ggg  aac  ccc  gaa  cag  agt  gca  atg  ctc  ccc  cag  ctg  aac  acc      152112
Leu  Gly  Asn  Pro  Glu  Gln  Ser  Ala  Met  Leu  Pro  Gln  Leu  Asn  Thr
2400                2405                          2410 ccc  agc  agg  agt  gcg  ctg  tcc  agc  gaa  ctg  tcc  ctg  gtc  ggg  gac      152157
Pro  Ser  Arg  Ser  Ala  Leu  Ser  Ser  Glu  Leu  Ser  Leu  Val  Gly  Asp
2415                2420                          2425
```

```
acc acg ggg gac acg cta gag aag ttt gtg gag ggc ttg tag              152199
Thr Thr Gly Asp Thr Leu Glu Lys Phe Val Glu Gly Leu
2430                2435                2440
```

<210> SEQ ID NO 2
<211> LENGTH: 7329
<212> TYPE: DNA
<213> ORGANISM: Homo sapiens
<220> FEATURE:
<221> NAME/KEY: CDS
<222> LOCATION: (1)..(7326)

<400> SEQUENCE: 2

```
atg gct gag aac ttg ctg gac gga ccg ccc aac ccc aaa aga gcc aaa     48
Met Ala Glu Asn Leu Leu Asp Gly Pro Pro Asn Pro Lys Arg Ala Lys
1               5                   10                  15 ctc agc tcg ccc ggt ttc tcg gcg aat gac agc aca gat ttt gga tca     96
Leu Ser Ser Pro Gly Phe Ser Ala Asn Asp Ser Thr Asp Phe Gly Ser
                20                  25                  30 ttg ttt gac ttg gaa aat gat ctt cct gat gag ctg ata ccc aat gga    144
Leu Phe Asp Leu Glu Asn Asp Leu Pro Asp Glu Leu Ile Pro Asn Gly
            35                  40                  45 gga gaa tta ggc ctt tta aac agt ggg aac ctt gtt cca gat gct gct    192
Gly Glu Leu Gly Leu Leu Asn Ser Gly Asn Leu Val Pro Asp Ala Ala
        50                  55                  60 tcc aaa cat aaa caa ctg tcg gag ctt cta cga gga ggc agc ggc tct    240
Ser Lys His Lys Gln Leu Ser Glu Leu Leu Arg Gly Gly Ser Gly Ser
65                  70                  75                  80 agt atc aac cca gga ata gga aat gtg agc gcc agc agc ccc gtg cag    288
Ser Ile Asn Pro Gly Ile Gly Asn Val Ser Ala Ser Ser Pro Val Gln
                85                  90                  95 cag ggc ctg ggt ggc cag gct caa ggg cag ccg aac agt gct aac atg    336
Gln Gly Leu Gly Gly Gln Ala Gln Gly Gln Pro Asn Ser Ala Asn Met
                100                 105                 110 gcc agc ctc agt gcc atg ggc aag agc cct ctg agc cag gga gat tct    384
Ala Ser Leu Ser Ala Met Gly Lys Ser Pro Leu Ser Gln Gly Asp Ser
            115                 120                 125 tca gcc ccc agc ctg cct aaa cag gca gcc agc acc tct ggg ccc acc    432
Ser Ala Pro Ser Leu Pro Lys Gln Ala Ala Ser Thr Ser Gly Pro Thr
        130                 135                 140 ccc gct gcc tcc caa gca ctg aat ccg caa gca caa aag caa gtg ggg    480
Pro Ala Ala Ser Gln Ala Leu Asn Pro Gln Ala Gln Lys Gln Val Gly
145                 150                 155                 160 ctg gcg act agc agc cct gcc acg tca cag act gga cct ggt atc tgc    528
Leu Ala Thr Ser Ser Pro Ala Thr Ser Gln Thr Gly Pro Gly Ile Cys
                165                 170                 175 atg aat gct aac ttt aac cag acc cac cca ggc ctc ctc aat agt aac    576
Met Asn Ala Asn Phe Asn Gln Thr His Pro Gly Leu Leu Asn Ser Asn
                180                 185                 190 tct ggc cat agc tta att aat cag gct tca caa ggg cag gcg caa gtc    624
Ser Gly His Ser Leu Ile Asn Gln Ala Ser Gln Gly Gln Ala Gln Val
            195                 200                 205 atg aat gga tct ctt ggg gct gct ggc aga gga agg gga gct gga atg    672
Met Asn Gly Ser Leu Gly Ala Ala Gly Arg Gly Arg Gly Ala Gly Met
        210                 215                 220 ccg tac cct act cca gcc atg cag ggc gcc tcg agc agc gtg ctg gct    720
Pro Tyr Pro Thr Pro Ala Met Gln Gly Ala Ser Ser Ser Val Leu Ala
225                 230                 235                 240 gag acc cta acg cag gtt tcc ccg caa atg act ggt cac gcg gga ctg    768
Glu Thr Leu Thr Gln Val Ser Pro Gln Met Thr Gly His Ala Gly Leu
                245                 250                 255
```

| | | |
|---|---|---|
| aac acc gca cag gca gga ggc atg gcc aag atg gga ata act ggg aac<br>Asn Thr Ala Gln Ala Gly Gly Met Ala Lys Met Gly Ile Thr Gly Asn<br>260 265 270 | | 816 |
| aca agt cca ttt gga cag ccc ttt agt caa gct gga ggg cag cca atg<br>Thr Ser Pro Phe Gly Gln Pro Phe Ser Gln Ala Gly Gly Gln Pro Met<br>275 280 285 | | 864 |
| gga gcc act gga gtg aac ccc cag tta gcc agc aaa cag agc atg gtc<br>Gly Ala Thr Gly Val Asn Pro Gln Leu Ala Ser Lys Gln Ser Met Val<br>290 295 300 | | 912 |
| aac agt ttg ccc acc ttc cct aca gat atc aag aat act tca gtc acc<br>Asn Ser Leu Pro Thr Phe Pro Thr Asp Ile Lys Asn Thr Ser Val Thr<br>305 310 315 320 | | 960 |
| aac gtg cca aat atg tct cag atg caa aca tca gtg gga att gta ccc<br>Asn Val Pro Asn Met Ser Gln Met Gln Thr Ser Val Gly Ile Val Pro<br>325 330 335 | | 1008 |
| aca caa gca att gca aca ggc ccc act gca gat cct gaa aaa cgc aaa<br>Thr Gln Ala Ile Ala Thr Gly Pro Thr Ala Asp Pro Glu Lys Arg Lys<br>340 345 350 | | 1056 |
| ctg ata cag cag cag ctg gtt cta ctg ctt cat gct cat aag tgt cag<br>Leu Ile Gln Gln Gln Leu Val Leu Leu Leu His Ala His Lys Cys Gln<br>355 360 365 | | 1104 |
| aga cga gag caa gca aac gga gag gtt cgg gcc tgc tcg ctc ccg cat<br>Arg Arg Glu Gln Ala Asn Gly Glu Val Arg Ala Cys Ser Leu Pro His<br>370 375 380 | | 1152 |
| tgt cga acc atg aaa aac gtt ttg aat cac atg acg cat tgt cag gct<br>Cys Arg Thr Met Lys Asn Val Leu Asn His Met Thr His Cys Gln Ala<br>385 390 395 400 | | 1200 |
| ggg aaa gcc tgc caa gtt gcc cat tgt gca tct tca cga caa atc atc<br>Gly Lys Ala Cys Gln Val Ala His Cys Ala Ser Ser Arg Gln Ile Ile<br>405 410 415 | | 1248 |
| tct cat tgg aag aac tgc aca cga cat gac tgt cct gtt tgc ctc cct<br>Ser His Trp Lys Asn Cys Thr Arg His Asp Cys Pro Val Cys Leu Pro<br>420 425 430 | | 1296 |
| ttg aaa aat gcc agt gac aag cga aac caa caa acc atc ctg ggg tct<br>Leu Lys Asn Ala Ser Asp Lys Arg Asn Gln Gln Thr Ile Leu Gly Ser<br>435 440 445 | | 1344 |
| cca gct agt gga att caa aac aca att ggt tct gtt ggc aca ggg caa<br>Pro Ala Ser Gly Ile Gln Asn Thr Ile Gly Ser Val Gly Thr Gly Gln<br>450 455 460 | | 1392 |
| cag aat gcc act tct tta agt aac cca aat ccc ata gac ccc agc tcc<br>Gln Asn Ala Thr Ser Leu Ser Asn Pro Asn Pro Ile Asp Pro Ser Ser<br>465 470 475 480 | | 1440 |
| atg cag cga gcc tat gct gct ctc gga ctc ccc tac atg aac cag ccc<br>Met Gln Arg Ala Tyr Ala Ala Leu Gly Leu Pro Tyr Met Asn Gln Pro<br>485 490 495 | | 1488 |
| cag acg cag ctg cag cct cag gtt cct ggc cag caa cca gca cag cct<br>Gln Thr Gln Leu Gln Pro Gln Val Pro Gly Gln Gln Pro Ala Gln Pro<br>500 505 510 | | 1536 |
| caa acc cac cag cag atg agg act ctc aac ccc ctg gga aat aat cca<br>Gln Thr His Gln Gln Met Arg Thr Leu Asn Pro Leu Gly Asn Asn Pro<br>515 520 525 | | 1584 |
| atg aac att cca gca gga gga ata aca aca gat cag cag ccc cca aac<br>Met Asn Ile Pro Ala Gly Gly Ile Thr Thr Asp Gln Gln Pro Pro Asn<br>530 535 540 | | 1632 |
| ttg att tca gaa tca gct ctt ccg act tcc ctg ggg gcc aca aac cca<br>Leu Ile Ser Glu Ser Ala Leu Pro Thr Ser Leu Gly Ala Thr Asn Pro<br>545 550 555 560 | | 1680 |
| ctg atg aac gat ggc tcc aac tct ggt aac att gga acc ctc agc act<br>Leu Met Asn Asp Gly Ser Asn Ser Gly Asn Ile Gly Thr Leu Ser Thr<br>565 570 575 | | 1728 |

```
ata cca aca gca gct cct cct tct agc acc ggt gta agg aaa ggc tgg      1776
Ile Pro Thr Ala Ala Pro Pro Ser Ser Thr Gly Val Arg Lys Gly Trp
            580                 585                 590 cac gaa cat gtc act cag gac ctg cgg agc cat cta gtg cat aaa ctc      1824
His Glu His Val Thr Gln Asp Leu Arg Ser His Leu Val His Lys Leu
595                 600                 605 gtc caa gcc atc ttc cca aca cct gat ccc gca gct cta aag gat cgc      1872
Val Gln Ala Ile Phe Pro Thr Pro Asp Pro Ala Ala Leu Lys Asp Arg
    610                 615                 620 cgc atg gaa aac ctg gta gcc tat gct aag aaa gtg gaa ggg gac atg      1920
Arg Met Glu Asn Leu Val Ala Tyr Ala Lys Lys Val Glu Gly Asp Met
625                 630                 635                 640 tac gag tct gcc aac agc agg gat gaa tat tat cac tta tta gca gag      1968
Tyr Glu Ser Ala Asn Ser Arg Asp Glu Tyr Tyr His Leu Leu Ala Glu
                645                 650                 655 aaa atc tac aag ata caa aaa gaa cta gaa gaa aaa cgg agg tcg cgt      2016
Lys Ile Tyr Lys Ile Gln Lys Glu Leu Glu Glu Lys Arg Arg Ser Arg
            660                 665                 670 tta cat aaa caa ggc atc ttg ggg aac cag cca gcc tta cca gcc ccg      2064
Leu His Lys Gln Gly Ile Leu Gly Asn Gln Pro Ala Leu Pro Ala Pro
675                 680                 685 ggg gct cag ccc cct gtg att cca cag gca caa cct gtg aga cct cca      2112
Gly Ala Gln Pro Pro Val Ile Pro Gln Ala Gln Pro Val Arg Pro Pro
    690                 695                 700 aat gga ccc ctg tcc ctg cca gtg aat cgc atg caa gtt tct caa ggg      2160
Asn Gly Pro Leu Ser Leu Pro Val Asn Arg Met Gln Val Ser Gln Gly
705                 710                 715                 720 atg aat tca ttt aac ccc atg tcc ttg ggg aac gtc cag ttg cca caa      2208
Met Asn Ser Phe Asn Pro Met Ser Leu Gly Asn Val Gln Leu Pro Gln
                725                 730                 735 gca ccc atg gga cct cgt gca gcc tcc cca atg aac cac tct gtc cag      2256
Ala Pro Met Gly Pro Arg Ala Ala Ser Pro Met Asn His Ser Val Gln
            740                 745                 750 atg aac agc atg ggc tca gtg cca ggg atg gcc att tct cct tcc cga      2304
Met Asn Ser Met Gly Ser Val Pro Gly Met Ala Ile Ser Pro Ser Arg
755                 760                 765 atg cct cag cct ccg aac atg atg ggt gca cac acc aac aac atg atg      2352
Met Pro Gln Pro Pro Asn Met Met Gly Ala His Thr Asn Asn Met Met
    770                 775                 780 gcc cag gcg ccc gct cag agc cag ttt ctg cca cag aac cag ttc ccg      2400
Ala Gln Ala Pro Ala Gln Ser Gln Phe Leu Pro Gln Asn Gln Phe Pro
785                 790                 795                 800 tca tcc agc ggg gcg atg agt gtg ggc atg ggg cag ccg cca gcc caa      2448
Ser Ser Ser Gly Ala Met Ser Val Gly Met Gly Gln Pro Pro Ala Gln
                805                 810                 815 aca ggc gtg tca cag gga cag gtg cct ggt gct gct ctt cct aac cct      2496
Thr Gly Val Ser Gln Gly Gln Val Pro Gly Ala Ala Leu Pro Asn Pro
            820                 825                 830 ctc aac atg ctg ggg cct cag gcc agc cag cta cct tgc cct cca gtg      2544
Leu Asn Met Leu Gly Pro Gln Ala Ser Gln Leu Pro Cys Pro Pro Val
835                 840                 845 aca cag tca cca ctg cac cca aca ccg cct cct gct tcc acg gct gct      2592
Thr Gln Ser Pro Leu His Pro Thr Pro Pro Ala Ser Thr Ala Ala
    850                 855                 860 ggc atg cca tct ctc cag cac acg aca cca cct ggg atg act cct ccc      2640
Gly Met Pro Ser Leu Gln His Thr Thr Pro Pro Gly Met Thr Pro Pro
865                 870                 875                 880 cag cca gca gct ccc act cag cca tca act cct gtg tcg tct tcc ggg      2688
Gln Pro Ala Ala Pro Thr Gln Pro Ser Thr Pro Val Ser Ser Ser Gly
```

```
                      885                 890                 895
cag act ccc acc ccg act cct ggc tca gtg ccc agt gct acc caa acc     2736
Gln Thr Pro Thr Pro Thr Pro Gly Ser Val Pro Ser Ala Thr Gln Thr
            900                 905                 910 cag agc acc cct aca gtc cag gca gca gcc cag gcc cag gtg acc ccg     2784
Gln Ser Thr Pro Thr Val Gln Ala Ala Ala Gln Ala Gln Val Thr Pro
            915                 920                 925 cag cct caa acc cca gtt cag ccc ccg tct gtg gct acc cct cag tca     2832
Gln Pro Gln Thr Pro Val Gln Pro Pro Ser Val Ala Thr Pro Gln Ser
    930                 935                 940 tcg cag caa cag ccg acg cct gtg cac gcc cag cct cct ggc aca ccg     2880
Ser Gln Gln Gln Pro Thr Pro Val His Ala Gln Pro Pro Gly Thr Pro
945                 950                 955                 960 ctt tcc cag gca gca gcc agc att gat aac aga gtc cct acc ccc tcc     2928
Leu Ser Gln Ala Ala Ala Ser Ile Asp Asn Arg Val Pro Thr Pro Ser
                965                 970                 975 tcg gtg gcc agc gca gaa acc aat tcc cag cag cca gga cct gac gta     2976
Ser Val Ala Ser Ala Glu Thr Asn Ser Gln Gln Pro Gly Pro Asp Val
            980                 985                 990 cct gtg ctg gaa atg aag acg gag acc caa gca gag gac act gag ccc     3024
Pro Val Leu Glu Met Lys Thr Glu Thr Gln Ala Glu Asp Thr Glu Pro
            995                 1000                1005 gat cct ggt gaa tcc aaa ggg gag ccc agg tct gag atg atg gag         3069
Asp Pro Gly Glu Ser Lys Gly Glu Pro Arg Ser Glu Met Met Glu
    1010                1015                1020 gag gat ttg caa gga gct tcc caa gtt aaa gaa gaa aca gac ata         3114
Glu Asp Leu Gln Gly Ala Ser Gln Val Lys Glu Glu Thr Asp Ile
    1025                1030                1035 gca gag cag aaa tca gaa cca atg gaa gtg gat gaa aag aaa cct         3159
Ala Glu Gln Lys Ser Glu Pro Met Glu Val Asp Glu Lys Lys Pro
    1040                1045                1050 gaa gtg aaa gta gaa gtt aaa gag gaa gaa gag agt agc agt aac         3204
Glu Val Lys Val Glu Val Lys Glu Glu Glu Glu Ser Ser Ser Asn
    1055                1060                1065 ggc aca gcc tct cag tca aca tct cct tcg cag ccg cgc aaa aaa         3249
Gly Thr Ala Ser Gln Ser Thr Ser Pro Ser Gln Pro Arg Lys Lys
    1070                1075                1080 atc ttt aaa cca gag gag tta cgc cag gcc ctc atg cca acc cta         3294
Ile Phe Lys Pro Glu Glu Leu Arg Gln Ala Leu Met Pro Thr Leu
    1085                1090                1095 gaa gca ctg tat cga cag gac cca gag tca tta cct ttc cgg cag         3339
Glu Ala Leu Tyr Arg Gln Asp Pro Glu Ser Leu Pro Phe Arg Gln
    1100                1105                1110 cct gta gat ccc cag ctc ctc gga att cca gac tat ttt gac atc         3384
Pro Val Asp Pro Gln Leu Leu Gly Ile Pro Asp Tyr Phe Asp Ile
    1115                1120                1125 gta aag aat ccc atg gac ctc tcc acc atc aag cgg aag ctg gac         3429
Val Lys Asn Pro Met Asp Leu Ser Thr Ile Lys Arg Lys Leu Asp
    1130                1135                1140 aca ggg caa tac caa gag ccc tgg cag tac gtg gac gac gtc tgg         3474
Thr Gly Gln Tyr Gln Glu Pro Trp Gln Tyr Val Asp Asp Val Trp
    1145                1150                1155 ctc atg ttc aac aat gcc tgg ctc tat aat cgc aag aca tcc cga         3519
Leu Met Phe Asn Asn Ala Trp Leu Tyr Asn Arg Lys Thr Ser Arg
    1160                1165                1170 gtc tat aag ttt tgc agt aag ctt gca gag gtc ttt gag cag gaa         3564
Val Tyr Lys Phe Cys Ser Lys Leu Ala Glu Val Phe Glu Gln Glu
    1175                1180                1185 att gac cct gtc atg cag tcc ctt gga tat tgc tgt gga cgc aag         3609
Ile Asp Pro Val Met Gln Ser Leu Gly Tyr Cys Cys Gly Arg Lys
```

```
Ile Asp Pro Val Met Gln Ser Leu Gly Tyr Cys Cys Gly Arg Lys
    1190            1195            1200 tat gag ttt tcc cca cag act ttg tgc tgc tat ggg aag cag ctg        3654
Tyr Glu Phe Ser Pro Gln Thr Leu Cys Cys Tyr Gly Lys Gln Leu
    1205            1210            1215 tgt acc att cct cgc gat gct gcc tac tac agc tat cag aat agg        3699
Cys Thr Ile Pro Arg Asp Ala Ala Tyr Tyr Ser Tyr Gln Asn Arg
    1220            1225            1230 tat cat ttc tgt gag aag tgt ttc aca gag atc cag ggc gag aat        3744
Tyr His Phe Cys Glu Lys Cys Phe Thr Glu Ile Gln Gly Glu Asn
    1235            1240            1245 gtg acc ctg ggt gac gac cct tca cag ccc cag acg aca att tca        3789
Val Thr Leu Gly Asp Asp Pro Ser Gln Pro Gln Thr Thr Ile Ser
    1250            1255            1260 aag gat cag ttt gaa aag aag aaa aat gat acc tta gac ccc gaa        3834
Lys Asp Gln Phe Glu Lys Lys Lys Asn Asp Thr Leu Asp Pro Glu
    1265            1270            1275 cct ttc gtt gat tgc aag gag tgt ggc cgg aag atg cat cag att        3879
Pro Phe Val Asp Cys Lys Glu Cys Gly Arg Lys Met His Gln Ile
    1280            1285            1290 tgc gtt ctg cac tat gac atc att tgg cct tca ggt ttt gtg tgc        3924
Cys Val Leu His Tyr Asp Ile Ile Trp Pro Ser Gly Phe Val Cys
    1295            1300            1305 gac aac tgc ttg aag aaa act ggc aga cct cga aaa gaa aac aaa        3969
Asp Asn Cys Leu Lys Lys Thr Gly Arg Pro Arg Lys Glu Asn Lys
    1310            1315            1320 ttc agt gct aag agg ctg cag acc aca aga ctg gga aac cac ttg        4014
Phe Ser Ala Lys Arg Leu Gln Thr Thr Arg Leu Gly Asn His Leu
    1325            1330            1335 gaa gac cga gtg aac aaa ttt ttg cgg cgc cag aat cac cct gaa        4059
Glu Asp Arg Val Asn Lys Phe Leu Arg Arg Gln Asn His Pro Glu
    1340            1345            1350 gcc ggg gag gtt ttt gtc cga gtg gtg gcc agc tca gac aag acg        4104
Ala Gly Glu Val Phe Val Arg Val Val Ala Ser Ser Asp Lys Thr
    1355            1360            1365 gtg gag gtc aag ccc ggg atg aag tca cgg ttt gtg gat tct ggg        4149
Val Glu Val Lys Pro Gly Met Lys Ser Arg Phe Val Asp Ser Gly
    1370            1375            1380 gaa atg tct gaa tct ttc cca tat cga acc aaa gct ctg ttt gct        4194
Glu Met Ser Glu Ser Phe Pro Tyr Arg Thr Lys Ala Leu Phe Ala
    1385            1390            1395 ttt gag gaa att gac ggc gtg gat gtc tgc ttt ttt gga atg cac        4239
Phe Glu Glu Ile Asp Gly Val Asp Val Cys Phe Phe Gly Met His
    1400            1405            1410 gtc caa gaa tac ggc tct gat tgc ccc cct cca aac acg agg cgt        4284
Val Gln Glu Tyr Gly Ser Asp Cys Pro Pro Pro Asn Thr Arg Arg
    1415            1420            1425 gtg tac att tct tat ctg gat agt att cat ttc ttc cgg cca cgt        4329
Val Tyr Ile Ser Tyr Leu Asp Ser Ile His Phe Phe Arg Pro Arg
    1430            1435            1440 tgc ctc cgc aca gcc gtt tac cat gag atc ctt att gga tat tta        4374
Cys Leu Arg Thr Ala Val Tyr His Glu Ile Leu Ile Gly Tyr Leu
    1445            1450            1455 gag tat gtg aag aaa tta ggg tat gtg aca ggg cac atc tgg gcc        4419
Glu Tyr Val Lys Lys Leu Gly Tyr Val Thr Gly His Ile Trp Ala
    1460            1465            1470 tgt cct cca agt gaa gga gat gat tac atc ttc cat tgc cac cca        4464
Cys Pro Pro Ser Glu Gly Asp Asp Tyr Ile Phe His Cys His Pro
    1475            1480            1485
```

-continued

| | | | | | | | | | | | | | |
|---|---|---|---|---|---|---|---|---|---|---|---|---|---|
| cct | gat | caa | aaa | ata | ccc | aag | cca | aaa | cga | ctg | cag | gag | tgg | tac | 4509 |
| Pro | Asp | Gln | Lys | Ile | Pro | Lys | Pro | Lys | Arg | Leu | Gln | Glu | Trp | Tyr | |
| | 1490 | | | | 1495 | | | | 1500 | | | | | | |
| aaa | aag | atg | ctg | gac | aag | gcg | ttt | gca | gag | cgg | atc | atc | cat | gac | 4554 |
| Lys | Lys | Met | Leu | Asp | Lys | Ala | Phe | Ala | Glu | Arg | Ile | Ile | His | Asp | |
| | 1505 | | | | 1510 | | | | 1515 | | | | | | |
| tac | aag | gat | att | ttc | aaa | caa | gca | act | gaa | gac | agg | ctc | acc | agt | 4599 |
| Tyr | Lys | Asp | Ile | Phe | Lys | Gln | Ala | Thr | Glu | Asp | Arg | Leu | Thr | Ser | |
| | 1520 | | | | 1525 | | | | 1530 | | | | | | |
| gcc | aag | gaa | ctg | ccc | tat | ttt | gaa | ggt | gat | ttc | tgg | ccc | aat | gtg | 4644 |
| Ala | Lys | Glu | Leu | Pro | Tyr | Phe | Glu | Gly | Asp | Phe | Trp | Pro | Asn | Val | |
| | 1535 | | | | 1540 | | | | 1545 | | | | | | |
| tta | gaa | gag | agc | att | aag | gaa | cta | gaa | caa | gaa | gaa | gag | gag | agg | 4689 |
| Leu | Glu | Glu | Ser | Ile | Lys | Glu | Leu | Glu | Gln | Glu | Glu | Glu | Glu | Arg | |
| | 1550 | | | | 1555 | | | | 1560 | | | | | | |
| aaa | aag | gaa | gag | agc | act | gca | gcc | agt | gaa | acc | act | gag | ggc | agt | 4734 |
| Lys | Lys | Glu | Glu | Ser | Thr | Ala | Ala | Ser | Glu | Thr | Thr | Glu | Gly | Ser | |
| | 1565 | | | | 1570 | | | | 1575 | | | | | | |
| cag | ggc | gac | agc | aag | aat | gcc | aag | aag | aag | aac | aac | aag | aaa | acc | 4779 |
| Gln | Gly | Asp | Ser | Lys | Asn | Ala | Lys | Lys | Lys | Asn | Asn | Lys | Lys | Thr | |
| | 1580 | | | | 1585 | | | | 1590 | | | | | | |
| aac | aag | aac | aaa | agc | agc | atc | agc | cgc | gcc | aac | aag | aag | aag | ccc | 4824 |
| Asn | Lys | Asn | Lys | Ser | Ser | Ile | Ser | Arg | Ala | Asn | Lys | Lys | Lys | Pro | |
| | 1595 | | | | 1600 | | | | 1605 | | | | | | |
| agc | atg | ccc | aac | gtg | tcc | aat | gac | ctg | tcc | cag | aag | ctg | tat | gcc | 4869 |
| Ser | Met | Pro | Asn | Val | Ser | Asn | Asp | Leu | Ser | Gln | Lys | Leu | Tyr | Ala | |
| | 1610 | | | | 1615 | | | | 1620 | | | | | | |
| acc | atg | gag | aag | cac | aag | gag | gtc | ttc | ttc | gtg | atc | cac | ctg | cac | 4914 |
| Thr | Met | Glu | Lys | His | Lys | Glu | Val | Phe | Phe | Val | Ile | His | Leu | His | |
| | 1625 | | | | 1630 | | | | 1635 | | | | | | |
| gct | ggg | cct | gtc | atc | aac | acc | ctg | ccc | ccc | atc | gtc | gac | ccc | gac | 4959 |
| Ala | Gly | Pro | Val | Ile | Asn | Thr | Leu | Pro | Pro | Ile | Val | Asp | Pro | Asp | |
| | 1640 | | | | 1645 | | | | 1650 | | | | | | |
| ccc | ctg | ctc | agc | tgt | gac | ctc | atg | gat | ggg | cgc | gac | gcc | ttc | ctc | 5004 |
| Pro | Leu | Leu | Ser | Cys | Asp | Leu | Met | Asp | Gly | Arg | Asp | Ala | Phe | Leu | |
| | 1655 | | | | 1660 | | | | 1665 | | | | | | |
| acc | ctc | gcc | aga | gac | aag | cac | tgg | gag | ttc | tcc | tcc | ttg | cgc | cgc | 5049 |
| Thr | Leu | Ala | Arg | Asp | Lys | His | Trp | Glu | Phe | Ser | Ser | Leu | Arg | Arg | |
| | 1670 | | | | 1675 | | | | 1680 | | | | | | |
| tcc | aag | tgg | tcc | acg | ctc | tgc | atg | ctg | gtg | gag | ctg | cac | acc | cag | 5094 |
| Ser | Lys | Trp | Ser | Thr | Leu | Cys | Met | Leu | Val | Glu | Leu | His | Thr | Gln | |
| | 1685 | | | | 1690 | | | | 1695 | | | | | | |
| ggc | cag | gac | cgc | ttt | gtc | tac | acc | tgc | aac | gag | tgc | aag | cac | cac | 5139 |
| Gly | Gln | Asp | Arg | Phe | Val | Tyr | Thr | Cys | Asn | Glu | Cys | Lys | His | His | |
| | 1700 | | | | 1705 | | | | 1710 | | | | | | |
| gtg | gag | acg | cgc | tgg | cac | tgc | act | gtg | tgc | gag | gac | tac | gac | ctc | 5184 |
| Val | Glu | Thr | Arg | Trp | His | Cys | Thr | Val | Cys | Glu | Asp | Tyr | Asp | Leu | |
| | 1715 | | | | 1720 | | | | 1725 | | | | | | |
| tgc | atc | aac | tgc | tat | aac | acg | aag | agc | cat | gcc | cat | aag | atg | gtg | 5229 |
| Cys | Ile | Asn | Cys | Tyr | Asn | Thr | Lys | Ser | His | Ala | His | Lys | Met | Val | |
| | 1730 | | | | 1735 | | | | 1740 | | | | | | |
| aag | tgg | ggg | ctg | ggc | ctg | gat | gac | gag | ggc | agc | agc | cag | ggc | gag | 5274 |
| Lys | Trp | Gly | Leu | Gly | Leu | Asp | Asp | Glu | Gly | Ser | Ser | Gln | Gly | Glu | |
| | 1745 | | | | 1750 | | | | 1755 | | | | | | |
| cca | cag | tca | aag | agc | ccc | cag | gag | tca | cgc | cgg | ctg | agc | atc | cag | 5319 |
| Pro | Gln | Ser | Lys | Ser | Pro | Gln | Glu | Ser | Arg | Arg | Leu | Ser | Ile | Gln | |
| | 1760 | | | | 1765 | | | | 1770 | | | | | | |
| cgc | tgc | atc | cag | tcg | ctg | gtg | cac | gcg | tgc | cag | tgc | cgc | aac | gcc | 5364 |
| Arg | Cys | Ile | Gln | Ser | Leu | Val | His | Ala | Cys | Gln | Cys | Arg | Asn | Ala | |
| | 1775 | | | | 1780 | | | | 1785 | | | | | | |

| | | | | | | | | | | |
|---|---|---|---|---|---|---|---|---|---|---|
| aac | tgc | tcg | ctg | cca | tcc | tgc | cag | aag | atg | aag | cgg | gtg | gtg | cag | 5409 |
| Asn | Cys | Ser | Leu | Pro | Ser | Cys | Gln | Lys | Met | Lys | Arg | Val | Val | Gln | |
| | 1790 | | | | 1795 | | | | | 1800 | | | | | |
| cac | acc | aag | ggc | tgc | aaa | cgc | aag | acc | aac | ggg | ggc | tgc | ccg | gtg | 5454 |
| His | Thr | Lys | Gly | Cys | Lys | Arg | Lys | Thr | Asn | Gly | Gly | Cys | Pro | Val | |
| | 1805 | | | | 1810 | | | | | 1815 | | | | | |
| tgc | aag | cag | ctc | atc | gcc | ctc | tgc | tgc | tac | cac | gcc | aag | cac | tgc | 5499 |
| Cys | Lys | Gln | Leu | Ile | Ala | Leu | Cys | Cys | Tyr | His | Ala | Lys | His | Cys | |
| 1820 | | | | | 1825 | | | | | 1830 | | | | | |
| caa | gaa | aac | aaa | tgc | ccc | gtg | ccc | ttc | tgc | ctc | aac | atc | aaa | cac | 5544 |
| Gln | Glu | Asn | Lys | Cys | Pro | Val | Pro | Phe | Cys | Leu | Asn | Ile | Lys | His | |
| 1835 | | | | | 1840 | | | | | 1845 | | | | | |
| aag | ctc | cgc | cag | cag | cag | atc | cag | cac | cgc | ctg | cag | cag | gcc | cag | 5589 |
| Lys | Leu | Arg | Gln | Gln | Gln | Ile | Gln | His | Arg | Leu | Gln | Gln | Ala | Gln | |
| 1850 | | | | | 1855 | | | | | 1860 | | | | | |
| ctc | atg | cgc | cgg | cgg | atg | gcc | acc | atg | aac | acc | cgc | aac | gtg | cct | 5634 |
| Leu | Met | Arg | Arg | Arg | Met | Ala | Thr | Met | Asn | Thr | Arg | Asn | Val | Pro | |
| 1865 | | | | | 1870 | | | | | 1875 | | | | | |
| cag | cag | agt | ctg | cct | tct | cct | acc | tca | gca | ccg | ccc | ggg | acc | ccc | 5679 |
| Gln | Gln | Ser | Leu | Pro | Ser | Pro | Thr | Ser | Ala | Pro | Pro | Gly | Thr | Pro | |
| 1880 | | | | | 1885 | | | | | 1890 | | | | | |
| aca | cag | cag | ccc | agc | aca | ccc | cag | acg | ccg | cag | ccc | cct | gcc | cag | 5724 |
| Thr | Gln | Gln | Pro | Ser | Thr | Pro | Gln | Thr | Pro | Gln | Pro | Pro | Ala | Gln | |
| 1895 | | | | | 1900 | | | | | 1905 | | | | | |
| ccc | caa | ccc | tca | ccc | gtg | agc | atg | tca | cca | gct | ggc | ttc | ccc | agc | 5769 |
| Pro | Gln | Pro | Ser | Pro | Val | Ser | Met | Ser | Pro | Ala | Gly | Phe | Pro | Ser | |
| 1910 | | | | | 1915 | | | | | 1920 | | | | | |
| gtg | gcc | cgg | act | cag | ccc | ccc | acc | acg | gtg | tcc | aca | ggg | aag | cct | 5814 |
| Val | Ala | Arg | Thr | Gln | Pro | Pro | Thr | Thr | Val | Ser | Thr | Gly | Lys | Pro | |
| 1925 | | | | | 1930 | | | | | 1935 | | | | | |
| acc | agc | cag | gtg | ccg | gcc | ccc | cca | ccc | ccg | gcc | cag | ccc | cct | cct | 5859 |
| Thr | Ser | Gln | Val | Pro | Ala | Pro | Pro | Pro | Pro | Ala | Gln | Pro | Pro | Pro | |
| 1940 | | | | | 1945 | | | | | 1950 | | | | | |
| gca | gcg | gtg | gaa | gcg | gct | cgg | cag | atc | gag | cgt | gag | gcc | cag | cag | 5904 |
| Ala | Ala | Val | Glu | Ala | Ala | Arg | Gln | Ile | Glu | Arg | Glu | Ala | Gln | Gln | |
| 1955 | | | | | 1960 | | | | | 1965 | | | | | |
| cag | cag | cac | ctg | tac | cgg | gtg | aac | atc | aac | aac | agc | atg | ccc | cca | 5949 |
| Gln | Gln | His | Leu | Tyr | Arg | Val | Asn | Ile | Asn | Asn | Ser | Met | Pro | Pro | |
| 1970 | | | | | 1975 | | | | | 1980 | | | | | |
| gga | cgc | acg | ggc | atg | ggg | acc | ccg | ggg | agc | cag | atg | gcc | ccc | gtg | 5994 |
| Gly | Arg | Thr | Gly | Met | Gly | Thr | Pro | Gly | Ser | Gln | Met | Ala | Pro | Val | |
| 1985 | | | | | 1990 | | | | | 1995 | | | | | |
| agc | ctg | aat | gtg | ccc | cga | ccc | aac | cag | gtg | agc | ggg | ccc | gtc | atg | 6039 |
| Ser | Leu | Asn | Val | Pro | Arg | Pro | Asn | Gln | Val | Ser | Gly | Pro | Val | Met | |
| 2000 | | | | | 2005 | | | | | 2010 | | | | | |
| ccc | agc | atg | cct | ccc | ggg | cag | tgg | cag | cag | gcg | ccc | ctt | ccc | cag | 6084 |
| Pro | Ser | Met | Pro | Pro | Gly | Gln | Trp | Gln | Gln | Ala | Pro | Leu | Pro | Gln | |
| 2015 | | | | | 2020 | | | | | 2025 | | | | | |
| cag | cag | ccc | atg | cca | ggc | ttg | ccc | agg | cct | gtg | ata | tcc | atg | cag | 6129 |
| Gln | Gln | Pro | Met | Pro | Gly | Leu | Pro | Arg | Pro | Val | Ile | Ser | Met | Gln | |
| 2030 | | | | | 2035 | | | | | 2040 | | | | | |
| gcc | cag | gcg | gcc | gtg | gct | ggg | ccc | cgg | atg | ccc | agc | gtg | cag | cca | 6174 |
| Ala | Gln | Ala | Ala | Val | Ala | Gly | Pro | Arg | Met | Pro | Ser | Val | Gln | Pro | |
| 2045 | | | | | 2050 | | | | | 2055 | | | | | |
| ccc | agg | agc | atc | tca | ccc | agc | gct | ctg | caa | gac | ctg | ctg | cgg | acc | 6219 |
| Pro | Arg | Ser | Ile | Ser | Pro | Ser | Ala | Leu | Gln | Asp | Leu | Leu | Arg | Thr | |
| 2060 | | | | | 2065 | | | | | 2070 | | | | | |
| ctg | aag | tcg | ccc | agc | tcc | cct | cag | cag | caa | cag | cag | gtg | ctg | aac | 6264 |
| Leu | Lys | Ser | Pro | Ser | Ser | Pro | Gln | Gln | Gln | Gln | Gln | Val | Leu | Asn | |

```
                    2075                2080                2085
att ctc aaa tca aac ccg cag cta atg gca gct ttc atc aaa cag    6309
Ile Leu Lys Ser Asn Pro Gln Leu Met Ala Ala Phe Ile Lys Gln
    2090                2095                2100 cgc aca gcc aag tac gtg gcc aat cag ccc ggc atg cag ccc cag    6354
Arg Thr Ala Lys Tyr Val Ala Asn Gln Pro Gly Met Gln Pro Gln
    2105                2110                2115 cct ggc ctc cag tcc cag ccc ggc atg caa ccc cag cct ggc atg    6399
Pro Gly Leu Gln Ser Gln Pro Gly Met Gln Pro Gln Pro Gly Met
    2120                2125                2130 cac cag cag ccc agc ctg cag aac ctg aat gcc atg cag gct ggc    6444
His Gln Gln Pro Ser Leu Gln Asn Leu Asn Ala Met Gln Ala Gly
    2135                2140                2145 gtg ccg cgg ccc ggt gtg cct cca cag cag cag gcg atg gga ggc    6489
Val Pro Arg Pro Gly Val Pro Pro Gln Gln Gln Ala Met Gly Gly
    2150                2155                2160 ctg aac ccc cag ggc cag gcc ttg aac atc atg aac cca gga cac    6534
Leu Asn Pro Gln Gly Gln Ala Leu Asn Ile Met Asn Pro Gly His
    2165                2170                2175 aac ccc aac atg gcg agt atg aat cca cag tac cga gaa atg tta    6579
Asn Pro Asn Met Ala Ser Met Asn Pro Gln Tyr Arg Glu Met Leu
    2180                2185                2190 cgg agg cag ctg ctg cag cag cag cag caa cag cag cag caa caa    6624
Arg Arg Gln Leu Leu Gln Gln Gln Gln Gln Gln Gln Gln Gln Gln
    2195                2200                2205 cag cag caa cag cag cag cag caa ggg agt gcc ggc atg gct ggg    6669
Gln Gln Gln Gln Gln Gln Gln Gly Ser Ala Gly Met Ala Gly
    2210                2215                2220 ggc atg gcg ggg cac ggc cag ttc cag cag cct caa gga ccc gga    6714
Gly Met Ala Gly His Gly Gln Phe Gln Gln Pro Gln Gly Pro Gly
    2225                2230                2235 ggc tac cca ccg gcc atg cag cag cag cag cgc atg cag cag cat    6759
Gly Tyr Pro Pro Ala Met Gln Gln Gln Gln Arg Met Gln Gln His
    2240                2245                2250 ctc ccc ctc cag ggc agc tcc atg ggc cag atg gcg gct cag atg    6804
Leu Pro Leu Gln Gly Ser Ser Met Gly Gln Met Ala Ala Gln Met
    2255                2260                2265 gga cag ctt ggc cag atg ggg cag ccg ggg ctg ggg gca gac agc    6849
Gly Gln Leu Gly Gln Met Gly Gln Pro Gly Leu Gly Ala Asp Ser
    2270                2275                2280 acc ccc aac atc cag caa gcc ctg cag cag cgg att ctg cag caa    6894
Thr Pro Asn Ile Gln Gln Ala Leu Gln Gln Arg Ile Leu Gln Gln
    2285                2290                2295 cag cag atg aag cag cag att ggg tcc cca ggc cag ccg aac ccc    6939
Gln Gln Met Lys Gln Gln Ile Gly Ser Pro Gly Gln Pro Asn Pro
    2300                2305                2310 atg agc ccc cag caa cac atg ctc tca gga cag cca cag gcc tcg    6984
Met Ser Pro Gln Gln His Met Leu Ser Gly Gln Pro Gln Ala Ser
    2315                2320                2325 cat ctc cct ggc cag cag atc gcc acg tcc ctt agt aac cag gtg    7029
His Leu Pro Gly Gln Gln Ile Ala Thr Ser Leu Ser Asn Gln Val
    2330                2335                2340 cgg tct cca gcc cct gtc cag tct cca cgg ccc cag tcc cag cct    7074
Arg Ser Pro Ala Pro Val Gln Ser Pro Arg Pro Gln Ser Gln Pro
    2345                2350                2355 cca cat tcc agc ccg tca cca cgg ata cag ccc cag cct tcg cca    7119
Pro His Ser Ser Pro Ser Pro Arg Ile Gln Pro Gln Pro Ser Pro
    2360                2365                2370 cac cac gtc tca ccc cag act ggt tcc ccc cac ccc gga ctc gca    7164
```

```
His His Val Ser Pro Gln Thr Gly Ser Pro His Pro Gly Leu Ala
    2375                2380                2385 gtc acc atg gcc agc tcc ata gat cag gga cac ttg ggg aac ccc     7209
Val Thr Met Ala Ser Ser Ile Asp Gln Gly His Leu Gly Asn Pro
    2390                2395                2400 gaa cag agt gca atg ctc ccc cag ctg aac acc ccc agc agg agt     7254
Glu Gln Ser Ala Met Leu Pro Gln Leu Asn Thr Pro Ser Arg Ser
    2405                2410                2415 gcg ctg tcc agc gaa ctg tcc ctg gtc ggg gac acc acg ggg gac     7299
Ala Leu Ser Ser Glu Leu Ser Leu Val Gly Asp Thr Thr Gly Asp
    2420                2425                2430 acg cta gag aag ttt gtg gag ggc ttg tag                         7329
Thr Leu Glu Lys Phe Val Glu Gly Leu
    2435                2440
```

<210> SEQ ID NO 3
<211> LENGTH: 2442
<212> TYPE: PRT
<213> ORGANISM: Homo sapiens

<400> SEQUENCE: 3

```
Met Ala Glu Asn Leu Leu Asp Gly Pro Pro Asn Pro Lys Arg Ala Lys
1               5                   10                  15

Leu Ser Ser Pro Gly Phe Ser Ala Asn Asp Ser Thr Asp Phe Gly Ser
            20                  25                  30

Leu Phe Asp Leu Glu Asn Asp Leu Pro Asp Glu Leu Ile Pro Asn Gly
        35                  40                  45

Gly Glu Leu Gly Leu Leu Asn Ser Gly Asn Leu Val Pro Asp Ala Ala
    50                  55                  60

Ser Lys His Lys Gln Leu Ser Glu Leu Leu Arg Gly Gly Ser Gly Ser
65                  70                  75                  80

Ser Ile Asn Pro Gly Ile Gly Asn Val Ser Ala Ser Ser Pro Val Gln
                85                  90                  95

Gln Gly Leu Gly Gly Gln Ala Gln Gly Gln Pro Asn Ser Ala Asn Met
            100                 105                 110

Ala Ser Leu Ser Ala Met Gly Lys Ser Pro Leu Ser Gln Gly Asp Ser
        115                 120                 125

Ser Ala Pro Ser Leu Pro Lys Gln Ala Ala Ser Thr Ser Gly Pro Thr
    130                 135                 140

Pro Ala Ala Ser Gln Ala Leu Asn Pro Gln Ala Lys Gln Val Gly
145                 150                 155                 160

Leu Ala Thr Ser Ser Pro Ala Thr Ser Gln Thr Gly Pro Gly Ile Cys
                165                 170                 175

Met Asn Ala Asn Phe Asn Gln Thr His Pro Gly Leu Leu Asn Ser Asn
            180                 185                 190

Ser Gly His Ser Leu Ile Asn Gln Ala Ser Gln Gly Gln Ala Gln Val
        195                 200                 205

Met Asn Gly Ser Leu Gly Ala Ala Gly Arg Gly Arg Gly Ala Gly Met
    210                 215                 220

Pro Tyr Pro Thr Pro Ala Met Gln Gly Ala Ser Ser Ser Val Leu Ala
225                 230                 235                 240

Glu Thr Leu Thr Gln Val Ser Pro Gln Met Thr Gly His Ala Gly Leu
                245                 250                 255

Asn Thr Ala Gln Ala Gly Gly Met Ala Lys Met Gly Ile Thr Gly Asn
            260                 265                 270

Thr Ser Pro Phe Gly Gln Pro Phe Ser Gln Ala Gly Gly Gln Pro Met
```

-continued

```
            275                 280                 285
Gly Ala Thr Gly Val Asn Pro Gln Leu Ala Ser Lys Gln Ser Met Val
290                 295                 300
Asn Ser Leu Pro Thr Phe Pro Thr Asp Ile Lys Asn Thr Ser Val Thr
305                 310                 315                 320
Asn Val Pro Asn Met Ser Gln Met Gln Thr Ser Val Gly Ile Val Pro
            325                 330                 335
Thr Gln Ala Ile Ala Thr Gly Pro Thr Ala Asp Pro Glu Lys Arg Lys
            340                 345                 350
Leu Ile Gln Gln Gln Leu Val Leu Leu Leu His Ala His Lys Cys Gln
            355                 360                 365
Arg Arg Glu Gln Ala Asn Gly Glu Val Arg Ala Cys Ser Leu Pro His
            370                 375                 380
Cys Arg Thr Met Lys Asn Val Leu Asn His Met Thr His Cys Gln Ala
385                 390                 395                 400
Gly Lys Ala Cys Gln Val Ala His Cys Ala Ser Ser Arg Gln Ile Ile
            405                 410                 415
Ser His Trp Lys Asn Cys Thr Arg His Asp Cys Pro Val Cys Leu Pro
            420                 425                 430
Leu Lys Asn Ala Ser Asp Lys Arg Asn Gln Gln Thr Ile Leu Gly Ser
            435                 440                 445
Pro Ala Ser Gly Ile Gln Asn Thr Ile Gly Ser Val Gly Thr Gly Gln
            450                 455                 460
Gln Asn Ala Thr Ser Leu Ser Asn Pro Asn Pro Ile Asp Pro Ser Ser
465                 470                 475                 480
Met Gln Arg Ala Tyr Ala Ala Leu Gly Leu Pro Tyr Met Asn Gln Pro
            485                 490                 495
Gln Thr Gln Leu Gln Pro Gln Val Pro Gly Gln Pro Ala Gln Pro
            500                 505                 510
Gln Thr His Gln Gln Met Arg Thr Leu Asn Pro Leu Gly Asn Asn Pro
            515                 520                 525
Met Asn Ile Pro Ala Gly Gly Ile Thr Thr Asp Gln Gln Pro Pro Asn
            530                 535                 540
Leu Ile Ser Glu Ser Ala Leu Pro Thr Ser Leu Gly Ala Thr Asn Pro
545                 550                 555                 560
Leu Met Asn Asp Gly Ser Asn Ser Gly Asn Ile Gly Thr Leu Ser Thr
            565                 570                 575
Ile Pro Thr Ala Ala Pro Pro Ser Ser Thr Gly Val Arg Lys Gly Trp
            580                 585                 590
His Glu His Val Thr Gln Asp Leu Arg Ser His Leu Val His Lys Leu
            595                 600                 605
Val Gln Ala Ile Phe Pro Thr Pro Asp Pro Ala Ala Leu Lys Asp Arg
            610                 615                 620
Arg Met Glu Asn Leu Val Ala Tyr Ala Lys Lys Val Glu Gly Asp Met
625                 630                 635                 640
Tyr Glu Ser Ala Asn Ser Arg Asp Glu Tyr Tyr His Leu Leu Ala Glu
            645                 650                 655
Lys Ile Tyr Lys Ile Gln Lys Glu Leu Glu Glu Lys Arg Arg Ser Arg
            660                 665                 670
Leu His Lys Gln Gly Ile Leu Gly Asn Gln Pro Ala Leu Pro Ala Pro
            675                 680                 685
Gly Ala Gln Pro Pro Val Ile Pro Gln Ala Gln Pro Val Arg Pro Pro
            690                 695                 700
```

-continued

```
Asn Gly Pro Leu Ser Leu Pro Val Asn Arg Met Gln Val Ser Gln Gly
705                 710                 715                 720

Met Asn Ser Phe Asn Pro Met Ser Leu Gly Asn Val Gln Leu Pro Gln
            725                 730                 735

Ala Pro Met Gly Pro Arg Ala Ala Ser Pro Met Asn His Ser Val Gln
            740                 745                 750

Met Asn Ser Met Gly Ser Val Pro Gly Met Ala Ile Ser Pro Ser Arg
            755                 760                 765

Met Pro Gln Pro Pro Asn Met Met Gly Ala His Thr Asn Asn Met Met
770                 775                 780

Ala Gln Ala Pro Ala Gln Ser Gln Phe Leu Pro Gln Asn Gln Phe Pro
785                 790                 795                 800

Ser Ser Ser Gly Ala Met Ser Val Gly Met Gly Gln Pro Pro Ala Gln
                805                 810                 815

Thr Gly Val Ser Gln Gly Gln Val Pro Gly Ala Ala Leu Pro Asn Pro
                820                 825                 830

Leu Asn Met Leu Gly Pro Gln Ala Ser Gln Leu Pro Cys Pro Pro Val
            835                 840                 845

Thr Gln Ser Pro Leu His Pro Thr Pro Pro Ala Ser Thr Ala Ala
            850                 855                 860

Gly Met Pro Ser Leu Gln His Thr Thr Pro Pro Gly Met Thr Pro Pro
865                 870                 875                 880

Gln Pro Ala Ala Pro Thr Gln Pro Ser Thr Pro Val Ser Ser Ser Gly
                885                 890                 895

Gln Thr Pro Thr Pro Thr Pro Gly Ser Val Pro Ser Ala Thr Gln Thr
            900                 905                 910

Gln Ser Thr Pro Thr Val Gln Ala Ala Ala Gln Ala Gln Val Thr Pro
            915                 920                 925

Gln Pro Gln Thr Pro Val Gln Pro Pro Ser Val Ala Thr Pro Gln Ser
            930                 935                 940

Ser Gln Gln Gln Pro Thr Pro Val His Ala Gln Pro Pro Gly Thr Pro
945                 950                 955                 960

Leu Ser Gln Ala Ala Ala Ser Ile Asp Asn Arg Val Pro Thr Pro Ser
                965                 970                 975

Ser Val Ala Ser Ala Glu Thr Asn Ser Gln Gln Pro Gly Pro Asp Val
                980                 985                 990

Pro Val Leu Glu Met Lys Thr Glu  Thr Gln Ala Glu Asp Thr Glu Pro
            995                 1000                 1005

Asp Pro Gly Glu Ser Lys Gly Glu Pro Arg Ser Glu  Met Met Glu
            1010                 1015                 1020

Glu Asp Leu Gln Gly Ala Ser  Gln Val Lys Glu Glu  Thr Asp Ile
            1025                 1030                 1035

Ala Glu  Gln Lys Ser Glu Pro  Met Glu Val Asp Glu  Lys Lys Pro
            1040                 1045                 1050

Glu Val  Lys Val Glu Val Lys  Glu Glu Glu Ser  Ser Ser Asn
            1055                 1060                 1065

Gly Thr  Ala Ser Gln Ser Thr  Ser Pro Ser Gln Pro  Arg Lys Lys
            1070                 1075                 1080

Ile Phe  Lys Pro Glu Glu Leu  Arg Gln Ala Leu Met  Pro Thr Leu
            1085                 1090                 1095

Glu Ala  Leu Tyr Arg Gln Asp  Pro Glu Ser Leu Pro  Phe Arg Gln
            1100                 1105                 1110
```

-continued

```
Pro Val Asp Pro Gln Leu Leu Gly Ile Pro Asp Tyr Phe Asp Ile
1115                1120                1125

Val Lys Asn Pro Met Asp Leu Ser Thr Ile Lys Arg Lys Leu Asp
1130                1135                1140

Thr Gly Gln Tyr Gln Glu Pro Trp Gln Tyr Val Asp Asp Val Trp
1145                1150                1155

Leu Met Phe Asn Asn Ala Trp Leu Tyr Asn Arg Lys Thr Ser Arg
1160                1165                1170

Val Tyr Lys Phe Cys Ser Lys Leu Ala Glu Val Phe Glu Gln Glu
1175                1180                1185

Ile Asp Pro Val Met Gln Ser Leu Gly Tyr Cys Cys Gly Arg Lys
1190                1195                1200

Tyr Glu Phe Ser Pro Gln Thr Leu Cys Cys Tyr Gly Lys Gln Leu
1205                1210                1215

Cys Thr Ile Pro Arg Asp Ala Ala Tyr Tyr Ser Tyr Gln Asn Arg
1220                1225                1230

Tyr His Phe Cys Glu Lys Cys Phe Thr Glu Ile Gln Gly Glu Asn
1235                1240                1245

Val Thr Leu Gly Asp Asp Pro Ser Gln Pro Gln Thr Thr Ile Ser
1250                1255                1260

Lys Asp Gln Phe Glu Lys Lys Lys Asn Asp Thr Leu Asp Pro Glu
1265                1270                1275

Pro Phe Val Asp Cys Lys Glu Cys Gly Arg Lys Met His Gln Ile
1280                1285                1290

Cys Val Leu His Tyr Asp Ile Ile Trp Pro Ser Gly Phe Val Cys
1295                1300                1305

Asp Asn Cys Leu Lys Lys Thr Gly Arg Pro Arg Lys Glu Asn Lys
1310                1315                1320

Phe Ser Ala Lys Arg Leu Gln Thr Thr Arg Leu Gly Asn His Leu
1325                1330                1335

Glu Asp Arg Val Asn Lys Phe Leu Arg Arg Gln Asn His Pro Glu
1340                1345                1350

Ala Gly Glu Val Phe Val Arg Val Val Ala Ser Ser Asp Lys Thr
1355                1360                1365

Val Glu Val Lys Pro Gly Met Lys Ser Arg Phe Val Asp Ser Gly
1370                1375                1380

Glu Met Ser Glu Ser Phe Pro Tyr Arg Thr Lys Ala Leu Phe Ala
1385                1390                1395

Phe Glu Glu Ile Asp Gly Val Asp Val Cys Phe Phe Gly Met His
1400                1405                1410

Val Gln Glu Tyr Gly Ser Asp Cys Pro Pro Pro Asn Thr Arg Arg
1415                1420                1425

Val Tyr Ile Ser Tyr Leu Asp Ser Ile His Phe Phe Arg Pro Arg
1430                1435                1440

Cys Leu Arg Thr Ala Val Tyr His Glu Ile Leu Ile Gly Tyr Leu
1445                1450                1455

Glu Tyr Val Lys Lys Leu Gly Tyr Val Thr Gly His Ile Trp Ala
1460                1465                1470

Cys Pro Pro Ser Glu Gly Asp Asp Tyr Ile Phe His Cys His Pro
1475                1480                1485

Pro Asp Gln Lys Ile Pro Lys Pro Lys Arg Leu Gln Glu Trp Tyr
1490                1495                1500

Lys Lys Met Leu Asp Lys Ala Phe Ala Glu Arg Ile Ile His Asp
```

1505                1510                1515

Tyr Lys Asp Ile Phe Lys Gln Ala Thr Glu Asp Arg Leu Thr Ser
        1520                1525                1530

Ala Lys Glu Leu Pro Tyr Phe Glu Gly Asp Phe Trp Pro Asn Val
        1535                1540                1545

Leu Glu Glu Ser Ile Lys Glu Leu Glu Gln Glu Glu Glu Glu Arg
        1550                1555                1560

Lys Lys Glu Glu Ser Thr Ala Ala Ser Glu Thr Thr Glu Gly Ser
        1565                1570                1575

Gln Gly Asp Ser Lys Asn Ala Lys Lys Lys Asn Asn Lys Lys Thr
        1580                1585                1590

Asn Lys Asn Lys Ser Ser Ile Ser Arg Ala Asn Lys Lys Lys Pro
        1595                1600                1605

Ser Met Pro Asn Val Ser Asn Asp Leu Ser Gln Lys Leu Tyr Ala
        1610                1615                1620

Thr Met Glu Lys His Lys Glu Val Phe Phe Val Ile His Leu His
        1625                1630                1635

Ala Gly Pro Val Ile Asn Thr Leu Pro Pro Ile Val Asp Pro Asp
        1640                1645                1650

Pro Leu Leu Ser Cys Asp Leu Met Asp Gly Arg Asp Ala Phe Leu
        1655                1660                1665

Thr Leu Ala Arg Asp Lys His Trp Glu Phe Ser Ser Leu Arg Arg
        1670                1675                1680

Ser Lys Trp Ser Thr Leu Cys Met Leu Val Glu Leu His Thr Gln
        1685                1690                1695

Gly Gln Asp Arg Phe Val Tyr Thr Cys Asn Glu Cys Lys His His
        1700                1705                1710

Val Glu Thr Arg Trp His Cys Thr Val Cys Glu Asp Tyr Asp Leu
        1715                1720                1725

Cys Ile Asn Cys Tyr Asn Thr Lys Ser His Ala His Lys Met Val
        1730                1735                1740

Lys Trp Gly Leu Gly Leu Asp Asp Glu Gly Ser Ser Gln Gly Glu
        1745                1750                1755

Pro Gln Ser Lys Ser Pro Gln Glu Ser Arg Arg Leu Ser Ile Gln
        1760                1765                1770

Arg Cys Ile Gln Ser Leu Val His Ala Cys Gln Cys Arg Asn Ala
        1775                1780                1785

Asn Cys Ser Leu Pro Ser Cys Gln Lys Met Lys Arg Val Val Gln
        1790                1795                1800

His Thr Lys Gly Cys Lys Arg Lys Thr Asn Gly Gly Cys Pro Val
        1805                1810                1815

Cys Lys Gln Leu Ile Ala Leu Cys Cys Tyr His Ala Lys His Cys
        1820                1825                1830

Gln Glu Asn Lys Cys Pro Val Pro Phe Cys Leu Asn Ile Lys His
        1835                1840                1845

Lys Leu Arg Gln Gln Gln Ile Gln His Arg Leu Gln Gln Ala Gln
        1850                1855                1860

Leu Met Arg Arg Arg Met Ala Thr Met Asn Thr Arg Asn Val Pro
        1865                1870                1875

Gln Gln Ser Leu Pro Ser Pro Thr Ser Ala Pro Pro Gly Thr Pro
        1880                1885                1890

Thr Gln Gln Pro Ser Thr Pro Gln Thr Pro Gln Pro Pro Ala Gln
        1895                1900                1905

```
Pro Gln Pro Ser Pro Val Ser Met Ser Pro Ala Gly Phe Pro Ser
    1910            1915                1920
Val Ala Arg Thr Gln Pro Thr Thr Val Ser Thr Gly Lys Pro
    1925            1930                1935
Thr Ser Gln Val Pro Ala Pro Pro Pro Ala Gln Pro Pro Pro
    1940            1945                1950
Ala Ala Val Glu Ala Ala Arg Gln Ile Glu Arg Glu Ala Gln Gln
    1955            1960                1965
Gln Gln His Leu Tyr Arg Val Asn Ile Asn Asn Ser Met Pro Pro
    1970            1975                1980
Gly Arg Thr Gly Met Gly Thr Pro Gly Ser Gln Met Ala Pro Val
    1985            1990                1995
Ser Leu Asn Val Pro Arg Pro Asn Gln Val Ser Gly Pro Val Met
    2000            2005                2010
Pro Ser Met Pro Pro Gly Gln Trp Gln Gln Ala Pro Leu Pro Gln
    2015            2020                2025
Gln Gln Pro Met Pro Gly Leu Pro Arg Pro Val Ile Ser Met Gln
    2030            2035                2040
Ala Gln Ala Ala Val Ala Gly Pro Arg Met Pro Ser Val Gln Pro
    2045            2050                2055
Pro Arg Ser Ile Ser Pro Ser Ala Leu Gln Asp Leu Leu Arg Thr
    2060            2065                2070
Leu Lys Ser Pro Ser Ser Pro Gln Gln Gln Gln Val Leu Asn
    2075            2080                2085
Ile Leu Lys Ser Asn Pro Gln Leu Met Ala Ala Phe Ile Lys Gln
    2090            2095                2100
Arg Thr Ala Lys Tyr Val Ala Asn Gln Pro Gly Met Gln Pro Gln
    2105            2110                2115
Pro Gly Leu Gln Ser Gln Pro Gly Met Gln Pro Gln Pro Gly Met
    2120            2125                2130
His Gln Gln Pro Ser Leu Gln Asn Leu Asn Ala Met Gln Ala Gly
    2135            2140                2145
Val Pro Arg Pro Gly Val Pro Gln Gln Gln Ala Met Gly Gly
    2150            2155                2160
Leu Asn Pro Gln Gly Gln Ala Leu Asn Ile Met Asn Pro Gly His
    2165            2170                2175
Asn Pro Asn Met Ala Ser Met Asn Pro Gln Tyr Arg Glu Met Leu
    2180            2185                2190
Arg Arg Gln Leu Leu Gln Gln Gln Gln Gln Gln Gln Gln Gln Gln
    2195            2200                2205
Gln Gln Gln Gln Gln Gln Gln Gly Ser Ala Gly Met Ala Gly
    2210            2215                2220
Gly Met Ala Gly His Gly Gln Phe Gln Gln Pro Gln Gly Pro Gly
    2225            2230                2235
Gly Tyr Pro Pro Ala Met Gln Gln Gln Arg Met Gln Gln His
    2240            2245                2250
Leu Pro Leu Gln Gly Ser Ser Met Gly Gln Met Ala Ala Gln Met
    2255            2260                2265
Gly Gln Leu Gly Gln Met Gly Gln Pro Gly Leu Gly Ala Asp Ser
    2270            2275                2280
Thr Pro Asn Ile Gln Gln Ala Leu Gln Gln Arg Ile Leu Gln Gln
    2285            2290                2295
```

-continued

```
Gln Gln Met Lys Gln Gln Ile Gly Ser Pro Gly Gln Pro Asn Pro
    2300                2305                2310

Met Ser Pro Gln Gln His Met Leu Ser Gly Gln Pro Gln Ala Ser
    2315                2320                2325

His Leu Pro Gly Gln Gln Ile Ala Thr Ser Leu Ser Asn Gln Val
    2330                2335                2340

Arg Ser Pro Ala Pro Val Gln Ser Pro Arg Pro Gln Ser Gln Pro
    2345                2350                2355

Pro His Ser Ser Pro Ser Pro Arg Ile Gln Pro Gln Pro Ser Pro
    2360                2365                2370

His His Val Ser Pro Gln Thr Gly Ser Pro His Pro Gly Leu Ala
    2375                2380                2385

Val Thr Met Ala Ser Ser Ile Asp Gln Gly His Leu Gly Asn Pro
    2390                2395                2400

Glu Gln Ser Ala Met Leu Pro Gln Leu Asn Thr Pro Ser Arg Ser
    2405                2410                2415

Ala Leu Ser Ser Glu Leu Ser Leu Val Gly Asp Thr Thr Gly Asp
    2420                2425                2430

Thr Leu Glu Lys Phe Val Glu Gly Leu
    2435                2440

<210> SEQ ID NO 4
<211> LENGTH: 85952
<212> TYPE: DNA
<213> ORGANISM: Homo sapiens
<220> FEATURE:
<221> NAME/KEY: CDS
<222> LOCATION: (1)..(94)
<220> FEATURE:
<221> NAME/KEY: CDS
<222> LOCATION: (24183)..(24817)
<220> FEATURE:
<221> NAME/KEY: CDS
<222> LOCATION: (32860)..(33036)
<220> FEATURE:
<221> NAME/KEY: CDS
<222> LOCATION: (34483)..(34744)
<220> FEATURE:
<221> NAME/KEY: CDS
<222> LOCATION: (36886)..(36999)
<220> FEATURE:
<221> NAME/KEY: CDS
<222> LOCATION: (38384)..(38629)
<220> FEATURE:
<221> NAME/KEY: CDS
<222> LOCATION: (42809)..(42902)
<220> FEATURE:
<221> NAME/KEY: CDS
<222> LOCATION: (44649)..(44786)
<220> FEATURE:
<221> NAME/KEY: CDS
<222> LOCATION: (47136)..(47253)
<220> FEATURE:
<221> NAME/KEY: CDS
<222> LOCATION: (48044)..(48218)
<220> FEATURE:
<221> NAME/KEY: CDS
<222> LOCATION: (53735)..(53812)
<220> FEATURE:
<221> NAME/KEY: CDS
<222> LOCATION: (54833)..(54942)
<220> FEATURE:
<221> NAME/KEY: CDS
<222> LOCATION: (56034)..(56171)
<220> FEATURE:
<221> NAME/KEY: CDS
<222> LOCATION: (56757)..(57194)
<220> FEATURE:
<221> NAME/KEY: CDS
```

```
<222> LOCATION: (58829)..(59008)
<220> FEATURE:
<221> NAME/KEY: CDS
<222> LOCATION: (59202)..(59346)
<220> FEATURE:
<221> NAME/KEY: CDS
<222> LOCATION: (61991)..(62109)
<220> FEATURE:
<221> NAME/KEY: CDS
<222> LOCATION: (64165)..(64404)
<220> FEATURE:
<221> NAME/KEY: CDS
<222> LOCATION: (65408)..(65496)
<220> FEATURE:
<221> NAME/KEY: CDS
<222> LOCATION: (67638)..(67718)
<220> FEATURE:
<221> NAME/KEY: CDS
<222> LOCATION: (69719)..(69775)
<220> FEATURE:
<221> NAME/KEY: CDS
<222> LOCATION: (71049)..(71126)
<220> FEATURE:
<221> NAME/KEY: CDS
<222> LOCATION: (73595)..(73662)
<220> FEATURE:
<221> NAME/KEY: CDS
<222> LOCATION: (75445)..(75595)
<220> FEATURE:
<221> NAME/KEY: CDS
<222> LOCATION: (75717)..(75863)
<220> FEATURE:
<221> NAME/KEY: CDS
<222> LOCATION: (76499)..(76612)
<220> FEATURE:
<221> NAME/KEY: CDS
<222> LOCATION: (77402)..(77567)
<220> FEATURE:
<221> NAME/KEY: CDS
<222> LOCATION: (79495)..(79659)
<220> FEATURE:
<221> NAME/KEY: CDS
<222> LOCATION: (80619)..(80780)
<220> FEATURE:
<221> NAME/KEY: CDS
<222> LOCATION: (83243)..(83524)
<220> FEATURE:
<221> NAME/KEY: CDS
<222> LOCATION: (83769)..(85949)

<400> SEQUENCE: 4 atg gcc gag aat gtg gtg gaa ccg ggg ccg cct tca gcc aag cgg cct      48
Met Ala Glu Asn Val Val Glu Pro Gly Pro Pro Ser Ala Lys Arg Pro
1               5                   10                  15 aaa ctc tca tct ccg gcc ctc tcg gcg tcc gcc agc gat ggc aca g        94
Lys Leu Ser Ser Pro Ala Leu Ser Ala Ser Ala Ser Asp Gly Thr
            20                  25                  30 gttagtttcg gcagccccgg ccttccacgt tcccttttaat cttttctact cggtgcgcct   154
ttattcttcc attttttttt tcttcctctc tctctagttc cctgccccctt aattaatttt   214 aaaggtattt gaatgagctg gtcgaagacg tccagtagcc caaccatttt ctttgcctcc    274
taatacattg attgcaacac tatgtcatat cggtgtgtgt tctggaatta gagctcgtaa    334
gtgggtgcta tatagaaatg gcctgtattg ttgctctcat gcaatttaat ttgggaaatg    394
ccaatgcatt tgtgtgtaag agctcctatg caatttaagt ttcattttttt ttgttcttgg   454 caaatgaatt tcgaatcctt tctctttact gtacttactg tgtttcctct actttccact   514
cttcgaaatt ttctctcctt tgcagaatat tttctgttga ggaatagggt gtaaaaaaat   574
cttgattttg tgtgtgcgag gtccaagatt tcaggttaga ggtgaagttt aacaattct    634 ttatcttacc taccattctt agctttttt tcctttttct tcttatttgc tttaagaatc    694
```

```
aatatggagc gcagttcatt tcacatctcc cagttctttg gtgtgagacc aaaatgtctg    754
aaactctggg ttttaggtt gggagaacag gggcatgttc tttgcagttt gcagtcactt    814
tctcatttta ggggaaataa gataaacaat tttgtggagt tacgtacctg gaaatcaagg    874
ttagaagttg aaagagttcc aatcatgaac tacaaacgtg aactgattgt acaaaagttt    934
aaaatgtgca ttaggtttgg tgtttgtgtg tgtctttgtc ttttacact tttaaacata    994 cttggagatc aagattttcg tttaaaagct ttacgaccag ttcattcagt tgtggactag   1054
ctcctttgtc aggagaagtt cagggagact tcttccatca tcccttcatt cttttcttac   1114
agttagttta atggtgttat cctgatgggt aaggaccttt tctttgctgg gataatgaag   1174
atgaagaatg gctggccatc tgacagtcca caagatgttc ccctttacta cggagcatct   1234
ctttaactcc ctgagagcag gctcagcgtc atccctccat ctgccagtga gagtgcataa   1294
tggagttaaa tgtacccttt gagtttgtag agaacttcga gagcatgttt ctaaataggc   1354
ttcatttcag agggtgaaaa tgggaagaca gagctaatgc tttgaattcg ttgcttttat   1414
aagaaagatg tgaaatgaat ttaagttaac ctgcaaaaat tgagaagtag gaatcttgcg   1474
agttcctcta cctaaggctt gtaacattga ttatgcatga actttgatct gtacctattc   1534
tatgaaggta ctgtagtctc cagggatttt tttagctggt ttttccttc agaattcata   1594 cacatacaca aacgtcgttg tattcctttg cacctactaa agtgccattc agaaacattt   1654
tttagatcat ctttagagac ttaatcacct gtagattttt gtggtgtttc tttcgtattt   1714
gtgtaatgtg gtagttttg cttttagtt tggtgtaac gtggtagtcg attttacatt   1774
ggagttagcc agtgacttgg aacgtagggg aaacttttt gtgtactttg agtagtcctg   1834
atttgagcag tttcgtcttg gagctgtatt gtttaaatac ttctgttcag gtgtgctact   1894
actttctcca tgtcggtctg ttttgctact tgaaatatct ttgaataatt acaagagttt   1954
taaatgtgtt aagtgggctt ttatagttta aaaaaaaact caacattgag attaattcat   2014
tcactcataa tgctaagagt ttatcttagt tacttttcta aattttgtaa tgagggttaa   2074
ctttaccccc ctccccaaat caagattcta ctccaggaat tctttggtgt acggtttta   2134 attgtaacca gtctgggttt ggggggaggg gagaagtgagt ataaagaaaa tactgtccct   2194
ctgttaactt acttcaagtt gggtaccatt gtaattttt tttttttttt ttttttttg   2254 agatggagtc tcattctgtc acccaggctg gagtgcagtg gtgcgatctc actacaacct   2314
ctgcctcctg ggttaaagca gttctgtctc agcctccta gtagctagga ctacaggcgc   2374
agaccaccac gcctggctga ttttgtatt tttagttgag acaggattc accatattgg   2434 tcaggctggt ctcgatctcc tgccctcaag tgatccaccc accttggcct cccgaagtgc   2494 tgggggttaca ggtatgagcc gcccggccag aggtaccatt atatcttgaa ttttttttt   2554 ttgacattct gcagtttgta atatgtttgc aggtaacttt tattggaggc acatcacctc   2614
ttaaaacttt taagtttcaa acttgtaact tttgattttt gagttgtcac ttgggtattt   2674
tataaatgtg aaagaaaatt atttcttgat attatggttt ttgtctagaa ctggttgaaa   2734
taagcccgaa attctagcac ctaaaacttt tttaaaaaaa gtgatttagg cttgcaaatt   2794
tcgtgatgta aatatatcca ccaagagcgt tctaatgtca gctttaaagg aaagaaaact   2854
ggaatccaat gggatgacat gctaaagtgt tacaaatcaa attattactt aaatctcaac   2914
ctctgaattg ctgtttaata ctcagatatt tccctaaaaa atttccaggt tgattcaaat   2974
aacttaggtt aaactcaact tttacgtgtt gggatgggga agagaagact tatttgtagc   3034
```

```
cttcacacct ttatgttcct gtttcagtat ttgcatttga tccattgaaa ttttttatttc    3094 atttggtatg gttagggtaa aacaaatcat ttgagaaatg acattttgtt ctccctctcc    3154
ctccaaaaaa aaaagattat gaaagccact tgtaaacttt ttttgtaaaa atgaccaaaa    3214
gactggaaaa gttaatgtta ggcaaatcct ggaaatatct tttggagctg tttctgatca    3274
tcttgagtga tggaaatgat gagggtcatc tgttgtcttc attactcagt gaacacgttt    3334
tgtcactgct tggtaaacgc ttaatgccgt atgcacttaa aaagcacctg gaaagatagg    3394
attttaggat ctggcatata attaagtagg gtaaagatcc ttctggtctt ggtacagttt    3454
tgtggccctg ggttttgtgc tttttttgttt tttgagtttt tcccccattt caaagacaca    3514
gggcagatag tgtgtaaagt atacctgctt tttgaccagt agattaatgt acacagtgga    3574
gaagtggtaa ggcttttttaa aatgtcagct ctacttttttt tttttttttt tttttttgag    3634
acagaggttt gctctcgttg cccaggctgg agtgcagtag ctcgatcttg gctcactgca    3694
atctcaacct cccaggttca agcgattctc tgcttcaccc tcctcagtag ctgggattgc    3754
aggtgtccac aaccatgccc agctaagttt tgtatttttt agtggagaca gtatttcacc    3814
attttggcca ggctggtctc gaactcctga cctcaggtga tccacccgcc tcagcctccc    3874
aaagtgctgg gaatacaggc gtgagccacc atgcccggct gtcagctcta ttttcttaaa    3934
atgccattgt gttagtggtt cgtcatccta accaaaacat tttgatcaag acctttattt    3994
ttccagctct gtaacttgtg atatgctatg ttttatttta ttttggcttg aatgtttaca    4054
taagagtttg cttctggagt cttgcagata tagctcctga tttagtgagg catttctctc    4114
ctcagtatta aattgcaaaa cattttacta aagtgcttta agtttttctg gcaattattc    4174
tcaaggcctt gtaagttcat ttataggact tcaagaaggt tgtctctggt tgatagtgag    4234
ataaagtgac ttttaagttg taaatcttga atgcgttaca atatgggggt cttattccag    4294
caggagttca tcttctatag cagaggttgg aattgtattg gcatgtccag tgaatggata    4354
atagggagga gggaggaaag ggtttctgcc ttggtggcct tttggcatta ttttgtgttt    4414
ttctttgctt ttctctctct tctttatttta ataaaaacaa aaaaatggaa acagttgaaa    4474
attaatgcaa agtggtattt gtagggacat taagtggtaa ataggaaaga gaaaagagt    4534 aggaagagtg ttgcagatac aagtgggagt gtaaaatact ttttcctggt atatttacaa    4594
aaacaatttg agagttattc tgccaattca tatacccagc aattaatgga aaagtaaaag    4654
atgctagttt tatgtttgtc cagattttag ggtttccttc tttgaagatt tctaaagttg    4714
aatatttttt taagtgaggc aagcagtaaa attaatgggc aaatgaaacc aattataccs    4774
agtctaaaat tttctttttt tttttgaggc agagtctcgc tttgtagctg ggactacagg    4834
cgcctgccac catgcccagc taatttttttg tattttttagt agagacgggg tttcaccatg    4894
ttggccatga tggtctcgat ctcctgacct tgtgaacctc ccatctctgc ctcccaaagt    4954
gctgggatta caggcgtgag ccaccgcgcc cagctaaaaa tttttttttt ttttaatact    5014
tttaagtttt aggatacatg tgcacaacgt gcaggtttgt tcacatatgta tacatgtgcc    5074 atgttggtgt gctgcaccca ttaactcgtc atttagcatt aggtatatct cctaatgcta    5134
tccctctccc ctccctgcta aaaattttt taacattgaa cttcgcaggt gattttttt    5194 cgcttaatag acggtagttt cattttgaaa ttttcatggg aaattactgc tcactttccc    5254
agaagcgctt aagaggataa ataataattg aggtgttaag cctcttctga gcaatttgga    5314
tataatttgt ttttagatct agattctttt ttataaatgt cccaaagcaa ttagaagtga    5374
ttgttttttt tgagacggag tctcgctctg tcgcccaggc tggagtgcag tggcgcgatc    5434
```

```
tcgggtcact gcaagctccg cctcccgggt tcaagccatt ctcctgcctc agcctcccga    5494
gtagctggga ctacaggcgc ccgccaccac acccggctaa ttttttgtat ttttagtaga    5554
gacgggtttc accgtgtta gcaaggatgg tctccataca ctgacctcgt gatccgccca    5614
cctcagcctc ccaaagtgct gggattacag gcgtgagcca tagcacctgg ccctagaagt    5674
aattttgttg agagagagag agtaaaacta aaagtactga aaagagtaag agagtagcta    5734
agagaatgag tattggagtc agactgctag agttcatagc ccaggcttgt atttattaac    5794
tgtgaacttt gggccaaata cttaacctgg ctcaacctcc tcacatttat tcctaaccac    5854
agccctgtaa ggtgggtgcg caccttatag gaatccacct tacttaccca ccttacagga    5914
ttgtggttag gaataaatga gaattctctt tatcagatgc ttaggactat gcttgcttct    5974
gtgtagtatg tgttcattgt taactgtttt taactttact gctaaatata tcagaaggaa    6034
agcagtggta gatggtttgg gggttgtttt tgttttttg atttgcaacg aagtcttgct    6094
ctgttgccca agctggagta cagtggcgtg atctcggcct atgacaacct ccgtctcccg    6154
gcttcaagcg attctcctgc tcagcctccg gagtagctag gactacagct gcgcagcacc    6214
atgcccggct aattttttgta ttttttagtag agacagggag tcctgacctc gtgatccacc    6274
cacctcggcc tcccaaaatg ttgggattac aggcatgagc caccgcgccc ggcctgtttt    6334
tgttttcgt ggatatacag tagtccccc ttatccttgc gggatacatt ccaagatctc    6394
cagtggatac ctgaaaccct gtatagtagt gaatataatt gtcatcagtc agaacacgtt    6454
tctgtccgtg tcttccacac acaaatttaa tgccttttcc atcttaacta atcacttgtc    6514
atgcactgtg gctgtgatgt ttgcagtttg aggtacaaca gcaaaactat cacgaatttt    6574
tttccttcac aatttcatgt atagatttga tctttgtaac ctccgcatac aattttttt    6634
cattccttat taagtcaaga actttcacct tcaagcaatt tacagcttct ctttggcata    6694
tccatatagc tgtcattgct acttttggac ttagggactg tcattaagta aaataagggt    6754
tacttaaaac tcaagcattg ccctgcccca tagtcagtct gacaatctga taactgagat    6814
ggctactaag tgacaaatgg ctggtagttt atacaggtga atacattaga cggaggggag    6874
attcactacc cggtcaggtg agatttcatc aggctactca gaatggcgca cagttttaaa    6934
cattgttgtg gctcacgcct gtaatcctgg cactttggga gattgaggca ggaggattgc    6994
ttgaggccag gcattcaaga ccagcctggg caatgtagtg ggaccccca tcccccacc    7054
atctctagaa aaaaaattta aaagtcagc aaggcatggt ggcatgcatc tgtagtccta    7114
gcttcttggg aggcttaagg tgtgaggatc tcttgagccc aggagttttg aggttacagt    7174
gagctatgat gacaccactg tacactccag cctaggtgac atagcaagac tctgtttcta    7234
aaacaacaaa aattagtgtt tatttctgca gttttctttg taatattttt gtaccacagg    7294
tgtttgaaat ggcagaaaat gaaacggggt aaggatgaac tcctgtatag atagactgga    7354
taaagagaaa gccaagtgca tgatgttcat agaggagtct taagagtaag ccttatgtca    7414
tctatccaaa tgttgttttc taggagtata agaatatagg aacagagctt aaaatggaaa    7474
aatactgtac agttagcctt ccgtatctga gggttccgtg tttgtggagt cagccacaga    7534
ttgaaaatat ttagggggaaa aaaatccatg gttgcatctg tactggacat gtacagactt    7594
tatttttcttg tcattattcc ctaaacaata cagtgcacca actatttatg ttgcatttac    7654
actgcattag gtattgtaaa taatccagaa agaattcaaa gtatatgggt gggtgtgtgt    7714
aggttatatg caaatactac atgtcccctt tatatcaggg actggagcat cctcagattt    7774
```

```
tggtatctgc agtggaggga gtggattctg gaaccaattc ccagcagata ccaagggaca    7834
accatatata tatagtatca tgacatcttg tatcatgtca cgtatatata tatcatatat    7894
attatcatgt cacgtataca agacatctta tatatcctat catgtaagat gtcttgtata    7954
cgtaagtaat agaaatgaaa atcagcagat agttaaggca taatgagaaa atggaaaaca    8014
ttgttcttgt tagaaatgtt taagaatggc ttcttgataa agaactgtgt taagcatatt    8074
cttcttctt tttagacaca gagtctcact ctgtttccta gacaggagtg cagtggtgca     8134
atcctggctc actgtagcct ccatctcctg ggttcaagct attctcctgc ctcaacctcc    8194
caagtagctg ggattacagg cacctgctac catgcctggc taatgtttgt attttagta    8254
gagatagggt ttcaccgtgt tggccaggct ggtctcgaac tcctgacctc agtctgccca    8314
cctcggcctc ccaaagtgct ggtattagag gcgagagcca cagtgcctgg ccaattaagc    8374
ataattttt ctattttca ttttcttaca tggatcttt tttttttt tgagacggag         8434
tctagctctg tcacccaggc tagagtgcag tgacacgatc tcggctcact gccagctccg    8494
cctcctgggt tcatgccatt ctcctgcctc agcctccta gtggctggga ctacaggcac     8554
ccgccaccat gcccggctaa ttttttgtat tttagtaga gatggggttt caccatgtta    8614
ggcaggatgg tctcgatctg ctgacttcat aatctaccct tctcggcctc ccaaagtgct    8674
gggattacag gggtaagcca ccgtgcccag ccacctgggt cttaaagaat aaattttctt    8734
gagatggagt cttgctgtgt tgcccaggct gaagttatcc tcctgcttcg gcctcctgag    8794
tagctgggat tgcagatgtg agccactatg cctgcctcta agaaactttc ttataaagga    8854
ggaagaagaa aagtagcagt gcagtgctcc aaagaatttt tttacaacac ttaaggaaga    8914
actaccttta acttgtagca ctagagactc tgtttcaaag aatgcacaag aatacttacc    8974
cttattactt gtaatatact ctcatatttt ctgttgcttt tttttcttt ctttttttt     9034
tttttttag tactggttgc agcctactat attgattttt atgacccact gttggctttt    9094
gagccataat ttgaagaata ctggcgtaga agagttgaca agatggcagt tattctgtat    9154
taggccaaca ttttctgtat gccaggaact tatcctctgt acattgttcc ttctttcctt    9214
cctggagttt atagataagg gaagaagact ggcattcacg gagtctggtg tgatcagcat    9274
tgtatttggg aagtacgtat atagtgggag gaacaggaga acctaaccca gtagttatcc    9334
tggtggctgt ctttgaggaa ttgtgtctga ttttgggatc tcacagatag agataggatt    9394
agtaaaaatg agcccaggct agaaaggaga ctgtgtgagg ccaggtatat cctgttctgg    9454
gaacctgtga gtgctgtctg actggtagaa tagccaaaaa cttgactgta gaggtgagca    9514
agggggccaa tcatggaggg cttataatac aggaatttag actttccatt ttacccattt    9574
aatggatggg gcagaattgt gctttaggca gttaagtaaa aggaggaata gtttgggaag    9634
aacagggaaa aacaggaggc agggagacca gtgaaacagc tgttttaggg ttccagccac    9694
ccttaccaca gaagatggaa agaagtgaaa agatttgagg gaagatggat gatcagcaga    9754
acttggtgac tgattagaag ttaggtagta agatggacaa atcaaggata attccccagt    9814
ttaaagtttg agcaacttgt tgggtgatga tttatttatt atttatttat ttattttgag    9874
acaatctctg acccaggttg gagtgcagtg gtgtgatctc agctcactgc aacctccgcc    9934
ttccgggttc aagcgattct catgcctcag cctcccaagt agctgggact aaaggtatcc    9994
accaccacgc ctggctaatt tttgtatttt tagtagagat ggggtttcac catgttgatc    10054
aggctggtct cgaactctgg cctcaagtga tctgctcgcc ttggcctccc aaaagtgctg    10114
ggattacagg catgagcagc tgtgcccagc tggataatta tttaataaat tggggagcat    10174
```

```
aggaagcata gtatttgtga agtgggtagg caggtgtgat gggggtagtg atgttacatt    10234
tggggcattt tgaagttggt ggttcttctg agttgagcag tcagtcactc ttcatttgct    10294
gcacctttat ctcattttag ccaacagaca ttgaatacct accaagtctt aggtatttgc    10354
aatgtaaaga caaattaagg tgccttctgc tgtcagagac ttcagagata cagtggggtt    10414
ggtatacatg tccacacagt tttcccgtaa gttatgcttt aaaaggtttt ttaaatgtta    10474
tatataaagg caggggatgg gttgcttttg acagagtagg tttggagcgt tgatggaaaa    10534
cttcatggag aaaatgtata tttgaacagg gttggtggaa attaacatac cttagaagta    10594
gggaaagttg gaagggtttt tcagatgaag ctaacatgtt tctgatgtgg ctagaatata    10654
cgctgtgtga tagggttttt catgggagag agatgggaaa ggatgttggg gttctattgt    10714
ggaaagagaa atatgctaag gaatttgcca tttatcttag catcaggata agaattgtat    10774
gagcagggga gtgacatggt tggggaaaga ctaattctgg taacaccgta cagagcagca    10834
gtaggtagaa cctatggcag gaagactagg agtacattat ttacctcttt tgaaatgagt    10894
ttgtcatttg ccttggaagt ttttggtaca ttgtaattaa caaagtgaat tgtttatttt    10954
gttcaagatc catgcttggt ttgccagttg ttataaatgt agaaaatata ccagatacca    11014
acttagaaac cattcactct ccttgttatt tacagatatg caaggttttt ttgttgttgt    11074
ttttgttttg ttttgttttt aaagggtatg tttctccatc taggattccc tgtaggcctt    11134
cccttgtaac aaatctcaag gtttgctcaa aatcaagaaa tgttcagtga cagttaagtt    11194
agcacacaat ttaggcttac tataaaacat gtccttgagt tgattcttaa ggtgggattt    11254
taataaataa tagtgtcttc atcatgtagt ttttttggtt tttttttttc atacagagtc    11314
ttgctctgtt gcccaggctg gagtgcagtg gtgtaatctt ggctcactgc aacctctgcc    11374
tccccggttc aagtgatttt cctgcctcag cctcccaagt agctgggatt acaggcgccc    11434
gccaccacac ccagctaatt tttgtatttt tagtagacac agggttttgc catgttggcc    11494
aggctgacct cgaactcctg acctcaggcg atccgcccgc ctcggcctcc caaagtgctg    11554
gggttacagg cgtgagccac catgtccggc ctcatgtagt tattttcaca agaagtgtca    11614
ctatattaat acattgaaaa agagcaaggt gaattgtcaa tgtgaatttt ctaaacatgg    11674
ccccaggtca cattcttgat caattaaagc acttcacctc tttaaaattc aagacttaag    11734
gctgggcgca gtggcctaca cctgtaatcc cagcactttg ggaggctgag gcaggtggat    11794
tacttgaggt caggaattca agaccagcct ggccaacatg gtgaaacccc atctctacta    11854
aaaatacaaa aattagctgg gcatggccgg cacggtggc ttacgcctgt aatcccagca    11914
ctttgggagg ccaagacggg cagatcacga ggtcaggaga ttgaaaccat cctgggtaac    11974
acggtgtaac cccgtctcta ctaaaaatac aaaaaatta ccccgtctc tactaaaaat    12034 acagaaaaat tagccgggcg tagtggcggg cgcctgtagt cccagctact caggaggctg    12094
aggcaggaga atggcgtgaa cccaggaggc ggagctagca gtgagccgag atcgtgccac    12154
tgcactccag cctaggtgac agagcgagac tccatctcag aaaaaaaaaa aaaaaaaaaa    12214
aaagccgggc gtggtggcag gcgcctgtag tcccagctac tcgggaggct gaggcaaggg    12274
aatctcttga acccgggagg cggaggttgc catgagctga gattgcacct gggccacgag    12334
agtgaaactg catctcaaaa aaaaaaaaat tcaatattga aatgttttgg gtttttttgt    12394
ttgtttgttt ctttttttga gatggagtct cactctgtca tccaggctgg agtgcagtgg    12454
tgcagtctcc actcactgca gcctccgcct cccgggttca agcgattctc ctgcttcagc    12514
```

```
ctcctgagta gctgggacta taggcacatg ccaccacagc cggctaattt ttgtattttt      12574
agtagagatg gggtttcact atgttggcca ggctggtctt gaactcctga cctcatgatc      12634
cacccacctc ggcctcccaa agtgttggga ttacaggcgt gagccaccac ccctggcgtg      12694
ttggggttta aaaagaataa acttcaagtt aatctcttcc caaagtataa gtatacctttt     12754 tgatgtcatg atagcaggac catgtgaaga gtacatattt tgaaatttgc ttgcacttt       12814 gccctttcac tctattggat ttcaaaattc aacagctgtc agcatttgta gctgtgtaat      12874
cctgtataat tatcatcttt tatccaaatt tgtataaaac ttacaagttt tcctaattt       12934 tttggagtat tagagatctt gcctgtcttt ccagcatgga tatttattt taattttctt       12994 aatgttcctt caaattacgt agtttgaaat gtttgtacat ctttatttcc ttgctagatg      13054
ggttgtttat atgattagat aattcttcat ttacagaggg ttaaagtaac tttttttaaa     13114
tgaagtactg aatagaggtt aggaaagttg ttggaacctg ataaatttgt aaaatttaca      13174
aaatttctca ttttaaaagc tacagtttta aaatttcatg cttttttaagc atccattgta     13234 agagtaggag tgtccaaaag caataagaac aagaaatctt tgtaagattg gtagtttcag      13294
tgtttagcca aaccattatc agaattagaa tgactaatgt tatgtaggtt tggttttcaa      13354
ctccattctt ttttttgttttc atttttttaaa aaattccaaa tctctaaccct ggccttggcg    13414 ctctgagtct tctgatctct gcccacctca tcactcactt tgttctcccc attttgttta      13474
tttcaattgc tgaactggct gagcttttac tctccccacc ttaggttgtt ccactcttca      13534
tctgtcaagc tcctactcat cctgtggact caaccactgg gttagatgaa agaaaagttt      13594
gacgtgtcca ctctttaaaa acattaagtg ttttttgttg tttgtttgag actgtcgtcc      13654
aggctgtagt gcagtggcgc aatcttggct cacggcagcc tcgacctcct gggctaaatg      13714
atcctcccac ctcagcctgt agctgcacca ccatgcctgg ctaatttta aattttttg        13774 tagaggcagg gtcttgctat gttgctcagg cttgtctaaa actcctgggc tcaagcagcc      13834
tgccttggcc tcccaaagtg ccatgattac agttgtgagc cacctaccag gtctggccta     13894
aaagcatttt tttattttta tttttttgagg tgggatctcg cactgtcacc caggctggag     13954
tgcagtagcg tgatctcggc ttactgcaac ctccgcctcc aaggttcggg tgattctcaa      14014
gcctcagcct cctgagtagc tgggattaca ggcgtgcacc atcaccccg gctcattttt       14074 gtatttttag tagcgatggg gtttcaccat gttggccagg ctggtctcaa actcctgatc      14134
tccgccagcc tcggccttcc aaagtgctga gattacaggc atgagccacg gtgcctgacc      14194
taaaagcatt ttaatgccac agagaaagcc agctaaaggg aggaggagca gtagatggat      14254
tctgtcttct aagtgggatt tgagaattga ctggatttta ataattaat aaaggtgttt       14314 tacttaatga acacagttta agagaactga gttgatttta cttcatttta cctaaagtac      14374
aaaggtaagt gtgtttactc aaataatatg tgagccttt aagtaaaaaa aaaaaaaagt      14434
gtaactgtga gagatactaa tatagtagaa ttagattttg agccaaaatt gttttaattt      14494
taaattacat tttgtgtcat agttaagtaa ctagaaaatt gtctgattta tgttcatagt     14554
acagtgtttg ggattatatt tttaatggtt ctaattttga aggttatgct tcatttatat      14614
ataatacttc atttgttcaa tttctcacgt atcattgaat tattttgatc ctttgatttt      14674
tggaaaggct aaatgaaccg agattatttt ttatttattt atttggagtt tggcttttgt      14734
tgcccaaact ggagtgcatt ggtgcagtct cggctcactg caacctctgc ctcctgggtt      14794
caagcgattc tcctgcctca gcctcccaag tagctgggat tacaggcatg tgccaccaca      14854
cccagctaat tttgtatttt ttttttgtag agacagagtt tttccgtgtt agtcaggctg      14914
```

```
gtcttgaact cccgacctca ggtgatagct tgcctcggcc tcccaaagtg ctgggattac   14974
aggcgtgagc caccacgccc ggccaccgag tttattttat aagggattat atggttacat   15034
ctgttgcaag gagcaaacca caagcaatat agaagacaac aagggtgatc tacagaatca   15094
gtatgtgata atgaaaggat gttttgactc aacactagtt tccacgtgtt taatccaaac   15154
tcagttgttg tttaaattgt taaatttcta atacacggtc cactgggtaa accatgtatt   15214
aggctaaact tttctttttc ttttttcttt tttttttttt tttttttga cagggtct     15274 cattctgtcg cccagtctgg agtgcagtgg cgtgatcatg gctcgctgca acctcaacct   15334
cctgggctca agcaatcctc ccatctcagc ctcccaagta gctgggacta cagatgtgca   15394
ccaccatgcc tggctaattt tcgtattttt tgttgacac tggtgtcctt ctacattcca    15454
ggctggcctt gaactcctgc gttcaagcaa ccctccagcc ttggccttcc aaagtggtag   15514
gattataggc gtgagccacg gtgcccaacc tatgctaaac ttttcacatc agatttatat   15574
gtgtcctgtc ccgttttact tcaccatgat tggactcagt gtacactcag atgaagaaac   15634
ttcaaaaaaa aaatactgct ccttgtgaag cagaagaaag attttactga aagtgatgtt   15694
tgtattggag catcattaaa ggcataaagg aacttgtgaa caaactactt ggtagaagca   15754
gcctggtgat gttgattggt tgatacttta ggaagcggga aatgtcttac tggagatagt   15814
tccttcattt caacagtcat ttgtgatact gttttttaat atttgccata ggatagttaa   15874
aaggtaatgg aacaaacttc agatttataa gtttttaatt aaatataaag ggggcaaaag   15934
tagataaata tcttaagagc tcaccttact gtctagaaaa aatacttgct ggcccagcgc   15994
cgtggcacac atatgtaagt aatcccagca ctttgggagg ccaaggtggg aggcttgcct   16054
gagcccagga gattcagacc agtctgggta acatggtgag accccatct caacaaaata    16114 aaaaattagg tgtggtgatg tgtgcctttg gtggcagcta ctaaggagga ttgcttgagc   16174
caggaggtga agctgcagtg tgctgtgatc ccgtcgctcc actccaggct gggcgacaga   16234
gcaagaccct gtctcaaaaa aaaaaaaaaa caaaaaaaaa cggaaaacat aagacagcaa   16294
tcaaatacaa tagatttggc ttcagtaaat gaaaaccctc actgtaggcc ctagaataac   16354
aagacttcta tattactaaa gctgattact gcttgatgaa ctctgtacat gtgatgtgac   16414
tagtatgaac ttctgaggtt gttgagatga atgagaataa acgtgaggtg ccaagaaaaa   16474
tgcctgacac attgaaagtg ctggataaat gtatgctgtc atcattgtaa gctgggctat   16534
ctcctaatag tgtaatgagt ccattgaata acaataggta acatgtttat agtgcttagt   16594
gtgtgccagg tactgttcta aacactttac atttattcac tcatttaatc acaaataaca   16654
tgaagtaggc actttgctgt tatgcagaga tggaaacaag gttatccctg catcttttt    16714 ttttggcagg ggaggagga cgggaacgga tggagttggt tttttttttt ggagcttctg    16774
agacccaagc ttcaggccat gctccccaa gcacctcccc accaccaccc cccaagatgt     16834
agtcttgctc tgtttcccag gctggagtgc aatggcgtga tctcagctaa acggaacttc   16894
tgcctcccgg gctcaagcaa ttctcctgcc ccggcctcct gagtagctgg gattacaggc   16954
gcctgccacc acgcccagct aattttttgta ttttagtag atgggggtt tcaccatctt    17014 ggccaggctc gaactcttga cctcaggtga tctgctcgcc tcggcctccc aaagtgctgg   17074
gattacaggt gtgacccact gtgcccatcc tgttccctgc cccccccccc tttttttta    17134 agttattgag acagagcctc acttggtcac ccaggctgga gtgcagtggc aggatcatag   17194
cgcactgcag cctcaacctc ctgggctcaa gcaggccctt tgagtaactg ggacctgtag   17254
```

```
gtgcatgcca gcatatccag ctaatttttt tttttttttt tttttttttt tttttttttt    17314
ttgagacaaa gtctcactct gttgcccaag ctggagtgca gtggtgtcat tgcaacctcc    17374
acctctcggg ttcaactgat tctcctgcct cagcctcccg actagctggg actacaggca    17434
tgctccacca ttcccggctg attttttat ttttagtaga gatgggattt cactatgttg     17494
gccaggctgg tcttgaacac ctggcctcaa gtgatccacc cgcctcggcc tcccaaagta    17554
aagtgctggg attgcagatg tgagctacca catccggcct atatccagct aattttaaa     17614 aataatattt ttgtagagag gtggtctttc tcccctcggc cttccaacgt actaggatta    17674
caggcgtgag ccaccttct ggctgtcttt tccttttat ttttcacac ttccagtggt      17734 ccttgggatc tgtgtatact ttagaatcat cttgtccagt ttcttgacaa acttctagaa    17794
gtttgattga tactgcattg aatctataga tcagtactgg ggaatgatgt ttttaatact    17854
gaggatttct aagtgtttga gatattctgt ttagtcagcc tttacttttg agtttacacc    17914
tgttttatat acattgtcag ttttttccta tgttataaat cttttttttt tttttttaa    17974 atttgagata gagtctcact cttgtcaccc aggccggaat gcagtggtac aatctctgct    18034
cactgcaaac tctgcctcct ggatgcaagc gattctcgtg cctcagcctt ctgagtagct    18094
gggactacag gcatgtgcca ccacgcgcag ctaattttgg tattttagt ggagaccggg     18154 tttcaccacg ttggccaggc tggtcttggc tggtcttaaa ctcctgacct ccagcagtcc    18214
acctgtctca gcctcccaaa gtgctaggat tacaggcgtg agccactgtg cccggctcta    18274
cattatttaa aaattattt gtaaccattt gttgctggca tacagaaatt cactttgata     18334
cgtttatatt tatggtataa ccagtcatct tgctaacctc tcacaatttc cagttgtatg    18394 tatttctta aaattgacaa cagttgtgta tattcatggg ttatagtgtg atgatatatg     18454
tatttgcttt gaacttctcta tgtcaacagt tatattatct acagacaata agttttgttt    18514 cttcctttt cctttctt tctttccttc tttttgtttt tgagacggag ttttgcttt        18574 gtcacccagg gtagagtgca atggcactat ctgggctcac cacaacctct gcctcccaag    18634
tcaagcgatt ctcctgcctc agcctcctga gtagctgagg ttacggcctg caccaccacg    18694
taccgctaat tttgtatttt tggtagagac ggggtttctc catgttgctc aggctggtct    18754
cgaacacccg acctcaggtg aacgcctgcc ttggcctgct aaagtgctgg gattacaggt    18814
gagaaccacc atgcccggac ttttttctct tttttttct tttttagaac ttgtaacctt     18874 ttttttttt tttttttttt tttttttgag acagagtctc actctgtcgc ccaggctgga    18934
gtgcagtggc gcgatgtcca ctcactgcaa gctccgcctc cgggttcac gccatcctcc     18994 tgcctcagcc tcccgagtag ctgggactac aggcatccgc caccgcgccc agctaatttt    19054
ttgtattttt tagtagagac ggggtttcac tgtgttagcc aggatggtct caatctcctg    19114
aactcgtgat ccgcccgcct tggcctccca aagtgctggg attacaagcg tgagccacca    19174
tgcctggcca cctatttttt tatgtgtgtg tgagacagtc tcgctctgtc acccagcctg    19234
gagtgcagtg gcactgtctc tgctcactgc aacctctgct cccctgggtt caagcgattc    19294
cttgcttcag cctcccaagt agctgggact acaggcgcct gccaccacac ccagctaatt    19354
ttttgttttg ttttgttttt agtagagatg tggtttcgct atattggcca ggctggtctc    19414
aagctcctga cctcaagtga tctgcccacc ttggcctccc aaagtgctgg gattacaggc    19474
gtgagccact gtgcctggcc aagatgaatc ttatattttc tttatccttt gttactatgg    19534
cgaatgacag tttatagatg ttctggtgtc ccctggattc ctgggattat cccaacttga    19594
tgatgatttt tgagcctttg gtttgctctt tttaaagagt cttgtttctg tgtccatgaa    19654
```

-continued

```
gaagattggc ctgtgttttt cttatattgg ccatgtgtaa ttttatatt gttttttttt    19714
tttagaagta tttgtgttag cttgaattgt attttccttg aaagtttggt gtagggcatg    19774
cctgtaaaca attcggatat ggtgctttct ttatggaaag attaaccaag ggcttatttt    19834
ctctagtagc agtaggatta cagtggtctg gcttcccatg tgcctattac ccagcttcag    19894
gtttactagt atattatact acccttcccc ccttttttgc tggagtattt taaagcaaat    19954
cctagccatg tcatttcacc agaaatattt caatgtatat ctttcagtaa aaaggattta    20014
ttttaaaata atgccattgt tatagtcaat aaagttaatg atttcttaat atcacccatt    20074
tctcagtctg tacctaaata tgtcttactc tcatttcaaa atgtgtgttt atagttggct    20134
tgtttgaatc aggattccac ccccccccca acttatgcta tggatttgtt ggagaaactg    20194
ggacattcca tatcctatat gatttctttt ttattaaggt ttgagtattt tctccggaat    20254
ttatttattt tgtatgtttt cttcatttgt ataaagttga tagtattgct ttatctttta    20314
attttctttt tttcttaacc ttcttgaagt tcgtctttg ttactccaaa aaactaactt     20374
ctagttttgg taatgctgtt acattcctat ttcctgtttc gtttatgctt ttgtctttga    20434
ttgtcttctt catattaata ctattttct aatataattt ggatacttaa ttcattatta     20494
gcaacctcag gagactcact ggagagttca ttaatttgta actttattta ttattattat    20554
tttttgaga cggagtctcg ctctgtcgcc caggctggag tgaagtggcg tgatctcggc     20614
tcactgcaaa ctctgtctcc cgggttcatg ccattctcct gcctcagcct cctgagtagc    20674
tgggactata ggcgcccgcc accacgcct gctaattttt tgtatttta gtagagatgg      20734
ggtttcaccg tgttatccag gatggtctcg atctcctgac ctcgtgatcc gcccacctcg    20794
gcctcccaaa gtgctgggat aacaggcgtg agccactgcg cccggccttt ttaactttat    20854
tttctaacat aggcctttag gttttgaaat atatttttta ttactcaatt tcctttgtga    20914
tttcttttgt aatttatcac tgcctgtttt taaaatttct aaagtggaga ttttttttgcc   20974
ctctatgttc agtatgctaa tgataaaata ttttcttgga tactccaggg gaaaagtaaa    21034
aattgcaaat aaagtatgat ctcagttttg taaatcacgt aagtataagg aaataatgaa    21094
ggaactatat cagtatatta gcaggcatt tttgaatagt ggttttaggt cagttttgtt     21154
acacatttgg gtatttgttg ttgttgttgt tgttgttgtt tgagatagga tctcgctctg    21214
tcacccaggc tagagtgcag tggtacattc acggctcact gcagcctcaa cttcccaagc    21274
tgccgctatc ctccttcctc agcctcccta gtagctgaga ccacaggtac aggccactag    21334
gcctggctaa gttttgtatt tttttgtgca gtttggtttt ctccatgttg cccaggctgg    21394
tctgctgagc tcgagccgtc tgccctcctt ggcctcacaa agtgttggga ttacaggttg    21454
tgagccaaag tgctcagcct tgtggcacat ttttgatgga ggagcccata tgatatttca    21514
aaaggaaaga gtaattctgt aaaactctgg actctaaatt atgccctgag atcttgggat    21574
acaatttgac ttagttcata tatgaccaca tgttggttta gttaatatat gaccatgtgc    21634
ttactatgtt gccagtaggc aaggagctgg tatataagtg gtaaaacatg tccttcgcga    21694
agaatgcatg gttggagtga ggggtggtca caagggatgg caagggagg agaggaggca     21754
aacccagaga taatttcagt gacatgataa aatgctaaaa gatacagaag gagcaggatt    21814
gggaagaaaa aaaaaaacta caagaagagg aagggcacat acaggaagag ttatacttag    21874
gaactaagat taattggatc aagtagacca ttaaggcaat attttgtctt caagggatgg    21934
tccattttttt aagaggataa tagctgtgga attttgttg ttgttagtag acaaggtctc     21994
```

```
acagtgccca gacttgatgt gaattcctgg gctcaagcta tcctcttgcc tcagcctcct    22054
gagtagcttg gactatagat gtgtaccact atgcccaaca cccagtaatg ccttttaat     22114 gtgaaaacta ctttagagaa ttgaaaggaa agaaaactca ataattttt atagtaggtt     22174 aatactgtca ataggtcaat caggagtaat tttcttcccc caggggatgt ttggtgatgt    22234
ctggagacag ttttgattgt cacaattggg atatgggtgc tactggcata agtagaaaga   22294
ccaggagtct cctaatgata atagagggca caagacaatc accctccacc cacaacaaag   22354
aattatcaca tagctcaaaa tgttaatagt gccagggttg agaaaccctg cattaatcta   22414
tacttagcac ccagttttgt ttgttctttt ttgagacagg atcttgctct gtcacccagg    22474
ctggagtgca gttgtgcagt taaagctcac tacaacctca aattcctgga ctcaagtaat   22534
cctcccacct tagcctcctg agtggctagg agtatagcct agtgccacca cacccagccg   22594
actttattgt ttgtagagac agggtcttgc tgtgttgacc tgggctgaag aattcctcct   22654
gccttggcct tctaaagtac tgagattaca ggtgtgagct accagggctg gtcttgcacc   22714
ctgtttttgg taggggtggt ttgtatggtg aaggagccag aggcatggtg ttgtacccta   22774
ttctggctag actttggtta aggaaagcta ttctgtaggc tacaggtcaa aaactccgcc   22834
tgttaaaggc ctactttgag gcaggtacta tataggaact tggtaaaaaa tggtggatag   22894
ccctctgctt aactggagca cacactgagt gttccacaaa tgacaggtct tttgtatcag   22954
ttgtgtgtct ttatgtatta caatatttaa aatgttttct ttccatcctg agtttagttt   23014
gtgtgtagat attttaactg ttcttctaag gaacttggga atattaatac agcttaattg   23074
catttctttt ttccatgact gtggatacaa acctttagct agcaactcat gtaataatgg   23134
gtgttgcact tttttttaa caaaaaataa aattttattt caactattat gctaattcta    23194
taacattatt tagaatgttt ttctttttt aattatcctt taagtttttgg gatacatgtg   23254 cagaacgtgc aggtttgtta cataggtata catgtgccat ggtggtttgc cgcacccatc    23314
aatccgtcat ctacattagg tatttgtcct aatgctatcc tctcctagcc ccccatcccc    23374
cagcaggccc tggtgtctga tgttcccctc tctgtgtcca tgtgttcgta tttaactccc    23434
acttatgagt gagaacatgc ggtgtttagt tttcttttcc tatgttttct gagaatgatg    23494
gtttccaggc ttcatccttg tccctgcaaa ggacatgaac tcatcctttt ttatggctgc    23554
atagtattcc atggtgtata tgtgccacat tttcttttatc cagtctgtca ttgatggggg   23614
gtgttgtact ttcaatccct ttttttcttg gtcttatttt aggtatagtt cttaagtgtt   23674
taagtttgtt gatataacca aatatcccct caatttaaaa aatctataaa atggttttag   23734
tatgacctaa aaaactacca tacaaatagt atatatatag ggctgtgtgt ggtggctcac   23794
acctgtaatc ccagcacttt ggaaggccaa tgcagacaga tagcttcagc tcaggagtgt   23854
aagaccagcc aggtcaacat ggcaagctcc gcctctacta aaaatacaaa atttagctcg   23914
gtgtggtggt gcgcacttgt agtcacagct acttgggagg ctgagatggt agaatcactt   23974
gaacctgtgg atagaggtta cagtaagcca agatcgcgca ccactgcact ccagcctgtg   24034
caacagagta agaccctgtc tcaaataaat agaaaaacat ggagtgaggt tgggaaatga   24094
catttaatgc ttattgagaa caatatagag cagttttta ttttggtttt gtcatacttt    24154
gacctttgtc ttttcccttt gcttttag at  ttt ggc tct cta ttt gac ttg      24205
                                   Asp Phe Gly Ser Leu Phe Asp Leu
                                        35 gag cac gac tta cca gat gaa tta atc aac tct aca gaa ttg gga cta                    24253
Glu His Asp Leu Pro Asp Glu Leu Ile Asn Ser Thr Glu Leu Gly Leu
40              45                  50                  55
```

```
acc aat ggt ggt gat att aat cag ctt cag aca agt ctt ggc atg gta      24301
Thr Asn Gly Gly Asp Ile Asn Gln Leu Gln Thr Ser Leu Gly Met Val
            60                  65                  70 caa gat gca gct tct aaa cat aaa cag ctg tca gaa ttg ctg cga tct      24349
Gln Asp Ala Ala Ser Lys His Lys Gln Leu Ser Glu Leu Leu Arg Ser
        75                  80                  85 ggt agt tcc cct aac ctc aat atg gga gtt ggt ggc cca ggt caa gtc      24397
Gly Ser Ser Pro Asn Leu Asn Met Gly Val Gly Gly Pro Gly Gln Val
            90                  95                 100 atg gcc agc cag gcc caa cag agc agt cct gga tta ggt ttg ata aat      24445
Met Ala Ser Gln Ala Gln Gln Ser Ser Pro Gly Leu Gly Leu Ile Asn
           105                 110                 115 agc atg gtc aaa agc cca atg aca cag gca ggc ttg act tct ccc aac      24493
Ser Met Val Lys Ser Pro Met Thr Gln Ala Gly Leu Thr Ser Pro Asn
120                 125                 130                 135 atg ggg atg ggc act agt gga cca aat cag ggt cct acg cag tca aca      24541
Met Gly Met Gly Thr Ser Gly Pro Asn Gln Gly Pro Thr Gln Ser Thr
                140                 145                 150 ggt atg atg aac agt cca gta aat cag cct gcc atg gga atg aac aca      24589
Gly Met Met Asn Ser Pro Val Asn Gln Pro Ala Met Gly Met Asn Thr
            155                 160                 165 ggg atg aat gcg ggc atg aat cct gga atg ttg gct gca ggc aat gga      24637
Gly Met Asn Ala Gly Met Asn Pro Gly Met Leu Ala Ala Gly Asn Gly
        170                 175                 180 caa ggg ata atg cct aat caa gtc atg aac ggt tca att gga gca ggc      24685
Gln Gly Ile Met Pro Asn Gln Val Met Asn Gly Ser Ile Gly Ala Gly
            185                 190                 195 cga ggg cga cag aat atg cag tac cca aac cca ggc atg gga agt gct      24733
Arg Gly Arg Gln Asn Met Gln Tyr Pro Asn Pro Gly Met Gly Ser Ala
200                 205                 210                 215 ggc aac tta ctg act gag cct ctt cag cag ggc tct ccc cag atg gga      24781
Gly Asn Leu Leu Thr Glu Pro Leu Gln Gln Gly Ser Pro Gln Met Gly
                220                 225                 230 gga caa aca gga ttg aga ggc ccc cag cct ctt aag gtaagtacag           24827
Gly Gln Thr Gly Leu Arg Gly Pro Gln Pro Leu Lys
            235                 240 ttttggtttg tgtgcacaat cggcatgcat gtgagtattg tcatgatgga tggagggttt    24887
gccttacatt gtatagcagt ttccactatt acacgccagg aatttactgt gctgtcataa    24947
gttttaagaa gtgcctgtat ttaagtaaaa cgtttatttt acagctggta ttctataact    25007
tcatacttcc aaatgattgc tggctaatgc tggttctctc tggcacaagt attggaatgt    25067
ttttatctca tttccaagtc cagtttagcc ttgtagcctc cttataaaat tacagttttg    25127
agatggctgg cattacactg tcttcagatg gatactccat tgttcctat tgctttgaat     25187 gtccctggtt ttcaagagat acattttattc tgagaaatgt attaactgtt attttttcttt  25247 attggttgat ggaaattaag gtgcatttgt tcatgtgaaa cctcaacagt gtagatgttt    25307
cagtgaacca gaacttggcc aaaagacttct gttagcttta ttaactagag aatgctaagt   25367
atattaaaaa tattttaaac ttttaaatgt ggatcctgta tacataaata aggcataatc    25427
acacatactt tagtgcttat ttcttcatat ttttctttac atattttatc tgtttttctt    25487
aaaatgggat cacactatgg ttgccagtgc ctggcatgta gttcgttttt gttgaatgag    25547
agatggcttc acttcgaaga tgaaattgga gataggtacg attttcacaa ggagtcaaga   25607
gcaagctttc tctgtaacag gaataaattg agcagacatc aggacttctg tgttcctgag    25667
aatcttgggt gcagtggctc atgcctgtaa tcccagcact ttgggaggcc aaggctagag    25727
```

```
gatcgcttga gcccaggagt taagagacca accaggtagc attgacccca tcttctattt    25787
aaggggaaaa aaaaaaaaag aaccttgatg gtgacagaga atgcaagtgt gaattgaaga    25847
cagatggaca aacttgtgtt gggggggaact gaggtgacat gtaggaattc aaaaacctta   25907
aattttttt tgctgcgaga atattgacaa gttaggattc tgttttagca ttcctttgta     25967
gattctccct ttctgcccct caccccccgcc accttttttt tttttttttg agacagggtc   26027
ttactctgtc acccaggctg gagtgcactg gcctaatcat ggcttactgc agcctcaacc    26087
taccaggctt aaacagtctt ctcgcctcag cctcctgagt agctggaact gaaggcacat    26147
accaccatgc ctggcttatt attatttttt tttttttttt tttttttttt aagagatggg    26207
gtctcactat gttgctcagg ctaatctcaa actcctcttg ggctcaagtg atcctcttgt    26267
ctcagcctcc caaagtgcca ggattacagg tgtgagccac tgcacccatc ctctgacact    26327
tttagattgc cgtgtcagtg tagtttactt agaatatttg gagtgagaac caaaaacaag    26387
gtaaattatt aagtacctct tctaggatct aggaacatag ctatgaagag agaaagtcct    26447
tgccaccgat gtttatattc tgttacggag aggagggatg acttacaata aaccctcact    26507
ggtggacaaa atactttagg gttaaagtag tgaatgaact tattttatgt aacctacttt    26567
ctactgtgca cataagatat aaattttaga gtatgccagg taagtgctat ggagaaaaat    26627
aaggaaaggc tcattgacat ctgcttgggg gtgtgggact attatggtta taatcttaat    26687
ttctttcaga aactgggttt atatagaagt gagcaaaaca aaaatccctg tccttgtgga    26747
gcttgtattt tgatgagaag gaggaattca aattttaaac ttctgttaaa cgatatttta    26807
tttccttatt tgatttttat tttgagaccg agtcttgctg ttgcccatgc tggagtgcag    26867
tggcgtgatc ttggatcact gcaacctctg cctcccgggt tcaggcagtt ctcctgcctc    26927
aggctccaag tagctgggac cacaggcatg cgccaccaag cctggctaat ttttgtattt    26987
ttagtagaga aggagtttca ccatgttgcc caggctcgtt gtgaactcct gacctcaagt    27047
gatctgccca cctcggcctc ccaaagtgtt gccaccgcac ctaggcctat tttcttattt    27107
taaatgaatc cacctatatt gatattttgt agagtactta tatcagtgtt tgacaaatga    27167
gggagcttta aatgtttaat aaatttaaca aatgttttaa gttatgtagg tttaggataa    27227
gataaccact taaggctgga tgcagcggtt cacacctaga atcattccag accagcccca    27287
gcaacatagt gagaccccca tctctaccaa aaacaaaaaa ttatccttgt gtcgtggcac    27347
acccacgcca gcagttgccc ttccactgta ccaagtccta aaattatctt gtagagcgaa    27407
ttatactcat tacatttctt aaactcctaa gacttgtgat atttaagaat taggatttaa    27467
ggtgtaagaa agttttcagt aagatttgat gactgtaacc ctgttggcaa atgacatcag    27527
cttttgcaca ccgttcttgt catggatgaa tctgtggttc aggaggtgca ggcaggtggt    27587
gacattacta ctacagctgt cttccaaaag tctgacctat ggtgatttat aggaagaaac    27647
ttggatcata ctgcctttta ccccaatctt tagattcagc ataaactaat caaagccaga    27707
atgttttaag ttacttttgt ttttgagaca ggatctcttc ctatcaccca ggctggagta    27767
cagtggcacc atcacagctc acttgcagcc ttgatctccc aggcttacgc gatcctccta    27827
cctcagactc ctaagtagct agtactacaa ggactgtcat gccctgccag ttatttttat    27887
ttttgttgag acagggtctc actatgttgt cttggcatca agcaatccac ctgccttggt    27947
cttccaaagt gctcagatta cagacagggg ccactaagcc tggccacatt ttttcaaga    28007
agaaaaaata ggcatggctc agtagttcac atctgtattc ctaccgcttt gggaggctga    28067
ggcaggagga tctcttgaag ccagaagttc gagatgtgcc tgggcaacat aatgagaccc    28127
```

```
catctctact tttctttttt cttttttctt tttttttcaaa aaagaaagaa tagttgtctg    28187
caggacgcat ttcttgtagc tgcctagaac tttgtgtggc ttcctcaccc tctccttttt    28247
agtttaggta gctatttgta tggtggtggg taattggaca tctggagcat attagctatg    28307
gagaaagaaa caagatcaaa taactatagt gtagcagaaa ttaagtacaa aatcttcctt    28367
attacattta gtgtggggag taaagaagca gggctcagga gatagaaggg gcagtgatct    28427
ggaggttggt tggtatttta ttttctaatt cctcagcaga tctgtgtggg agatggaaaa    28487
acaaaagcta gagaatcttt tttggtcaca gtgaccaaaa gtgtcaggaa gaaattactg    28547
ccagctgatc agcaatcagt gtagtctgtg tatttaaacc catagtctgc catagaggag    28607
cttggagttt ccaggtaatg catcgtgatc aagggaacaa gcagtgtcag gaattggttg    28667
aaattcagtt ggtctaggca ggcaaggcat gcaatcatga aggaccagat tgtttgggga    28727
aatatttgga taaagacatt acatttatta acaagagaca acaacacagc ttagaaattc    28787
caacattttg ttgattcaga taataggact cttgagggca taatttattg tcttagtctt    28847
ttattgtttg tcatgcgggt tctgtgatag aatgactttc atactatatc tatcatgaat    28907
tttcatgcta ataagaaaca ggttaaacaa ctcccccatg tataggtatg gatattattg    28967
gagccacata ggataaatac tagtagttta aaaaaaacat aggtagcagc agcacttgca    29027
gtcagatttg taactaccaa aagtagcctg gacttgattt aaacctgttt ctgcattcta    29087
ttgcccctgc aatcttttgg ccatatttac atagaatcaa gaaggttttt ttctttcttc    29147
ttcttctttt tttttttttt tttttttttt ggagacagag tttcgttctt gtcgcccagg    29207
caggagtgca atggcccaat cttggctcat tgcaacctct gcctcccagg tttaagtgat    29267
tctcctgcct cagtctcccg agtaggtggg attgcaggtg tgtgctacca cgcccagata    29327 attttgtat tattagtaga gacaggg ttt taccatgttg gccaggctgg tttcaaactc    29387
ctgacctcag gtgatccatc caccgccacc tctcaaagtg ctgggattac aggcgtgagc    29447
caccgtgccc gaccaagaaa ttatcttctc tgaatgcttc tcatttcagg ccacctcatt    29507
cttttatgct tccatcaaac tgccacttgt aaattacttg taaatcattc ttgtaaatta    29567
cttaccttag tctctgaatt tcatctggaa aatgaaaatg ttcttaact ttttttttc    29627 atttttggt aatagtataa agaagattaa tttacatttt tttgtttttt ttaatagagg    29687
caaactgctg aaccaaaaaa gatgtcatat tcatagattt gcagagtata gatattgcat    29747
atgatttaaa gaacgaattt taggccaggc atggtgggag atgcctgtaa tcccagcact    29807
taggcagaag gattgcttga ggctaggagt tcagtcaact cctgggcaac atctctacaa    29867
aaataaaaac aaaaattagc tgggcatggt ggtgcaagct tgtagtccca tctgcttggg    29927
aggctgagat gggagaattg cttgagccca gaggttggga attataatga gctatgataa    29987
tgcaactgca ctccaaccta ggcaacagag tgagaccctg tctttttata taaaaagtaa    30047
aagaaaaatt ttattaagag ctttgtacct gtccaaaaca gatgcttcac agaggtagta    30107
acatttgaaa ttacaaggat gagtagaatc tgcaggtgtt tcttagttag gttgtactat    30167
ctaaggaacc aacagaaaat gcctctctgt gaacttggtg tttatttcca ggttggcatt    30227
aaggagtcaa ataggaaaga aaatgtgcta ctgttcagtt gtagggaaag ggaaaagctt    30287
gaggcaaatg ctggaggctc aaggagcgtg atactttcag actttaagaa atcagtacag    30347
gaaatatata agataccata gataggtagt cagacttcat aaaaggcttt gtatacgtac    30407
tgtggggttg attttttttct tttatagagg caggtgaaaa cagaagacag gcaaacctgt    30467
```

-continued

```
tgtccacagt ctgtacaagc actgtgatag gtttgagtta agacagtcac agtaggtagg   30527
aatacatggg aagggtttta gtgtctatgt gtgcttttag aggtagaatt gaaggaccct   30587
ttgattggtc ttagcagaca gaaatctggt atgaatcctt taattgggca gtagctatag   30647
tatcttgagt tattctgagt gtttgctcaa tgtttctagt agtgatgatg acttgtagtt   30707
gggatcctat gtgtaatttg gcagaagagg acggtggctt caaactttgt ttgggatata   30767
aagttgaccc cattttgaat tatttttaaaa taatttgaaa gattaatgaa aatgcattt   30827 tataactttc attattagta aaacgtttga ctttagaata atgctgtttt tcaattaatt   30887
attattatag tataatggct ccaggtgaac ttaacataaa tatagaacat aaactactt   30947 ttaaagtaca gagggagccg gcacagtggc taacgcctgt aatcccagca ctttgggagg   31007
ccgaggtggg cagatcactt gaggtcagga gttcaaggcc agccttgcca acatggcgaa   31067
accccgtctc gactgaaagt aaaaaaatta gctgagtatg gcggcgcacg cctgtagtcc   31127
cagctactca ggctgaggca ggataaccgc ttgaacccag gaggcagagg ttgcagtgag   31187
ccgaaattgc accactgcgc cccagcctgg gcgacagagc gagactttgt ctcaaaaaca   31247
gagaagtaca taagggttgc aaagtcaaat gacttgaagg gccaagcagg tgacttagca   31307
ggtgacttaa tagagcagct aggttttaaaa cagcaaggaa tagtgtggag tctgacttc   31367 cgcatgctct atgtaaagga gtcagaatca gaagttttaa aaaacactgt catcagtgtc   31427
cctacacaaa aaaggacata ttcccaaacc atcagttttc tacttttat acaaacaaaa   31487 tacaggaata attattcaaa tgaggccaag catggtggtt cacgcctata atcgcagcac   31547
tttgggaagc tgtggtggga ggattgctag agcccgggaa tttgagacca gcctgggcaa   31607
catggcaaga ccctgtctct atttttaat agtcaaaaaa aagaagaaga agaaaacatt   31667
caaatgcttg aacatgacaa aggggttaga tggcttatta agttgaattc gccatgtagc   31727
atcatgtgtg acgtaatgga aatgaatggc aaaccttgtt taacagaatt aaatgaagat   31787
gattaaaagt atttctaaaa catcttatt tcaaatattt atgaaaataa ctctgtacat   31847
ttaccatacc caaggcccct aaatcttaat tttgatctta atcttgaaaa tgtattgttg   31907
ttagcatact ttgtatagtg ggttttttt gtttgtttgt ttttgagaca gggtctcact   31967
ctgttgccga ggctggagtg cagtggcctg atcatggctt acttgcagcc tcaacctccc   32027
aggctcaggt gatcctccta cctcagcctc ctgagtagct gggaccacag gcacatgcca   32087
ccacatccag cttttctttc cttttttttt ttttttttt ttttgagat ggagtctcac   32147 tctgtcgccc aggctggagt gcagcggcgt gatctcggct cactgcaagc tccgcctccc   32207
gggttcactc cattctcctg cctcagcctc ccgactagct gggactacag gcgcccgcca   32267
ccacacccgg ctaatttttt gtattttag tagagacggg gtttcaccat gttagccagg   32327
atagtctcta tctcctgacc tcatgatcct cccgcttcgg cctcccaaag tgctgagatt   32387
acaggtgtga gccactgcgc ccggctgttt ttggggttt ttttttgta ttttggtacc   32447 gatgggtttt caccatgttc cccaggctgt tgtcaaactc ctgacctcaa gaaccctcc   32507 tgccttggcc tcgcaaagtg gtgggattac aggtatgagt cgccaggccc ggccacttgg   32567 tttttttgcca tcatggctcc ctacaacctc tacctcccag gcttcactga taatcccact   32627
ttagccttcc aattagctgg gactataggc ttgcgccacc atgtccagat ttttgtattt   32687
tttagtagag atggggtttt gtcacgttgc ccaagctgta gtgtctttc taatagaagc   32747 tgagaatttc ctttgaaact gtctttgtga acttggaagt gaaatcagaa aaggaataat   32807
aatgtcttaa attttattgc ttattttgtt ttcttttgtt tcttactctt ag atg gga   32865
```

```
                                            Met Gly
                                                245
atg atg aac aac ccc aat cct tat ggt tca cca tat act cag aat cct    32913
Met Met Asn Asn Pro Asn Pro Tyr Gly Ser Pro Tyr Thr Gln Asn Pro
        250                 255                 260 gga cag cag att gga gcc agt ggc ctt ggt ctc cag att cag aca aaa    32961
Gly Gln Gln Ile Gly Ala Ser Gly Leu Gly Leu Gln Ile Gln Thr Lys
        265                 270                 275 act gta cta tca aat aac tta tct cca ttt gct atg gac aaa aag gca    33009
Thr Val Leu Ser Asn Asn Leu Ser Pro Phe Ala Met Asp Lys Lys Ala
        280                 285                 290 gtt cct ggt gga gga atg ccc aac atg gtgagtacta atccattaca          33056
Val Pro Gly Gly Gly Met Pro Asn Met
        295                 300 gacttgtttt caaactggca ttttgacaaa agaattgtgt taaactttca cccttctgtt  33116
atatatgctg ggatttgtac ccactaggag cctaaattga tatgtacttg atgatccctg  33176
tgaggaggct tgtgcttcct ttccatttct ctgttttttt tgttccatgt ggttattgat  33236
cagtgagcat gttgatccaa acaggagtaa gtgaactgct acaatgaagt tttaggggcc  33296
tgccattcag caacttggtc ttgtgagcgt ttccatacga tacgaaagcg aaccttttca  33356
cttttggggg aaggaatctc tggcaaagga tccgaactct cagtgaccat atttaccaat  33416
attatttgat tctactacac ccaagtaaat tccctctcaa aagtaatgta ttgttttaaa  33476
cagcaatttt tgttaaataa aatttcagg aacttctagt gttattttg tacagtcaaa    33536
ctactagtag taaatgtgtc tgcattcaac tttggaaaaa cattgtctga aaaaatcctc  33596
tttcagatgt tttagttttg tcctttgtgt cattatgttt atggactgcc tatatttgag  33656
atactctgcc aagtactgga gttatacaga tgaatgaaac atgtcatctc tgtcccgaga  33716
aatgttcact tttttttttt tttttttttt tttttttttt tgagacggag tttagctctt  33776
gttgcccagg ctggagtgca gtggtacgat ctcggctcac tgcaacttct ccctcctggt  33836
ttcaagcaac tctcctgcct cagccttctg agtagctggg attacaggca tgtgccatca  33896
tgcccggcta actttgtatt tttagtagag acagggtttc tccatgttgg tcaggctgat  33956
ctcgaactcc cgacctcagg tgatccgcct gcctcggcct cccaacgtgc tagggttaca  34016
ggcgtgagcc accgcgcccg gcctgaaatc ttcacttttt aatttaaaaa actaaattta  34076
tcccagagtt tagaaaaact agttttttcac caacccgaaa gacccctctg ctgagtctct  34136
tgaggagttc ttcattgctc tttaaaacct aatttgggtg tgcttttaac tacagacacc  34196
ctctcaccct tccctctccc gctggagttt accatgtcct tctctctgct tttgctctct  34256
gtgtattata catacttata tcacttcgta atgtcatttt ttttcttatt aaattgagct  34316
tcttaaaggt aggagccatg gtttatgcat tccctgtgtc aaaaaatgga gtctggctta  34376
tagtagacta accataaagg ttttcattga aaatatccac atctctattt attaagaaat  34436
agcacattat gactcctacc attaaatata ttgttatatc tctcag ggt caa cag      34491
                                                    Gly Gln Gln
                                                            305 cca gcc ccg cag gtc cag cag cca ggc ctg gtg act cca gtt gcc caa   34539
Pro Ala Pro Gln Val Gln Gln Pro Gly Leu Val Thr Pro Val Ala Gln
        310                 315                 320 ggg atg ggt tct gga gca cat aca gct gat cca gag aag cgc aag ctc   34587
Gly Met Gly Ser Gly Ala His Thr Ala Asp Pro Glu Lys Arg Lys Leu
        325                 330                 335 atc cag cag cag ctt gtt ctc ctt ttg cat gct cac aag tgc cag cgc   34635
Ile Gln Gln Gln Leu Val Leu Leu Leu His Ala His Lys Cys Gln Arg
```

-continued

|     |     |     | 340 |     |     |     | 345 |     |     |     | 350 |     |     |     |       |
| --- | --- | --- | --- | --- | --- | --- | --- | --- | --- | --- | --- | --- | --- | --- | ----- |
| cgg | gaa | cag | gcc | aat | ggg | gaa | gtg | agg | cag | tgc | aac | ctt | ccc | cac | tgt   34683 |
| Arg | Glu | Gln | Ala | Asn | Gly | Glu | Val | Arg | Gln | Cys | Asn | Leu | Pro | His | Cys   |
|     |     |     | 355 |     |     |     | 360 |     |     |     | 365 |     |     |     |       | cgc aca atg aag aat gtc cta aac cac atg aca cac tgc cag tca ggc 34731
Arg Thr Met Lys Asn Val Leu Asn His Met Thr His Cys Gln Ser Gly
370                 375                 380                 385 aag tct tgc caa g gtaagtggac ccacagggtt actgtactta gcaatttta       34784
Lys Ser Cys Gln cagccaggga gaagaaggaa aatgtgatca agtctatttt gtggtgatgg atatgtttaa 34844
taccttaatt gtggtgatgg tgtctgtatg tacaaagtca ccaaaatgta tacattagac 34904
caggtgtggt gtctcacact tacaatccca gcactttggt aggccaaatg gggaggattg 34964
cttgaggcca ggagtttgag accagcctgg acaacatagc aagacctcgc cgggcatgat 35024
gatgcacctg tagtcctagc tgagggacta agaaggctga ggaaggagga ttgcttgagc 35084
ccaggaagtc aaggctgcag ggggctatga ttgcgccact gtactccagc tgggtgaca  35144
atgtgagacc atgtctttaa aaaaggttgg gcgcagtggc tcatgcctgt catcccagca 35204
ctttgggaga ctgaggtggg cagatcactt gaggtcagga gttcaagacc agcctgggca 35264
atatggtgaa acctcgtctc tacaaaaaaa tactaaagaa aatcagccag atgtctgggt 35324
gtgttcctgt agtcccagct acttgggaga ttgaggtggg aggatggctt gagcccaaga 35384
gggcaggggt tggtgtgatt cgacatcata ccactgcact ccagcctgga cgatagaacc 35444
aaaccctgtt tcaaaaaaaa aacagtgtac atatgtgtaa ttttttaaaa ttattttatt 35504
ttatttattt gttttttgag acagagtctc gctctgtttc ccaggctgga gtgtggtggc 35564
acaatctcgg ctcactgcaa actccacctt ccaggttcat gccattctcc cgcctcagcc 35624
tcccaagtaa ctgggactac aggcaggcgc ctaccaccat gcccggctaa ttttttgtat 35684
ttttagtgga gacggggttt taccgtgttg gccaggatcg tctcaatctc ctgaccttgt 35744
ggtccacccg ccttggcctc ccaaagtgtt aggattacag gcgtgagcca ccacgcttgg 35804
ccaatatgtg caatttaaaa atatttata ccccaaagca tttagaaaat tccattgtct 35864
aaaatgcatca tcacagttaa ctcactcggt aaaggtcgtc ttggctgcgt ccattctgtg 35924
gcaattacga ataaagctgc cataaacaaa atcaattttg agactccttt actgatagtg 35984
acgttatttt aggaaatgat aaaaacacag tttttttttt gagatggagt ctcgctctgt 36044
cgcccaggct ggagtgcagt ggtgtgatct cagctcaccg caagctccgc ctcctgggtt 36104
catgccattc tcctgcctca gcctcccgag tagatgggac tacaggcgcc cgccaccatg 36164
gcggctaatt ttttttgtat ttttggtaga cgggggtttt cactgtgtta gccaggatgg 36224
tctctatctc ctgacctcgt gatccgcccg cctcggcctc ccaaagtgct ggaattacag 36284
gcgtgagcca ccgcgcccgg ccaaaacaca ctatcgtttt tgtgagcaag tatctaagga 36344
tgtgagaaga gaataaattt taaggtctt cccatgtggt gatcctcata gactttgatt   36404
tttatttgcc ctagcatagc atactttaaa tgttattgag ggtttgctaa ctgtcatgta 36464
ggcaagtgtt caatttaata caatttactg cagtcatttt tacccgatct aatacaattt 36524
gtatgaagtc attaaaaagt gttcttatag gcatgtgtgt cataacattg gtttagagta 36584
catttgctta gaataaagta ggttgtgtat agcatggtga aaaatgaggg ctcttaagcc 36644
agactgcttg aggttgaatc tcactttgag tactctgtga ctttgtgcaa attgcttacc 36704
cattcttttt gcctttcttg actgtgaatt ctgagtatta ataggagcta ccttataggg 36764

```
ctgttaggaa gatgaaataa gttaatgcat ttatgttact tattaagtgg tcaacaagtt    36824
agctattatt aatgtaaaaa cattaacctg ctcttgaaaa aatatgtttt cttctcttta    36884 g tg  gca cac tgt gca tct tct cga caa atc att tca cac tgg aag aat    36932
  Val Ala His Cys Ala Ser Ser Arg Gln Ile Ile Ser His Trp Lys Asn
  390             395                 400                 405 tgt aca aga cat gat tgt cct gtg tgt ctc ccc ctc aaa aat gct ggt       36980
Cys Thr Arg His Asp Cys Pro Val Cys Leu Pro Leu Lys Asn Ala Gly
                410                 415                 420 gat aag aga aat caa cag c gtaagtgatg aaatcttttg aaggtttata            37029
Asp Lys Arg Asn Gln Gln
            425 tgaaaagttt taaagtctca ccagtgccat ttatagtact acttgattat gtgagggacc    37089 tgtggtgttg tactatgttg aataaatgtt ttttccctt ttaattttc tgcttcccta      37149 gtgcatagaa ttgaactgct tagggagttt gaggctgcag tgagctatgg tcatgttact    37209 gcgctccagc ctgagtgatg gagtgagaac ctgcctcaat taaaaaaaaa aaaaaagaa     37269 agaaaaaaca gtgcagtggc tcatgcctgt catcccaaca gttttggaag ccaaggcaag    37329 aggattccca ggagttcaag accagcctag gcaacttagc aagaccttgt atcttccaaa    37389 aactttaaaa attagttgtg tgtggtgtgc ctggctgaga tgagaggatt gcttgaatcc    37449 aggaggtgga ggctgtagtg agctatgatt gtggcacagc agtccagcct gggtgacaca    37509 aggatacct gtcttaaaa aaacaaaac aaacaaaac aaaaaaaca actgaacact          37569 gcttaacatc caaataaga tccaggaact ctcaatactt attatttata caaacagcaa     37629 taggtaaatt tatgttctgc tttgaaccta tgaaaattta aagaccgttg ctttggcatt    37689 gggcaagtta ttctttttata ctatacttgt gatctaaacg ttccaggtac ttggaaatta  37749 ttttaaaaag aaaaaatatg agattatttt tataatattg ggatatagaa gagcttttttt  37809 tttttaagag aaaagacgag attaacactt taaaattgta actaccacat ctctatagca    37869 acaaaaattt aagcttttag ggttaaagga caaatttggg aagtattgta cagcatttga    37929 aaatggaatt aaatttttata acaagaattg ggaatagaaa atagacaatt caccagagac   37989 gggaggagag aggggaactc ccaatataat tcactattaa gaagagaaat aaggtatcgt    38049 ttctctcctg tagtgtaggc agaaatgatg ctgccgggtg ttggcagttg aatggctcca    38109 aagcattcat acagtgttgg tcggaacatt aataaagccc tttgggaagg ctattgggca    38169 ttcagaatca aaagcctttt ataccagtgg tcccctttac caatcagttc tgcatctaga    38229 aatttcttcc aggaaataat ggaagacaag atccacatac tcagatgttt cataatcacg    38289 taacaataat tttgtggggt ttttttattag acatgttagt cttttttttc tcaccagcat   38349 taatttgtaa tactatatct tttgtcttct ctag ca  att ttg act gga gca ccc    38403
                                         Pro Ile Leu Thr Gly Ala Pro
                                                                430 gtt gga ctt gga aat cct agc tct cta ggg gtg ggt caa cag tct gcc       38451
Val Gly Leu Gly Asn Pro Ser Ser Leu Gly Val Gly Gln Gln Ser Ala
435             440                 445                 450 ccc aac cta agc act gtt agt cag att gat ccc agc tcc ata gaa aga       38499
Pro Asn Leu Ser Thr Val Ser Gln Ile Asp Pro Ser Ser Ile Glu Arg
                455                 460                 465 gcc tat gca gct ctt gga cta ccc tat caa gta aat cag atg ccg aca       38547
Ala Tyr Ala Ala Leu Gly Leu Pro Tyr Gln Val Asn Gln Met Pro Thr
                470                 475                 480 caa ccc cag gtg caa gca aag aac cag cag aat cag cag cct ggg cag       38595
Gln Pro Gln Val Gln Ala Lys Asn Gln Gln Asn Gln Gln Pro Gly Gln
            485                 490                 495
```

```
tct ccc caa ggc atg cgg ccc atg agc aac atg a gtaagtttgt         38639
Ser Pro Gln Gly Met Arg Pro Met Ser Asn Met
  500             505 gtcatcctaa taacatggta ttggttgtgt cagtaaatga catctataaa cacagtgttg  38699
ttagctcctt tttatttttt ctgctacatg atttttttaag taattttttta aagattacag  38759 tgtaaaaggt cccttacagt tcatctacga gaggtaactg ccactggttt gtatcttcct  38819
tgatcctttt ttgcattata tgagttcaga tttgcagaaa tgagatccca tatgttattc  38879
cacaacaaac tttgattaat actgtgtaga cgggccgggc atggtggcta acacctgtaa  38939
tcccagcaca ttgggaggcc aaggtgggtg atcacaagg tcaggagttt gagaccagcc  38999
tgaccaacat agtgaaaccc cgtctctact aaaaatacaa aaattagtag ggtgtggtgg  39059
tgcgtgcctg taatcctagc tacacgagag gctgagacag gagaatggct tgaacctggg  39119
aggcagaggt tgcagtgagc tgagattgag ccattgcact ccagcctggg tgacagagca  39179
agactccatc tcaaaaaaaa aaaaaatact atgtagacat ctttcatagt cagtattcca  39239
tgtatcattt taaatggttg tatagtatgt cattctttca ttctttttttt ttttttttttt  39299 tttgagatgg agtctcgctc tgttgtcagg ctggaatgca gtggcacgat ctcggctcac  39359
tgcaacctct gcctcccggg ttcaagcgaa tctcctgcct tagcctcctg agtagctggg  39419
actacaggcg cgtgccacca tgcccagcta atttttgtat ttttagtaga ggtgggggttt  39479 tcaccatgtt ggccatgatg atctcaatct cttgacctcg tgatccaccc acctgggcct  39539
cccaaaatgc tgggattaca ggcgtgagct actgcacccg gcccaacaat ctcttacaga  39599
tggacattga gatctccaat tattctgctg ctttaaacta tacaacagaa attgtgtttt  39659
gacttgaggc atttttgggct gaaacatata gaaatgagtg tagttggtaa tgatttcctc  39719
atgtctggca ggaggaatag tgtgcctttt caaatagttt ttttgtgact tgtttgcctc  39779
acttcctgtt ttatgactga gagggaagag ggagaagtgt tccagtatcc taatttgggg  39839
atatatatgt ttctctgatt gcatatgata acattggaag aattgttcta atatcttaat  39899
tttgggatat gtatgtttct ctaattgcat atgataaaat caaacagctt ttttctgtgt  39959
ctatccctct gctgtcaagc agttcaaata tctaagctat tttgtttgag tagttagaca  40019
tccagcattg tagagaccag gtcttgtcca ggttggtctt gaactcctgg tcttaagcaa  40079
tcctcctgcc ttggcctccc agagtgctgg gattacaggc atgagccacc gcacctggcc  40139
taagattatc cccccccca cccccacccc ggaaacagag tctcgctgtg tcaccgaggc  40199
tggagtacag tggcacgatc ttggctcact gcaacttccg cctcctgggt tcaagcagtt  40259
cttcctgcct cagcctccca aatagctggg attagaggca cctgccacca cacccagcta  40319 atttttttt tggaacgaag ttttgccatg ttggccaggc tggtcttgaa ctcctgacct  40379
caggtgatct gcctgcctca acctcccaaa gtgctgtgat tacagacatg aaccactgtg  40439
cctgaccctc taagattatt ttttaataca gattgagtat ccctttttcct aaatgcttga  40499 aagcagagta ctttagattt ttttcggagt ttggaatgtt tatatttgct ggttgagttg  40559
agaatcccaa atccaaaaat caaaatgctg cattgagcat ttcccttgaa tatcattcac  40619
aaagttttgg atttctgtat ttgggatgcc aaccaaccca tactgctatt ttttactttc  40679
ttcctatttt ccactgctgt gttctgttgc tcccatttttt ggttttttgaa ttaatcttca  40739 ggacattttt tcttttctgt ttttcttttac tatataataa cagtatttc aaaccagtga  40799 tctgctttta agcacatgtt gagccactgt gcagtaaagt ttaatgctcc tgttttcaaa  40859
```

```
actgttgaac aactgttttg tcagaaactg aaagttatga gagtgaaatg caaacatttt    40919
tagacccatc aattttgatt ttgactttta ataatttaag atctaaaatg ctagatagtg    40979
acatggagct tcttgtattc aagtttgtaa gtcagatttt gcagtcactg gcatgactat    41039
tttagacagt tgtgctaatg ctcattgtac cagaccattt ctattttaat attctttaga    41099
ttcttcattc ctgccctgtt gttattgttt attacttggt ctgttgattt cattcttttc    41159
tttttttttt tttttttttct gatttcattc ttgaaagtag tattttcaag gaggatgttt    41219
ttcttgagtt ttacctaatc agggacttag ataagttttc ttagataaat tatggataac    41279
tagaaacgta cgtgtgtgtt tgagtttggt ctcgctgtgt gcatgtgtgt ttttgagact    41339
gggtctgata actggaaacg tacgtgtgtg tgtgtgtgag attggtctca ctgtgtgtgt    41399
atgtgtgtgt ttgagactgg gtctcgctgt gtcacccagg ctggagtgca gtagtgcgat    41459
cttggcctgc atcctctgcc tcctgggctc aagcggtact cccacctcag cctcccaagt    41519
agctgggacc acatacgtgc accaccacgc ctggctaatt tttgtatgtt ttgtagagac    41579
agggtttcgc catgtggccc aggctggtct tgaactcctg agctcaagtg atcgcctgcc    41639
tcgacctccc aaagcagttt gtgtttttcg ttacttccat gacaaccagt actaactagt    41699
taaataatta ttgagtgacg agttttttaag caggactagg aaaagggatg aggagcaatc    41759
ttgccttttc aggcttcctt ttacctcttc tgtattgaaa ataacatgta cagcggtaat    41819
ggaaagttgg acctggacac tagcatattt tcccctcttg ttttatatct tctgtcttgg    41879
aatgagcatt gctttttct ttcttctttt cttttcttt ttgagacaac atctcactct    41939
gtcgccagg ctggagtgta gtggcgccat ctcggctcac tgcaacctcc gcctcctggg    41999
ttcaagcgat gctcctgcct cagcctccaa gagtagctgg gactaggcgc acaccaccac    42059
cttttgtgt tttcttttag tagagacagg gtttcaccac attggccagg ctggtcttga    42119
actgctgact tcgtgatccg cccacctcgg cctcccaaag tgctgggatt acaggacgcc    42179
cagccagcat tgcttttta tctcccattc catgttacgc agaatgcact tacctttttc    42239
cttaagtttt agtaggttgt tgtcttcccc tggcctggaa tttcattact gtaattgggt    42299
agttcccttt tgttttcaa agttatgttt atagttccta ttatagctct tttcctctca    42359
ttatattatc ttgcctatgt acttttatat atatgcacaa ttatttgaat gataattttg    42419
ggggatttt gccccccattt cttcgtgtct tttatttag aattagattt aagattactc    42479
aagttccctt tgtttttatt tcttctggtc tcctgaagtg ctgagattac aggcgtgagc    42539
ctctgcgcct ggtcacattt gctttttttt tttaagttat gtttcgtttt ctatgattta    42599
ctgttgggtg cttcatcttt ttcttacctg tttgtaaggg tgcttcaaat cagcctttac    42659
atatgtgttg ccagttatat tgtcaattat ttattgtata tgctgcaaat ttttttttctg    42719
atttgtcatt tgtttcttaa ctttatagta tttattgtat ggtggctgtt gtatttattt    42779
ctgtctcctg ttatttcatt ttgacttag gt  gct agt cct atg gga gta aat     42831
                                   Ser Ala Ser Pro Met Gly Val Asn
                                                 510             515
gga ggt gta gga gtt caa acg ccg agt ctt ctt tct gac tca atg ttg     42879
Gly Gly Val Gly Val Gln Thr Pro Ser Leu Leu Ser Asp Ser Met Leu
    520                 525                 530
cat tca gcc ata aat tct caa aa  gtaagtctta acgtgattta taccctgggt    42932
His Ser Ala Ile Asn Ser Gln Asn
    535                 540
cacattacaa atactactgg ttaacaattc attgtttgac tttgaacttt agttcctcg    42992
gtttgaggat gtctttgaat acagatagat gtttgagtcc attctttctt ttttcgctct    43052
```

```
gtagcccagg ctagagtgca gtggcatgat ctcagctcac tgcaacctct gcctcctggt    43112
tctggttaaa gcaattctcc tgcctcagcc tcctgagtag ctgggattac aggaacacac    43172
caccatgccc agctaatttt tgtacttttg gtagagacag ggtttcactg tgttggccag    43232
gctgttcttg aactcctgac ctcgcgatcc gtctgcctca gtctcccgaa gtgctgggat    43292
tgcaggcgtg agccaccacg cctagcccac tctttcttct ttctacagcc ttaatcgaaa    43352
ttgtattgat tttctagtgt agcctacacc ttccctaata cagtaggatg ttgcaaggtt    43412
acagctccat aatagcctta tcctgatgtt aagaattagt ccaccagcct gggcaatatg    43472
tcaagacgtc ttctctacaa gaaaatacaa aaagttaac ggggcatggt ggcgtgcacc     43532
tgtagtccca gctactgatg aggctgaggt gggaggagca cttgaggctg ggaggtcgag    43592
gctctggtga gccgtgatta caccactgca ccctagtctg ggtgacagcg agactgtgtc    43652
tcaaaagata aaaattatta ttttaaaaag agaggtagtc catcatccaa agcattccct    43712
gaggtgagct gtgttaaaat gacagcttag tctgataaca caagccttag aaaactaagt    43772
atgggccgag catggcagct cccctgtaat cccagcactt gggaggccg aggcaggcag     43832 attgcttgat cttagaagct caagaccagc ctgggcaaca tggcgaaatc ctgtctctgc    43892
tagaaataag aaaattagcc gggcatggtg gcatccacct gtaatcccag ctactcagga    43952
ggctgaggca ggagaatcgc ttgaacccg gaggcagagg ttgcagtgag ctgagatcat     44012
gccactgcac tccagcctgg gtgacagagc gacacgccat ctcaagaagg aaaaaaaaat    44072
ggctgggctc agtggctcac gcctgtaatc tcagcacttt ggaggccca ggtgggtgga     44132 tcacttgagg tcaggagttt gagaccagcc tagccaacat gatgaaaccc catctctact    44192
aaaatacaaa attagccgga cgtggtggcg ggtgcctgta atcccaccaa ctcaagaggc    44252
tgaggcagga gaatcgcttg aacccagaag gcagagattg cagtgatctg ggattgcacc    44312
actacagtcc agcctgggca acagagcaag actttgtctc aaaaaaaaaa aaaaaaaaa    44372 ggcattacag acaaaaccca gaaatgaag tcttatgata tcttgtgtta ggacatcatc     44432 ctgcccctcca agaaaataca acttacccctc acacaggtat gaacatgcac agtttaaaat  44492
cagtctagtc acacacttct ccctgcctag ctccttaatg cgaatagaag tgacatagca    44552
tattgattcc attacaataa tcagtgtcag cttgaattaa atgaggtctt ctcctacctt    44612
tcttcactaa aactatttgg tgacccccttt ttgaag c cca atg atg agt gaa aat   44667
                                          Pro Met Met Ser Glu Asn
                                                              545
```

```
gcc agt gtg ccc tcc ctg ggt cct atg cca aca gca gct caa cca tcc       44715
Ala Ser Val Pro Ser Leu Gly Pro Met Pro Thr Ala Ala Gln Pro Ser
    550                 555                 560 act act gga att cgg aaa cag tgg cac gaa gat att act cag gat ctt       44763
Thr Thr Gly Ile Arg Lys Gln Trp His Glu Asp Ile Thr Gln Asp Leu
    565                 570                 575 cga aat cat ctt gtt cac aaa ct  gtaagtaaga ttgtggacac gtctcattcg     44816
Arg Asn His Leu Val His Lys Leu
580                 585
```

```
taaagagatg ttacgtcaac atgttttcaa tctcctgggc atttaattac taaaggaata    44876
ttagcaattt ttctgtagca tggaggttga tgttgatact tctactcttg tggatttctt    44936
gctgctgctg cttttttcct tctcaacctt tcccaccatc atctatggta gtctttcagc    44996
tttaatggta tgtgaactat tctgtctagt gacagtaaat aatatattaa acattgtttt    45056
tagctattgc ctttgcaaaa cttatatatc taagaaaaac taggcctcag ctcattaaaa    45116
```

```
tattgcattg ataacatcct tttctgttac tcctggtaga gcaggggttt tttgtttgtt    45176
tgagatggag tctcactctg ttgcccaggc tggagtgcag tggcacgatc ttggttcact    45236
gcagacttcg cctcccaggt gccagtgatt ctcctgtctc agccgcccag gtagctggga    45296
ctacaggcac gtgccacctc acctggctaa ttttttgtatt tttagtagag acggggtttc    45356
actgtgttgg tcacgctgac ttcaaattcc tgacatcaag tgatccgcct gcctcagctt    45416
cccaaagtgc taggattaca ggtgtgagcc accacgcctg tcctggtaga gcttttatta    45476
tgtaaaaatc tggtagggtg gactctctgg tcttctcgtc ctccagatgt gcacatggca    45536
gtttattttt gagaagttga tatatttcag gcactctccc cttacgaact ccatcttaat    45596
ctaaagagtt tttgtcagat gaaggagggg gaggcatata gagcaaggta atgaaatgtg    45656
ctcagcatca taaaaggta gagcttggac cttgccaatt acagagttta cccttcaaac     45716
accatgcagt attttttctt ggagaagtct tttcatttca ctttcagtta atagcagggt    45776
cgtctttact gtatccatat ttttttaattg actgaggaac tatttatcat tttgtcttaa    45836
tttattttta tgttatgtca aactaccaat tatatacgtt tcatttagga attttttttt    45896
cctcccacga acccatgctt gctaatcatt taggattctt tgtttgtttg ttttttgtttt    45956 tgttttttgag actgagtctt tctctgtcgc ccaggctgga gtgcagtgtc gtgatctcgg    46016
ctggctactg caacctcccg tctcctgggt tcaagcgttt ctcctgtctc atcctcccaa    46076
gtagctgggg ttacaggtgt tgccaccac acctggctga tatttgtatt tttagtagag     46136
atggggtttc gccgtgttgg ccaggctggt ctcgaactcc tgacctcagg tgatccacct    46196
gccttggcct cccaaagggc tgggattata ggcgttgagc cactgtgtcc agccaggaat    46256
tcttcagtgg tagcactaag taacggaatt tgacaaggaa agaacttcac aagtttaatg    46316
aaattattcc tttaataaag aataaccgat ctcttatttt gtgacagact attcaggaac    46376
tttttattta tggacagaga tgattatttg gggttgatca tttgacttta cgttaaaagt    46436
ttattatata tgctcgagtt ttctaccaac ttggtattat tctggacttc catttatatc    46496
ttcttgatct ggttccttca agtcctatgc aactgagtac gggatgtcca ataaaaatta    46556
gtgcctaaag atcacatttg tcagtcataa gagatactag tgcaaaacat tttgttaggg    46616
aattgcatga aagtgaaaaa ctgaatctaa cagaatcatt acgcatttct ggtctgtcca    46676
cttcaggttt ttggtttttt gtttgttttt tataagcctt tgtcagaaca gttcaagttt    46736
ttgatgtttt aacattttag agtggttact gaattttatt tcagtaagct aaataataaa    46796
tttagaagag cagatggaac tctgaaggct acttgatact atgacaaggc ctgttttcct    46856
cactgtcttt agtatgtaac ccaaagtaat attttgcttt atgtctagag taacagggac    46916
caaagagtat ttttttataga gtcatttctt atattgtgaa cggaaatata gacaaaaatt    46976
cttttgttta tcacaaaaag ataatttcat ttcagtaagt aatatatatc accttgccat    47036 tatttttttct tttcctctat gtgttcagtg tataaaaatc agaaaaatac taattaaatg    47096
ctgacatgat attacagtgg taggatttttc tttttccag c gtc caa gcc ata ttt   47151
                                              Val Gln Ala Ile Phe
                                                            590 cct acg ccg gat cct gct gct tta aaa gac aga cgg atg gaa aac cta      47199
Pro Thr Pro Asp Pro Ala Ala Leu Lys Asp Arg Arg Met Glu Asn Leu
         595                 600                 605 gtt gca tat gct cgg aaa gtt gaa ggg gac atg tat gaa tct gca aac      47247
Val Ala Tyr Ala Arg Lys Val Glu Gly Asp Met Tyr Glu Ser Ala Asn
    610                 615                 620 aat cga gtgagtgtct ggttttttttc tattaatagc caagattgaa cctgttgtgg      47303
Asn Arg
```

```
Asn Arg
625 ttattttatt cctctttagc atgtacaagt agtacatatg cttcagacgg gggacacgct    47363 gtagctatcc cgtcttattg tccccaagca tagttaggat accaaagcag tttcttaagt    47423 gtatgtcatc aagaatctta tgttttcct cctaatacag tgcactcatg tggcacttta    47483 tctggttgtc ctgtcaacct aaaaagtggc tgagctggcc gagtgcagtg gctcggtgcc    47543 tgtaatccca gcagtttgaa agtctgaggt gggcggatca cttgagccta ggagttggag    47603 accagcccgg gcaacatagc aaaaccccat ctctacaaaa aattagccag gcatggtggc    47663 acgtgcctgt tgtcccagct gctcaaaagg ctgaggtggg ggaatcacca gagccttgga    47723 agtcaagctg cagtgattcg ggattgcgct gctggtgaca gagggagacc ttgtctctct    47783 caaaaacagg agtggggtgg tgctgagctg ttaccagctg tgttctcttt tcactagaat    47843 ataatgaagt agcgacttaa ctgttgttca cggtagttca gattctctac ataagttgaa    47903 ctttcctttc taaattggca ccagttctta atgcagcata taaatgaaa ctaatatcta    47963 ttctcagttt atttttctg ttacctggtg gtagttcctt ttttcctcat ctcccttatt    48023 ttacttcaac aattcaaaag gcg gaa tac tac cac ctt cta gct gag aaa atc    48076
                       Ala Glu Tyr Tyr His Leu Leu Ala Glu Lys Ile
                                    630                  635 tat aag atc cag aaa gaa cta gaa gaa aaa cga agg acc aga cta cag    48124
Tyr Lys Ile Gln Lys Glu Leu Glu Glu Lys Arg Arg Thr Arg Leu Gln
        640                 645                 650 aag cag aac atg cta cca aat gct gca ggc atg gtt cca gtt tcc atg    48172
Lys Gln Asn Met Leu Pro Asn Ala Ala Gly Met Val Pro Val Ser Met
        655                 660                 665 aat cca ggg cct aac atg gga cag ccg caa cca gga atg act tct a      48218
Asn Pro Gly Pro Asn Met Gly Gln Pro Gln Pro Gly Met Thr Ser
670                 675                 680 gtaagtggtt tttgttatat ttctgtttga gagaaattga taataaaata gtttctatct    48278
aaagtcatta atttctgtaa gcttgtgtaa ctattctaga gttttttaaa taaccatttg    48338
cctttgcaaa gaaataact catctactag taaaaacaga agcagaacaa gtatatttaa    48398
gatgtctggg catggtactt aacataccct gataatctgg aattgttttt agagcccaag    48458
gtgtaaactt ctctaatagt gacatctaga aagcaatagc ctacatacag atgttcacag    48518
atttctctga gactggcttg tgtggtaagt agccagtaaa tgtttgtagg ctgaccaggt    48578
tcaggagccc tgtaacacac ataatatcat attacactgt cacactttct acttgacata    48638
aaatattcta agtctaggaa ctcttttttt ttttttcttt ttcttttttt ttgaggcaga    48698
gtctcactcc gtcacccagg ctggagtacg gtggcatgat cttggatcac tgcagcctcc    48758
gcctcccagg ttcaagcaat tctcccacct cagccttccg agtagctggg attacaggca    48818
catgccacca cgcctgtcta atttttgtat ttttcgtaga cagggtttt gccatgttg    48878 gcctagctga tctcaaactc ctggcctcaa atgatccgcc cacctggca tcccaaagta    48938 ctaggattac aggcatgagc caccactccc tgcctagaag catcatttaa aattacattt    48998
tgacagcttc agtttctgat tatagcatca ttgttgacct gatgaattaa ccagatagcc    49058
aagactatga taaatagtct tactcaatcg ttgacttatt ggtacgatca aagtagtgaa    49118
atatggagca ggcacaccat tttcaggaat ggcacaggct gtaagtgctg tgagcaaggc    49178
tgtgatagga aaacctgca tttactgagt taggaaatgc taatgacctc taagaagtgc    49238
caactgagcc agcgggcagt aaacctcata cgatcagtag attataggtg ggctgagaag    49298
```

```
ttcatctctt tcattcattg aagtagtaaa gtagagaacc attggttacc actggccttt    49358
agcagcctca tttgctaact gaagtgtgcc aggtactgtt ttgtaatgtg taaaaagttg    49418
ggaggagcaa cattgctgag gaaatagtat acatggaggc tgcccaatag taaggaaaaa    49478
cacagatttt ttgagtagtt agaacaaatt ttcaggaatg aaaaagtcaa gattagagtt    49538
gagactgctt cagtacatga tttggacttg agtagtaact aaagattaaa aaaagtagac    49598
aggctgggtg cggtggttca tgcctgtact cccagcactt tgggaggccg aggcgggtag    49658
atcatgacgt caggagatgg agaccatcct ggctaacacg gtgaaacccc atctctacta    49718
aaaatacaaa acaattagcc gggcatggtg gcgggcacct gtagtcccag ctactcaaga    49778
ggctgaggca ggagaacagt gtgaacccgg gaggcggagc ttgcagtgag ccgagattgt    49838
gcctctgcac tccagcctgg gcaacagagc gagactctgt ctcaaaaaaa aaacaagtgg    49898
acatacctga gatacttggt tttggtagaa tttactcaag ttctgggtga agttctgagc    49958 caagttaaa gtctgtgaga tattaaattg tattctaatg tcagtataaa cagtatggta    50018
ctgatgtaag caggaataag tggtagtgga actgagtatc agccttaagt atatgttgac    50078
ctttagctcg tactaaatct gacattttgt agaatgagat tcttaccta acctgataca    50138 cagaaaataa tagaagcata aaagtggtcg ggcatggtgg tggctcacgc ctgtaatccc    50198
agctctttgg gaggctgagg ctgcagatca cttgagctta ggagttcaga accagcctgg    50258
gcaacatggt gaaactctgt ctctataaaa aatacaaaaa ttagccaggc atggaggtgt    50318
gtgcctgtag tcccagctac tcaggaggat gaggcaggaa catcacttga gcccaggagg    50378
tcaaggctgc agtgagctgt gattgtgcca ctgcacttaa gcctggacaa cagagtgaga    50438
tcctgtcttt aaataaataa ataaggtttg taaactttga aaaacaaaa ttgaaagaac    50498 tacgtagaat gttgaagaaa acataacatt ctcatcttca tgtttcttta acatttgttt    50558
ttttgttgtt ggttttgttt ttgttttttt tttgaaacag tctctctttg tcactcaggc    50618
tgaagtgcag tggcaccatc taagctcact gcaacctctg cctcccagat tcagttgatt    50678
cttgtacctc agcatcccca gcagctggaa ttacaggcat gcatcaccac acctaactaa    50738
tgttttgtat tttcagtaga cagggtttt cacaccatgt tggccaacct agtctcgaac    50798
tcccggcctc aagtgatccg cgtaccttgg tcttgcaaag tgctgggatt acaggcttga    50858
gccatcacac ctggccacgt ttgattttt tgttttaata caagaatac agttattata    50918 gaatcagaga gtggcaatgg caggactatg tgtattggcc taaaatatg cccatagtaa    50978 acttatgtaa cgtgtaccat cttgaaaaaa taatcccggt tgttaatgga gttgaaggta    51038
ggtaactctt tccttattaa ttttttgcaa agatacgaag tttcaggaaa agctgatgac    51098
agaagtatgc atgttatagt ctgagttttt ttaagtgtgg catatgccct agaaaaagtt    51158
ctggaagaag taaatactaa tctctgaaca tgggcttctg atggggcag tggaattcca    51218 ggatacttgt gttgtgtgat aaagggtttt tgattatttg acttaatgca tatagtttgc    51278
attaagggca tatatattga aatgtgaaag atggacattt ttgtttgtgt atattttctt    51338
tacctctaaa tatttatata tatacatttt tgagatgggg tctgtttcgc ccagcctgga    51398
gtgcagtggt gtgatctcgg ctcactgcat cctccatgcc tcccaagctc aagcaatcct    51458
cccacttcag cccccccaagt agctgggacc acaggcacac gccaccatgc ctggctaatt    51518 ttttttttatt ttttagtaga aacagggttt ctgtatgttg cccagactag tctcgaactc    51578
ctgagctcaa gatatccacc cacctcggcc tcccaaaatg ctgaaattac aggtgtgacc    51638
cactgcgccc agcctttaaa tatttatctt aaaaaatagt atcaagatgt tcctttaaat    51698
```

-continued

```
aattcatcaa gtttccttaa aatgacaaga gctgcctcat ggagcaataa tagatacatt      51758
cgtatctgca tcatatgggg caaatgtggg cagtaggatt gcggttttat ttttaaacca      51818
ttttcatttg attagtctca aatacttaaa aatcagaaga ttttgcattt aaaaagtctg      51878
aatttctggc tgctttaaaa aaaaaaggac atgtctggca gacttgaccc cctttctcct      51938
acagtgacac ctgtctatag ctgcactcat ggctgactct agaagagctg tgttttctct      51998
ccacttcagt cctcaccatt ctctattgtt ttgggtactt aaaacagttt tacttggtat      52058
tagctgcttg gcacttgcca tttagcttgg aacacctatc catattgttg acttgaaaaa      52118
aaagttactc atatcttagg tgaaaacatt gttttgtaga tagtgtgcgt gaatacagat      52178
atgtgtgggg aggaagagga aaggtttatc tcaaggtcat ttgttggatc ctgattcatt      52238
tttctattga ttttttaattt ttatgtaatg agcatggatt atgcatatac ttcttataaa     52298
gcttgcagag ttacagataa aagtttatat gaataaatgt tgagcatttc ctctctcagt      52358
tttgctcatt tactaaaggt tgaaatttgt ctgaagggat ggacatctcc ttagaagagc      52418
agcaggtctt cctctcctat gcctgaggct tgaatgtaca gcccttgatg gagggtatgg      52478
ccagggtgga gccaggtcac tacagacatc tgtccttttcc gagggtgctg taaaaatatt     52538
ttctctgtgc actatgttga aagtactaca ctagagcatg tgcagataat ccaggaaaaa      52598
gaccttagaa tttatgtatt tatattttag gttttttttg agacgagtc tcgctctgtc       52658 gcccaggctg gagtgcagtg gcacgatctc agcttactgc aagctccacc tcccggggtc      52718 atgcccggg ttcacgccat tctcctgcct cagcctcccg agtagctggg actacaggcg       52778
cctgccacca cgcccggcta ttttttttgta tttttagtag acagggtttt caccgtgcta     52838
tctaggatgg tctcgatctc ctgacctcgt gatccgcccg cctcggcctc ccaaagtgct      52898
gggattacag gatattttat ttttttaaga attatttctg ttttttgtatt taagaggtac     52958 atgatatgta gtgtggtata atatgcatat tatttaaaat caatgttcac agtttatgtg     53018
cataaaaacg ttgtgctaca tgatcaaatt cggccaccat tagacatgat tcatagctat      53078
tatccatgga gatactctgt tgcatgccaa ccagactcag actttgttaa acaataacat     53138
attaaatgct atgatggcct caattttttt ttttttttt gagacagagt cttgctccat       53198
cgcccaggct ggagtgcagt cgtgtgatct tggctcactg caacctccgc cttccaggtt      53258
catgcgattc tcctgcctca gcctcctgag tagctgggat tacaggtgcc tgccaccacg      53318
cctggctaat ttttttgtat ttttagtaga caggggttt cgccatgttg gctaggctgg       53378
ttttgaactc ctgacctcaa gtgatccacc cacctcagcc tcccaaagtg ccaggattac      53438
aggcgtgagc cactgtgcct ggcctataat ggcttcaata gcttattttt ctatcaacat     53498
tgaaagcacc cgggctcata aggaatacc aacaaatcca cttggaggca ttttttctgta     53558 ttccagaaat aacattttct tcaagcttct gtctagttca gagctttatt ttgtgattca     53618
tactcaattt tcaaggtat tattaaaaat attttgtggg gtttgtgtgt gcagtgagtt      53678
tttgtttggt taagggaaga tggtgcaaag atacttattt ctcttttta ctctag at        53736
                                                                         Asn
                                                                         685 ggc cct cta cct gac cca agt atg atc cgt ggc agt gtg cca aac cag          53784
Gly Pro Leu Pro Asp Pro Ser Met Ile Arg Gly Ser Val Pro Asn Gln
                690                 695                 700 atg atg cct cga ata act cca caa tct g gtaaatagtg aaaaaaattt              53832
Met Met Pro Arg Ile Thr Pro Gln Ser
705                 710
```

| | |
|---|---|
| tttttatttta aaagaatccc cggtgtactg caagataata cttgctacct gaacacccgc | 53892 |
| tttatgccaa cagcaagtgt catgattacc tgcccataga ggaagagggg gtgaagagca | 53952 |
| ggttggctgg cagatcacag ggcaggtgac attaaatgat caagtatcca ttaaaaaaca | 54012 |
| actgcaggct gggcatggtg gctcacgctt gtaatcccag cactttggga ggccgaggct | 54072 |
| ggtgtaccac ctgaggtcaa agtacgagac cagcctggcc aatgtggtga aaccctgtct | 54132 |
| ctactaaaaa tacaaaaaaa ttagccggtt gtagtggcac gggcctgtaa tcccatttac | 54192 |
| tctggaggct gaggctggag aatcacttga acccaggagg cggagtttgc agtgaggcga | 54252 |
| gatcgcgcca ctggacccca gcctgagtga cagcaagact tcgtctcaaa aaaaaaaaa | 54312 |
| aaagcagatt gtaaaatttg taaaattcag tttggagatc ctgttagttg ataatgtctg | 54372 |
| tttactgcta ctgtgaatga gacagattta tttatactta gaaggttgaa agccagttta | 54432 |
| ttagtcctga tagaatcagg gccaggtgcg gtggctcacg cctgtaatcc cagcactttg | 54492 |
| ggaggctgag gcgggcagat cacaaggtca ggagatagag accatcctgg ctaacacagt | 54552 |
| gaaaccccg tctctactaa aaatacaaaa aattagctgg gtgtggtggc ggacgcctgt | 54612 |
| agtcccagct actcaggagg ctgaggcagg agaatggtgt gaacccaggt ggcagagctt | 54672 |
| gcagtgagcg gagattgcgc cactgcactc cagcctgggc gacagagcaa gactccgtct | 54732 |
| caaaaaaaaa aaaagataca gaatcagaca taagaattct atctttttatt attcaatttc | 54792 |

| acaaaggcat tcagatctaa cattttgctc atattcacag gt ttg aat caa ttt | 54846 |
| | Gly Leu Asn Gln Phe | |
| | 715 | |
| ggc cag atg agc atg gcc cag ccc cct att gta ccc cgg caa acc cct | 54894 |
| Gly Gln Met Ser Met Ala Gln Pro Pro Ile Val Pro Arg Gln Thr Pro | |
| 720 725 730 | |
| cct ctt cag cac cat gga cag ttg gct caa cct gga gct ctc aac ccg | 54942 |
| Pro Leu Gln His His Gly Gln Leu Ala Gln Pro Gly Ala Leu Asn Pro | |
| 735 740 745 | |

| | |
|---|---|
| gttagtttga cgtctttggt aatctctttg gcctttacct ggtattttga aaatcctgtt | 55002 |
| tgttcctact ttataaattc tcacagtcat ttaaacagac cataactcct agttcttctg | 55062 |
| taattcttct gtatttaact ctactagaaa gctgaccaaa aaacgaaaac agccagtccc | 55122 |
| ttgtccctgg agtgtcagtg tttagtggcc tgcatgcgtt ttcacggtca cttctcttcc | 55182 |
| ctgatgtctg tcttccctcc tccaggcaga gaactgtctt gcaaggttga tggtgcgttt | 55242 |
| ttgcctggtt cttgaactcg gagaagagag actaggcttc tcctgctcct tatgcgaact | 55302 |
| cttaaccagt ccatctctct accttgaccc taaccctcct gctgcccttt agagttagct | 55362 |
| ggtgcctctg attcttgacc cttttggggg ttcctgagca ttactacttc tcactaatct | 55422 |
| gccattttca acagggagtt ctgtccttca ttttaaccta taagacagat ggtcttagct | 55482 |
| tatgaagttt ttggcctttg gtactcgaga tttctttctt taaggcctga atttgtgtag | 55542 |
| ggtaattttg gaaatgacat gtaacagtgc tagagcattt gtggaccatg aatgctacca | 55602 |
| gattctgcta caacttgtaa gattttcttg tttttacata ttatgggtct tagaatttgt | 55662 |
| gttattacat cactgacatg acctcatgaa attgtgatta actctcctca cttaacagag | 55722 |
| catgcaaaga aaattacctg ctatccttgt gctaggcata tttgtgtacc aagagaatgt | 55782 |
| gtgttccatc ctcttactat ttcttggagt aggcctaggt aaactgtgag gctatttctc | 55842 |
| tttatcttgg cacaagagtc agttgttcta caactttctt ccttctcctc ttcagccctc | 55902 |
| ttcacctata ctcctgtctt tggcttttct ctacttaata agcctgacgt taggagcatt | 55962 |
| tgatgatttt agttatagta gaataactat aatgaagcag tttggtgatt tgtgtttttt | 56022 |

```
tttttttca g cct atg ggc tat ggg cct cgt atg caa cag cct tcc aac    56072
          Pro Met Gly Tyr Gly Pro Arg Met Gln Gln Pro Ser Asn
                  750                 755                 760 cag ggc cag ttc ctt cct cag act cag ttc cca tca cag gga atg aat    56120
Gln Gly Gln Phe Leu Pro Gln Thr Gln Phe Pro Ser Gln Gly Met Asn
                765                 770                 775 gta aca aat atc cct ttg gct ccg tcc agc ggt caa gct cca gtg tct    56168
Val Thr Asn Ile Pro Leu Ala Pro Ser Ser Gly Gln Ala Pro Val Ser
                780                 785                 790 caa gtatgtctca taagtggatt tttcacttat ttttgattct tgaaacttct          56221
Gln cttgatgtag gttttttatag gagagagtgg cagcaaatag tgggtgaaaa cagatgattt 56281 tttaaaaaat aacaattttg gacttagggt attctgaaca tgaagagatt attctgtgac  56341
atagcaatgg tgttaattgt tacaaagtag gaaataattt aaatggatag ttttaattgt  56401
ttttactagt gaacactta aaataaatct tagaattaaa cacaatgtag aaggaaatct  56461
ggctgaaaag agcataggca ggccctagag cactctgcac tcaattctgc cattttctg   56521 cggtggctga ggccattctg ctgaatggtt tgaagtctct ttagttaagt actatcttga  56581
tggtgctgtc caaagataca tgcccagtaa tagggtattt tacacatttt gaaatagaca  56641
cattgctact ctttgtttaa tcagtttgtg tcctaaattt atatatcatg cctatgtaag  56701
tatttcctta attctgttct gaattgctgt cttgttatgt tttttatttt aacag gca   56759
                                                              Ala caa atg tct agt tct tcc tgc ccg gtg aac tct cct ata atg cct cca    56807
Gln Met Ser Ser Ser Ser Cys Pro Val Asn Ser Pro Ile Met Pro Pro
795                 800                 805                 810 ggg tct cag ggg agc cac att cac tgt ccc cag ctt cct caa cca gct    56855
Gly Ser Gln Gly Ser His Ile His Cys Pro Gln Leu Pro Gln Pro Ala
                815                 820                 825 ctt cat cag aat tca ccc tcg cct gta cct agt cgt acc ccc acc cct    56903
Leu His Gln Asn Ser Pro Ser Pro Val Pro Ser Arg Thr Pro Thr Pro
                830                 835                 840 cac cat act ccc cca agc ata ggg gct cag cag cca cca gca aca aca    56951
His His Thr Pro Pro Ser Ile Gly Ala Gln Gln Pro Pro Ala Thr Thr
                845                 850                 855 att cca gcc cct gtt cct aca cct cct gcc atg cca cct ggg cca cag    56999
Ile Pro Ala Pro Val Pro Thr Pro Pro Ala Met Pro Pro Gly Pro Gln
860                 865                 870 tcc cag gct cta cat ccc cct cca agg cag aca cct aca cca cca aca    57047
Ser Gln Ala Leu His Pro Pro Pro Arg Gln Thr Pro Thr Pro Pro Thr
875                 880                 885                 890 aca caa ctt ccc caa caa gtg cag cct tca ctt cct gct gca cct tct    57095
Thr Gln Leu Pro Gln Gln Val Gln Pro Ser Leu Pro Ala Ala Pro Ser
                895                 900                 905 gct gac cag ccc cag cag cag cct cgc tca cag cag agc aca gca gcg    57143
Ala Asp Gln Pro Gln Gln Gln Pro Arg Ser Gln Gln Ser Thr Ala Ala
                910                 915                 920 tct gtt cct acc cca aca gca ccg ctg ctt cct ccg cag cct gca act    57191
Ser Val Pro Thr Pro Thr Ala Pro Leu Leu Pro Pro Gln Pro Ala Thr
                925                 930                 935 cca gtaagtagag atttggattt aggcagaatc attagagcta tactgtagta         57244
Pro ttatattact tctgggccat ttccattctc ttttgcttta tctcttactg ttttctccac  57304
aagtagaatg taatctattt ttcattaggg acttttgtat cctgttttgc cttcctgtga  57364
tagtacctat cgtagcagga gcataaagat tttatttagc tctgactttg accattatgt  57424
```

-continued

```
ttcatgttgt accctgaggt ctgaaggtac gtaaaggggt acgacaaggg gacacaatcc    57484
ttctccttat ttagtatatt atttagtgca gcacataaat tttacatata tttaaggaat    57544
cttttttcaaa cagtttgagc cataaaacct agagattgaa tttaaaaatt gcagatttgg   57604
acgggcgcgg tggtgtacac ttttcatcct agcactttgg gaggctgtgg caggcagatc    57664
acttgaggtc aggagttcaa gaccagcctg gccaacatgg tgaaaccctg tctctacaaa    57724
aaaataacaa aaattagcca gacatggtag cgggtgcctg taatcccagc tactcgggag    57784
actgaggcag gagaatggct tgaacctggg aggtggaggt tgcagtgatc cgagattgcg    57844
ccactgcact ctagcctagg cgacagagtg aaactccgtc taaaaaaaaa aaaaaaaatt    57904
gcagatttat gagtccttgt ggcccaaacc aaagtttaaa aataagatga gagaattata    57964
gacccagaac aacctgtagc ttccttgtga gaggttggtt atgtatataa taaaaatcca    58024
aattctcatc taatagttga atccttatta atagaacttt ttttaagggt ttagaagctt    58084
ctactttgat accgatatta atatatatcg gtatccaata gttctcagcc atgttgatga    58144
actgagaagt tccatgagtc acagccgttt tataaagtac tgtacttgac ggatggctgg    58204
ttcatcgtgg cctctgatag acaaggaagg acagaatgag agaggaacca gtggatctgc    58264
ttgattttat tctttataaa atcaaggata cttccagaaa atactgactt ctcattaaga    58324
gatttcttat gacaagcctt aggataaaga tagggaatgc cagtttatct cattagaatc    58384
tagcgattca aaacagccac tctctgggac atcattatat ttattgtctc cttttctgta    58444
cctttgaaac tttctctggt gagaaggtaa aaacaagcca gtctttctta ttttctttca    58504
ctcatttctg tataaatgtg agctcctctg aagcagacat ctttgaaatc cccacacact    58564
gccagataat gatagttatc aatgaaatag ttgctggttc tttgatgtac aatcagccaa    58624
ccagtattta caagtcttaa ttctcctgtt cttaagcata attaagggag gtgaaatggg    58684
cagagcaaat gaaagcacca tgaataaata taagccaaga aataggtggc taattctgct    58744
atcctgttgc ttaccttaca ttctgattgt atcgttggca gactctgcgt gtgtctcacc    58804
```

| | | | | | | | |
|---|---|---|---|---|---|---|---|
| tacttcccttt tttttctgc | ccag | ctt | tcc | cag | cca | gct | gta | agc | att | gaa | 58855 |
| | | Leu | Ser | Gln | Pro | Ala | Val | Ser | Ile | Glu | |
| | | | | 940 | | | | 945 | | | |
| gga | cag | gta | tca | aat | cct | cca | tct | act | agt | agc | aca | gaa | gtg | aat | tct | 58903 |
| Gly | Gln | Val | Ser | Asn | Pro | Pro | Ser | Thr | Ser | Ser | Thr | Glu | Val | Asn | Ser | |
| | 950 | | | | | 955 | | | | | 960 | | | | | |
| cag | gcc | att | gct | gag | aag | cag | cct | tcc | cag | gaa | gtg | aag | atg | gag | gcc | 58951 |
| Gln | Ala | Ile | Ala | Glu | Lys | Gln | Pro | Ser | Gln | Glu | Val | Lys | Met | Glu | Ala | |
| 965 | | | | | 970 | | | | | 975 | | | | | 980 | |
| aaa | atg | gaa | gtg | gat | caa | cca | gaa | cca | gca | gat | act | cag | ccg | gag | gat | 58999 |
| Lys | Met | Glu | Val | Asp | Gln | Pro | Glu | Pro | Ala | Asp | Thr | Gln | Pro | Glu | Asp | |
| | | | | 985 | | | | | 990 | | | | | 995 | | |
| att | tca | gag | gtgagagtag ggcaattact gtttgatttg gttaggacct | | | | | | | | | | | | | 59048 |
| Ile | Ser | Glu | | | | | | | | | | | | | | |

```
cagtatagga acccaagttt taaaaaatat tgcagaaaaa tattttgata attagatctc    59108
atggcataga ttttgcatga gaagggtgt tcagattact gattcccaac tagatatctt     59168
tggaatacta aaaattctta cgttttcttt   tag                               59219
```

| | | | | | | | |
|---|---|---|---|---|---|---|---|
| | | tct | aaa | gtg | gaa | gac | tgt | 59219 |
| | | Ser | Lys | Val | Glu | Asp | Cys | |
| | | 1000 | | | | 1005 | | |
| aaa | atg | gaa | tct | acc | gaa | aca | gaa | gag | aga | agc | act | gag | tta | aaa | 59264 |
| Lys | Met | Glu | Ser | Thr | Glu | Thr | Glu | Glu | Arg | Ser | Thr | Glu | Leu | Lys | |
| 1010 | | | | | 1015 | | | | | 1020 | | | | | |
| act | gaa | ata | aaa | gag | gag | gaa | gac | cag | cca | agt | act | tca | gct | acc | 59309 |

```
Thr Glu Ile Lys Glu   Glu Glu Asp Gln Pro  Ser Thr Ser Ala Thr
            1025                   1030             1035 cag tca tct ccg gct   cca gga cag tca aag  aaa aag a gtgagtctct          59356
Gln Ser Ser Pro Ala   Pro Gly Gln Ser Lys  Lys Lys
            1040                   1045 gaagccattc gttctggagg tagctgaaga aaccaaagac ccagggcaga attgcggtca        59416
tgcctcttgg gcctcagaag ttgccattat tgtgatttca ttaacctgga agccctgggc        59476
ctggtctctt cattgttact aataattttt ctttctttt ttttttttta atattcactt         59536
gcagcaacca atgagttaag tcattcccct catttcttca gggttccctg tgttagtaca        59596
ccctaaaaat tgtctcattt ttcaggagag agaaatgttt gtaaatagcc ttgactaaaa        59656
tgcaggaaag aatagcaata gtaatagcat ttgtcattca cctgctgtgt gctaagtatc        59716
cacattgtct catttaataa tttctttctt tcttttcctt tcttttttg tttgaatcg          59776
gattctcact tttgttgttc aggctggagt gcagtggcgg gatctgagct cactgcaacc        59836
tccacctccc aggttcaagc gattctcctg cctcagcctc ccgagtatct gggactgcat        59896
gcgcatgcca ccatgcccgt ctaattttg tatttttagt agagacagga tttcaccgtg         59956
ttggccagga tggtctcgat ctcttgacct ggtgatccac ccgcttcgag ctcccaaagt        60016
gctgggatta caggcatgag ctaccacacc cggcctcatt taataatttc acaacagctc        60076
tgaggttatt ggcctgaagc ttagcaaagt taagtaactt tccacaggtt actcagctga        60136
ccctactgcc tgggccagga agcagaccca ggcagtctga ggcagagtgc tcaaatccag        60196
ccattccaac aagtgttaat tgactatttt aggactagaa cttttgtggc tctagtgatc        60256
tgcaaaaggc accaggtagg acatacctga ggagtgagtc tgctggctct tacagatgat        60316
atatattgaa aagtgttcca ttaatacaat gtgttgtaaa atgttgggat taaaaaatta       60376
ttttcatttt aaaaataaga cttgtatata ttgaggtgtt ttaatatggg ctgtaacaaa        60436
cccagtctta ctattggcaa tctctcttta aaatgtgtgt tccctcatgc ctgtaatccc        60496
accgctttgg gaggccgagc gggcagatca cttgaggtca ggagttcaag accagcctgg       60556
ccaatatggt gaaactctgt ctctactaaa agtacaaaag ttagccgggt gtggtggctc       60616
tcacccgtag tcccatctac ttgggaggct gaggcagaag aatcacttga acccgggaga       60676
tggaaggagg ttgcagtgag ccaagatggc gccactgcac tccagcctga gtgacagaga       60736
gtaattgtct caaacaaata aataaaataa aatgtctaat ttcacaagtt tattcaaata       60796
gtccttattt ttagcacagc taaatatgag tgacaagcat cttcgtagtc tggtttcccc       60856
ccactccatg gcaaccccc agaggtgaaa attatctgaa gtaacaaata tactctaccg        60916
atgatgaaat ttttttttgcc aattaagaaa aaataaggcc cttgctgaaa ttgaaagctt      60976
tttaaatcac tggcttctca aagaactgtt tgattccatt tgggacacac caacaaattt       61036
ttccggactt tttgggaaat atcattgaga acacatttga acttaatttg atcaactaag       61096
tctattattt tagcaatacc attttgttc tctcttcttt taaacttaaa cctaacattt        61156
gtcattaaaa tagtacatgt ctcttttct ttggctctaa ataccaagc atttgaacga         61216
aggagtcttc tcttctgtgc ccctgactcc ttgtagtata agacaatacc tgatctagtc       61276
tagtttctga cttgttaaat actgatgtca tgaagaaaga cttttctgtt cttgcttgac      61336
tgcatctccc tcttaacacg agtatcttgt gcactctttt tttttttttt tttttttg        61396
agatggggcc tcattctgtt gcctaggctg gagtgcagtg gcgccatctc ggctcactgc       61456
aacatctgcc tcccgagttc aagcagttct cttgcctcaa gcctcctgag tagctgagac       61516
```

```
tagcatgcca ccatgtccga ctaatttttt atatttttag tagagacgag gtttcaccat   61576
gttggccagg ctgaaacttc tgacctcaaa gtgatctgcc cacctcagcc tccaccgtgc   61636
ctggtcccat ggactcttat ttggcaaagt ctcttcataa atttttagaa gcctttggat   61696
tctgcttcta attgaccgag tctgtcttca ctgactttgt gactgaaaag ttaagctgag   61756
ggtgaagagt gttttaaggt gataagacac aatgttttt aggagctgtc tgaaacaaag    61816
cggggcttag aatctagaat cagtgattga gcctgtagtg atatttccat ggggacagag   61876
tggttaattt tgttattgat tcttgagatg cttttagagc ttcaggctga atgatttttt   61936
aaagttcttc tgcttaattg gtaactaatt tcaaatgcac ttttttttt  taag  tt      61992
                                                            Ile ttc aaa cca gaa gaa cta cga cag gca ctg atg cca act ttg gag          62037
Phe Lys Pro Glu Glu Leu Arg Gln Ala Leu Met Pro Thr Leu Glu
    1050             1055                 1060 gca ctt tac cgt cag gat cca gaa tcc ctt ccc ttt cgt caa cct          62082
Ala Leu Tyr Arg Gln Asp Pro Glu Ser Leu Pro Phe Arg Gln Pro
    1065             1070                 1075 gtg gac cct cag ctt tta gga atc cct gtaagtattt ggtggtactt            62129
Val Asp Pro Gln Leu Leu Gly Ile Pro
    1080             1085 ttgattttat tttttaattt gataacagct ttattgagag ataattcaca ttccaaacag   62189
tatagccact catttcaaat ttgtaattca gtgattttt ttttttcccc ctgagacagg    62249
gtcttattct ggttgcctag gctggagtgc agtggcacga tcgtggctca ctactgtctc   62309
cacctcccgg gctcaggtga ttctcccacc tcagcatcct gagtagctgg ataactaca    62369 ttcatgtgcc acctcacctg gctagttttt tgtatttttt agtagagacg gggtttcgcc   62429
atgttgccca ggctggtctt gaacgcctgg actcaagcaa taggcccatc tcagcctccc   62489
agagtgctgg aattacaggt gtgagccact gggcctggcc taattcaggg agttttagta   62549
tattcacaga gttgtgcatg acactttcat tttcatcatc tgaaaaaaat cctttaccat   62609
taacagtcac tcactatttt ctcccatagc accccaatcc tagacatcac cagactgcat   62669
tctgtctctg gatttgtctg ttctacatgt ttcattaaat tggaacatac agtatgtgat   62729
tctttgtgcc aggacgttcc ttagcataat gttttcaagg ttcatccatg ttgtagcatg   62789
aatcagtagc acatacctat ttatagccca ataatattcc attatttttc tttacctgtt   62849
gatgagttga tagacattta ggttgtttac acgttttgac tattaagata ggactgtagt   62909
gaacattgtg tggatttaag ttttttatttc tccttggtat ttacctagga gtggaattcc   62969
tgggttatat agtttgttta cttttttgtt gttgttattt gttttttgtt ttttgagat    63029 ggagtttcac tcttgttgcc caggctagag tgcaatggcg caatctcagt tcacctcaac   63089 ctcccctcc cgggttcaag cagttctcct acctctcagc ctcccgagta gctgggatta    63149
caggcatgtg ccaccatgcc cggctaattt tgtattttta gtagagatgg ggtttctgta   63209
tgttggtcag gctggtctca aactcccaac ctcagatgat ccaccacct cggcctccca    63269 gaatgcccag attacaggcg tgagccaccg cacccggcca ctttcgttgt tcaagagca    63329 ataggtcata gcagaaaaaa ggaccgtggt tagctttgtt tttaaagttg cctccatata   63389
ctaggctgct ggcagatttc atttggtggt tttaaactgt tacttggccg ggcacggtgg   63449
ctaacgcctg taatcccaac acttttggag gccaaggcag gcagatcact tgagttcagg   63509
agttggagac cagcctcacc aacatggtga accccatct ctactaaaaa tataaaaagt    63569
aactgggcgt ggtggtgcac gcctgtaatc ctggctactt gggaggctga ggcaggtgaa   63629
```

```
tagtttgaac gaccctggga ggcagaggtt gcactgagcc aagattgcac cactgcactc    63689
cagcctgggc aacatgttga cagagactcc atctcaaagg tcaagtgctt ccaggggcaa    63749
aagcctttta ggacttttcc tctcttgtat cttgctgtga tttcagatgg aacattttaa    63809
gttctgtggg cttagtttcc tcattgtaca ccccttctag tactaaaatt ttaaatgtct    63869
ttgactttac tgatctcaca tgtactttca taaagaacct gaagttgctt cagtagaata    63929
tcagcctgat gtctagaaag tccatagtag ttctgtttct ctgcccttg agtagtttaa     63989 tatctctgta aactaatatt taaagaagtg atggacatca gtcacctctt ggggaatata    64049
gacaggccag aaactaaaac actgcctgga aaattaacaa tgataatgga tgatactcca    64109
tctcccgtaa aaatagtgag acttgagtaa tgtttgatgt cacttgtctt tctag gat    64167
                                                                Asp tac ttt gat att gtg aag agc ccc atg gat ctt tct acc att aag           64212
Tyr Phe Asp Ile Val Lys Ser Pro Met Asp Leu Ser Thr Ile Lys
    1090            1095            1100 agg aag tta gac act gga cag tat cag gag ccc tgg cag tat gtc           64257
Arg Lys Leu Asp Thr Gly Gln Tyr Gln Glu Pro Trp Gln Tyr Val
1105            1110            1115 gat gat att tgg ctt atg ttc aat aat gcc tgg tta tat aac cgg           64302
Asp Asp Ile Trp Leu Met Phe Asn Asn Ala Trp Leu Tyr Asn Arg
1120            1125            1130 aaa aca tca cgg gta tac aaa tac tgc tcc aag ctc tct gag gtc           64347
Lys Thr Ser Arg Val Tyr Lys Tyr Cys Ser Lys Leu Ser Glu Val
1135            1140            1145 ttt gaa caa gaa att gac cca gtg atg caa agc ctt gga tac tgt           64392
Phe Glu Gln Glu Ile Asp Pro Val Met Gln Ser Leu Gly Tyr Cys
1150            1155            1160 tgt ggc aga aag gtaagaaatg tgtttcagat ttgactttaa cttttctggg           64444
Cys Gly Arg Lys
    1165 atacctagaa taatatagtg ggtgactggga taagagaata tcctgcttct ggctttgaca   64504 tggctttttt tttttttttt ttttttcctt tttgacaggg tcttattctc ccaggctgga    64564 gtgcagtggt gaggtcatag ctcactgcag cttcaacctc ctgggctcaa gcaattctcc    64624 cacctcagcc tcctgagcag ctgggactac agccgtacgc caccatgcct ggctgatttt    64684 ttaaatttgt tttgtagaaa cagggtctca tgatgttgct caggctagtc ttgaactcct    64744 gggctcaagc agtcctcctg cctcggcctc ccaaagtgct ggaattacag tcatgagcca    64804 cctctcccag ccaacacagt ctttctctta ctgtgtgcca cagtagtaat atctcttaat    64864 atgaaatggg ctttctttaa aggcattttt tcagagtggc aattgtatgg aaaagttgac    64924 taattaaata atcaacagac tgttaactca tctggagtag gggcattctt atattcacct    64984 gtgggtgcag attcctcagc atgtgctggc tttcctgtac ataccaattc acattattgg    65044 ttttttgttt ttaaaataag actatggtct tgctgtgttg cctaagctgg tctggaactc    65104 ttgggctcac gcagtcttcc cacctcagct tctgagcact gcaggcatgt gccaccctgc    65164 ccagctattc ctgttaggtt cttttggtaaa gtgatggaag gatatgactg ctaagcctac   65224 ctcagcgttt tgaaataatg tggtagtaaa ctgagaatga ttttcaggaa ctgaattagc    65284 ccatcattat taacataaat gagaactaag acaccactga cttctgtttc tgacttgcca    65344 ttcttactgt tctagcttgt ccttaaggcc tctgtgcttt ttaacaaatg gtttctttg     65404 cag ttg gag ttc tct cca cag aca ctg tgt tgc tac ggc aaa cag          65449
    Leu Glu Phe Ser Pro Gln Thr Leu Cys Cys Tyr Gly Lys Gln
        1170            1175            1180
```

| | |
|---|---|
| ttg tgc aca ata cct cgt gat gcc act tat tac agt tac cag aac<br>Leu Cys Thr Ile Pro Arg Asp Ala Thr Tyr Tyr Ser Tyr Gln Asn<br>                1185                      1190                   1195 | 65494 |
| ag  gtaagcttgg ccaggtgtgg accatggtcc atgtgtccac atgtccaggg<br>Arg | 65546 |
| agtgcatgcg gatgggccag cacacataca gtcatggttc atgtgtatct tgcttgaaga | 65606 |
| cagctgtata gcacaagttc tgttttttgc cttctgcctt tgtttgcaga acaataaaat | 65666 |
| tttctatcag agtagccttg catcagttac ctgggttcct cccaagagct tgagaagtta | 65726 |
| agcaactttg tgagttgttg gcctagatgg gtctatatcc caggccccac ttctctttct | 65786 |
| actgtgtgtt tgttgatcac cacagcctga ggcaaaactg agaagatttt taaactttta | 65846 |
| actgaaactc gctagacagc ttttttggaaa tatttccttt ttagatgagg cctatcccta | 65906 |
| agtagttgtt attagaatat atgaaaacag gattctggag tcttttcttt gcctcatatt | 65966 |
| aagcaaatta aaaggaaaac ctcacatagc tctctgtacc ttacttttcc caacccagcc | 66026 |
| ttgtatgtga cagaggatga tttgagtcta ataaacgagg cacctctgcc taattttctc | 66086 |
| ctgcccaatc aatggctgta atcacataaa tctcattcac taatctatct taaccacaat | 66146 |
| ttgtctcctg ttttcagtga tcagctacaa gtatagcttg cattgggtgt ttatttgggg | 66206 |
| ctctgataca ataataacaa ggctggatga tattaatacc ctttatttgt ttgttaatac | 66266 |
| caaatccatg gtgttggttt ttgctgaact tgtgtgttgc agatgcattt ctagctttga | 66326 |
| aaagtcactt aaacttttc ttttatttac aaaaagttag gcgtgcttct aatgctttgt | 66386 |
| agacctaatg ctttgatttt gcagtgagta aaaatctagc tctttactca tttgaaacct | 66446 |
| agaaaaggtg ggactcaagt tgttataagt accttatgtt taaaaaagca agtaactgga | 66506 |
| catgaaactt ttctcatgtt tactaaaaca gtagtctaaa gtgtttatct ttgcaccaag | 66566 |
| ccatctttaa tcaggtacct gcacacatca tttccttttg aaatgtatca cttgatggct | 66626 |
| gtagtcagta tttaactgct tgtgcaggct tttcaataaa cagttttttt tctttctttg | 66686 |
| ttgagacagg gtctcactct gtcactcagg ctggagtgca gtggcgcaat cttagctcac | 66746 |
| tgcaacctct gcctcccggg ttcaagcgat tctcctgcct cagccttcca aatagttggg | 66806 |
| attacaggtg tgtgccacca tgccttgctt attttttgtat ttttagtaga cagggtttt | 66866 |
| cagcatgttg gccaggctgg tctcgatctc ctgacctcag atgatccacc ctctcagcct | 66926 |
| tccaaagtgc taggattata ggtatgagcc accacgcctg gcaatggttg ttttagatta | 66986 |
| ttgttttctg cagttgtatc tatagtgggc ttttggggtg ggggtgggg gtctgtggtt | 67046 |
| ttttgttttg taagtgggaa gaggtgtgat tcctgtattt aggtaatgag tagcagttct | 67106 |
| tctctccctg gtatatttat ccttcttcct cctttt gatt atttacatca catagcgtta | 67166 |
| attgctgaaa tgaaggata tgggtctgtg taattgaaac atttgctttt atttgcagta | 67226 |
| atcatttgct acttgtgatc ccatttgaga tatttaatgc taatctgtgc tttgccttgg | 67286 |
| ctttctgctt tgtgttgttc tgtcttgctt ttatgttttt tgttgtcttg caatccctca | 67346 |
| tttcttcgtt tgttttgtgt ttttttttct ccctcatgct tgtcgttgtc tgcacttggc | 67406 |
| tttgattgca aaaaaaaaaa caaaaaaaaa caaaaaaaca aacaaaaaaa ccaaaaccca | 67466 |
| aactgtgggg cccatatatc tgcatcattg aatgtccttg tcgccgttga tgacctgctc | 67526 |
| tctgctcccg tccccctcct tggcctgctg tgattggtgg cttcgttgct tggcttgggc | 67586 |
| tgtgttgtgt gaacggaaca gttcaccccca gtatggcctt cttgccgaca g g tat<br>                                                                                                      Tyr | 67641 |
| cat ttc  tgt gag aag tgt ttc  aat gag atc caa ggg  gag agc gtt | 67686 |

```
His Phe Cys Glu Lys Cys Phe Asn Glu Ile Gln Gly Glu Ser Val
1200                1205                1210 tct ttg ggg gat gac cct tcc cag cct caa ac  gtaagtaact         67728
Ser Leu Gly Asp Asp Pro Ser Gln Pro Gln Thr
1215                    1220 gcattatttt gaaaagtgct aattagtttg ttgtccagtg attatgcaca gcttatttct   67788
aaatgaactt aagctatgct gttgaatatg gtagccatta ccacatgtt gctatttaaa    67848
tgcatattaa tttaaataaa aattgtttat cacatggaat actcacattt caactgttca   67908
gtagctatct gtgtctggtg ctaccatat tggtcaacac agagaacata tccatcatag    67968
tagaaagctc tttgagacat caatgaatta gggaatatgt cagcaatggg caatcatctt   68028
agttctagta aaagtattct gtataggaag caatcagctt ctcttcgaaa aattggaggt   68088
tagtacaaga aaacatcatt attaactgtt ctgagtttga gggtgattga actgatgacc   68148
accttacacc cttctcttgt aggttaacag aagacccaag tcactattgt agtgaataat   68208
agactttaac agcatgccgg ggtttaagag atttgcttgt gctttgcagt ctcacaagct   68268
cttaccattt ggtaaatggc caagaaaaaa atttcaaaca tatagtctaa tagtttaatc   68328
tctggccagg cgtggtggct catgcctgtc atctcagcac tttgggaggc caaggcgggc   68388
ggatcacgag gtcaggagat cgagaccatc ctggctaaca cggtgaagcc ctgtctctac   68448
taaaaataca aaaaattagc cgggcatggt ggtgggcgcc tgtagtccca gctactcggg   68508
aggctgaggc aggagaacgg cgtgaacccg ggaggtggag cttgcagtga gctgagattg   68568
ggccactgca ttccagcctg ggcgacagag cgagagtctg tctcaaaata aataaaagaa   68628
aaaagaaaa aagtaactta agatgtaggc agtcattaga attcaaactg ggactgtcta    68688
agaaggaaaa actgttcagt gtaattttaa tattattgaa agttcatatt tacttctgtt   68748
caggacgttg cacaaaaatt tggaattctc ttgttcctag taaaaatggg gcttctgaga   68808
aaagctggtt aattttttcta aattgcgttc taaagatagc agtgtctggg tgctagctag  68868
gagagtagat actaggagcc tttgatcctt gaaacatttt gacatttggt taagccagga   68928
aggttagctc tagggtaagt ttccttgatg caggaagaga cgtaagcctt gtcattgaac   68988
tctcaggtgg cttaccaaat agtctaaacc ttaaggcagt acatctctaa ctttgaaaag   69048
agtaggaaca agacccttcc caattctgca ggcctgtagt ggatccaagt gtctatttct   69108
aactcccaga ttgttctggt gctgctcatc ttcagattgc acttggagta gcaagacagg   69168
ccattcagga aaatgctatt aacagagatg aatgaatctc taggccataa ctagtataag   69228
aaacggtttt caatgtggac atgtcctcat ttttgtaagg aagtataaca gaagtccaag   69288
ttggtccccc taatgttgat tctagttgga gaatgtggat cctagttgga gaatggtaag   69348
actgttagct tttgtatgta gtgaggctat gagcagtgtg ttatgctggg tttcaggatg   69408
ggaagccatg ataccctaaca ccaagaatag taacagacaa gatttttaaaa ggaaaagaag  69468
aaacagtatt tctagttctt cctgggttct ccatttctga taagaggaaa tttatttact   69528
atgaagtcct atagaatatt cctttacata aacatgcatt ttgtgtgagc caagaataca   69588
cctatttaaa tgtgtattct taaaaaacct gaatctctat ataggggtgaa gtttgttcct   69648
ttggttagaa cagcagtcag attgctcatc tctatcactt tttctcattg tgtcccttt    69708
ctctccttag t aca  ata aat aaa gaa caa  ttt tcc aag aga aaa  aat    69755
             Thr Ile Asn Lys Glu Gln Phe Ser Lys Arg Lys Asn
                 1225                1230               1235 gac aca ctg gat cct gaa ct  gtaagtacga tcccttgaa tagtcagtac         69805
Asp Thr Leu Asp Pro Glu Leu
```

```
                1240
gctttggctt tcttttttcc ctttcattct cttgaagttt gcatgaccaa tcagatgatc  69865
ctatattctt gggctaaatc tacataacat acatctaatg gatagtaaaa ccatggaaaa  69925
cactgaagta ctaaggaaca ttatttctta atgttaattt taatgttctt aatgttgaat  69985
gtgaaacatt aaagatctaa acttctagtt tgcagtgagg ccttttagat catggaggac  70045
tgacatgtat gtcttctaga tgttcctaaa atggatggga tggtatttgg atttatttgg  70105
aattttcagc accaggaatc tgtcttaaaa attagccagg ttttggccgg gcacggtggc  70165
tcacgcctgt aatcccagca ctttgggagg ccgaggcggg cagatcacga ggtcaggaga  70225
tcgagaccat cccggctaaa acggtgaaac cccgtctcta ctaaaaatac aaaaaattag  70285
ccgggcgtag tggcgggcgc ctgtagtccc agctacttgg gaggctgagg caggagaatg  70345
gcgtgaacct gggaggcgga gcttgcagtg agccgagatc ccgccactgc actccagcct  70405
gggcgacaga gcgagactcc gtctcaaaaa aaaaaaaaa aaaaaattag ccaggtttgg  70465
ccgggcacag tggcccacat ctgtaatccc agcactttgg gaggccaagg caggatcacc  70525
caaggtcaag agttcgagac cagcctggcc aacatggcaa atcccgtct ctactacaaa  70585 tatataaatt agctgtgcgt ggtggtgcgc gcctgtaatc ccagctactc gggaggctga  70645
ggcaggagaa tcgctggaac ccggaggca ggggttgaag tgagctgata tgacgccact  70705
gcactccagc ctgggcgaca cagagagact ccatctcaga aaacaaaaca aaaacagcc  70765 aggcatgata gtatgtgcct atcctagcca ggtagctgag aggccaaggc aggaaaatgg  70825
cttgagccca ggagtttaag gttgtagtga gctgtgatca tgccacccac tccagcctgt  70885
acaacagaga ccctatctct aaaaaaatag aaactttatt aaaactattt tcagttcttt  70945
ggtcatgacc ttggctgtct ttgtcagaag tcatgggaaa tattgcaagt tttcatttgg  71005
ttaaggtttg gggttaattt tggaattggc tctgctcttc cag g ttt gtt gaa     71058
                                                   Phe Val Glu
                                                          1245 tgt aca gag tgc gga aga aag atg cat cag atc tgt gtc ctt cac       71103
Cys Thr Glu Cys Gly Arg Lys Met His Gln Ile Cys Val Leu His
         1250              1255              1260 cat gag atc atc tgg cct gct gg gtaagtctta acgttgttac tttctctgga   71156
His Glu Ile Ile Trp Pro Ala Gly
                1265 attttctttt atcgtgaata ttaacaagtt ttttattcta tgcaattgac tgtattatat  71216 cttcaaagtt actatcttta aattgttttc tttgggtttg gccacgataa ttatagttcg  71276 cttttaaaa attaagtaac ctagtatcca aaaatagatt tttatcttat ttttatgcat   71336 tcttcttagc catataaata tattttattc tgctggattg tttattaaaa ttatattgta  71396 gttattacac atcaaaagta aatatttatg gccaggcgag gtggctcacg cctgtaatcc  71456 cagcactttg ggaggccgag gcgggcggat cacctgagga caggggttcc agaccagcct  71516 gaccaacatg gcaaaacctc gtgtctactg aaaatacaaa aattagcctg gcgtggtggt  71576 gcacgcctgt aatccagcta ctcaggaggg aggctgaggg aagagaatca cttgaacctg  71636 tgaggggag gttgcagtga gctgagatca cgccactgca ctccagcctg gtgacagag   71696 tgagactctg tctcaaagaa aaagtaaat gcttttgttc cggcatctag aaactaggat   71756 catgctgctg gcatgaatag gtctggcccc ggtaagggtc accatttggt tagggcagga   71816 acagcaagtt ataaggctgc agtcatagtg taattgccta gtaaaaggga ggggccatcg   71876 ctctgtacaa gaggaactaa tcccagccat gttccaaagg aagcgggtat atgggacatc   71936
```

-continued

```
cagtgcctct cattaagatg ggatctccat ctcttctgct ctgttcttgg gctgattgtt    71996
gttcctgatt tggaggttac aagaaagggc aggctaattg acagatttca ctttctcttt    72056
tttcaccgtt attttcacat agaaaataac actaaggaaa ataggtgatg gtttagtgga    72116
tactttattt tcagtgtgac ttgtctttta agtgtgcctt tttagtgctt tccttaacag    72176
atttcgtaag aatgattaag agacttcttg tggttcttct aatttaggat cagtcaactg    72236
aatgaaaata atctgttatt actgtgttaa gcttgctttt tcttaaaagt aatttatgtt    72296
cattataaaa tttgaatagt atgacagttt atgaagtaaa aagcgacggt ctcagcttct    72356
ctcttcccac ccagattcct cactacagga ataacactct tttgtacata caatcataca    72416
ttttcttttt ttctttttt gagacagagt tcgctcttg ttgcccaggc tggagtgcag    72476
tggcgcgatc tcggctcact gcaacctctg cctcccaggt tcaagtgatt ctcctgcctc    72536
agcctcccta gtagctggga ttataggtgt gtgccaccat gcccggctaa ttttgtatt    72596
ttggtagaga cagggtttca tcatattggt caggctggtc ttgaactccc gacctcaggt    72656
gatccaccca cctcggcctc ccgaagtgct gggattacag catgagccac tgcacctggc    72716
acatttctt gatttatgtg tatttaattt ttaattttg tattttgtta taagtcatag    72776
acttttttaa ttgagtctca ctttcatcac ccaggctgga gtgcaatggt gtgatctcag    72836
ctcactgcaa cctccacctc ctgggttcag gcaattctcc tgcctcagcc tctcctgcct    72896
cagcctctcg agtagctggg attacaggca cataccacca tgtctgacca attcttgtat    72956
ttttactaga cacagggttt cattatgttg gtcagggtgg tcttgaactc ctgacctcaa    73016
aagatccacc cacctcgacc tcccaaagta ctgggattac aggcgggagc caccacgcct    73076
ggctggtcat agacactcat ttatgtctgc tgcatttta atggatgcat agtattctgt    73136
aacatactat aatccattta tttacttggt tgatgaacaa gttatacaa gaaactactt    73196
aggagacaaa tatcatgtgc atttgcagta gctgaatcta ttggttctac tctcaaaatg    73256
tactttccaa ctagtagcat ataggaaatg tcacctctta ggatttttct ccctatcac    73316
attagcaaaa cctatcttga tttgtaatcc ttgatcatct tttcctgtgt aaaccaattt    73376
atatgcccctt catgttctt catgtctgtt gcttgatttt caattatctt ttttattctt    73436
actgatttct aaaagctctt tgtgtattag ttttattaac tcttcattag aaatttagaa    73496
atacttctgc tagattgtct tttgaatttt aactttttgt tagtataaat tcaacggttt    73556
atctaagttg tgtaagcaaa gttttggttt acatttag a ttc gtc tgt gat ggc    73610
                                            Phe Val Cys Asp Gly
                                                          1270
tgt tta aag aaa agt gca cga act agg aaa gaa aat aag ttt tct          73655
Cys Leu Lys Lys Ser Ala Arg Thr Arg Lys Glu Asn Lys Phe Ser
1275                1280                 1285
gct aaa a gtaagtttta ttcttaaagg taaattttgg caaaacttat ctgaagccta    73712
Ala Lys
1290
gataagaaac catccaaagt gaattacttt gttttaatc acagtaatag agtaaaaata    73772
aaataattct ataatctcct tatagttgat ctgtaatata ttttttggtg tgaaatttat    73832
tagaccaaag aaaaaaattt ccaaggaacg gatttgtaga atgcacaaga tacgtgtttt    73892
tcctgttcct atattttcc ctatttgggg catttcataa aggaggaata aggtgtggaa    73952
atgattggcc ggaattgcca tctctcagtt tgtttattta ttattttta tttttattttt    74012
tgagagtctc actctgtccc ccaggctgca cagtgcagtg gcacgatctc agctcactgc    74072
```

```
aacctccgcc tcccaggttc atgtgatttt tctgtcttag cctccagtgt agctgggact    74132
acaggcatgt gcctccacac ccagctaatt tttgtaattt attagagatg gcgttttgcc    74192
atgttggcca ggctgatctc aaactcctga tcacaggtga tccacccacc ttggcctccc    74252
aaagtactgg gattacaggc gtgaaccacc atgcccaacc cctcagttca caccattat     74312 atgggctacc ttttggcctt atgtgattgt tttctactgt gccaggagga tgtcaaaaat    74372
tttatcatgt aagtaattaa cactaataat ctaaatgtag tatttgattt agttttgggg    74432
tgttttactg atctacagat tattttgatt cttgtaaggt ttctcaaaat gctcaacctt    74492
cgttacttta aaatattact gcaatctagg caaagtacat agagatgttc attgtttata    74552
tatttgtgtg tgtgtgtgtg tgtgtgtgta tatatatata tatatatata tatatatata    74612
tatatatata tatatatata atgtttggtt ggttgggttt tttgttttttt ggaaacaagg   74672 tttcactgtg ttgtccaggc tgatcttgaa ctcctggatt caagcaatcc tcccacctca    74732
gcctcccaaa gtacaaggat taggattatg ggtgtgagcc ttgtctcctg gccattgttc    74792
tatttctgtt tgtttttgtt tttttttttg tttttttttt tttttttttt tttttgagac    74852
agagtctcgc tgtcgcccat agtggcgcag tctcagctca ctgcagcctc tgcctcccgg    74912
gttcaagcga ttctcgtgcc tcagcctccc aagtagctgg aattacaggc gtgcaccacc    74972
atgcctggct aattttttgta tttttagtag agacggggtt tcagcatgtt ggccaggctg    75032
gtctcgaact cctgacctca ggtgatgcgc ccacctcagc ctcccaaagt gctgggatta    75092
caggcatgag ctaccgcacc cggcccctgt tctgtatttt tataaactct tccaaaattg    75152
gaaatttttc aaaatgagaa gttggggaaa atgatatta gaaattattg agtactgtgt     75212
ctgctttaat agcacatgta ttaaaattag aatgatatga agattagcat gttccctgca    75272
ctcatatgac atgtaaatct gcaaagtagt gactactttg ctatgatttt ttaaaatttc    75332
accaagttat cctgtttgta ttgaaaaaag tacaaatgag atttgaggtt gaaccttaag    75392
actaacaaca gtaaatttgc acctcagtaa cttttaactt ttacattcct ag gg   ttg    75449
                                                          Arg Leu cca tct   acc aga ctt ggc acc  ttt cta gag aat cgt  gtg aat gac        75494
Pro Ser   Thr Arg Leu Gly Thr  Phe Leu Glu Asn Arg  Val Asn Asp
    1295              1300                  1305 ttt ctg   agg cga cag aat cac  cct gag tca gga gag  gtc act gtg        75539
Phe Leu   Arg Arg Gln Asn His  Pro Glu Ser Gly Glu  Val Thr Val
    1310              1315                  1320 aga gta   gtt cat gct tct gac  aaa acc gtg gaa gta  aaa cca ggc        75584
Arg Val   Val His Ala Ser Asp  Lys Thr Val Glu Val  Lys Pro Gly
    1325              1330                  1335 atg aaa   gca ag  gtatctagtc atttcacttt tcttctcctc gtggatccaa          75635
Met Lys   Ala Arg
    1340 aattgctcat acatggttac tattggtgat tccagtctga atgagttatg ttgtggttcc      75695 cccaccatct caattgtata g g ttt gtg gac  agt gga gag atg gca   gaa       75744
                       Phe Val Asp  Ser Gly Glu Met Ala   Glu
                           1345                    1350 tcc ttt   cca tac cga acc aaa gcc ctc  ttt gcc ttt gaa gaa   att       75789
Ser Phe   Pro Tyr Arg Thr Lys Ala Leu  Phe Ala Phe Glu Glu   Ile
    1355              1360                   1365 gat ggt   gtt gac ctg tgc ttc ttt ggc  atg cat gtt caa gag   tat       75834
Asp Gly   Val Asp Leu Cys Phe Phe Gly  Met His Val Gln Glu   Tyr
    1370              1375                   1380 ggc tct   gac tgc cct cca ccc aac cag  ag  gtatgactag ctcacagtgg       75883
Gly Ser   Asp Cys Pro Pro Pro Asn Gln  Arg
```

```
                    1385              1390
ctagctccgg atttgtgtgg gagttccaac ttataatagg tggaaaagca taacaggcaa    75943
gaaaatgttt agtgtgtttg gtttggaaat gcaaaatctc aagtgtccag taattttaaa    76003
gtgaaacaga ttaaaaagca aaccccccaaa caaaataacc gctcaatact gctcttctgt    76063
ggtcatagta ataaaggata tgaatagcaa cctgaaattg gaatttgaaa acaaacgtac    76123
tactcttcag aaaatgagct taaatctgga ttaagtagct atgtgaaaat atatcataca    76183
aatcgggtgg gaatttcttt tctccaaaaa tagtataaag gcaataataa aaacgtatag    76243
ggatcaccaa atactgattg atgtgtatgt gccaggcact gctagttact acaaatagaa    76303
ggaaaccaca ggctcactga acttccctga agggttcacg gcggagtcgc ctacctgcct    76363
gtgatgagct tcacaaataa cgatgtgagc aaagagcctg ggagagtgag agggtgttat    76423
taggcacatg gagtaaagaa ctcattatgt gacctgactt ttttttttcct cttcatttct    76483 cttcattttg tatag g aga gta tac ata tct tac ctc gat agt gtt cat    76532
              Arg Val Tyr Ile Ser Tyr Leu Asp Ser Val His
                  1395                    1400 ttc ttc cgt cct aaa tgc ttg agg act gca gtc tat cat gaa atc    76577
Phe Phe Arg Pro Lys Cys Leu Arg Thr Ala Val Tyr His Glu Ile
        1405                1410                1415 cta att gga tat tta gaa tat gtc aag aaa tta gg gtaagcatat    76622
Leu Ile Gly Tyr Leu Glu Tyr Val Lys Lys Leu Gly
        1420                1425 tttgataatg gctttttttc tttaactagc atggcattct ggtgagatat aggttaaata    76682
tgcaaatata taactcttgg ccttttttc ctcattttag ttcttacgta acaattctct    76742
taactttgtt ggagcccctt tgaagttaat gtcagtagag agaaatggat atgttggccc    76802
tagtttcacc catccaacat tagttttgtt tgtaagctaa gccattgggt ccactttgct    76862
ttgaagtttg atttgtgccc ctcatttgag ggcagaattt taactgcatt tgatccttt    76922 acaacctggg tatgaagacc aaaaacagtt ctggagatac ttcttacctt tagagtatgt    76982
atgtcattgg aaacattcac tccctcatct tgaagtctgt ttctctgaac agtgtgcctt    77042
ttaatttagc tcttgttaaa tgggtccatt ttcctttgca gtgtaatctt catttggtct    77102
taacatgcag acttagggtt tttggatcca gggctaagtc acccacttcg tggctgagat    77162
tcgcaacatc ccaccatggc ctccaaaaat aagtaggcaa tatgagatcc attgttacta    77222
ctgtgagtta tgcctaattt tggcctcaca atgttaatct cattctgggt tatatataca    77282
ctgtgttatc ttgggaaaaa ttattggtat ctatatcaac tccaacttgt ggtttaaaat    77342
gtagccttct agaatagatt atctcttttc cttaatgttc tttctctttg tattgttag    77401 t tac aca aca ggg cat att tgg gca tgt cca cca agt gag gga gat    77447
  Tyr Thr Thr Gly His Ile Trp Ala Cys Pro Pro Ser Glu Gly Asp
      1430                1435                1440 gat tat atc ttc cat tgc cat cct cct gac cag aag ata ccc aag    77492
Asp Tyr Ile Phe His Cys His Pro Pro Asp Gln Lys Ile Pro Lys
1445                1450                1455 ccc aag cga ctg cag gaa tgg tac aaa aaa atg ctt gac aag gct    77537
Pro Lys Arg Leu Gln Glu Trp Tyr Lys Lys Met Leu Asp Lys Ala
1460                1465                1470 gta tca gag cgt att gtc cat gac tac aag gtcagttggg acatagggggc    77587
Val Ser Glu Arg Ile Val His Asp Tyr Lys
1475                1480 caggtgctga caatagatct ggaaatgcac taatgttgct gctctttgtt ctgtcattta    77647 acttttttttt tttttttttt tttttttga gacggagtct cgctctgtca cgcaggctgg    77707
```

```
agtgcagtga cacgattttg gctcacttca agctccgcct cctgggttca tgccattctc    77767
ctgcctcagc ctcctgagta gctgggacta caggctcctg ccatcacacc cggctaaatt    77827
ttttgtatt tttagtagag acggggtttc accgtgttag ccaggatggt ctcgatctcc     77887
tgaccttgtg atccgcccgc cttggcctcc caaagtgctg ggattacagg catgagccac    77947
cgtgcccagc ctttttttt ttttttaaa caaaagtctt gcttgttcta cctcttgcat      78007
gtaattccta aaaatgctaa tttgattgct tttattttgt atattcaaaa ttttcaata     78067
taagaaaaac caggttttga agagcggtag atcaagaaat ccctgtttta aacatgtaac    78127
caaaatttta ttttatttat ttttgggggg agggtgggga tagagttggg gtatcgccat    78187
gctgcccagg ctggacttga actcttggcc tcaagcattc caaagtgctg ggattacagg    78247
catgagccac tgtgcccggc cttaaaatat atcttttgt tttggttttt tgttggtttg     78307
gtttgggttg gttagggttt tagggtgtg ggtgttttgt tttcagaaag ggtcactctc     78367
tgtcacccag gctagggtgc agtggcatga tacccgctca ttgcaacctg tgcctcccag    78427
gctcaagcca tcctcccatc tcagcttcct gagttgctgg gactaggtgc acactacgag    78487
agctagctga ttttttgtata tttttttgtag agacaggatg tcaccatgtt gcccaggctg   78547
gtctcaaact cctgagctca agtgatctgc ccacctcagc ctcccaaagt gctaggatta    78607
taggcatgag ccacatcacc cagccaaaaa tatattctcc cttttttttt tttgacgga    78667
gtttcaggct ggagtgcaat ggtgcagtct cctgggttca agtgatggtc ctacctcagc    78727
ctcccgagta gctgggatta caggcatgca ccaccaagcc aggctaattt tttctatttt    78787
tagtagagac ggggtttctc cacattggtc aggctggtct cgaactcctg acctcaggtg    78847
atccacctgc ctcggcctcc caaagtgctg ggattacagg tgtgagtcac tgcacctggc    78907
caaaaatata ttcttaatta acagtattat gttattcata aatataggtt gtctcatgat    78967
acagacttgt cttcctcaat ttagtagttc aactaaataa agaagttttc ctaagcagcc    79027
cagcaaatca ttctgcagca gatactattt ccagtatttg tagttttggt cattttgaac    79087
aaagctgtca gtaaaagctg ctgaaattca aaggatgggt gtgaggaggg catgcttcat    79147
accacatatt ctgtgataag gagtggtagg ggccatggca tgcatgatgg tgctaccacc    79207
ctgacgttga tcctggcagg ataattgcca cttggttata taaaggcaga taagctccct    79267
gtttttgtgg gtagaagaaa tagaaaaccg gaaatattga ctttaggcca ggccttttca    79327
ctatttattt ttctaaatac tccctggctt acggcttagg tataaagtct ctgccagctt    79387
tcaagacatt ttaagctttc atgtttcttg tcagccatga ttattctgta taatcaatgc    79447
tttaaaagaa catagaaatt cctatatgta catgcatgtt tcacag gat  att ttt      79503
                                                    Asp  Ile Phe
                                                    1485 aaa caa gct act gaa gat aga tta aca agt gca aag gaa ttg cct           79548
Lys Gln Ala Thr Glu Asp Arg Leu Thr Ser Ala Lys Glu Leu Pro
         1490                1495                1500 tat ttc gag ggt gat ttc tgg ccc aat gtt ctg gaa gaa agc att           79593
Tyr Phe Glu Gly Asp Phe Trp Pro Asn Val Leu Glu Glu Ser Ile
        1505                1510                1515 aag gaa ctg gaa cag gag gaa gaa gag aga aaa cga gag gaa aac           79638
Lys Glu Leu Glu Gln Glu Glu Glu Glu Arg Lys Arg Glu Glu Asn
        1520                1525                1530 acc agc aat gaa agc aca gat gtaagggcat tgagtttcct ttgaaacttc         79689
Thr Ser Asn Glu Ser Thr Asp
        1535
```

```
tatcatgatt ctaatattta atccagaagt gcacttaaac tttcaattgg gttttaaagc   79749
tttcaggtgt aaaagagctc tttaagttgg acaagaaata ttggcttaga gaggttatta   79809
gggttctgtt tcagtggtat taaactttta aagcatcaga gccccttta aaatggcatc    79869 tcagactttg agtaatgtga aatgataaaa gaaactgaag gaaatcctga aaaactgata   79929
gaagattact tatctgaagg actaggttat gaatattata ggccttgtgg gtcacatatc   79989
tctggcatat tttctgtctt ttaaaaacac actctttta aatgtaaaaa accattctta    80049
gctatacaaa ataggcctga gccagaattt aagttactaa gcctggctta gtaacctcac   80109
cagttatttc cccatagcat atctcgaatt acctccattg aatttaactt aacaaaaggc   80169
acccttaaat agtctgttaa caaactctta cagccttgtc atttagtatt tgtaggctca   80229
taacatttta gaatatgagt ggaaggaaat aaaaccaagg tcttctggct ccccactttg   80289
atacactctt cactacccca aagtgccacc ccttccttgt tccctagccc caatctggga   80349
tacattcaat caatctacag ggtctgcaca ttctgtggcc tcttctaggc aaaaagctaa   80409
agggctgcca ttgccttaaa gatcactggg agaaaattag gtcaaataac aactttaagg   80469
agaaagaata agtgaagaga acagctagta aaataagtta caggcataag attatgatat   80529
ctagtttcaa agaagggaga tattctgtgc tattcccaaa ttacttaaca aaaaccttat   80589
tttcttgtct cctttgtgct actctgcag gtg  acc aag  gga gac  agc  aaa aat  80642
                                Val  Thr Lys  Gly Asp  Ser  Lys Asn
                                1540           1545 gct  aaa aag  aag aat  aat aag  aaa acc  agc aaa  aat aag  agc agc   80687
Ala  Lys Lys  Lys Asn  Asn Lys  Lys Thr  Ser Lys  Asn Lys  Ser Ser
     1550         1555          1560 ctg  agt agg  ggc aac  aag aag  aaa ccc  ggg atg  ccc aat  gta tct   80732
Leu  Ser Arg  Gly Asn  Lys Lys  Lys Pro  Gly Met  Pro Asn  Val Ser
     1565         1570          1575 aac gac  ctc tca  cag aaa  cta tat  gcc acc  atg gag  aag cat  aaa   80777
Asn Asp  Leu Ser  Gln Lys  Leu Tyr  Ala Thr  Met Glu  Lys His  Lys
         1580          1585         1590 gag gtaagatgca gccacccaga gttggggaaa acggcaaga tttctggcca              80830
Glu ggcatggtgg ctcacacctg taatcccagc actttgggag gccaaggcgg gtggatcacc    80890
tgaggtcagg agttcaagac cagcctgacc aacacggtga aaccttgctc tactaaaaat    80950
acaaaattag ctgggcatgg tggcacatgc ctgtaatccc agctactcag gaggctgagg    81010
caggagaatt gcttgaacct gagaagcgga gattgcagtg agccgaggtc actccattgc    81070
actccagcct gggcaacaag agcgaaactc cacctcagaa aaagaaataa gaatgaata     81130 aaaacactga ctgttcgctg gcgtggtgg ctcatgcctg taatcccagc actttggagg     81190
ttgaggcagg cggatcactt gaggtcagga gttgagacc agcctggcca acatggcgaa     81250
ccgaaacccc gtctctacta aaaatacaaa aattagcctg gcgtggtggc acacacctgt    81310
aatccttggg atgctgggt gggaggatca cttgaacctg ggaggcagag gttgcagtgc    81370
acttacagcc tgggtgacag aacgagactc tgtttcaaaa aataaaaaga tttaaccttt    81430
ctgaaagtga attagtaaat agaattggag aaaagttaaa cttccacata tggacttaca    81490 accccttct caaaactttt tgagttattt catcatttac attgtttagt tgttcttgca     81550
gtcatttggg aaaataactg ggtaaggttt ttttttctc tctttaatat catataattg     81610
ataacgaaag ccaggagaat tgaagagtaa ttcctctcag ggtttgtcca atggtagtaa    81670
tctcgattgt tcagtcagac tcctcatttt actatctcgg ttctcagaca tataatcaag    81730
```

```
ttcttatagg aagtggtaat taagttgaga gggaaatgaa ggcttgattt caggttgtaa    81790
ttccgtacct aaaaattggt taaacagtct ctttgggaga gaaatagtta acaaaatctt    81850
ttttagagag gaatttgtta taatgatgtt atcatggtga acacctatat acataggtgt    81910
tcaaagtatc ttttccccca ctgctccccc catcaccacc ccttttttgt tagcctagaa    81970
taatgggcta cgatgtaata atggtaataa ccattatctc agccatgcta gtgaaatgga    82030
aggattcctg agttctaata cgttaggtaa tgattattaa caattaatag ttactagcta    82090
tttcaagcag taagtaatgc cacagaatcc taggcagttg ggaaaagccc ttagaatata    82150
ttgtaatagg tttgacttaa attgtggaca cattccatgg ctgtttaaat ttaggttgta    82210
aatccaagta ttggcctggt tgtagggtga cagaagcagc gaacattgct ggccagagac    82270
tgtgagtgtg gctgccagtg tgcacagatg ttgaataatc tgttatcagt acagcagttt    82330
ctcacaagtt cctaatttct taaggggatg ttttacattt tattacttta ataggtgttt    82390
atagttatat actaattaat gtcaaataca tatgtaatac cagcttttta tacctttac     82450 actaatggtt atgagaattg atggttgtta caagtttttt caaacttcaa tgaacaagaa    82510
ttttattgct ttgtcaacaa agactaagat tttttatcca ttccattccc ttccaaacct    82570
gtaggaaaag ttacacagga aagttgcata ggggaccttc atgagtccag gccagttgtt    82630
tttcatactg tctccatatt tggatttgtc tggtttgttg taattagatt gaggttaaac    82690
catggattgc atcttaaagt agactgcctt gaggcaaaat gtccactgtg catggtgcta    82750
tacctcaccc agaccattgt tactctgaag gagttactga atgaaggaga aaaaaatcac    82810
aggatgtgca tttcagttct atttatagtc agtctcaaga gaccaaagag gtaaagcagg    82870
aaaaggaaca ggaggcgtat ggtggtgaaa ctaactcagc attcgccagt ctcattggtg    82930
ctcagcctgc tgtacctgct cacacctgta atcccagcac tctgggaggc tgaggcaggc    82990
agatcacttg agcttaggag tttgagacca gcctgggcaa catggcgaag cctcgtctct    83050
acaaaaaatg cagaaattag ccaggtgtgg tggtgtgggc ctgtggtctc agctattcag    83110
gaggccatgg tgggataatt gcttgagccc aggaggcaga ggttgtagtg agccaagatc    83170
acgccactgc attccagcct ggatgacaga gcgaggccct gtctcaaaaa aaagagactg    83230 tctgttttc ag gtc ttc ttt gtg atc cgc ctc att gct ggc cct gct        83278
             Val Phe Phe Val Ile Arg Leu Ile Ala Gly Pro Ala
                1595              1600              1605 gcc aac tcc ctg cct ccc att gtt gat cct gat cct ctc atc ccc         83323
Ala Asn Ser Leu Pro Pro Ile Val Asp Pro Asp Pro Leu Ile Pro
1610              1615              1620 tgc gat ctg atg gat ggt cgg gat gcg ttt ctc acg ctg gca agg         83368
Cys Asp Leu Met Asp Gly Arg Asp Ala Phe Leu Thr Leu Ala Arg
        1625              1630              1635 gac aag cac ctg gag ttc tct tca ctc cga aga gcc cag tgg tcc         83413
Asp Lys His Leu Glu Phe Ser Ser Leu Arg Arg Ala Gln Trp Ser
        1640              1645              1650 acc atg tgc atg ctg gtg gag ctg cac acg cag agc cag gac cgc         83458
Thr Met Cys Met Leu Val Glu Leu His Thr Gln Ser Gln Asp Arg
        1655              1660              1665 ttt gtc tac acc tgc aat gaa tgc aag cac cat gtg gag aca cgc         83503
Phe Val Tyr Thr Cys Asn Glu Cys Lys His His Val Glu Thr Arg
        1670              1675              1680 tgg cac tgt act gtc tgt gag gtaggcaccg ggttgtggga aggaggaggt        83554
Trp His Cys Thr Val Cys Glu
                1685 gagctccgca gggttgttct gaggggccat gcagccacgt attttataga ggcctgtggg   83614
```

```
                                                           -continued atgctagggg cttggcctcg tgtttgaggg gcagagctga agaggctagt ttttgttcta  83674 cgaaagggc ttttctagcc caaacaatat ctaaaatact tttgaatgac ttaaatcttg   83734
gagagtttac gtgcacctcc tgttttttcc ctag gat tat gac ttg tgt atc      83786
                                     Asp Tyr Asp Leu Cys Ile
                                         1690 acc tgc tat aac act aaa aac cat gac cac aaa atg gag aaa cta       83831
Thr Cys Tyr Asn Thr Lys Asn His Asp His Lys Met Glu Lys Leu
    1695                1700                1705 ggc ctt ggc tta gat gat gag agc aac aac cag cag gct gca gcc       83876
Gly Leu Gly Leu Asp Asp Glu Ser Asn Asn Gln Gln Ala Ala Ala
1710            1715                1720 acc cag agc cca ggc gat tct cgc cgc ctg agt atc cag cgc tgc       83921
Thr Gln Ser Pro Gly Asp Ser Arg Arg Leu Ser Ile Gln Arg Cys
    1725                1730                1735 atc cag tct ctg gtc cat gct tgc cag tgt cgg aat gcc aat tgc       83966
Ile Gln Ser Leu Val His Ala Cys Gln Cys Arg Asn Ala Asn Cys
1740            1745                1750 tca ctg cca tcc tgc cag aag atg aag cgg gtt gtg cag cat acc       84011
Ser Leu Pro Ser Cys Gln Lys Met Lys Arg Val Val Gln His Thr
    1755                1760                1765 aag ggt tgc aaa cgg aaa acc aat ggc ggg tgc ccc atc tgc aag       84056
Lys Gly Cys Lys Arg Lys Thr Asn Gly Gly Cys Pro Ile Cys Lys
1770            1775                1780 cag ctc att gcc ctc tgc tgc tac cat gcc aag cac tgc cag gag       84101
Gln Leu Ile Ala Leu Cys Cys Tyr His Ala Lys His Cys Gln Glu
    1785                1790                1795 aac aaa tgc ccg gtg ccg ttc tgc cta aac atc aag cag aag ctc       84146
Asn Lys Cys Pro Val Pro Phe Cys Leu Asn Ile Lys Gln Lys Leu
1800            1805                1810 cgg cag caa cag ctg cag cac cga cta cag cag gcc caa atg ctt       84191
Arg Gln Gln Gln Leu Gln His Arg Leu Gln Gln Ala Gln Met Leu
    1815                1820                1825 cgc agg agg atg gcc agc atg cag cgg act ggt gtg gtt ggg cag       84236
Arg Arg Arg Met Ala Ser Met Gln Arg Thr Gly Val Val Gly Gln
1830            1835                1840 caa cag ggc ctc cct tcc ccc act cct gcc act cca acg aca cca       84281
Gln Gln Gly Leu Pro Ser Pro Thr Pro Ala Thr Pro Thr Thr Pro
    1845                1850                1855 act ggc caa cag cca acc acc ccg cag acg ccc cag ccc act tct       84326
Thr Gly Gln Gln Pro Thr Thr Pro Gln Thr Pro Gln Pro Thr Ser
1860            1865                1870 cag cct cag cct acc cct ccc aat agc atg cca ccc tac ttg ccc       84371
Gln Pro Gln Pro Thr Pro Pro Asn Ser Met Pro Pro Tyr Leu Pro
    1875                1880                1885 agg act caa gct gct ggc cct gtg tcc cag ggt aag gca gca ggc       84416
Arg Thr Gln Ala Ala Gly Pro Val Ser Gln Gly Lys Ala Ala Gly
1890            1895                1900 cag gtg acc cct cca acc cct cct cag act gct cag cca ccc ctt       84461
Gln Val Thr Pro Pro Thr Pro Pro Gln Thr Ala Gln Pro Pro Leu
    1905                1910                1915 cca ggg ccc cca cct gca gca gtg gaa atg gca atg cag att cag       84506
Pro Gly Pro Pro Pro Ala Ala Val Glu Met Ala Met Gln Ile Gln
1920            1925                1930 aga gca gcg gag acg cag cgc cag atg gcc cac gtg caa att ttt       84551
Arg Ala Ala Glu Thr Gln Arg Gln Met Ala His Val Gln Ile Phe
    1935                1940                1945 caa agg cca atc caa cac cag atg ccc ccg atg act ccc atg gcc       84596
Gln Arg Pro Ile Gln His Gln Met Pro Pro Met Thr Pro Met Ala
```

```
                1950                1955                1960
ccc atg ggt atg aac cca cct ccc atg acc aga ggt ccc agt ggg    84641
Pro Met Gly Met Asn Pro Pro Pro Met Thr Arg Gly Pro Ser Gly
    1965                1970                1975 cat ttg gag cca ggg atg gga ccg aca ggg atg cag caa cag cca    84686
His Leu Glu Pro Gly Met Gly Pro Thr Gly Met Gln Gln Gln Pro
    1980                1985                1990 ccc tgg agc caa gga gga ttg cct cag ccc cag caa cta cag tct    84731
Pro Trp Ser Gln Gly Gly Leu Pro Gln Pro Gln Gln Leu Gln Ser
    1995                2000                2005 ggg atg cca agg cca gcc atg atg tca gtg gcc cag cat ggt caa    84776
Gly Met Pro Arg Pro Ala Met Met Ser Val Ala Gln His Gly Gln
    2010                2015                2020 cct ttg aac atg gct cca caa cca gga ttg ggc cag gta ggt atc    84821
Pro Leu Asn Met Ala Pro Gln Pro Gly Leu Gly Gln Val Gly Ile
    2025                2030                2035 agc cca ctc aaa cca ggc act gtg tct caa caa gcc tta caa aac    84866
Ser Pro Leu Lys Pro Gly Thr Val Ser Gln Gln Ala Leu Gln Asn
    2040                2045                2050 ctt ttg cgg act ctc agg tct ccc agc tct ccc ctg cag cag caa    84911
Leu Leu Arg Thr Leu Arg Ser Pro Ser Ser Pro Leu Gln Gln Gln
    2055                2060                2065 cag gtg ctt agt atc ctt cac gcc aac ccc cag ctg ttg gct gca    84956
Gln Val Leu Ser Ile Leu His Ala Asn Pro Gln Leu Leu Ala Ala
    2070                2075                2080 ttc atc aag cag cgg gct gcc aag tat gcc aac tct aat cca caa    85001
Phe Ile Lys Gln Arg Ala Ala Lys Tyr Ala Asn Ser Asn Pro Gln
    2085                2090                2095 ccc atc cct ggg cag cct ggc atg ccc cag ggg cag cca ggg cta    85046
Pro Ile Pro Gly Gln Pro Gly Met Pro Gln Gly Gln Pro Gly Leu
    2100                2105                2110 cag cca cct acc atg cca ggt cag cag ggg gtc cac tcc aat cca    85091
Gln Pro Pro Thr Met Pro Gly Gln Gln Gly Val His Ser Asn Pro
    2115                2120                2125 gcc atg cag aac atg aat cca atg cag gcg ggc gtt cag agg gct    85136
Ala Met Gln Asn Met Asn Pro Met Gln Ala Gly Val Gln Arg Ala
    2130                2135                2140 ggc ctg ccc cag cag caa cca cag cag caa ctc cag cca ccc atg    85181
Gly Leu Pro Gln Gln Gln Pro Gln Gln Gln Leu Gln Pro Pro Met
    2145                2150                2155 gga ggg atg agc ccc cag gct cag cag atg aac atg aac cac aac    85226
Gly Gly Met Ser Pro Gln Ala Gln Gln Met Asn Met Asn His Asn
    2160                2165                2170 acc atg cct tca caa ttc cga gac atc ttg aga cga cag caa atg    85271
Thr Met Pro Ser Gln Phe Arg Asp Ile Leu Arg Arg Gln Gln Met
    2175                2180                2185 atg caa cag cag cag caa cag gga gca ggg cca gga ata ggc cct    85316
Met Gln Gln Gln Gln Gln Gln Gly Ala Gly Pro Gly Ile Gly Pro
    2190                2195                2200 gga atg gcc aac cat aac cag ttc cag caa ccc caa gga gtt ggc    85361
Gly Met Ala Asn His Asn Gln Phe Gln Gln Pro Gln Gly Val Gly
    2205                2210                2215 tac cca cca cag cag cag cag cgg atg cag cat cac atg caa cag    85406
Tyr Pro Pro Gln Gln Gln Gln Arg Met Gln His His Met Gln Gln
    2220                2225                2230 atg caa caa gga aat atg gga cag ata ggc cag ctt ccc cag gcc    85451
Met Gln Gln Gly Asn Met Gly Gln Ile Gly Gln Leu Pro Gln Ala
    2235                2240                2245 ttg gga gca gag gca ggt gcc agt cta cag gcc tat cag cag cga    85496
```

| | |
|---|---|
| Leu Gly Ala Glu Ala Gly Ala Ser Leu Gln Ala Tyr Gln Gln Arg<br>    2250                  2255                  2260 | |
| ctc ctt cag caa cag atg ggg tcc cct gtt cag ccc aac ccc atg<br>Leu Leu Gln Gln Gln Met Gly Ser Pro Val Gln Pro Asn Pro Met<br>2265                  2270                  2275 | 85541 |
| agc ccc cag cag cat atg ctc cca aat cag gcc cag tcc cca cac<br>Ser Pro Gln Gln His Met Leu Pro Asn Gln Ala Gln Ser Pro His<br>2280                  2285                  2290 | 85586 |
| cta caa ggc cag cag atc cct aat tct ctc tcc aat caa gtg cgc<br>Leu Gln Gly Gln Gln Ile Pro Asn Ser Leu Ser Asn Gln Val Arg<br>2295                  2300                  2305 | 85631 |
| tct ccc cag cct gtc cct tct cca cgg cca cag tcc cag ccc ccc<br>Ser Pro Gln Pro Val Pro Ser Pro Arg Pro Gln Ser Gln Pro Pro<br>2310                  2315                  2320 | 85676 |
| cac tcc agt cct tcc cca agg atg cag cct cag cct tct cca cac<br>His Ser Ser Pro Ser Pro Arg Met Gln Pro Gln Pro Ser Pro His<br>2325                  2330                  2335 | 85721 |
| cac gtt tcc cca cag aca agt tcc cca cat cct gga ctg gta gct<br>His Val Ser Pro Gln Thr Ser Ser Pro His Pro Gly Leu Val Ala<br>2340                  2345                  2350 | 85766 |
| gcc cag gcc aac ccc atg gaa caa ggg cat ttt gcc agc ccg gac<br>Ala Gln Ala Asn Pro Met Glu Gln Gly His Phe Ala Ser Pro Asp<br>2355                  2360                  2365 | 85811 |
| cag aat tca atg ctt tct cag ctt gct agc aat cca ggc atg gca<br>Gln Asn Ser Met Leu Ser Gln Leu Ala Ser Asn Pro Gly Met Ala<br>2370                  2375                  2380 | 85856 |
| aac ctc cat ggt gca agc gcc acg gac ctg gga ctc agc acc gat<br>Asn Leu His Gly Ala Ser Ala Thr Asp Leu Gly Leu Ser Thr Asp<br>2385                  2390                  2395 | 85901 |
| aac tca gac ttg aat tca aac ctc tca cag agt aca cta gac ata<br>Asn Ser Asp Leu Asn Ser Asn Leu Ser Gln Ser Thr Leu Asp Ile<br>2400                  2405                  2410 | 85946 |
| cac tag<br>His | 85952 |

<210> SEQ ID NO 5
<211> LENGTH: 7245
<212> TYPE: DNA
<213> ORGANISM: Homo sapiens
<220> FEATURE:
<221> NAME/KEY: CDS
<222> LOCATION: (1)..(7242)

<400> SEQUENCE: 5

| | |
|---|---|
| atg gcc gag aat gtg gtg gaa ccg ggg ccg cct tca gcc aag cgg cct<br>Met Ala Glu Asn Val Val Glu Pro Gly Pro Pro Ser Ala Lys Arg Pro<br>1                 5                    10                  15 | 48 |
| aaa ctc tca tct ccg gcc ctc tcg gcg tcc gcc agc gat ggc aca gat<br>Lys Leu Ser Ser Pro Ala Leu Ser Ala Ser Ala Ser Asp Gly Thr Asp<br>               20                    25                  30 | 96 |
| ttt ggc tct cta ttt gac ttg gag cac gac tta cca gat gaa tta atc<br>Phe Gly Ser Leu Phe Asp Leu Glu His Asp Leu Pro Asp Glu Leu Ile<br>        35                    40                  45 | 144 |
| aac tct aca gaa ttg gga cta acc aat ggt ggt gat att aat cag ctt<br>Asn Ser Thr Glu Leu Gly Leu Thr Asn Gly Gly Asp Ile Asn Gln Leu<br>50                  55                  60 | 192 |
| cag aca agt ctt ggc atg gta caa gat gca gct tct aaa cat aaa cag<br>Gln Thr Ser Leu Gly Met Val Gln Asp Ala Ala Ser Lys His Lys Gln<br>65                     70                  75                  80 | 240 |
| ctg tca gaa ttg ctg cga tct ggt agt tcc cct aac ctc aat atg gga<br>Leu Ser Glu Leu Leu Arg Ser Gly Ser Ser Pro Asn Leu Asn Met Gly | 288 |

```
                         85                   90                     95
gtt ggt ggc cca ggt caa gtc atg gcc agc cag gcc caa cag agc agt       336
Val Gly Gly Pro Gly Gln Val Met Ala Ser Gln Ala Gln Gln Ser Ser
                100                 105                  110 cct gga tta ggt ttg ata aat agc atg gtc aaa agc cca atg aca cag       384
Pro Gly Leu Gly Leu Ile Asn Ser Met Val Lys Ser Pro Met Thr Gln
                115                 120                  125 gca ggc ttg act tct ccc aac atg ggg atg ggc act agt gga cca aat       432
Ala Gly Leu Thr Ser Pro Asn Met Gly Met Gly Thr Ser Gly Pro Asn
        130                 135                  140 cag ggt cct acg cag tca aca ggt atg atg aac agt cca gta aat cag       480
Gln Gly Pro Thr Gln Ser Thr Gly Met Met Asn Ser Pro Val Asn Gln
145                 150                  155                  160 cct gcc atg gga atg aac aca ggg atg aat gcg ggc atg aat cct gga       528
Pro Ala Met Gly Met Asn Thr Gly Met Asn Ala Gly Met Asn Pro Gly
                165                 170                  175 atg ttg gct gca ggc aat gga caa ggg ata atg cct aat caa gtc atg       576
Met Leu Ala Ala Gly Asn Gly Gln Gly Ile Met Pro Asn Gln Val Met
                180                 185                  190 aac ggt tca att gga gca ggc cga ggg cga cag aat atg cag tac cca       624
Asn Gly Ser Ile Gly Ala Gly Arg Gly Arg Gln Asn Met Gln Tyr Pro
                195                 200                  205 aac cca ggc atg gga agt gct ggc aac tta ctg act gag cct ctt cag       672
Asn Pro Gly Met Gly Ser Ala Gly Asn Leu Leu Thr Glu Pro Leu Gln
        210                 215                  220 cag ggc tct ccc cag atg gga gga caa aca gga ttg aga ggc ccc cag       720
Gln Gly Ser Pro Gln Met Gly Gly Gln Thr Gly Leu Arg Gly Pro Gln
225                 230                  235                  240 cct ctt aag atg gga atg atg aac aac ccc aat cct tat ggt tca cca       768
Pro Leu Lys Met Gly Met Met Asn Asn Pro Asn Pro Tyr Gly Ser Pro
                245                 250                  255 tat act cag aat cct gga cag cag att gga gcc agt ggc ctt ggt ctc       816
Tyr Thr Gln Asn Pro Gly Gln Gln Ile Gly Ala Ser Gly Leu Gly Leu
                260                 265                  270 cag att cag aca aaa act gta cta tca aat aac tta tct cca ttt gct       864
Gln Ile Gln Thr Lys Thr Val Leu Ser Asn Asn Leu Ser Pro Phe Ala
                275                 280                  285 atg gac aaa aag gca gtt cct ggt gga gga atg ccc aac atg ggt caa       912
Met Asp Lys Lys Ala Val Pro Gly Gly Gly Met Pro Asn Met Gly Gln
        290                 295                  300 cag cca gcc ccg cag gtc cag cag cca ggc ctg gtg act cca gtt gcc       960
Gln Pro Ala Pro Gln Val Gln Gln Pro Gly Leu Val Thr Pro Val Ala
305                 310                  315                  320 caa ggg atg ggt tct gga gca cat aca gct gat cca gag aag cgc aag      1008
Gln Gly Met Gly Ser Gly Ala His Thr Ala Asp Pro Glu Lys Arg Lys
                325                 330                  335 ctc atc cag cag cag ctt gtt ctc ctt ttg cat gct cac aag tgc cag      1056
Leu Ile Gln Gln Gln Leu Val Leu Leu Leu His Ala His Lys Cys Gln
                340                 345                  350 cgc cgg gaa cag gcc aat ggg gaa gtg agg cag tgc aac ctt ccc cac      1104
Arg Arg Glu Gln Ala Asn Gly Glu Val Arg Gln Cys Asn Leu Pro His
                355                 360                  365 tgt cgc aca atg aag aat gtc cta aac cac atg aca cac tgc cag tca      1152
Cys Arg Thr Met Lys Asn Val Leu Asn His Met Thr His Cys Gln Ser
        370                 375                  380 ggc aag tct tgc caa gtg gca cac tgt gca tct tct cga caa atc att      1200
Gly Lys Ser Cys Gln Val Ala His Cys Ala Ser Ser Arg Gln Ile Ile
385                 390                  395                  400 tca cac tgg aag aat tgt aca aga cat gat tgt cct gtg tgt ctc ccc      1248
```

```
Ser His Trp Lys Asn Cys Thr Arg His Asp Cys Pro Val Cys Leu Pro
            405                 410                 415 ctc aaa aat gct ggt gat aag aga aat caa cag cca att ttg act gga    1296
Leu Lys Asn Ala Gly Asp Lys Arg Asn Gln Gln Pro Ile Leu Thr Gly
                420                 425                 430 gca ccc gtt gga ctt gga aat cct agc tct cta ggg gtg ggt caa cag    1344
Ala Pro Val Gly Leu Gly Asn Pro Ser Ser Leu Gly Val Gly Gln Gln
            435                 440                 445 tct gcc ccc aac cta agc act gtt agt cag att gat ccc agc tcc ata    1392
Ser Ala Pro Asn Leu Ser Thr Val Ser Gln Ile Asp Pro Ser Ser Ile
        450                 455                 460 gaa aga gcc tat gca gct ctt gga cta ccc tat caa gta aat cag atg    1440
Glu Arg Ala Tyr Ala Ala Leu Gly Leu Pro Tyr Gln Val Asn Gln Met
465                 470                 475                 480 ccg aca caa ccc cag gtg caa gca aag aac cag cag aat cag cag cct    1488
Pro Thr Gln Pro Gln Val Gln Ala Lys Asn Gln Gln Asn Gln Gln Pro
                485                 490                 495 ggg cag tct ccc caa ggc atg cgg ccc atg agc aac atg agt gct agt    1536
Gly Gln Ser Pro Gln Gly Met Arg Pro Met Ser Asn Met Ser Ala Ser
            500                 505                 510 cct atg gga gta aat gga ggt gta gga gtt caa acg ccg agt ctt ctt    1584
Pro Met Gly Val Asn Gly Gly Val Gly Val Gln Thr Pro Ser Leu Leu
        515                 520                 525 tct gac tca atg ttg cat tca gcc ata aat tct caa aac cca atg atg    1632
Ser Asp Ser Met Leu His Ser Ala Ile Asn Ser Gln Asn Pro Met Met
530                 535                 540 agt gaa aat gcc agt gtg ccc tcc ctg ggt cct atg cca aca gca gct    1680
Ser Glu Asn Ala Ser Val Pro Ser Leu Gly Pro Met Pro Thr Ala Ala
545                 550                 555                 560 caa cca tcc act act gga att cgg aaa cag tgg cac gaa gat att act    1728
Gln Pro Ser Thr Thr Gly Ile Arg Lys Gln Trp His Glu Asp Ile Thr
                565                 570                 575 cag gat ctt cga aat cat ctt gtt cac aaa ctc gtc caa gcc ata ttt    1776
Gln Asp Leu Arg Asn His Leu Val His Lys Leu Val Gln Ala Ile Phe
            580                 585                 590 cct acg ccg gat cct gct gct tta aaa gac aga cgg atg gaa aac cta    1824
Pro Thr Pro Asp Pro Ala Ala Leu Lys Asp Arg Arg Met Glu Asn Leu
        595                 600                 605 gtt gca tat gct cgg aaa gtt gaa ggg gac atg tat gaa tct gca aac    1872
Val Ala Tyr Ala Arg Lys Val Glu Gly Asp Met Tyr Glu Ser Ala Asn
610                 615                 620 aat cga gcg gaa tac tac cac ctt cta gct gag aaa atc tat aag atc    1920
Asn Arg Ala Glu Tyr Tyr His Leu Leu Ala Glu Lys Ile Tyr Lys Ile
625                 630                 635                 640 cag aaa gaa cta gaa gaa aaa cga agg acc aga cta cag aag cag aac    1968
Gln Lys Glu Leu Glu Glu Lys Arg Arg Thr Arg Leu Gln Lys Gln Asn
                645                 650                 655 atg cta cca aat gct gca ggc atg gtt cca gtt tcc atg aat cca ggg    2016
Met Leu Pro Asn Ala Ala Gly Met Val Pro Val Ser Met Asn Pro Gly
            660                 665                 670 cct aac atg gga cag ccg caa cca gga atg act tct aat ggc cct cta    2064
Pro Asn Met Gly Gln Pro Gln Pro Gly Met Thr Ser Asn Gly Pro Leu
        675                 680                 685 cct gac cca agt atg atc cgt ggc agt gtg cca aac cag atg atg cct    2112
Pro Asp Pro Ser Met Ile Arg Gly Ser Val Pro Asn Gln Met Met Pro
        690                 695                 700 cga ata act cca caa tct ggt ttg aat caa ttt ggc cag atg agc atg    2160
Arg Ile Thr Pro Gln Ser Gly Leu Asn Gln Phe Gly Gln Met Ser Met
705                 710                 715                 720
```

| | |
|---|---|
| gcc cag ccc cct att gta ccc cgg caa acc cct cct ctt cag cac cat<br>Ala Gln Pro Pro Ile Val Pro Arg Gln Thr Pro Pro Leu Gln His His<br>                    725                    730                735 | 2208 |
| gga cag ttg gct caa cct gga gct ctc aac ccg cct atg ggc tat ggg<br>Gly Gln Leu Ala Gln Pro Gly Ala Leu Asn Pro Pro Met Gly Tyr Gly<br>                    740                    745                750 | 2256 |
| cct cgt atg caa cag cct tcc aac cag ggc cag ttc ctt cct cag act<br>Pro Arg Met Gln Gln Pro Ser Asn Gln Gly Gln Phe Leu Pro Gln Thr<br>        755                    760                    765 | 2304 |
| cag ttc cca tca cag gga atg aat gta aca aat atc cct ttg gct ccg<br>Gln Phe Pro Ser Gln Gly Met Asn Val Thr Asn Ile Pro Leu Ala Pro<br>    770                    775                    780 | 2352 |
| tcc agc ggt caa gct cca gtg tct caa gca caa atg tct agt tct tcc<br>Ser Ser Gly Gln Ala Pro Val Ser Gln Ala Gln Met Ser Ser Ser Ser<br>785                    790                    795                800 | 2400 |
| tgc ccg gtg aac tct cct ata atg cct cca ggg tct cag ggg agc cac<br>Cys Pro Val Asn Ser Pro Ile Met Pro Pro Gly Ser Gln Gly Ser His<br>                    805                    810                815 | 2448 |
| att cac tgt ccc cag ctt cct caa cca gct ctt cat cag aat tca ccc<br>Ile His Cys Pro Gln Leu Pro Gln Pro Ala Leu His Gln Asn Ser Pro<br>        820                    825                    830 | 2496 |
| tcg cct gta cct agt cgt acc ccc acc cct cac cat act ccc cca agc<br>Ser Pro Val Pro Ser Arg Thr Pro Thr Pro His His Thr Pro Pro Ser<br>    835                    840                    845 | 2544 |
| ata ggg gct cag cag cca cca gca aca aca att cca gcc cct gtt cct<br>Ile Gly Ala Gln Gln Pro Pro Ala Thr Thr Ile Pro Ala Pro Val Pro<br>850                    855                    860 | 2592 |
| aca cct cct gcc atg cca cct ggg cca cag tcc cag gct cta cat ccc<br>Thr Pro Pro Ala Met Pro Pro Gly Pro Gln Ser Gln Ala Leu His Pro<br>865                    870                    875                880 | 2640 |
| cct cca agg cag aca cct aca cca cca aca aca caa ctt ccc caa caa<br>Pro Pro Arg Gln Thr Pro Thr Pro Pro Thr Thr Gln Leu Pro Gln Gln<br>                    885                    890                895 | 2688 |
| gtg cag cct tca ctt cct gct gca cct tct gct gac cag ccc cag cag<br>Val Gln Pro Ser Leu Pro Ala Ala Pro Ser Ala Asp Gln Pro Gln Gln<br>        900                    905                    910 | 2736 |
| cag cct cgc tca cag cag agc aca gca gcg tct gtt cct acc cca aca<br>Gln Pro Arg Ser Gln Gln Ser Thr Ala Ala Ser Val Pro Thr Pro Thr<br>    915                    920                    925 | 2784 |
| gca ccg ctg ctt cct ccg cag cct gca act cca ctt tcc cag cca gct<br>Ala Pro Leu Leu Pro Pro Gln Pro Ala Thr Pro Leu Ser Gln Pro Ala<br>930                    935                    940 | 2832 |
| gta agc att gaa gga cag gta tca aat cct cca tct act agt agc aca<br>Val Ser Ile Glu Gly Gln Val Ser Asn Pro Pro Ser Thr Ser Ser Thr<br>945                    950                    955                960 | 2880 |
| gaa gtg aat tct cag gcc att gct gag aag cag cct tcc cag gaa gtg<br>Glu Val Asn Ser Gln Ala Ile Ala Glu Lys Gln Pro Ser Gln Glu Val<br>                    965                    970                975 | 2928 |
| aag atg gag gcc aaa atg gaa gtg gat caa cca gaa cca gca gat act<br>Lys Met Glu Ala Lys Met Glu Val Asp Gln Pro Glu Pro Ala Asp Thr<br>        980                    985                    990 | 2976 |
| cag ccg gag gat att tca gag tct  aaa gtg gaa gac tgt  aaa atg gaa<br>Gln Pro Glu Asp Ile Ser Glu Ser  Lys Val Glu Asp Cys  Lys Met Glu<br>    995                      1000                  1005 | 3024 |
| tct acc  gaa aca gaa gag aga  agc act gag tta aaa  act gaa ata<br>Ser Thr  Glu Thr Glu Glu Arg  Ser Thr Glu Leu Lys  Thr Glu Ile<br>    1010                    1015                  1020 | 3069 |
| aaa gag gag gaa gac cag cca agt act tca gct acc cag tca tct<br>Lys Glu Glu Glu Asp Gln Pro Ser Thr Ser Ala Thr Gln Ser Ser<br>1025                    1030                  1035 | 3114 |

| | | | | | | | | | | | | |
|---|---|---|---|---|---|---|---|---|---|---|---|---|
| ccg | gct | cca | gga | cag | tca | aag | aaa | aag | att | ttc | aaa | cca gaa gaa | 3159 |
| Pro | Ala | Pro | Gly | Gln | Ser | Lys | Lys | Lys | Ile | Phe | Lys | Pro Glu Glu |
| | 1040 | | | | 1045 | | | | 1050 | | | |

| cta | cga | cag | gca | ctg | atg | cca | act | ttg | gag | gca | ctt | tac cgt cag | 3204 |
|---|---|---|---|---|---|---|---|---|---|---|---|---|---|
| Leu | Arg | Gln | Ala | Leu | Met | Pro | Thr | Leu | Glu | Ala | Leu | Tyr Arg Gln |
| | 1055 | | | | 1060 | | | | 1065 | | | |

| gat | cca | gaa | tcc | ctt | ccc | ttt | cgt | caa | cct | gtg | gac | cct cag ctt | 3249 |
|---|---|---|---|---|---|---|---|---|---|---|---|---|---|
| Asp | Pro | Glu | Ser | Leu | Pro | Phe | Arg | Gln | Pro | Val | Asp | Pro Gln Leu |
| 1070 | | | | 1075 | | | | 1080 | | | | |

| tta | gga | atc | cct | gat | tac | ttt | gat | att | gtg | aag | agc | ccc atg gat | 3294 |
|---|---|---|---|---|---|---|---|---|---|---|---|---|---|
| Leu | Gly | Ile | Pro | Asp | Tyr | Phe | Asp | Ile | Val | Lys | Ser | Pro Met Asp |
| 1085 | | | | 1090 | | | | 1095 | | | | |

| ctt | tct | acc | att | aag | agg | aag | tta | gac | act | gga | cag | tat cag gag | 3339 |
|---|---|---|---|---|---|---|---|---|---|---|---|---|---|
| Leu | Ser | Thr | Ile | Lys | Arg | Lys | Leu | Asp | Thr | Gly | Gln | Tyr Gln Glu |
| 1100 | | | | 1105 | | | | 1110 | | | | |

| ccc | tgg | cag | tat | gtc | gat | gat | att | tgg | ctt | atg | ttc | aat aat gcc | 3384 |
|---|---|---|---|---|---|---|---|---|---|---|---|---|---|
| Pro | Trp | Gln | Tyr | Val | Asp | Asp | Ile | Trp | Leu | Met | Phe | Asn Asn Ala |
| 1115 | | | | 1120 | | | | 1125 | | | | |

| tgg | tta | tat | aac | cgg | aaa | aca | tca | cgg | gta | tac | aaa | tac tgc tcc | 3429 |
|---|---|---|---|---|---|---|---|---|---|---|---|---|---|
| Trp | Leu | Tyr | Asn | Arg | Lys | Thr | Ser | Arg | Val | Tyr | Lys | Tyr Cys Ser |
| 1130 | | | | 1135 | | | | 1140 | | | | |

| aag | ctc | tct | gag | gtc | ttt | gaa | caa | gaa | att | gac | cca | gtg atg caa | 3474 |
|---|---|---|---|---|---|---|---|---|---|---|---|---|---|
| Lys | Leu | Ser | Glu | Val | Phe | Glu | Gln | Glu | Ile | Asp | Pro | Val Met Gln |
| 1145 | | | | 1150 | | | | 1155 | | | | |

| agc | ctt | gga | tac | tgt | tgt | ggc | aga | aag | ttg | gag | ttc | tct cca cag | 3519 |
|---|---|---|---|---|---|---|---|---|---|---|---|---|---|
| Ser | Leu | Gly | Tyr | Cys | Cys | Gly | Arg | Lys | Leu | Glu | Phe | Ser Pro Gln |
| 1160 | | | | 1165 | | | | 1170 | | | | |

| aca | ctg | tgt | tgc | tac | ggc | aaa | cag | ttg | tgc | aca | ata | cct cgt gat | 3564 |
|---|---|---|---|---|---|---|---|---|---|---|---|---|---|
| Thr | Leu | Cys | Cys | Tyr | Gly | Lys | Gln | Leu | Cys | Thr | Ile | Pro Arg Asp |
| 1175 | | | | 1180 | | | | 1185 | | | | |

| gcc | act | tat | tac | agt | tac | cag | aac | agg | tat | cat | ttc | tgt gag aag | 3609 |
|---|---|---|---|---|---|---|---|---|---|---|---|---|---|
| Ala | Thr | Tyr | Tyr | Ser | Tyr | Gln | Asn | Arg | Tyr | His | Phe | Cys Glu Lys |
| 1190 | | | | 1195 | | | | 1200 | | | | |

| tgt | ttc | aat | gag | atc | caa | ggg | gag | agc | gtt | tct | ttg | ggg gat gac | 3654 |
|---|---|---|---|---|---|---|---|---|---|---|---|---|---|
| Cys | Phe | Asn | Glu | Ile | Gln | Gly | Glu | Ser | Val | Ser | Leu | Gly Asp Asp |
| 1205 | | | | 1210 | | | | 1215 | | | | |

| cct | tcc | cag | cct | caa | act | aca | ata | aat | aaa | gaa | caa | ttt tcc aag | 3699 |
|---|---|---|---|---|---|---|---|---|---|---|---|---|---|
| Pro | Ser | Gln | Pro | Gln | Thr | Thr | Ile | Asn | Lys | Glu | Gln | Phe Ser Lys |
| 1220 | | | | 1225 | | | | 1230 | | | | |

| aga | aaa | aat | gac | aca | ctg | gat | cct | gaa | ctg | ttt | gtt | gaa tgt aca | 3744 |
|---|---|---|---|---|---|---|---|---|---|---|---|---|---|
| Arg | Lys | Asn | Asp | Thr | Leu | Asp | Pro | Glu | Leu | Phe | Val | Glu Cys Thr |
| 1235 | | | | 1240 | | | | 1245 | | | | |

| gag | tgc | gga | aga | aag | atg | cat | cag | atc | tgt | gtc | ctt | cac cat gag | 3789 |
|---|---|---|---|---|---|---|---|---|---|---|---|---|---|
| Glu | Cys | Gly | Arg | Lys | Met | His | Gln | Ile | Cys | Val | Leu | His His Glu |
| 1250 | | | | 1255 | | | | 1260 | | | | |

| atc | atc | tgg | cct | gct | gga | ttc | gtc | tgt | gat | ggc | tgt | tta aag aaa | 3834 |
|---|---|---|---|---|---|---|---|---|---|---|---|---|---|
| Ile | Ile | Trp | Pro | Ala | Gly | Phe | Val | Cys | Asp | Gly | Cys | Leu Lys Lys |
| 1265 | | | | 1270 | | | | 1275 | | | | |

| agt | gca | cga | act | agg | aaa | gaa | aat | aag | ttt | tct | gct | aaa agg ttg | 3879 |
|---|---|---|---|---|---|---|---|---|---|---|---|---|---|
| Ser | Ala | Arg | Thr | Arg | Lys | Glu | Asn | Lys | Phe | Ser | Ala | Lys Arg Leu |
| 1280 | | | | 1285 | | | | 1290 | | | | |

| cca | tct | acc | aga | ctt | ggc | acc | ttt | cta | gag | aat | cgt | gtg aat gac | 3924 |
|---|---|---|---|---|---|---|---|---|---|---|---|---|---|
| Pro | Ser | Thr | Arg | Leu | Gly | Thr | Phe | Leu | Glu | Asn | Arg | Val Asn Asp |
| 1295 | | | | 1300 | | | | 1305 | | | | |

| ttt | ctg | agg | cga | cag | aat | cac | cct | gag | tca | gga | gag | gtc act gtt | 3969 |
|---|---|---|---|---|---|---|---|---|---|---|---|---|---|
| Phe | Leu | Arg | Arg | Gln | Asn | His | Pro | Glu | Ser | Gly | Glu | Val Thr Val |
| 1310 | | | | 1315 | | | | 1320 | | | | |

| aga | gta | gtt | cat | gct | tct | gac | aaa | acc | gtg | gaa | gta | aaa cca ggc | 4014 |
|---|---|---|---|---|---|---|---|---|---|---|---|---|---|
| Arg | Val | Val | His | Ala | Ser | Asp | Lys | Thr | Val | Glu | Val | Lys Pro Gly |

```
                                1325                1330                1335
atg aaa gca agg ttt gtg gac agt gga gag atg gca gaa tcc ttt        4059
Met Lys Ala Arg Phe Val Asp Ser Gly Glu Met Ala Glu Ser Phe
    1340                1345                1350 cca tac cga acc aaa gcc ctc ttt gcc ttt gaa gaa att gat ggt        4104
Pro Tyr Arg Thr Lys Ala Leu Phe Ala Phe Glu Glu Ile Asp Gly
1355                1360                1365 gtt gac ctg tgc ttc ttt ggc atg cat gtt caa gag tat ggc tct        4149
Val Asp Leu Cys Phe Phe Gly Met His Val Gln Glu Tyr Gly Ser
    1370                1375                1380 gac tgc cct cca ccc aac cag agg aga gta tac ata tct tac ctc        4194
Asp Cys Pro Pro Pro Asn Gln Arg Arg Val Tyr Ile Ser Tyr Leu
1385                1390                1395 gat agt gtt cat ttc ttc cgt cct aaa tgc ttg agg act gca gtc        4239
Asp Ser Val His Phe Phe Arg Pro Lys Cys Leu Arg Thr Ala Val
    1400                1405                1410 tat cat gaa atc cta att gga tat tta gaa tat gtc aag aaa tta        4284
Tyr His Glu Ile Leu Ile Gly Tyr Leu Glu Tyr Val Lys Lys Leu
1415                1420                1425 ggt tac aca aca ggg cat att tgg gca tgt cca cca agt gag gga        4329
Gly Tyr Thr Thr Gly His Ile Trp Ala Cys Pro Pro Ser Glu Gly
    1430                1435                1440 gat gat tat atc ttc cat tgc cat cct cct gac cag aag ata ccc        4374
Asp Asp Tyr Ile Phe His Cys His Pro Pro Asp Gln Lys Ile Pro
1445                1450                1455 aag ccc aag cga ctg cag gaa tgg tac aaa aaa atg ctt gac aag        4419
Lys Pro Lys Arg Leu Gln Glu Trp Tyr Lys Lys Met Leu Asp Lys
    1460                1465                1470 gct gta tca gag cgt att gtc cat gac tac aag gat att ttt aaa        4464
Ala Val Ser Glu Arg Ile Val His Asp Tyr Lys Asp Ile Phe Lys
1475                1480                1485 caa gct act gaa gat aga tta aca agt gca aag gaa ttg cct tat        4509
Gln Ala Thr Glu Asp Arg Leu Thr Ser Ala Lys Glu Leu Pro Tyr
    1490                1495                1500 ttc gag ggt gat ttc tgg ccc aat gtt ctg gaa gaa agc att aag        4554
Phe Glu Gly Asp Phe Trp Pro Asn Val Leu Glu Glu Ser Ile Lys
1505                1510                1515 gaa ctg gaa cag gag gaa gaa gag aga aaa cga gag gaa aac acc        4599
Glu Leu Glu Gln Glu Glu Glu Glu Arg Lys Arg Glu Glu Asn Thr
    1520                1525                1530 agc aat gaa agc aca gat gtg acc aag gga gac agc aaa aat gct        4644
Ser Asn Glu Ser Thr Asp Val Thr Lys Gly Asp Ser Lys Asn Ala
1535                1540                1545 aaa aag aag aat aat aag aaa acc agc aaa aat aag agc agc ctg        4689
Lys Lys Lys Asn Asn Lys Lys Thr Ser Lys Asn Lys Ser Ser Leu
    1550                1555                1560 agt agg ggc aac aag aag aaa ccc ggg atg ccc aat gta tct aac        4734
Ser Arg Gly Asn Lys Lys Lys Pro Gly Met Pro Asn Val Ser Asn
1565                1570                1575 gac ctc tca cag aaa cta tat gcc acc atg gag aag cat aaa gag        4779
Asp Leu Ser Gln Lys Leu Tyr Ala Thr Met Glu Lys His Lys Glu
    1580                1585                1590 gtc ttc ttt gtg atc cgc ctc att gct ggc cct gct gcc aac tcc        4824
Val Phe Phe Val Ile Arg Leu Ile Ala Gly Pro Ala Ala Asn Ser
1595                1600                1605 ctg cct ccc att gtt gat cct gat cct ctc atc ccc tgc gat ctg        4869
Leu Pro Pro Ile Val Asp Pro Asp Pro Leu Ile Pro Cys Asp Leu
    1610                1615                1620 atg gat ggt cgg gat gcg ttt ctc acg ctg gca agg gac aag cac        4914
```

```
              Met Asp Gly Arg Asp Ala Phe Leu Thr Leu Ala Arg Asp Lys His
                  1625                1630                1635 ctg gag ttc tct tca ctc cga aga gcc cag tgg tcc acc atg tgc         4959
Leu Glu Phe Ser Ser Leu Arg Arg Ala Gln Trp Ser Thr Met Cys
    1640                1645                1650 atg ctg gtg gag ctg cac acg cag agc cag gac cgc ttt gtc tac         5004
Met Leu Val Glu Leu His Thr Gln Ser Gln Asp Arg Phe Val Tyr
    1655                1660                1665 acc tgc aat gaa tgc aag cac cat gtg gag aca cgc tgg cac tgt         5049
Thr Cys Asn Glu Cys Lys His His Val Glu Thr Arg Trp His Cys
    1670                1675                1680 act gtc tgt gag gat tat gac ttg tgt atc acc tgc tat aac act         5094
Thr Val Cys Glu Asp Tyr Asp Leu Cys Ile Thr Cys Tyr Asn Thr
    1685                1690                1695 aaa aac cat gac cac aaa atg gag aaa cta ggc ctt ggc tta gat         5139
Lys Asn His Asp His Lys Met Glu Lys Leu Gly Leu Gly Leu Asp
    1700                1705                1710 gat gag agc aac aac cag cag gct gca gcc acc cag agc cca ggc         5184
Asp Glu Ser Asn Asn Gln Gln Ala Ala Ala Thr Gln Ser Pro Gly
    1715                1720                1725 gat tct cgc cgc ctg agt atc cag cgc tgc atc cag tct ctg gtc         5229
Asp Ser Arg Arg Leu Ser Ile Gln Arg Cys Ile Gln Ser Leu Val
    1730                1735                1740 cat gct tgc cag tgt cgg aat gcc aat tgc tca ctg cca tcc tgc         5274
His Ala Cys Gln Cys Arg Asn Ala Asn Cys Ser Leu Pro Ser Cys
    1745                1750                1755 cag aag atg aag cgg gtt gtg cag cat acc aag ggt tgc aaa cgg         5319
Gln Lys Met Lys Arg Val Val Gln His Thr Lys Gly Cys Lys Arg
    1760                1765                1770 aaa acc aat ggc ggg tgc ccc atc tgc aag cag ctc att gcc ctc         5364
Lys Thr Asn Gly Gly Cys Pro Ile Cys Lys Gln Leu Ile Ala Leu
    1775                1780                1785 tgc tgc tac cat gcc aag cac tgc cag gag aac aaa tgc ccg gtg         5409
Cys Cys Tyr His Ala Lys His Cys Gln Glu Asn Lys Cys Pro Val
    1790                1795                1800 ccg ttc tgc cta aac atc aag cag aag ctc cgg cag caa cag ctg         5454
Pro Phe Cys Leu Asn Ile Lys Gln Lys Leu Arg Gln Gln Gln Leu
    1805                1810                1815 cag cac cga cta cag cag gcc caa atg ctt cgc agg agg atg gcc         5499
Gln His Arg Leu Gln Gln Ala Gln Met Leu Arg Arg Arg Met Ala
    1820                1825                1830 agc atg cag cgg act ggt gtg gtt ggg cag caa cag ggc ctc cct         5544
Ser Met Gln Arg Thr Gly Val Val Gly Gln Gln Gln Gly Leu Pro
    1835                1840                1845 tcc ccc act cct gcc act cca acg aca cca act ggc caa cag cca         5589
Ser Pro Thr Pro Ala Thr Pro Thr Thr Pro Thr Gly Gln Gln Pro
    1850                1855                1860 acc acc ccg cag acg ccc cag ccc act tct cag cct cag cct acc         5634
Thr Thr Pro Gln Thr Pro Gln Pro Thr Ser Gln Pro Gln Pro Thr
    1865                1870                1875 cct ccc aat agc atg cca ccc tac ttg ccc agg act caa gct gct         5679
Pro Pro Asn Ser Met Pro Pro Tyr Leu Pro Arg Thr Gln Ala Ala
    1880                1885                1890 ggc cct gtg tcc cag ggt aag gca gca ggc cag gtg acc cct cca         5724
Gly Pro Val Ser Gln Gly Lys Ala Ala Gly Gln Val Thr Pro Pro
    1895                1900                1905 acc cct cct cag act gct cag cca ccc ctt cca ggg ccc cca cct         5769
Thr Pro Pro Gln Thr Ala Gln Pro Pro Leu Pro Gly Pro Pro Pro
    1910                1915                1920
```

```
gca gca gtg gaa atg gca atg cag att cag aga gca gcg gag acg      5814
Ala Ala Val Glu Met Ala Met Gln Ile Gln Arg Ala Ala Glu Thr
1925            1930                1935 cag cgc cag atg gcc cac gtg caa att ttt caa agg cca atc caa      5859
Gln Arg Gln Met Ala His Val Gln Ile Phe Gln Arg Pro Ile Gln
    1940            1945                1950 cac cag atg ccc ccg atg act ccc atg gcc ccc atg ggt atg aac      5904
His Gln Met Pro Pro Met Thr Pro Met Ala Pro Met Gly Met Asn
1955            1960                1965 cca cct ccc atg acc aga ggt ccc agt ggg cat ttg gag cca ggg      5949
Pro Pro Pro Met Thr Arg Gly Pro Ser Gly His Leu Glu Pro Gly
    1970            1975                1980 atg gga ccg aca ggg atg cag caa cag cca ccc tgg agc caa gga      5994
Met Gly Pro Thr Gly Met Gln Gln Gln Pro Pro Trp Ser Gln Gly
1985            1990                1995 gga ttg cct cag ccc cag caa cta cag tct ggg atg cca agg cca      6039
Gly Leu Pro Gln Pro Gln Gln Leu Gln Ser Gly Met Pro Arg Pro
    2000            2005                2010 gcc atg atg tca gtg gcc cag cat ggt caa cct ttg aac atg gct      6084
Ala Met Met Ser Val Ala Gln His Gly Gln Pro Leu Asn Met Ala
2015            2020                2025 cca caa cca gga ttg ggc cag gta ggt atc agc cca ctc aaa cca      6129
Pro Gln Pro Gly Leu Gly Gln Val Gly Ile Ser Pro Leu Lys Pro
    2030            2035                2040 ggc act gtg tct caa caa gcc tta caa aac ctt ttg cgg act ctc      6174
Gly Thr Val Ser Gln Gln Ala Leu Gln Asn Leu Leu Arg Thr Leu
2045            2050                2055 agg tct ccc agc tct ccc ctg cag cag caa cag gtg ctt agt atc      6219
Arg Ser Pro Ser Ser Pro Leu Gln Gln Gln Gln Val Leu Ser Ile
    2060            2065                2070 ctt cac gcc aac ccc cag ctg ttg gct gca ttc atc aag cag cgg      6264
Leu His Ala Asn Pro Gln Leu Leu Ala Ala Phe Ile Lys Gln Arg
2075            2080                2085 gct gcc aag tat gcc aac tct aat cca caa ccc atc cct ggg cag      6309
Ala Ala Lys Tyr Ala Asn Ser Asn Pro Gln Pro Ile Pro Gly Gln
    2090            2095                2100 cct ggc atg ccc cag ggg cag cca ggg cta cag cca cct acc atg      6354
Pro Gly Met Pro Gln Gly Gln Pro Gly Leu Gln Pro Pro Thr Met
2105            2110                2115 cca ggt cag cag ggg gtc cac tcc aat cca gcc atg cag aac atg      6399
Pro Gly Gln Gln Gly Val His Ser Asn Pro Ala Met Gln Asn Met
    2120            2125                2130 aat cca atg cag gcg ggc gtt cag agg gct ggc ctg ccc cag cag      6444
Asn Pro Met Gln Ala Gly Val Gln Arg Ala Gly Leu Pro Gln Gln
2135            2140                2145 caa cca cag cag caa ctc cag cca ccc atg gga ggg atg agc ccc      6489
Gln Pro Gln Gln Gln Leu Gln Pro Pro Met Gly Gly Met Ser Pro
    2150            2155                2160 cag gct cag cag atg aac atg aac cac aac acc atg cct tca caa      6534
Gln Ala Gln Gln Met Asn Met Asn His Asn Thr Met Pro Ser Gln
2165            2170                2175 ttc cga gac atc ttg aga cga cag caa atg atg caa cag cag cag      6579
Phe Arg Asp Ile Leu Arg Arg Gln Gln Met Met Gln Gln Gln Gln
    2180            2185                2190 caa cag gga gca ggg cca gga ata ggc cct gga atg gcc aac cat      6624
Gln Gln Gly Ala Gly Pro Gly Ile Gly Pro Gly Met Ala Asn His
2195            2200                2205 aac cag ttc cag caa ccc caa gga gtt ggc tac cca cca cag cag      6669
Asn Gln Phe Gln Gln Pro Gln Gly Val Gly Tyr Pro Pro Gln Gln
    2210            2215                2220
```

```
cag cag cgg atg cag cat cac atg caa cag atg caa caa gga aat    6714
Gln Gln Arg Met Gln His His Met Gln Gln Met Gln Gln Gly Asn
    2225                2230                2235 atg gga cag ata ggc cag ctt ccc cag gcc ttg gga gca gag gca    6759
Met Gly Gln Ile Gly Gln Leu Pro Gln Ala Leu Gly Ala Glu Ala
    2240                2245                2250 ggt gcc agt cta cag gcc tat cag cag cga ctc ctt cag caa cag    6804
Gly Ala Ser Leu Gln Ala Tyr Gln Gln Arg Leu Leu Gln Gln Gln
    2255                2260                2265 atg ggg tcc cct gtt cag ccc aac ccc atg agc ccc cag cag cat    6849
Met Gly Ser Pro Val Gln Pro Asn Pro Met Ser Pro Gln Gln His
    2270                2275                2280 atg ctc cca aat cag gcc cag tcc cca cac cta caa ggc cag cag    6894
Met Leu Pro Asn Gln Ala Gln Ser Pro His Leu Gln Gly Gln Gln
    2285                2290                2295 atc cct aat tct ctc tcc aat caa gtg cgc tct ccc cag cct gtc    6939
Ile Pro Asn Ser Leu Ser Asn Gln Val Arg Ser Pro Gln Pro Val
    2300                2305                2310 cct tct cca cgg cca cag tcc cag ccc ccc cac tcc agt cct tcc    6984
Pro Ser Pro Arg Pro Gln Ser Gln Pro Pro His Ser Ser Pro Ser
    2315                2320                2325 cca agg atg cag cct cag cct tct cca cac cac gtt tcc cca cag    7029
Pro Arg Met Gln Pro Gln Pro Ser Pro His His Val Ser Pro Gln
    2330                2335                2340 aca agt tcc cca cat cct gga ctg gta gct gcc cag gcc aac ccc    7074
Thr Ser Ser Pro His Pro Gly Leu Val Ala Ala Gln Ala Asn Pro
    2345                2350                2355 atg gaa caa ggg cat ttt gcc agc ccg gac cag aat tca atg ctt    7119
Met Glu Gln Gly His Phe Ala Ser Pro Asp Gln Asn Ser Met Leu
    2360                2365                2370 tct cag ctt gct agc aat cca ggc atg gca aac ctc cat ggt gca    7164
Ser Gln Leu Ala Ser Asn Pro Gly Met Ala Asn Leu His Gly Ala
    2375                2380                2385 agc gcc acg gac ctg gga ctc agc acc gat aac tca gac ttg aat    7209
Ser Ala Thr Asp Leu Gly Leu Ser Thr Asp Asn Ser Asp Leu Asn
    2390                2395                2400 tca aac ctc tca cag agt aca cta gac ata cac tag                7245
Ser Asn Leu Ser Gln Ser Thr Leu Asp Ile His
    2405                2410
```

<210> SEQ ID NO 6
<211> LENGTH: 2414
<212> TYPE: PRT
<213> ORGANISM: Homo sapiens

<400> SEQUENCE: 6

Met Ala Glu Asn Val Val Glu Pro Gly Pro Pro Ser Ala Lys Arg Pro
1               5                   10                  15

Lys Leu Ser Ser Pro Ala Leu Ser Ala Ser Ala Ser Asp Gly Thr Asp
            20                  25                  30

Phe Gly Ser Leu Phe Asp Leu Glu His Asp Leu Pro Asp Glu Leu Ile
        35                  40                  45

Asn Ser Thr Glu Leu Gly Leu Thr Asn Gly Gly Asp Ile Asn Gln Leu
    50                  55                  60

Gln Thr Ser Leu Gly Met Val Gln Asp Ala Ala Ser Lys His Lys Gln
65                  70                  75                  80

Leu Ser Glu Leu Leu Arg Ser Gly Ser Ser Pro Asn Leu Asn Met Gly
                85                  90                  95

```
Val Gly Gly Pro Gly Gln Val Met Ala Ser Gln Ala Gln Gln Ser Ser
                100                 105                 110

Pro Gly Leu Gly Leu Ile Asn Ser Met Val Lys Ser Pro Met Thr Gln
            115                 120                 125

Ala Gly Leu Thr Ser Pro Asn Met Gly Met Gly Thr Ser Gly Pro Asn
        130                 135                 140

Gln Gly Pro Thr Gln Ser Thr Gly Met Met Asn Ser Pro Val Asn Gln
145                 150                 155                 160

Pro Ala Met Gly Met Asn Thr Gly Met Asn Ala Gly Met Asn Pro Gly
                165                 170                 175

Met Leu Ala Ala Gly Asn Gly Gln Gly Ile Met Pro Asn Gln Val Met
            180                 185                 190

Asn Gly Ser Ile Gly Ala Gly Arg Gly Arg Gln Asn Met Gln Tyr Pro
        195                 200                 205

Asn Pro Gly Met Gly Ser Ala Gly Asn Leu Leu Thr Glu Pro Leu Gln
    210                 215                 220

Gln Gly Ser Pro Gln Met Gly Gly Gln Thr Gly Leu Arg Gly Pro Gln
225                 230                 235                 240

Pro Leu Lys Met Gly Met Met Asn Asn Pro Asn Pro Tyr Gly Ser Pro
                245                 250                 255

Tyr Thr Gln Asn Pro Gly Gln Gln Ile Gly Ala Ser Gly Leu Gly Leu
            260                 265                 270

Gln Ile Gln Thr Lys Thr Val Leu Ser Asn Asn Leu Ser Pro Phe Ala
        275                 280                 285

Met Asp Lys Lys Ala Val Pro Gly Gly Met Pro Asn Met Gly Gln
    290                 295                 300

Gln Pro Ala Pro Gln Val Gln Gln Pro Gly Leu Val Thr Pro Val Ala
305                 310                 315                 320

Gln Gly Met Gly Ser Gly Ala His Thr Ala Asp Pro Glu Lys Arg Lys
                325                 330                 335

Leu Ile Gln Gln Gln Leu Val Leu Leu Leu His Ala His Lys Cys Gln
            340                 345                 350

Arg Arg Glu Gln Ala Asn Gly Glu Val Arg Gln Cys Asn Leu Pro His
        355                 360                 365

Cys Arg Thr Met Lys Asn Val Leu Asn His Met Thr His Cys Gln Ser
    370                 375                 380

Gly Lys Ser Cys Gln Val Ala His Cys Ala Ser Ser Arg Gln Ile Ile
385                 390                 395                 400

Ser His Trp Lys Asn Cys Thr Arg His Asp Cys Pro Val Cys Leu Pro
                405                 410                 415

Leu Lys Asn Ala Gly Asp Lys Arg Asn Gln Gln Pro Ile Leu Thr Gly
            420                 425                 430

Ala Pro Val Gly Leu Gly Asn Pro Ser Ser Leu Gly Val Gly Gln Gln
        435                 440                 445

Ser Ala Pro Asn Leu Ser Thr Val Ser Gln Ile Asp Pro Ser Ser Ile
    450                 455                 460

Glu Arg Ala Tyr Ala Ala Leu Gly Leu Pro Tyr Gln Val Asn Gln Met
465                 470                 475                 480

Pro Thr Gln Pro Gln Val Gln Ala Lys Asn Gln Asn Gln Gln Pro
                485                 490                 495

Gly Gln Ser Pro Gln Gly Met Arg Pro Met Ser Asn Met Ser Ala Ser
            500                 505                 510

Pro Met Gly Val Asn Gly Gly Val Gly Val Gln Thr Pro Ser Leu Leu
```

```
                515                 520                 525
Ser Asp Ser Met Leu His Ser Ala Ile Asn Ser Gln Asn Pro Met Met
530                 535                 540

Ser Glu Asn Ala Ser Val Pro Ser Leu Gly Pro Met Pro Thr Ala Ala
545                 550                 555                 560

Gln Pro Ser Thr Thr Gly Ile Arg Lys Gln Trp His Glu Asp Ile Thr
                565                 570                 575

Gln Asp Leu Arg Asn His Leu Val His Lys Leu Val Gln Ala Ile Phe
                580                 585                 590

Pro Thr Pro Asp Pro Ala Ala Leu Lys Asp Arg Arg Met Glu Asn Leu
                595                 600                 605

Val Ala Tyr Ala Arg Lys Val Glu Gly Asp Met Tyr Glu Ser Ala Asn
610                 615                 620

Asn Arg Ala Glu Tyr Tyr His Leu Leu Ala Glu Lys Ile Tyr Lys Ile
625                 630                 635                 640

Gln Lys Glu Leu Glu Glu Lys Arg Arg Thr Arg Leu Gln Lys Gln Asn
                645                 650                 655

Met Leu Pro Asn Ala Ala Gly Met Val Pro Val Ser Met Asn Pro Gly
                660                 665                 670

Pro Asn Met Gly Gln Pro Gln Pro Gly Met Thr Ser Asn Gly Pro Leu
                675                 680                 685

Pro Asp Pro Ser Met Ile Arg Gly Ser Val Pro Asn Gln Met Met Pro
690                 695                 700

Arg Ile Thr Pro Gln Ser Gly Leu Asn Gln Phe Gly Gln Met Ser Met
705                 710                 715                 720

Ala Gln Pro Pro Ile Val Pro Arg Gln Thr Pro Leu Gln His His
                725                 730                 735

Gly Gln Leu Ala Gln Pro Gly Ala Leu Asn Pro Pro Met Gly Tyr Gly
                740                 745                 750

Pro Arg Met Gln Gln Pro Ser Asn Gln Gly Gln Phe Leu Pro Gln Thr
                755                 760                 765

Gln Phe Pro Ser Gln Gly Met Asn Val Thr Asn Ile Pro Leu Ala Pro
                770                 775                 780

Ser Ser Gly Gln Ala Pro Val Ser Gln Ala Gln Met Ser Ser Ser Ser
785                 790                 795                 800

Cys Pro Val Asn Ser Pro Ile Met Pro Pro Gly Ser Gln Gly Ser His
                805                 810                 815

Ile His Cys Pro Gln Leu Pro Gln Pro Ala Leu His Gln Asn Ser Pro
                820                 825                 830

Ser Pro Val Pro Ser Arg Thr Pro Thr Pro His His Thr Pro Pro Ser
                835                 840                 845

Ile Gly Ala Gln Gln Pro Pro Ala Thr Thr Ile Pro Ala Pro Val Pro
850                 855                 860

Thr Pro Pro Ala Met Pro Pro Gly Pro Gln Ser Gln Ala Leu His Pro
865                 870                 875                 880

Pro Pro Arg Gln Thr Pro Thr Pro Pro Thr Thr Gln Leu Pro Gln Gln
                885                 890                 895

Val Gln Pro Ser Leu Pro Ala Ala Pro Ser Ala Asp Gln Pro Gln Gln
                900                 905                 910

Gln Pro Arg Ser Gln Gln Ser Thr Ala Ala Ser Val Pro Thr Pro Thr
                915                 920                 925

Ala Pro Leu Leu Pro Pro Gln Pro Ala Thr Pro Leu Ser Gln Pro Ala
930                 935                 940
```

-continued

```
Val Ser Ile Glu Gly Gln Val Ser Asn Pro Pro Ser Thr Ser Thr
945                 950                 955                 960

Glu Val Asn Ser Gln Ala Ile Ala Glu Lys Gln Pro Ser Gln Glu Val
            965                 970                 975

Lys Met Glu Ala Lys Met Glu Val Asp Gln Pro Glu Pro Ala Asp Thr
            980                 985                 990

Gln Pro Glu Asp Ile Ser Glu Ser Lys Val Glu Asp Cys Lys Met Glu
        995                 1000                1005

Ser Thr Glu Thr Glu Glu Arg Ser Thr Glu Leu Lys Thr Glu Ile
    1010                1015                1020

Lys Glu Glu Glu Asp Gln Pro Ser Thr Ser Ala Thr Gln Ser Ser
    1025                1030                1035

Pro Ala Pro Gly Gln Ser Lys Lys Ile Phe Lys Pro Glu Glu
    1040                1045                1050

Leu Arg Gln Ala Leu Met Pro Thr Leu Glu Ala Leu Tyr Arg Gln
    1055                1060                1065

Asp Pro Glu Ser Leu Pro Phe Arg Gln Pro Val Asp Pro Gln Leu
    1070                1075                1080

Leu Gly Ile Pro Asp Tyr Phe Asp Ile Val Lys Ser Pro Met Asp
    1085                1090                1095

Leu Ser Thr Ile Lys Arg Lys Leu Asp Thr Gly Gln Tyr Gln Glu
    1100                1105                1110

Pro Trp Gln Tyr Val Asp Asp Ile Trp Leu Met Phe Asn Asn Ala
    1115                1120                1125

Trp Leu Tyr Asn Arg Lys Thr Ser Arg Val Tyr Lys Tyr Cys Ser
    1130                1135                1140

Lys Leu Ser Glu Val Phe Glu Gln Glu Ile Asp Pro Val Met Gln
    1145                1150                1155

Ser Leu Gly Tyr Cys Cys Gly Arg Lys Leu Glu Phe Ser Pro Gln
    1160                1165                1170

Thr Leu Cys Cys Tyr Gly Lys Gln Leu Cys Thr Ile Pro Arg Asp
    1175                1180                1185

Ala Thr Tyr Tyr Ser Tyr Gln Asn Arg Tyr His Phe Cys Glu Lys
    1190                1195                1200

Cys Phe Asn Glu Ile Gln Gly Glu Ser Val Ser Leu Gly Asp Asp
    1205                1210                1215

Pro Ser Gln Pro Gln Thr Thr Ile Asn Lys Glu Gln Phe Ser Lys
    1220                1225                1230

Arg Lys Asn Asp Thr Leu Asp Pro Glu Leu Phe Val Glu Cys Thr
    1235                1240                1245

Glu Cys Gly Arg Lys Met His Gln Ile Cys Val Leu His His Glu
    1250                1255                1260

Ile Ile Trp Pro Ala Gly Phe Val Cys Asp Gly Cys Leu Lys Lys
    1265                1270                1275

Ser Ala Arg Thr Arg Lys Glu Asn Lys Phe Ser Ala Lys Arg Leu
    1280                1285                1290

Pro Ser Thr Arg Leu Gly Thr Phe Leu Glu Asn Arg Val Asn Asp
    1295                1300                1305

Phe Leu Arg Arg Gln Asn His Pro Glu Ser Gly Glu Val Thr Val
    1310                1315                1320

Arg Val Val His Ala Ser Asp Lys Thr Val Glu Val Lys Pro Gly
    1325                1330                1335
```

```
Met Lys Ala Arg Phe Val Asp Ser Gly Glu Met Ala Glu Ser Phe
1340                1345                1350

Pro Tyr Arg Thr Lys Ala Leu Phe Ala Phe Glu Glu Ile Asp Gly
    1355                1360                1365

Val Asp Leu Cys Phe Phe Gly Met His Val Gln Glu Tyr Gly Ser
    1370                1375                1380

Asp Cys Pro Pro Pro Asn Gln Arg Arg Val Tyr Ile Ser Tyr Leu
    1385                1390                1395

Asp Ser Val His Phe Phe Arg Pro Lys Cys Leu Arg Thr Ala Val
    1400                1405                1410

Tyr His Glu Ile Leu Ile Gly Tyr Leu Glu Tyr Val Lys Lys Leu
    1415                1420                1425

Gly Tyr Thr Thr Gly His Ile Trp Ala Cys Pro Pro Ser Glu Gly
    1430                1435                1440

Asp Asp Tyr Ile Phe His Cys His Pro Pro Asp Gln Lys Ile Pro
    1445                1450                1455

Lys Pro Lys Arg Leu Gln Glu Trp Tyr Lys Lys Met Leu Asp Lys
    1460                1465                1470

Ala Val Ser Glu Arg Ile Val His Asp Tyr Lys Asp Ile Phe Lys
    1475                1480                1485

Gln Ala Thr Glu Asp Arg Leu Thr Ser Ala Lys Glu Leu Pro Tyr
    1490                1495                1500

Phe Glu Gly Asp Phe Trp Pro Asn Val Leu Glu Glu Ser Ile Lys
    1505                1510                1515

Glu Leu Glu Gln Glu Glu Glu Arg Lys Arg Glu Glu Asn Thr
    1520                1525                1530

Ser Asn Glu Ser Thr Asp Val Thr Lys Gly Asp Ser Lys Asn Ala
    1535                1540                1545

Lys Lys Lys Asn Asn Lys Lys Thr Ser Lys Asn Lys Ser Ser Leu
    1550                1555                1560

Ser Arg Gly Asn Lys Lys Lys Pro Gly Met Pro Asn Val Ser Asn
    1565                1570                1575

Asp Leu Ser Gln Lys Leu Tyr Ala Thr Met Glu Lys His Lys Glu
    1580                1585                1590

Val Phe Phe Val Ile Arg Leu Ile Ala Gly Pro Ala Ala Asn Ser
    1595                1600                1605

Leu Pro Pro Ile Val Asp Pro Asp Pro Leu Ile Pro Cys Asp Leu
    1610                1615                1620

Met Asp Gly Arg Asp Ala Phe Leu Thr Leu Ala Arg Asp Lys His
    1625                1630                1635

Leu Glu Phe Ser Ser Leu Arg Arg Ala Gln Trp Ser Thr Met Cys
    1640                1645                1650

Met Leu Val Glu Leu His Thr Gln Ser Gln Asp Arg Phe Val Tyr
    1655                1660                1665

Thr Cys Asn Glu Cys Lys His His Val Glu Thr Arg Trp His Cys
    1670                1675                1680

Thr Val Cys Glu Asp Tyr Asp Leu Cys Ile Thr Cys Tyr Asn Thr
    1685                1690                1695

Lys Asn His Asp His Lys Met Glu Lys Leu Gly Leu Gly Leu Asp
    1700                1705                1710

Asp Glu Ser Asn Asn Gln Gln Ala Ala Ala Thr Gln Ser Pro Gly
    1715                1720                1725

Asp Ser Arg Arg Leu Ser Ile Gln Arg Cys Ile Gln Ser Leu Val
```

-continued

```
                1730                1735                1740

His Ala Cys Gln Cys Arg Asn Ala Asn Cys Ser Leu Pro Ser Cys
        1745                1750                1755

Gln Lys Met Lys Arg Val Val Gln His Thr Lys Gly Cys Lys Arg
        1760                1765                1770

Lys Thr Asn Gly Gly Cys Pro Ile Cys Lys Gln Leu Ile Ala Leu
        1775                1780                1785

Cys Cys Tyr His Ala Lys His Cys Gln Glu Asn Lys Cys Pro Val
        1790                1795                1800

Pro Phe Cys Leu Asn Ile Lys Gln Lys Leu Arg Gln Gln Gln Leu
        1805                1810                1815

Gln His Arg Leu Gln Gln Ala Gln Met Leu Arg Arg Arg Met Ala
        1820                1825                1830

Ser Met Gln Arg Thr Gly Val Val Gly Gln Gln Gln Gly Leu Pro
        1835                1840                1845

Ser Pro Thr Pro Ala Thr Pro Thr Thr Pro Thr Gly Gln Gln Pro
        1850                1855                1860

Thr Thr Pro Gln Thr Pro Gln Pro Thr Ser Gln Pro Gln Pro Thr
        1865                1870                1875

Pro Pro Asn Ser Met Pro Pro Tyr Leu Pro Arg Thr Gln Ala Ala
        1880                1885                1890

Gly Pro Val Ser Gln Gly Lys Ala Ala Gly Gln Val Thr Pro Pro
        1895                1900                1905

Thr Pro Pro Gln Thr Ala Gln Pro Pro Leu Pro Gly Pro Pro Pro
        1910                1915                1920

Ala Ala Val Glu Met Ala Met Gln Ile Gln Arg Ala Ala Glu Thr
        1925                1930                1935

Gln Arg Gln Met Ala His Val Gln Ile Phe Gln Arg Pro Ile Gln
        1940                1945                1950

His Gln Met Pro Pro Met Thr Pro Met Ala Pro Met Gly Met Asn
        1955                1960                1965

Pro Pro Pro Met Thr Arg Gly Pro Ser Gly His Leu Glu Pro Gly
        1970                1975                1980

Met Gly Pro Thr Gly Met Gln Gln Gln Pro Pro Trp Ser Gln Gly
        1985                1990                1995

Gly Leu Pro Gln Pro Gln Gln Leu Gln Ser Gly Met Pro Arg Pro
        2000                2005                2010

Ala Met Met Ser Val Ala Gln His Gly Gln Pro Leu Asn Met Ala
        2015                2020                2025

Pro Gln Pro Gly Leu Gly Gln Val Gly Ile Ser Pro Leu Lys Pro
        2030                2035                2040

Gly Thr Val Ser Gln Gln Ala Leu Gln Asn Leu Leu Arg Thr Leu
        2045                2050                2055

Arg Ser Pro Ser Ser Pro Leu Gln Gln Gln Gln Val Leu Ser Ile
        2060                2065                2070

Leu His Ala Asn Pro Gln Leu Leu Ala Ala Phe Ile Lys Gln Arg
        2075                2080                2085

Ala Ala Lys Tyr Ala Asn Ser Asn Pro Gln Pro Ile Pro Gly Gln
        2090                2095                2100

Pro Gly Met Pro Gln Gly Gln Pro Gly Leu Gln Pro Pro Thr Met
        2105                2110                2115

Pro Gly Gln Gln Gly Val His Ser Asn Pro Ala Met Gln Asn Met
        2120                2125                2130
```

```
Asn Pro Met Gln Ala Gly Val Gln Arg Ala Gly Leu Pro Gln Gln
    2135            2140            2145

Gln Pro Gln Gln Gln Leu Gln Pro Pro Met Gly Gly Met Ser Pro
    2150            2155            2160

Gln Ala Gln Gln Met Asn Met Asn His Asn Thr Met Pro Ser Gln
    2165            2170            2175

Phe Arg Asp Ile Leu Arg Arg Gln Gln Met Met Gln Gln Gln Gln
    2180            2185            2190

Gln Gln Gly Ala Gly Pro Gly Ile Gly Pro Gly Met Ala Asn His
    2195            2200            2205

Asn Gln Phe Gln Gln Pro Gln Gly Val Gly Tyr Pro Pro Gln Gln
    2210            2215            2220

Gln Gln Arg Met Gln His His Met Gln Gln Met Gln Gln Gly Asn
    2225            2230            2235

Met Gly Gln Ile Gly Gln Leu Pro Gln Ala Leu Gly Ala Glu Ala
    2240            2245            2250

Gly Ala Ser Leu Gln Ala Tyr Gln Gln Arg Leu Leu Gln Gln Gln
    2255            2260            2265

Met Gly Ser Pro Val Gln Pro Asn Pro Met Ser Pro Gln Gln His
    2270            2275            2280

Met Leu Pro Asn Gln Ala Gln Ser Pro His Leu Gln Gly Gln Gln
    2285            2290            2295

Ile Pro Asn Ser Leu Ser Asn Gln Val Arg Ser Pro Gln Pro Val
    2300            2305            2310

Pro Ser Pro Arg Pro Gln Ser Gln Pro Pro His Ser Ser Pro Ser
    2315            2320            2325

Pro Arg Met Gln Pro Gln Pro Ser Pro His His Val Ser Pro Gln
    2330            2335            2340

Thr Ser Ser Pro His Pro Gly Leu Val Ala Ala Gln Ala Asn Pro
    2345            2350            2355

Met Glu Gln Gly His Phe Ala Ser Pro Asp Gln Asn Ser Met Leu
    2360            2365            2370

Ser Gln Leu Ala Ser Asn Pro Gly Met Ala Asn Leu His Gly Ala
    2375            2380            2385

Ser Ala Thr Asp Leu Gly Leu Ser Thr Asp Asn Ser Asp Leu Asn
    2390            2395            2400

Ser Asn Leu Ser Gln Ser Thr Leu Asp Ile His
    2405            2410
```

METHOD FOR PREDICTING RESPONSIVENESS TO CANCER TREATMENT USING P300-INHIBITING COMPOUND

TECHNICAL FIELD

The present invention relates to a method for predicting responsiveness to the treatment of cancer with a compound inhibiting p300 and a method for selecting a candidate for the treatment of cancer by using functional suppression of CBP as an index. The present invention also relates to a method for treating cancer having functional suppression of CBP with a compound inhibiting p300. The present invention further relates to a reagent for detecting the presence or absence of functional suppression of CBP, which is used in these methods. The present invention further relates to a method for screening for a compound for use in the treatment of cancer having functional suppression of CBP by using inhibition of p300 as an index.

BACKGROUND ART

Tyrosine kinase inhibitors are effective against solid tumors with activating mutations in tyrosine kinase gene, such as EGFR mutations or ALK fusion found in lung adenocarcinoma (NPL 1). We and other researchers have recently identified RET oncogene fusions in lung adenocarcinoma (NPL 2). This supports the importance of tyrosine kinase gene as a therapeutic target.

Meanwhile, inactivating somatic mutations in genes encoding chromatin-regulating protein subunits (e.g., histone acetyltransferases CBP/CREBBP and p300/EP300, histone methyltransferases MLL2 and SETD2, histone demethylases JARID1C and UTX, and chromatin remodeling factors BRG1, ARID1A, ARID2, PBRM1, and SNF5) have been largely attractive since they were first identified by the genome-wide sequencing analysis of cancer cells. These mutations are considered to inhibit functions in transcription or DNA double-strand break repair and thought to be crucial to the development and/or progression of cancer.

Unfortunately, therapeutic strategies for specifically targeting cancer cells having these mutations have not yet been developed.

CITATION LIST

Non Patent Literature

[NPL 1] Pao W, Girard N. Lancet Oncol. 2011; February; 12 (2): 175-80
[NPL 2] Shaw A T, et al., Nat Rev Cancer. 2013; November; 13 (11): 772-87

SUMMARY OF INVENTION

Technical Problem

The present invention has been made in light of these circumferences, and an object of the present invention is to develop a therapeutic strategy for specifically targeting cancer cells having functional suppression of CBP.

Solution to Problem

Synthetic lethality therapy is a very promising method for treating cancer. For example, BRCA1 and BRCA2 genes are in the relationship of synthetic lethality with PARP1 gene. The growth of BRCA1-deficient or BRCA2-deficient cancer cells depends on the functions of the PARP1 protein. Now, these findings have been translated to the clinic through the development of PARP inhibitors to treat BRCA1/BRCA2-deficient tumors (Chan D A, et al., Nat Rev Drug Discov. 2011; 10: 351-64). In addition, the synthetic lethality therapy has been proposed for the treatment of cancer deficient in a gene involved in DNA mismatch repair or cell metabolism (Muller F L, et al., Nature. 2012; 488: 337-42, Chan D A, et al., Sci Transl Med. 2011; 3: 94ra70, and Martin S A, et al., Cancer Cell. 2010; 17: 235-48). The present inventors have conducted diligent studies in order to apply the synthetic lethality therapy to a therapeutic strategy for specifically killing cancer cells harboring CBP mutations.

As a result, the present inventors have found that suppression of p300 protein expression or functional inhibition of this protein in cancer cells harboring CBP mutations remarkably suppresses the growth of the cancer cells, whereas such suppression of growth does not occur in CBP-proficient cells. Also, the percentage of cells positive to Annexin V/PI staining was increased in cancer cells whose growth was suppressed, demonstrating that apoptosis was induced. Furthermore, an experiment using mice in which cancer cells harboring CBP mutations were transplanted has also demonstrated the in vivo inhibitory effect of suppression of p300 expression on the growth of cancer cells harboring CBP mutations.

From these results, the present inventors have found that CBP and p300 are in the relationship of synthetic lethality, and treatment inhibiting p300 (particularly, its histone acetyltransferase activity) is a promising approach for the treatment of cancer having functional suppression of CBP. The present inventors have also revealed that this therapeutic strategy achieves efficient treatment based on companion diagnostics because a p300 inhibitor can be administered to a cancer patient selected with functional suppression of CBP as an index.

The present inventors have further found that screening for a drug useful in the treatment of CBP-mutated cancer can be performed by using whether or not to inhibit p300 as an index. On the basis of these findings, the present invention has been completed.

Thus, the present invention relates to synthetic lethality therapy for specifically targeting cancer cells having functional suppression of CBP such as CBP mutations, and companion diagnostics for the synthetic lethality therapy, and more specifically provides the following aspects:

(1) A method for predicting responsiveness to the treatment of cancer with a compound inhibiting p300, comprising using a biological sample derived from a cancer patient, detecting the presence or absence of functional suppression of CBP contained in the biological sample, and determining the patient with the detected functional suppression of CBP as responsive to the treatment of cancer with the compound inhibiting p300.

(2) A method for selecting a candidate for the treatment of cancer with a compound inhibiting p300, comprising using a biological sample derived from a cancer patient, detecting the presence or absence of functional suppression of CBP in the biological sample, and selecting the patient with the detected functional suppression of CBP as the candidate for the treatment of cancer with the compound inhibiting p300.

(3) A method for treating cancer having functional suppression of CBP, comprising using a biological sample derived from a cancer patient, detecting the presence or absence of functional suppression of CBP contained in the biological sample, and administering a compound inhibiting p300 to the patient with the detected functional suppression of CBP.

(4) A reagent for detecting the presence or absence of functional suppression of CBP in a method according to any of (1) to (3), the reagent comprising any of the following molecules (a) to (c) as an active ingredient:
(a) an oligonucleotide primer specifically binding to the CBP gene,
(b) an oligonucleotide probe specifically binding to the CBP gene, and
(c) an antibody specifically binding to the CBP protein.

(5) A method for screening for a compound for use in the treatment of cancer having functional suppression of CBP, the method comprising the step of selecting the compound by using whether or not to inhibit p300 as an index.

(6) A therapeutic agent for cancer in which functional suppression of CBP has been detected, comprising a compound inhibiting p300.

Advantageous Effects of Invention

According to the present invention, responsiveness to the treatment of cancer with a p300 inhibitor can be efficiently predicted with functional suppression of CBP as an index. According to the present invention, the presence or absence of functional suppression of CBP (e.g., inactivating mutations or reduction in expression) in a biological sample derived from a cancer patient is detected, and the patient having the functional suppression of CBP is selected. Then, this selected patient can be subjected to the treatment of cancer with a p300 inhibitor. Therefore, treatment results of cancer patients can be largely improved. Use of a probe or a primer for the CBP gene and an antibody against CBP allows companion diagnostics to be efficiently performed by such detection of the presence or absence of functional suppression of CBP.

BRIEF DESCRIPTION OF DRAWINGS

FIG. 1A is a photograph showing results of Western blotting. FIG. 1B is a graph showing cell survival rates. FIG. 1C is a graph showing colony formation rates.

FIG. 3A is a graph showing survival rates of lung cancer cell lines. FIG. 3B is a graph showing IC50 of C646 against the lung cancer cell lines. FIG. 3C is a graph showing survival rates of lymphoma cell lines. FIG. 3D is a graph showing IC50 of C646 against the lymphoma cell lines.

FIG. 5A shows results obtained at 96 hours after transfection with sip300. FIG. 5B shows results obtained at 48 hours and 96 hours after C464 treatment.

DESCRIPTION OF EMBODIMENTS

<Method for Predicting Responsiveness to Treatment of Cancer and Method for Selecting Candidate for Treatment of Cancer>

In the present invention, tumor, malignant tumor, cancer, malignant neoplasm, carcinoma, sarcoma, and the like are collectively referred to as "tumor" or "cancer". In the present invention, it has been found that CBP and p300 are in the relationship of synthetic lethality in cancer cells, and inhibition of p300 in cancer cells having functional suppression of CBP can suppress the growth of the cancer cells. On the basis of this finding, responsiveness to the treatment of cancer with a compound inhibiting p300 can be evaluated with functional suppression of CBP as an index. Thus, the present invention provides a method for predicting responsiveness to the treatment of cancer with a compound inhibiting p300, comprising using a biological sample derived from a cancer patient, detecting the presence or absence of functional suppression of CBP contained in the biological sample, and determining the patient with the detected functional suppression of CBP as responsive to the treatment of cancer with the compound inhibiting p300.

Such a patient with the detected functional suppression of CBP is suitable for the treatment of cancer with the compound inhibiting p300. Efficient treatment can be performed by selecting a patient responsive to and a patient nonresponsive to the treatment of cancer with the compound inhibiting p300 with functional suppression of CBP as an index. Thus, the present invention provides even a method for selecting a candidate for the treatment of cancer with a compound inhibiting p300, comprising using a biological sample derived from a cancer patient, detecting the presence or absence of functional suppression of CBP in the biological sample, and selecting the patient with the detected functional suppression of CBP as the candidate for the treatment of cancer with the compound inhibiting p300.

Figure 7:
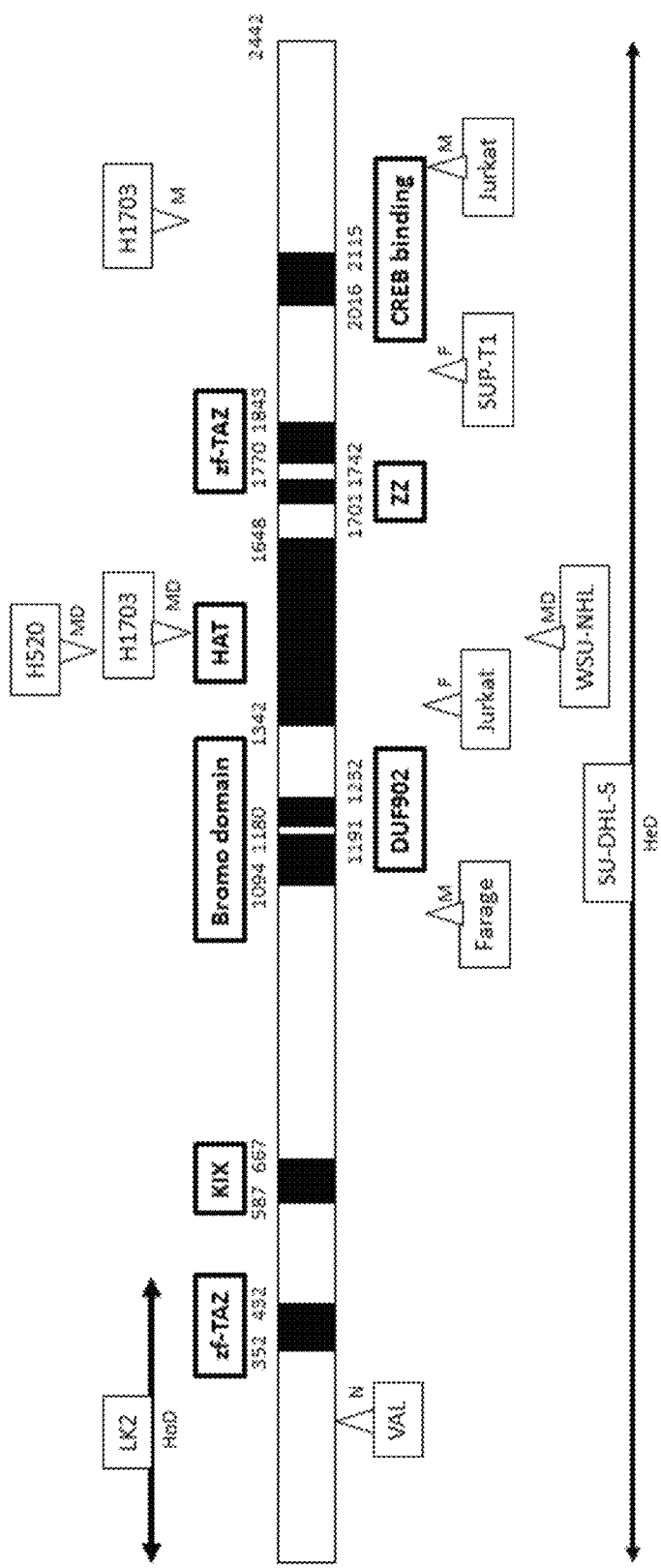
FIG. 7 is a diagram showing CBP mutations in a lung cancer cell line and a lymphoma cell line. In the diagram, "HoD" denotes homozygous deletion; "HeD" denotes heterozygous deletion; "N" denotes nonsense mutation; "F" denotes frame shift mutation; "MD" denotes intradomain missense mutation; and "M" denotes missense mutation.

In the present invention, the "cancer patient" may be not only a human affected by cancer but a human suspected of having cancer. In the method of the present invention, the cancer patient in which the presence or absence of functional suppression of CBP is to be detected is not particularly limited, and every cancer patient can be used as this subject. The cancer found to have functional suppression of CBP may be, for example, lung cancer, bladder cancer, lymphoma, or adenoid cystic cancer. A 10% subset of lung cancer, a 13% subset of bladder cancer, a 20 to 40% subset of lymphoma, and a 7% subset of adenoid cystic cancer are known to have CBP mutations. Therefore, according to the method of the present invention, a cancer patient having such a frequency can be selected as the "candidate for the treatment".

to, for example, a missense mutation in the histone acetyltransferase (HAT) domain (1342- to 1648-positions in the amino acid sequence represented by SEQ ID NO: 3) of CBP, a nonsense mutation over the whole region, or complete or partial deletion of the gene. The inactivating mutation is not limited thereto as long as the mutation causes inactivation of CBP. Examples of the CBP mutations are shown in Table 1 and FIG. 7. In Table 1, the abbreviations are as follows: SCC: small-cell carcinoma AdC: adenocarcinoma; SqC: squamous cell carcinoma; LCC: large cell carcinoma; NT: not tested; and ND: not detected. The mark * denotes aberrant size. The mark † denotes that the corresponding noncancerous tissue DNA is unavailable.

TABLE 1

| Sample | Histology | Exon (change) | Predicted in gene product change | Expression mRNA | Protein | p53 mutation |
|---|---|---|---|---|---|---|
| Cell line | | | | | | |
| H209 | SCC | 4-32 (Homozygous deletion) | Fusion | + | +* | IVS6-2 A/G |
| H1963† | SCC | 1-3 (Homozygous deletion) | Null | − | − | Val147Asp His214Arg |
| LK-2† | SqC | 3 (Homozygous deletion) | Trancation | + | +* | Val272Met |
| H2122 | AdC | 3 (A248C: Heterozygous) | Asn83Thr | + | + | Gln16Len Cys176Phe |
| H322† | AdC | 15 (C2678T: Heterozygous) | Ser893Leu | + | + | Arg248leu |
| H520† | SqC | 27 (C4336T: Heterozygous) | Arg1446Cys | + | + | Trp146stop |
| H1703† | SqC | 28 (G4416T: Heterozygous) 32 (A6524G: Heterozygous) | Trp1472Cys Asn2175Ser | + | + | IVS8 + 1G/T |
| H1184† | SCC | 32 (G5503T: Heterozygous) | Glu1835 stop | + | + | Asp259Val |
| Lu65† | LCC | 32 (A6332G: Heterozygous) | Asn2111Ser | + | + | Glu11Gln |
| Surgical specimen | | | | | | |
| Na98T | AdC | 3 (DG91 or 92: Heterozygous) | Trancation | + | NT | Gly271Lys |
| N501T | AdC | 8 (C1651A: Heterozygous) | Leu551Ile | NT | NT | His193Tyr |
| S31T | SCC | 26 (G4232A: Homozygous) | Gly1411Glu | NT | NT | ND |
| Na79T | SqC | 31 (C4926G: Heterozygous) | Silent | + | NT | ND |
| T10-28T | SqC | 32 (C6131G: Heterozygous) | Ala2044Gly | NT | NT | Tyr220Cys |

The "biological sample" used in the present invention is not particularly limited as long as the presence or absence of functional suppression of CBP can be detected in the biological sample. A cancer biopsy specimen is preferred. Protein extracts or nucleic acid extracts (mRNA extracts, cDNA or cRNA preparations prepared from the mRNA extracts, etc.) obtained from these samples may be used.

In the present invention, both "CBP" and "p300" are histone acetyltransferases that are involved in chromatin regulation. These enzymes are in a paralogous relationship. The typical nucleotide sequence of human-derived natural CBP genomic DNA is shown in SEQ ID NO: 1. The typical nucleotide sequence of human-derived natural CBP cDNA is shown in SEQ ID NO: 2. The typical amino acid sequence of human-derived natural CBP protein is shown in SEQ ID NO: 3. The typical nucleotide sequence of human-derived natural p300 genomic DNA is shown in SEQ ID NO: 4. The typical nucleotide sequence of human-derived natural p300 cDNA is shown in SEQ ID NO: 5. The typical amino acid sequence of human-derived natural p300 protein is shown in SEQ ID NO: 6. It should be understood that even CBP or p300 having no mutation may vary in sequence among individuals due to polymorphism, etc.

In the present invention, the "functional suppression of CBP" includes both of inactivation of CBP or reduction in CBP activity and reduction in CBP expression. The inactivation of CBP is typically attributed to an inactivating mutation in CBP. The inactivating mutation may occur due The reduction in CBP expression includes both of reduction in expression at the transcriptional level and reduction in expression at the translational level.

In the present invention, examples of the approach for "detecting functional suppression of CBP" include, but are not particularly limited to, methods described below.

—Detection of CBP Mutation—

In the present invention, the phrase "detecting a mutation" means to detect a mutation in genomic DNA as a rule and includes even to detect change in base in a transcription product or change in amino acid in a translation product (i.e., indirect detection) when the mutation in genomic DNA is reflected to such change in the transcription product or the translation product.

A preferred embodiment of the method of the present invention is a method for detecting a mutation by directly determining the nucleotide sequence of a CBP gene region in a cancer patient. In the present invention, the "CBP gene region" means a given region in the genomic DNA containing the CBP gene. This region also includes the expression control regions (e.g., a promoter region and an enhancer region) of the CBP gene, the 3'-untranslated region of the CBP gene, and the like. Mutations in these regions may influence, for example, the transcriptional activity of the CBP gene.

In this method, first, a DNA sample is prepared from a biological sample derived from a cancer patient. Examples of the DNA sample include a genomic DNA sample and a cDNA sample prepared from RNA by reverse transcription.

The method for extracting genomic DNA or RNA from the biological sample is not particularly limited and can be appropriately selected for use from approaches known in the art. Examples of the method for extracting the genomic DNA include SDS phenol method (method which involves denaturing proteins of a tissue preserved in a urea-containing solution or ethanol using a proteolytic enzyme (proteinase K), a surfactant (SDS), and phenol, and precipitating and extracting DNA from the tissue with ethanol), and DNA extraction method using Clean Columns® (manufactured by Hermes-NexTec GmbH), AquaPure® (manufactured by Bio-Rad Laboratories, Inc.), ZR Plant/Seed DNA Kit (manufactured by Zymo Research Corp.), AquaGenomic Solution® (manufactured by MoBiTec GmbH), prepGEM® (manufactured by ZyGEM NZ, Ltd.), or BuccalQuick® (manufactured by TrimGen Corp.). Examples of the method for extracting the RNA include extraction method using phenol and a chaotropic salt (more specifically, extraction method using a commercially available kit such as TRIzol (manufactured by Invitrogen Corp.) or IISOGEN® (manufactured by Wako Pure Chemical Industries, Ltd.)), and methods using other commercially available kits (RNAPrep total RNA extraction kit (manufactured by Beckman Coulter Inc.), RNeasy Mini (manufactured by Qiagen N.V.), RNA Extraction Kit (manufactured by Pharmacia Biotech Inc.), etc.). Examples of the reverse transcriptase for use in preparing cDNA from the extracted RNA include, but are not particularly limited to, reverse transcriptase derived from retrovirus such as RAV (Rous associated virus) or AMV (avian myeloblastosis virus), and reverse transcriptase derived from mouse retrovirus such as MMLV (Moloney murine leukemia virus).

In this embodiment, subsequently, DNA containing a mutation site in the CBP gene region is isolated, and the nucleotide sequence of the isolated DNA is determined. The isolation of the DNA can be carried out by, for example, PCR with the genomic DNA or the RNA as a template using a pair of oligonucleotide primers designed to flank the mutation site in the CBP gene region. The determination of the nucleotide sequence of the isolated DNA can be carried out by a method generally known to those skilled in the art, such as Maxam-Gilbert method or Sanger method.

The determined nucleotide sequence of the DNA or the cDNA can be compared with a control (e.g., the nucleotide sequence of DNA or cDNA derived from a noncancerous tissue of the same patient) to determine the presence or absence of a mutation in the CBP gene region in the cancer cells of the cancer patient.

The method for detecting a mutation in the CBP gene region can be carried out by various methods capable of detecting mutations, in addition to the method for directly determining the nucleotide sequence of DNA or cDNA.

The detection of a mutation according to the present invention can also be carried out by, for example, the following method: first, a DNA or cDNA sample is prepared from the biological sample. Subsequently, a reporter fluorescent dye- and quencher fluorescent dye-labeled oligonucleotide probe having a nucleotide sequence complementary to a nucleotide sequence containing the mutation in the CBP gene region is prepared. Then, the oligonucleotide probe is hybridized to the DNA sample, and the nucleotide sequence containing the mutation in the CBP gene region is further amplified with the DNA sample hybridized with the oligonucleotide probe as a template. The fluorescence emitted by the reporter fluorescent dye as a result of degradation of the oligonucleotide probe by the amplification is detected. Subsequently, the detected fluorescence is compared with the control. Examples of such a method include double dye probe method, so-called TaqMan® probe method.

In a further alternative method, a DNA or cDNA sample is prepared from the biological sample. Subsequently, a nucleotide sequence containing the mutation in the CBP gene region is amplified with the DNA sample as a template in a reaction system containing an intercalator that emits fluorescence when inserted to between DNA double strands. The temperature of the reaction system is changed, and variation in the intensity of fluorescence emitted by the intercalator is detected. The detected variation in the fluorescence intensity caused by the change in the temperature is compared with the control. Examples of such a method include HRM (high resolution melting) method.

In a further alternative method, first, a DNA or cDNA sample is prepared from the biological sample. Subsequently, DNA containing the mutation site in the CBP gene region is amplified. Further, the amplified DNA is cleaved with restriction enzymes. Subsequently, the DNA fragment is separated according to its size. Subsequently, the detected size of the DNA fragment is compared with the control. Examples of such a method include a method based on restriction fragment length polymorphism (RFLP) and PCR-RFLP.

In a further alternative method, first, a DNA or cDNA sample is prepared from the biological sample. Subsequently, DNA containing the mutation site in the CBP gene region is amplified. Further, the amplified DNA is dissociated into single-stranded DNA. Subsequently, the single-stranded DNA thus obtained by dissociation is separated on a non-denaturing gel. The mobility of the separated single-stranded DNA on the gel is compared with the control. Examples of such a method include PCR-SSCP (single-strand conformation polymorphism).

In a further alternative method, first, a DNA or cDNA sample is prepared from the biological sample. Subsequently, DNA containing the mutation site in the CBP gene region is amplified. Further, the amplified DNA is separated on a gel in which the concentration of a DNA denaturant is gradually elevated. Subsequently, the mobility of the separated DNA on the gel is compared with the control. Examples of such a method include denaturant gradient gel electrophoresis (DGGE).

A further alternative method is a method using DNA containing the mutation site in the CBP gene region prepared from the biological sample, and a substrate with an immobilized oligonucleotide probe hybridizing to the DNA. Examples of such a method include DNA array method.

In a further alternative method, first, a DNA or cDNA sample is prepared from the biological sample. Also, an "oligonucleotide primer having a nucleotide sequence complementary to a base immediately 3' to the base of the mutation site in the CBP gene region and a 3'-nucleotide sequence thereof" is prepared. Subsequently, ddNTP primer extension reaction is performed with the DNA as a template using the primer. Subsequently, the primer extension reaction product is subjected to mass spectrometry in a mass spectrometer. Subsequently, the genotype is determined from the results of mass spectrometry. Subsequently, the determined genotype is compared with the control. Examples of such a method include MALDI-TOF/MS.

In a further alternative method, first, a DNA or cDNA sample is prepared from the biological sample. Subsequently, an oligonucleotide probe consisting of 5'-"a nucleotide sequence complementary to the base of the mutation site in the CBP gene region and a 5'-nucleotide sequence thereof"-"a nucleotide sequence that does not hybridize to a base immediately 3' to the mutation site in the CBP gene region and a 3'-nucleotide sequence thereof"-3' (flap) is prepared. Also, an "oligonucleotide probe having a nucleotide sequence complementary to the base of the mutation site in the CBP gene region and a 3'-nucleotide sequence thereof" is prepared. Subsequently, these two types of oligonucleotide probes are hybridized to the prepared DNA. Subsequently, the hybridized DNA is cleaved with a single-stranded DNA-cleaving enzyme to liberate the flap. Examples of the single-stranded DNA-cleaving enzyme include, but are not particularly limited to, cleavase. In this method, a fluorescence reporter- and fluorescence quencher-labeled oligonucleotide probe having a sequence complementary to the flap is then hybridized to the flap. Subsequently, the intensity of the generated fluorescence is measured. Subsequently, the measured fluorescence intensity is compared with the control. Examples of such a method include Invader method.

In a further alternative method, first, a DNA or cDNA sample is prepared from the biological sample. Subsequently, DNA containing the mutation site in the CBP gene region is amplified. The amplified DNA is dissociated into single-stranded DNA. Only one of the single DNA strands thus obtained by dissociation is separated. Subsequently, extension reaction is performed by one base at a time from near the base of the mutation site in the CBP gene region. Pyrophosphate generated during this reaction is enzymatically allowed to emit light, and the intensity of the luminescence is measured. Then, the measured fluorescence intensity is compared with the control. Examples of such a method include pyrosequencing method.

In a further alternative method, first, a DNA or cDNA sample is prepared from the biological sample. Subsequently, DNA containing the mutation site in the CBP gene region is amplified. Subsequently, an "oligonucleotide primer having a nucleotide sequence complementary to a base immediately 3' to the base of the mutation site in the CBP gene region and a 3'-nucleotide sequence thereof" is prepared. Subsequently, single-nucleotide extension reaction is performed with the amplified DNA as a template using the prepared primer in the presence of a fluorescently labeled nucleotide. The degree of polarization of fluorescence is measured. Subsequently, the measured degree of polarization of fluorescence is compared with the control. Examples of such a method include AcycloPrime method.

In a further alternative method, first, a DNA or cDNA sample is prepared from the biological sample. Subsequently, DNA containing the mutation site in the CBP gene region is amplified. Subsequently, an "oligonucleotide primer having a nucleotide sequence complementary to a base immediately 3' to the base of the mutation site in the CBP gene region and a 3'-nucleotide sequence thereof" is prepared. Subsequently, single-nucleotide extension reaction is performed with the amplified DNA as a template using the prepared primer in the presence of a fluorescently labeled nucleotide. Subsequently, the base species used in the single-nucleotide extension reaction is determined. Subsequently, the determined base species is compared with the control. Examples of such a method include SNuPE method.

Provided that the mutation involves change (e.g., substitution, deletion, or insertion) in amino acid in the CBP protein, the sample prepared from the biological sample may be the protein. In such a case, for example, a method using a molecule (e.g., an antibody) specifically binding to a site having change in amino acid caused by the mutation can be utilized for detecting the mutation. The method for detecting the protein using an antibody will be described later.

—Detection of Reduction in CBP Expression—

In the present invention, the "reduction in CBP expression" usually means a lower expression level as compared with a control (e.g., an expression level in the noncancerous tissue of a healthy person or the same patient).

In the method for detecting the CBP expression level at the transcriptional level, first, RNA or cDNA is prepared by the method described above from a biological sample derived from a cancer patient. Subsequently, an oligonucleotide primer and an oligonucleotide probe are used in amplification reaction and hybridization reaction, respectively, to detect the amplification product or the hybridization product. For example, RT-PCR, Northern blotting, dot blotting, DNA array method, in situ hybridization, RNase protection assay, or mRNA-seq can be used as such a method. Those skilled in the art can design an oligonucleotide primer or an oligonucleotide probe suitable for each method by a routine method on the basis of the nucleotide sequence (e.g., SEQ ID NO: 2) of CBP cDNA.

In the method for detecting the CBP expression level at the translational level, first, a protein sample is prepared from a biological sample derived from a cancer patient. Subsequently, an antibody specific for the CBP protein is used in antigen-antibody reaction to detect the binding of the antibody to the CBP protein. When the antibody specific for CBP is labeled, the CBP protein can be detected directly. When this antibody is not labeled, a labeled molecule (e.g., secondary antibody or protein A) that recognizes this antibody is further allowed to act on the antigen-antibody complex, and the CBP protein can be detected indirectly through the use of the label of the molecule. For example, immunohistochemical (immunostaining) method, Western blotting, ELISA, flow cytometry, imaging cytometry, radioimmunoassay, immunoprecipitation, or analysis method using an antibody array can be used as such a method. The immunohistochemistry also has the advantage that additional information such as the morphology or distributed state of cancer cells in a tissue can be obtained at the same time.

The antibody used is not particularly limited by its type, origin, etc., and is preferably a monoclonal antibody. An oligoclonal antibody (a mixture of several to several tens of antibodies) or a polyclonal antibody can also be used as long as CBP can be detected with sufficient specificity. Alternatively, a functional antibody fragment such as Fab, Fab', F(ab')2, Fv, scFv, sc(Fv)2, dsFv, or diabody, or a multimer thereof (e.g., a dimer, a trimer, a tetramer, or a polymer) can also be used. The anti-CBP antibody may be a commercially available product.

The detection of the CBP protein can also be carried out by use of mass spectrometry (MS). Particularly, liquid chromatography coupled to mass spectrometer (LC/MS) analysis is sensitive and is therefore advantageous. The mass spectrometry measurement can be carried out, for example, by preparing proteins from the biological sample, labeling the proteins, fractionating the proteins, subjecting the protein fractions to mass spectrometry, and identifying the CBP protein from the mass spectrometry value. An isotope labeling reagent known in the art can be used as the label, and an appropriate labeling reagent can be obtained as a commercially available product. Also, the fractionation can be carried out by a method known in the art and can be carried out using, for example, a commercially available strong cation column.

—Others—

It is known in the art that promoter hypermethylation is partly responsible for reduction in gene expression. Thus, the presence or absence of functional suppression of CBP can be possibly detected with CBP gene promoter methylation as an index. The promoter methylation can be detected by use of a method known in the art, for example, a method which involves directly detecting, by sequencing, change in nucleotide sequence treated with bisulfite having the activity of converting methylated cytosine to uracil, or an indirect detection method using a restriction endonuclease that can recognize (or cleave) a nucleotide sequence before bisulfite treatment but cannot recognize (or cleave) a nucleotide sequence treated with bisulfite.

In this way, when the functional suppression of CBP, for example, loss-of-function inactivating mutation in CBP, has been detected, when the reduction in CBP expression has been detected, or when any of other phenomena that cause inactivation of CBP or reduction in CBP expression (e.g., promoter hypermethylation) has been detected, the patient can be determined as responsive to the treatment of cancer with the compound inhibiting p300 and can be selected as the candidate for the treatment of cancer with the compound inhibiting p300. In this context, the "responsiveness to the treatment of cancer" is an index for deciding whether or not the compound inhibiting p300 can exert therapeutic effects on cancer. The determination of the responsiveness may include not only the determination of the presence or absence of the responsiveness but the evaluation of the degree of the found responsiveness (e.g., evaluation concluding that high responsiveness can be expected or moderate responsiveness can be expected). Thus, according to the degree of functional suppression of CBP, for example, a patient may be selected as a treatment candidate at a level where moderate responsiveness can be expected.

On the other hand, when no functional suppression of CBP has been found, the patient can be excluded from the candidate for the treatment of cancer with the compound inhibiting p300. This can improve the response rate of the treatment.

When p300, which is a target of this treatment, is not normally expressed, there is the risk that the treatment of cancer with the compound inhibiting p300 cannot be effectively carried out. Thus, the normal expression of p300 can also be used as an additional index in the prediction of responsiveness to the treatment of cancer or the selection of a cancer patient. The approach for detecting the expression of p300 is the same as in the detection of CBP expression described above.

<Method for Treating Cancer>

The present invention also provides a method for treating cancer having functional suppression of CBP, comprising using a biological sample derived from a cancer patient, detecting the presence or absence of functional suppression of CBP contained in the biological sample, and administering a compound inhibiting p300 to the patient with the detected functional suppression of CBP.

The "compound inhibiting p300" for use in this treatment is not particularly limited and may be a compound known in the art or may be a compound that is identified by screening mentioned later.

The compound inhibiting p300 can be administered orally or parenterally (e.g., intravenously, intraarterially, or locally) to the cancer patient in various forms such as tablets, powders, granules, capsules, or solutions according to its characteristics. The dose is not particularly limited as long as the amount is effective for treating cancer by inhibiting p300. The dose can be appropriately selected according to the properties of the compound as well as the age, body weight, symptoms, and health conditions of the cancer patient, the severity of the cancer, etc. The frequency of administration is not particularly limited and can be appropriately selected according to a purpose. For example, a daily dose may be administered once a day or may be administered in several portions. In the case of administering the compound inhibiting p300 to a human, the dose ranges from approximately 0.01 mg/kg body weight to approximately 500 mg/kg body weight, preferably from approximately 0.1 mg/kg body weight to approximately 100 mg/kg body weight, per day. In the case of the compound inhibiting p300 to a human, preferably, this compound is administered in one portion or in two to four portions per day, and this administration is preferably repeated at appropriate intervals. Alternatively, the daily dose may exceed the amount described above, if necessary, at a physician's discretion.

This can further inhibit p300 in cancer cells having functional suppression of CBP in the cancer patient and can treat the cancer by the effect of synthetic lethality.

Examples of the cancer targeted by the treatment include, but are not limited to, lung cancer, bladder cancer, lymphoma, and adenoid cystic cancer.

<Reagent for Detecting Presence or Absence of Functional Suppression of CBP>

The present invention also provides a reagent for detecting the presence or absence of functional suppression of CBP in any of the methods described above, the reagent comprising any of the following molecules (a) to (c) as an active ingredient:

(a) an oligonucleotide primer specifically binding to the CBP gene,
(b) an oligonucleotide probe specifically binding to the CBP gene, and
(c) an antibody specifically binding to the CBP protein.

The polynucleotide primer can be designed on the basis of nucleotide sequence information (e.g., SEQ ID NO: 1 or 2) on the CBP genomic DNA or cDNA such that the primer is suitable for the approach described above or the region to be amplified and such that the formation of an amplification product of a gene other than the CBP gene is prevented as much as possible. Those skilled in the art can carry out such oligonucleotide primer design by a routine method. The length of the oligonucleotide primer is usually 15 to 50 bases long, preferably 15 to 30 bases long, and may be longer than these lengths according to an approach and a purpose.

The polynucleotide probe described above can be designed on the basis of nucleotide sequence information (e.g., SEQ ID NO: 1 or 2) on the CBP genomic DNA or cDNA such that the primer is suitable for the approach described above or the region to be hybridized and such that hybridization to a gene other than the CBP gene is prevented as much as possible. Those skilled in the art can carry out such oligonucleotide probe design by a routine method. The length of the oligonucleotide probe is usually 15 to 200 bases long, preferably 15 to 100 bases long, more preferably 15 to 50 bases long, and may be longer than these lengths according to an approach and a purpose.

Preferably, the oligonucleotide probe is appropriately labeled for use. Examples of the labeling method can include a method which involves labeling the 5' end of the oligonucleotide by phosphorylation with $^{32}P$ using T4 polynucleotide kinase, and a method which involves incorporating a substrate base labeled with an isotope (e.g., $^{32}P$), a fluorescent dye, or biotin into the oligonucleotide using a DNA polymerase such as Klenow enzyme and a primer such as a random hexamer oligonucleotide (random prime method, etc.).

The oligonucleotide primer and the oligonucleotide probe of the present invention can be prepared using, for example, a commercially available oligonucleotide synthesizer. The oligonucleotide probe can also be prepared as a double-stranded DNA fragment obtained by restriction enzyme treatment or the like. The oligonucleotide primer and the oligonucleotide probe of the present invention do not have to be consist of natural nucleotides (deoxyribonucleotide (DNA) and/or ribonucleotide (RNA)) and may be composed partially or wholly of non-natural nucleotides. Examples of the non-natural nucleotides include PNA (polyamide nucleic acid), LNA® (locked nucleic acid), ENA® (2'-O,4'-C-ethylene-bridged nucleic acid), and complexes thereof.

The polyclonal antibody serving as the antibody specifically binding to the CBP protein described above can be obtained by immunizing an immunization animal with an antigen (e.g., the CBP protein, a partial peptide thereof, or cells expressing the protein or the partial peptide) and purifying the polyclonal antibody from the antisera of the animal by a conventional approach (e.g., salting-out, centrifugation, dialysis, or column chromatography). The monoclonal antibody serving as this antibody can be prepared by hybridoma method or recombinant DNA method.

Typical examples of the hybridoma method include the method of Kohler and Milstein (Kohler & Milstein, Nature 1975; 256: 495). In this method, antibody-producing cells for use in a cell fusion step are spleen cells, lymph node cells, peripheral leukocytes, or the like of the animal (e.g., mouse, rat, hamster, rabbit, monkey, or goat) immunized with an antigen (e.g., the CBP protein, a partial peptide thereof, or cells expressing the protein or the partial peptide). Antibody-producing cells obtained by the action of the antigen in a medium on these cells or lymphocytes or the like described above isolated in advance from an unimmunized animal may also be used. Various cell lines known in the art can be used as myeloma cells. The antibody-producing cells and the myeloma cells may be derived from different animal species as long as these cells can be fused. Preferably, the antibody-producing cells and the myeloma cells are derived from the same animal species. The hybridomas are produced by, for example, the cells fusion between spleen cells obtained from a mouse immunized with the antigen and mouse myeloma cells and can be obtained by subsequent screening for hybridomas producing the monoclonal antibody specific for the CBP protein. The monoclonal antibody against the CBP protein can be obtained by the culture of the hybridomas or from the ascitic fluid of a mammal that has received the hybridomas.

The recombinant DNA method is an approach which involves cloning DNA encoding the antibody from the hybridomas, B cells, or the like, incorporating this DNA into an appropriate vector, and transferring this vector to host cells (e.g., a mammalian cell line, E. coli, yeast cells, insect cells, or plant cells), followed by the production of the antibody of the present invention as a recombinant antibody (e.g., P. J. Delves, Antibody Production: Essential Techniques, 1997 WILEY, P. Shepherd and C. Dean Monoclonal Antibodies, 2000 OXFORD UNIVERSITY PRESS, and Vandamme A M, et al., Eur. J. Biochem. 1990; 192: 767-775). For the expression of the DNA encoding the antibody, DNA encoding the heavy chain and DNA encoding the light chain may be incorporated into separate expression vectors, which can then be used in the transformation of host cells, or DNA encoding the heavy chain and DNA encoding the light chain may be incorporated into a single expression vector, which can then be used in the transformation of host cells (see WO94/11523). The antibody can be obtained in a substantially pure and homogenous form by culturing the host cells and separating and/or purifying the antibody from the inside or the culture solution of the host cells. The separation and/or purification of the antibody can employ a method for use in usual polypeptide purification. If a transgenic animal (e.g., cattle, goat, sheep, or pig) harboring the antibody gene is prepared by use of a transgenic animal preparation technique, the monoclonal antibody derived from the antibody gene may be obtained in large amounts from the milk of the transgenic animal.

On the basis of the antibody thus obtained or the gene thereof, a functional antibody fragment such as Fab, Fab', F(ab')2, Fv, scFv, sc(Fv)2, dsFv, or diabody, or a multimer thereof (e.g., a dimer, a trimer, a tetramer, or a polymer) can be prepared.

In the case of directly detecting the amount of the antibody bound with the CBP protein, the obtained anti-CBP antibody is used either directly or after being labeled with, for example, an enzyme, a radioisotope, a fluorescent dye, or an avidin-biotin system. On the other hand, in the case of carrying out an indirect detection method for detecting the amount of the antibody bound with the CBP protein using a secondary antibody or the like, the obtained anti-CBP antibody (primary antibody) does not have to be labeled. For this detection, a labeled molecule (e.g., secondary antibody or protein A) that recognizes the antibody can be used.

The reagent of the present invention can optionally contain additional components acceptable for reagents, such as sterilized water, saline, a buffer, and a preservative, according to the need, in addition to the molecule described above as an active ingredient.

<Method for Screening for Compound for Use in Treatment of Cancer>

The present invention also provides a method for screening for a compound for use in the treatment of cancer having functional suppression of CBP, the method comprising the step of selecting the compound by using whether or not to inhibit p300 as an index.

Examples of the test compound that is applied to the screening system of the present invention include, but are not particularly limited to, synthetic low-molecular compound libraries, expression products of gene libraries, peptide libraries, siRNA, antibodies, substances released by bacteria, extracts and culture supernatants of cells (microbes, plant cells, or animal cells), purified or partially purified polypeptides, marine organism-, plant-, or animal-derived extracts, and random phage peptide display libraries. The test compound may be a derivative of a p300 inhibitor (e.g., a C646 derivative) known in the art.

In the present invention, the "inhibition of p300" includes both of inhibition of p300 activity and inhibition of p300 expression. Since the loss of the histone acetyltransferase activity of p300 is considered to contribute to the synthetic lethality of CBP and p300, the inhibition of p300 used as an index of screening is preferably inhibition of the histone acetyltransferase activity of p300. For example, a detection method using a radioisotope (Lau O D, et al., J. Biol. Chem. 2000; 275: 21953-21959), a method which involves fluorescently detecting CoA-SH generated as by-products during histone acetyltransferase reaction (Gao T, et al., Methods Mol Biol. 2013; 981: 229-38), and a detection method using NADH (Berndsen C E, Denu J M. Methods. 2005; 36: 321-331) can be used for detecting the histone acetyltransferase activity.

In the screening, the test compound can be allowed to act on this detection system, followed by the detection of histone acetyltransferase activity. As a result of the detection, when the activity is decreased as compared with the histone acetyltransferase activity of p300 in a control (e.g., without the addition of the test compound), the activity of p300 can be evaluated as being inhibited.

As CBP and p300 are in a paralogous relationship, the compound obtained by screening is preferably more specific for p300 from the viewpoint of reduction in adverse reactions, etc. Whether or not to be specific for p300 can be evaluated by, for example, a binding experiment or an activity inhibition experiment on each molecule. Thus, the screening of the present invention may comprise the step of selecting the compound by using whether or not to be more specific for p300 as an index.

In the case of detecting the inhibition of p300 expression, for example, the test compound can be allowed to act on cells expressing p300, followed by the detection of the p300 expression at the transcriptional level or translational level by the method described above. Alternatively, a reporter assay system based on an expression construct containing a reporter gene linked downstream of a p300 promoter may be used. As a result of the detection, when the expression is decreased as compared with the expression of p300 (or the expression of the reporter as a substitute therefor in the reporter system) in a control (e.g., without the addition of the test compound), the expression of p300 can be evaluated as being inhibited.

The compound identified by the screening of the present invention can be mixed with a pharmacologically acceptable carrier and formulated by a pharmaceutical method known in the art to prepare a pharmaceutical product. Examples of the pharmacologically acceptable carrier include, but are not limited to, sterilized water, saline, plant oils, solvents, bases, emulsifiers, suspending agents, surfactants, stabilizers, flavoring agents, fragrances, excipients, vehicles, antiseptics, binders, diluents, tonicity agents, soothing agents, expanders, disintegrants, buffers, coating agents, lubricants, colorants, sweeteners, thickeners, corrigents, solubilizers, and other additives.

EXAMPLES

Hereinafter, the present invention will be described further specifically with reference to Examples. However, the present invention is not intended to be limited by these Examples.

[Example 1] Development of Therapeutic Strategy Based on Synthetic Lethality of Cancer Having CBP Mutation 1. Material and Method
(1) Cell Line
A549, H1299, H157, SQ5, H1703, LK2, H520 (NSCLC), RL, Loucy, RC-K8, U2932, Ramos, Farage, SUP-T1, WSU-NHL, VAL, SUDHL5, Jurkat, TE8, and TE10 were separately cultured in RPMI-1640 or DMEM supplemented with 10% fetal bovine serum (FBS). MRC-5 cells (normal fibroblasts), HEK293T cells (immortalized renal epithelial cells), and RPE-1 cells (immortalized retinal epithelial cells) were separately cultured in DMEM supplemented with 10% FBS.
(2) Short Interfering RNA (siRNA)
ON-TARGET plus SMARTpool siRNA (GE Healthcare Dharmacon Inc.) was used in knockdown of various proteins. Lipofectamine RNAiMAX (Invitrogen Corp.) was used in transfection. Non-targeting siRNA (L-001810-10) was used as a negative control.
(3) Immunoblot Analysis
Immunoblotting was performed as described in the literature (Ogiwara H, et al., Oncogene 2011; 5; 30: 2135-46) using antibodies specific for the following proteins: CBP (Santa Cruz Biotechnology, Inc.; sc-369X), p300 (Santa Cruz Biotechnology, Inc.; sc-48343X), H3 (Active Motif; 39163), H3K18ac (Millipore Corp.; 07-354), β-actin (Cell Signaling Technology, Inc.; 4970), cleaved PARP (Cell Signaling Technology, Inc.; 5625), p21/CDKN1A (Cell Signaling Technology, Inc.; 2947), and LC3B (Cell Signaling Technology, Inc.; 3868).
(4) Cell Survival Assay
The effect of siRNA knockdown on the survival of cancer cells was evaluated using clonogenic survival assay. Each cancer cell line was transfected with siRNA (50 nM) using Lipofectamine RNAiMAX (Invitrogen Corp.). Two days later, the cells were trypsinized, counted, reseeded in specified numbers in 6-well culture dishes, and further cultured for 12 days (or for 14 days for knockdown of various HATs) to allow colony formation. The cells were then fixed for 5 minutes in a solution containing 50% (v/v) methanol/0.01% (w/v) Crystal Violet, and the number of colonies was counted.

The viability was determined by examining intracellular ATP level using CellTiter-Glo Luminescent Cell Viability Assay kit (Promega Corp.). Each cancer cell line was transfected with siRNA (50 nM) using Lipofectamine RNAiMAX (Invitrogen Corp.). Two days later, the cells were trypsinized, counted, and reseeded in specified numbers in 96-well plate. In order to measure the cell viability, CellTiter-Glo Luminescent Cell Viability Assay kit (Promega Corp.) was added to the cells, and fluorescence was measured using Envision (PerkinElmer, Inc.).
(5) Cell-Cycle Analysis
Cells were trypsinized, centrifuged, washed with PBS, and fixed in 70% ice-cold ethanol. The cells were then centrifuged again and incubated in PBS containing 200 µg/ml RNase A and 5 µg/ml propidium iodide. The cell-cycle distribution was analyzed by Guava flow cytometry (Millipore Corp.).
(6) Apoptosis Analysis by Annexin V/PI Staining
In order to detect apoptotic cells by flow cytometry, Annexin V-FITC/PI apoptosis detection kit (F. Hoffmann-La Roche, Ltd.) was used according to the manufacturer's instruction manual. Briefly, the cell pellet was suspended in a 1× binding buffer and incubated with Annexin V-FITC and PI for 20 minutes in the dark. Subsequently, the fluorescence of the cells was analyzed by flow cytometry.
(7) Production of shRNA Lentivirus
In order to prepare tet-inducible cell lines, each cell line was transduced with shRNA-expressing lentivirus vector-derived pTRIPZ (Open Biosystems). 293T cells were cotransfected with shRNA-encoding plasmids and packaging plasmids using Trans-Lentiviral™ Packaging System (Open Biosystems). On the next day, the medium was replaced with a fresh growth medium, and the supernatant containing the lentivirus was recovered and concentrated by centrifugation.
(8) In Vivo Analysis
The numbers of tet-inducible cell lines LK2-shp300 cells and LK2-shNT cells ($2 \times 10^6$ cells/mouse in 50% Matrigel; BD Biosciences) were counted, and the cells of each line were re-suspended in a 1:1 mixture of a medium and Matrigel (BD Biosciences) on ice. The cells were subcutaneously injected into the flanks of 7-week-old female BALB/c-nu/nu mice (CLEA Japan, Inc.) using a protocol approved by the Ethical Committee on Animal Experiments at the National Cancer Center. Three weeks later when tumor size reached 200 mm$^3$ or larger, the mice were randomly divided into 2 groups and fed with either a diet containing doxycycline (200 ppm) or a control diet. Tumor growth was measured twice a week using a caliper. The volume of the transplanted tumor was calculated every 3 to 4 days using a caliper according to the following formula: $V=L \times W^2/2$ wherein V represents volume (mm$^3$), L represents the largest diameter (mm), and W represents the smallest diameter (mm). At the end of the experiment, the mice were sacrificed according to standard protocols.

(9) Statistical Analysis

All experiments were performed in triplicate. Data are shown as the mean±SD. The differences between drug-treated cells and untreated cells were evaluated using Student's t-test. Statistically significant differences are indicated by asterisks ("*", $P<0.05$; "", $P<0.01$; "*", $P<0.001$; "****", $P<0.0001$).

2. Results (1) p300-Dependent Growth of CBP-Mutated Cancer Cells

Figure 1:
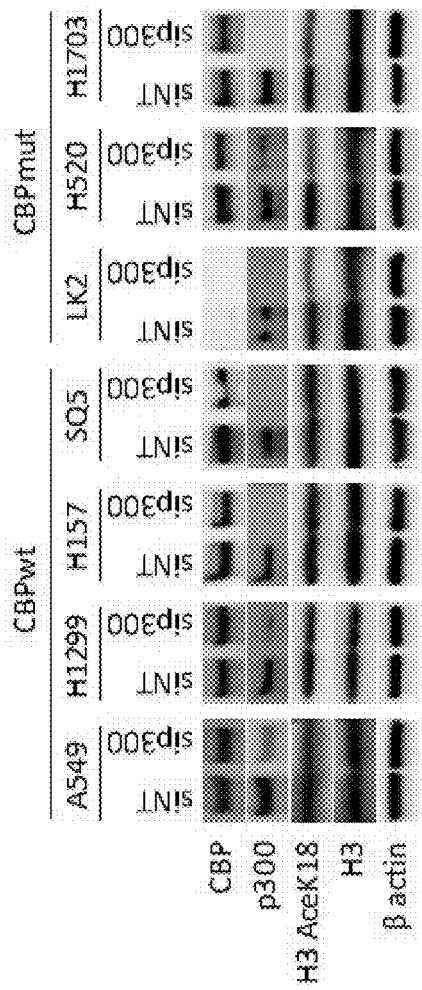
FIG. 1 is a diagram showing the effect of suppression of p300 expression on cancer cell lines having CBP mutations.
Figure 1:
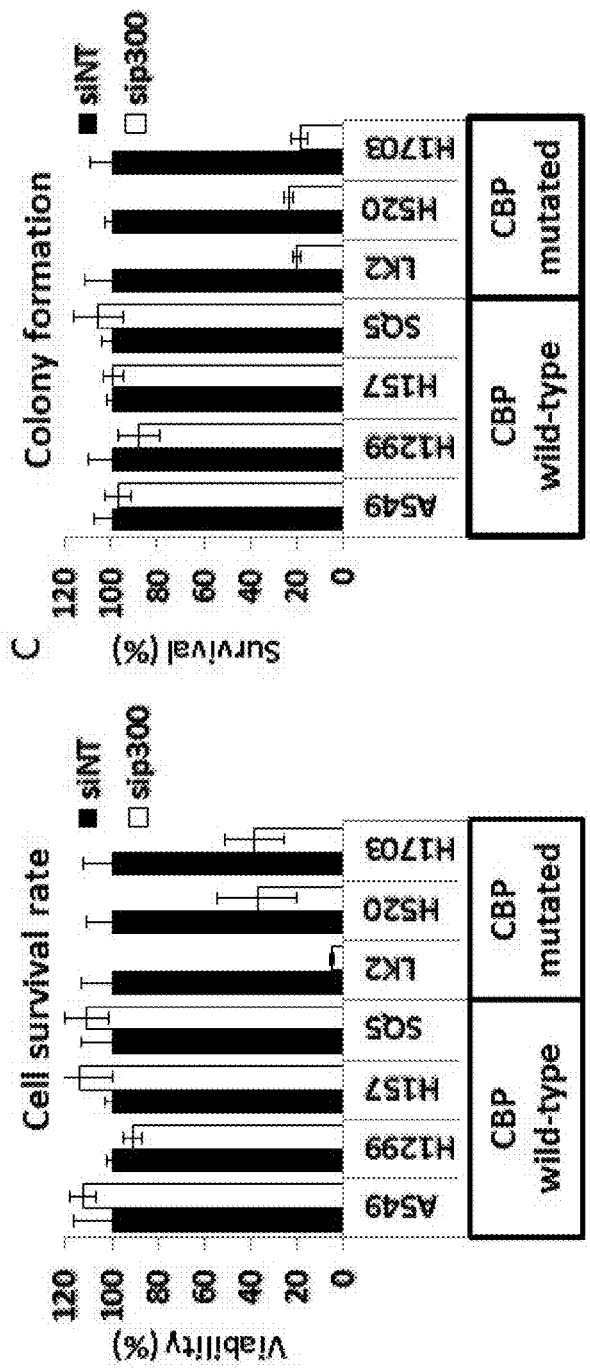
Figure 2:
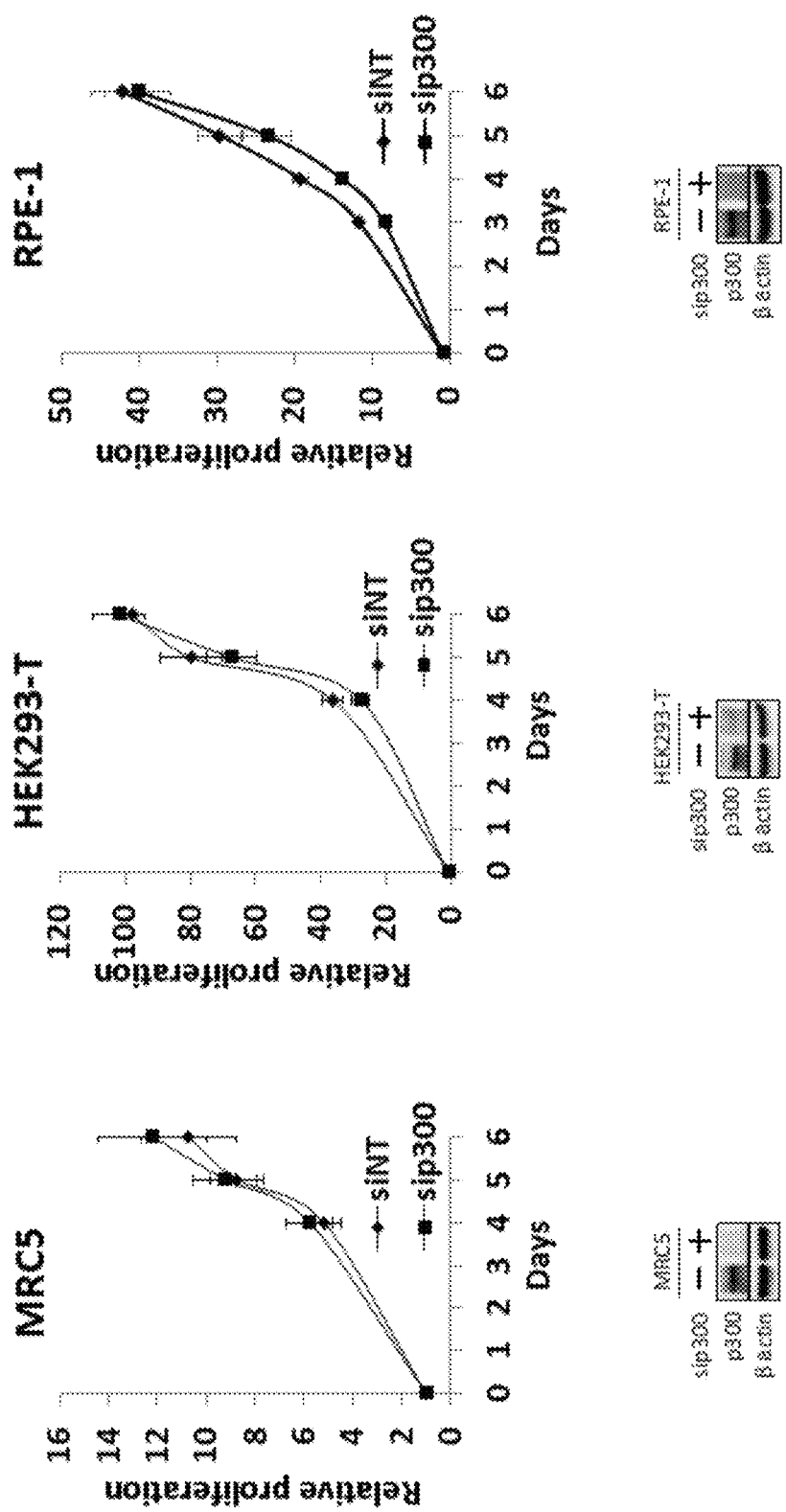
FIG. 2 is a diagram showing the effect of suppression of p300 expression on normal cell lines. The upper graphs show results of detecting the cell growth of each normal cell line. The lower photographs show siRNA-mediated depletion of p300 in each normal cell line.

We compared the effect of siRNA-mediated p300 depletion on growth of CBP-proficient and CBP-mutated cancer cell lines, using a cell growth assay and clonogenic survival assay (FIGS. 1A to 1C). As a result, suppression of cell growth and colony formation in all CBP-mutated cells tested, but not in CBP proficient cell lines.

p300 knockdown did not affect the growth of the non-cancerous fibroblast line MRC5, the immortalized renal epithelial cell line HEK293T, and the immortalized retinal epithelial cells RPE-1 expressing CBP and p300 (FIG. 2).

These results suggested that CBP-mutated cancer cells depend on p300 for growth.

(2) Sensitivity of CBP-Mutated Lung Cancer and Lymphoma to p300 Inhibitor C646

Figure 3:
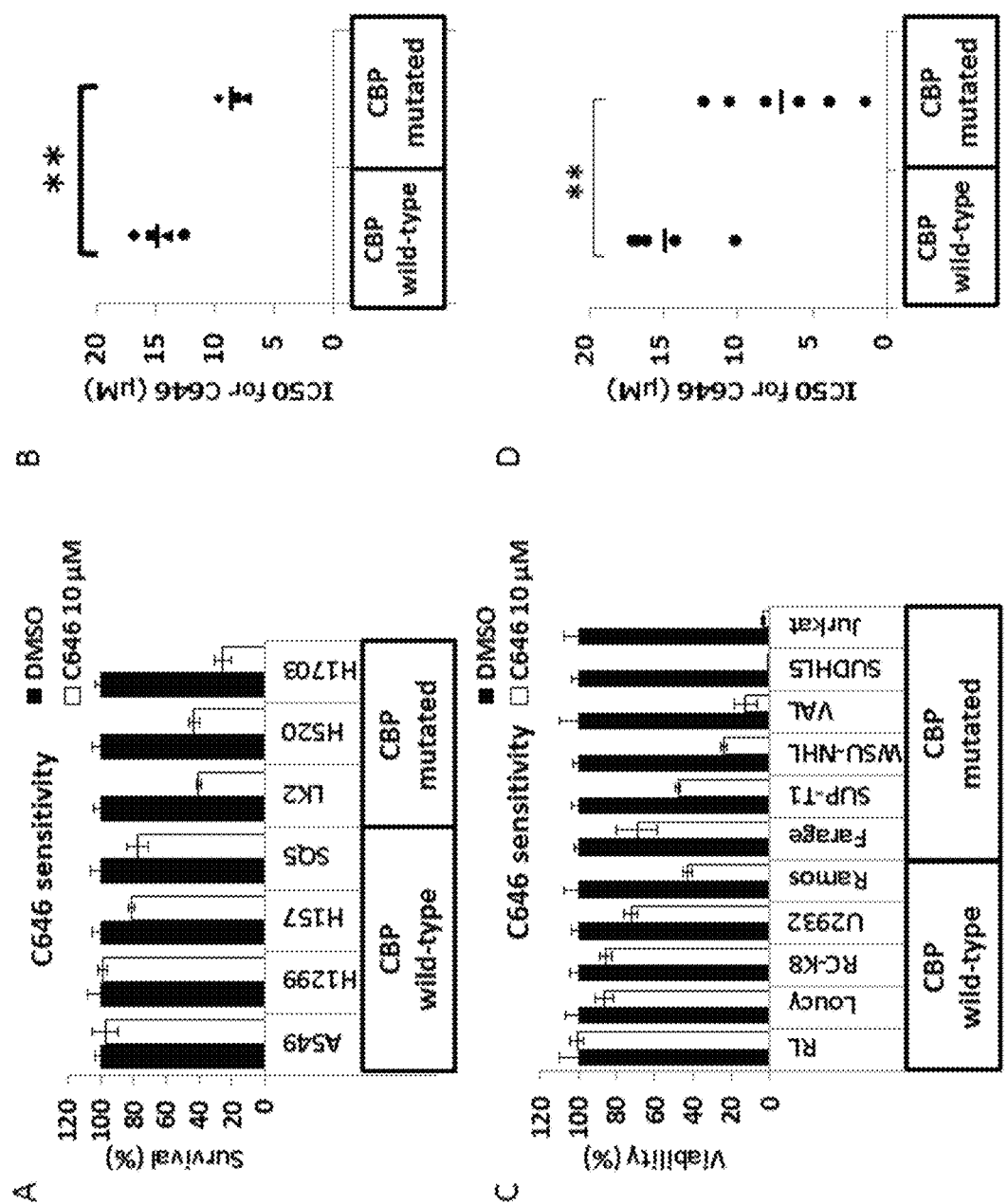
FIG. 3 is a diagram showing the sensitivity of cancer cell lines having CBP mutations to a p300 inhibitor C646.

We next examined the influence of a p300 inhibitor C646 on CBP-mutated lung cancer cells and lymphoma cells. As a result, higher sensitivity of the CBP-mutated cancer cells to C646 than that of the CBP-proficient cancer cells was observed (FIGS. 3A and 3C). The IC$_{50}$ value for C646 in CBP-mutated cancer cells has a low tendency relative to CBP-proficient cancer cells (Student's t test, $p<0.01$) (FIGS. 3B and 3D). These results suggested that inhibition of the histone acetyltransferase activity of p300 specifically causes a lethal effect on CBP-mutated cancer cells.

(3) Induction of Apoptosis by p300 Depletion in CBP-Mutated Cancer Cell

Figure 4:
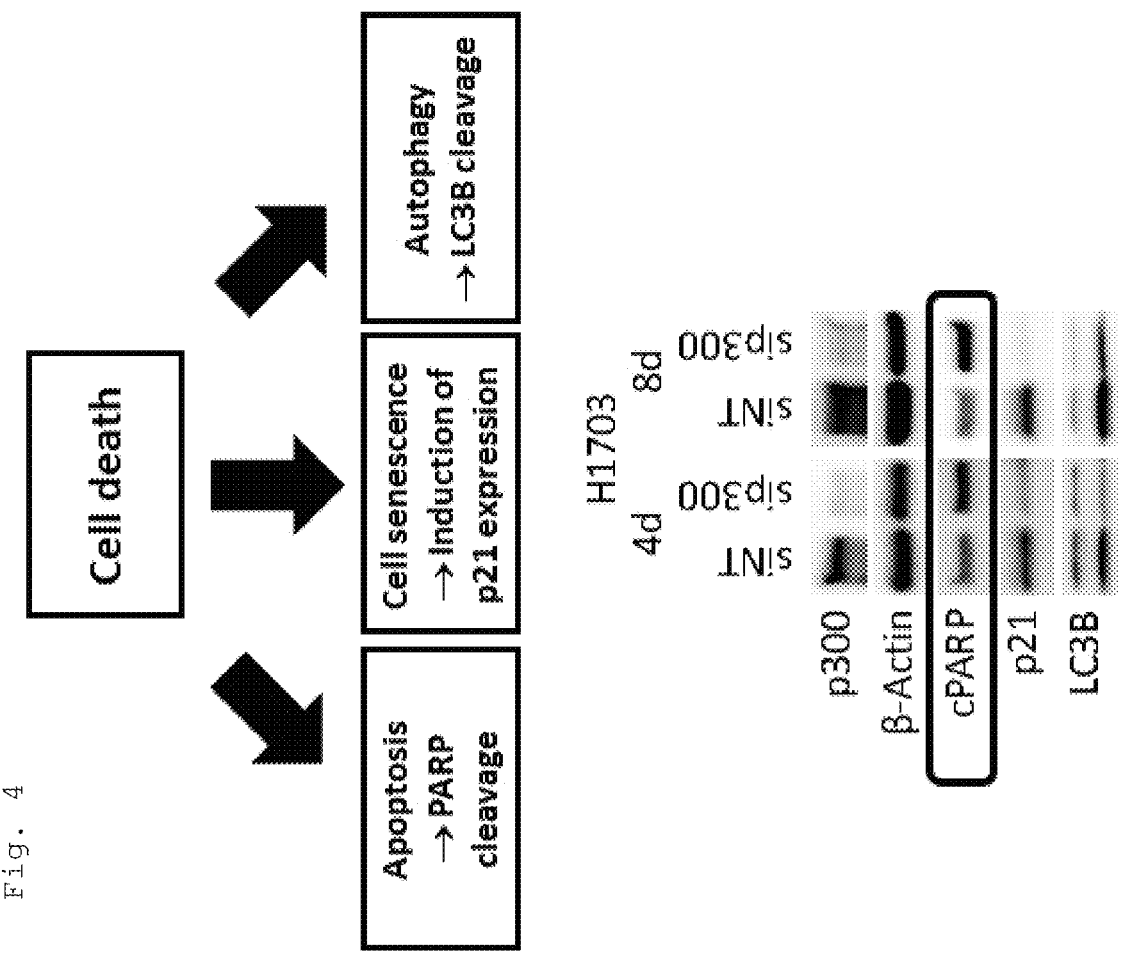
FIG. 4 is a diagram showing the mechanism underlying the cell death of cancer cell lines having CBP mutations by suppression of p300 expression. The upper diagram shows the general relationship of cell death with apoptosis, cell senescence, and autophagy. The lower photograph shows the change in various markers.
Figure 5:
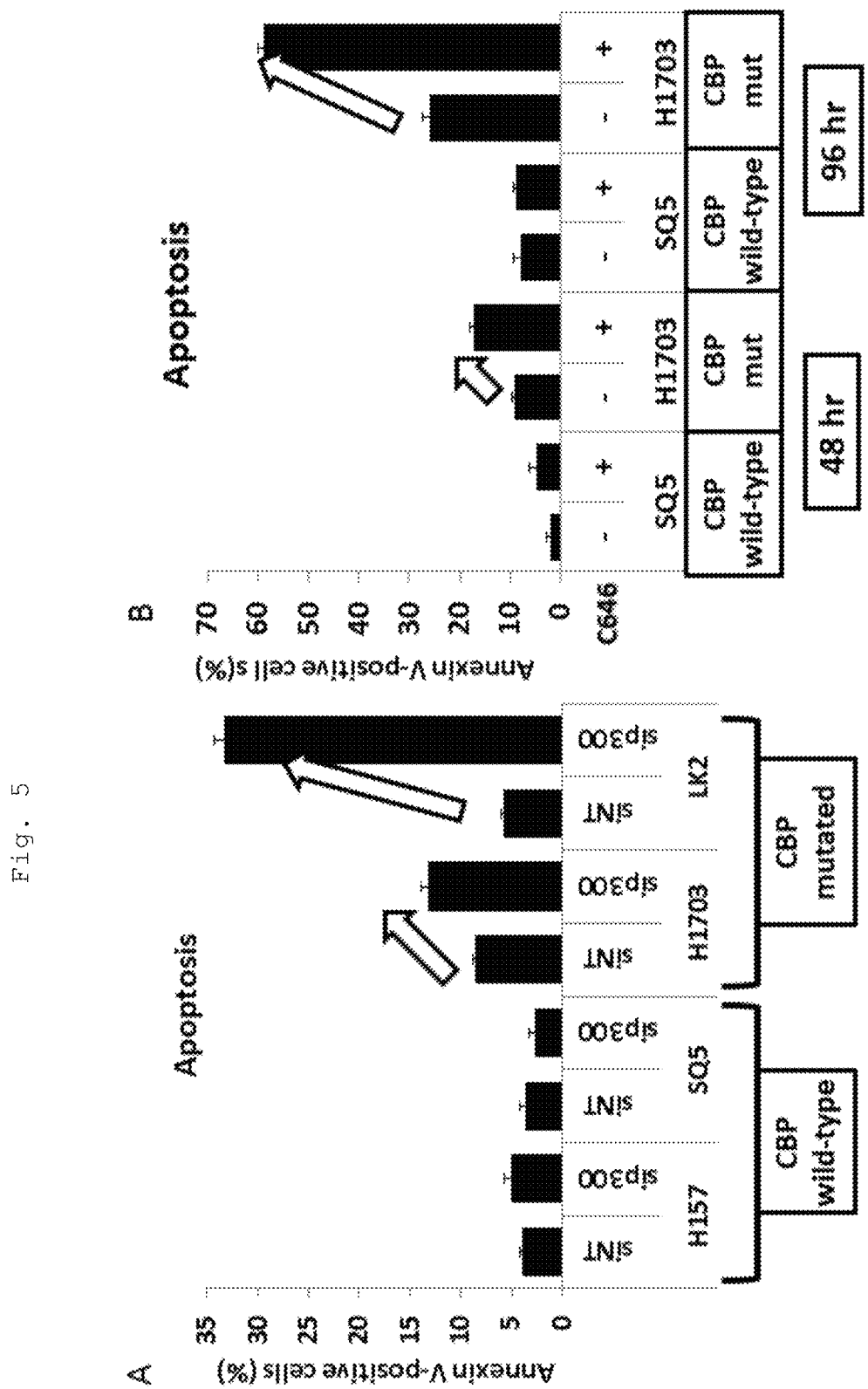
FIG. 5 is a graph showing results of detecting the induction of apoptosis of cancer cell lines having CBP mutations by suppression of p300 expression by using Annexin V stainability as an index.

We next examined the mechanism underlying inhibition by p300 depletion or inhibition in CBP-mutated cancer cells. siRNA-mediated depletion of p300 in CBP-mutated H1703 cells increased the amount of cleaved PARP (biomarker of apoptosis), but did not increase the amount of p21/CDKN1A (biomarker of cell senescence) or LC3B (biomarker of autophagy) (FIG. 4). Consistent with this, by the flow cytometry analysis of cells stained with Annexin V, p300 depletion by siRNA—was confirmed to increase the percentage of Annexin V-positive apoptotic cells in CBP-mutated H1703 cells and LK2 cells, but not to increase the percentage of Annexin V-positive apoptotic cells in CBP-proficient H157 cells and SQ5 cells (FIG. 5A).

In consideration of the results of using the p300 inhibitor C646 described above (FIG. 5B), these results suggest that depletion or inhibition of p300 specifically suppresses the growth of CBP-mutated cancer cells by inducing apoptosis.

(4) In Vivo p300-Dependent Growth of CBP-Mutated Cancer Cells

Figure 6:
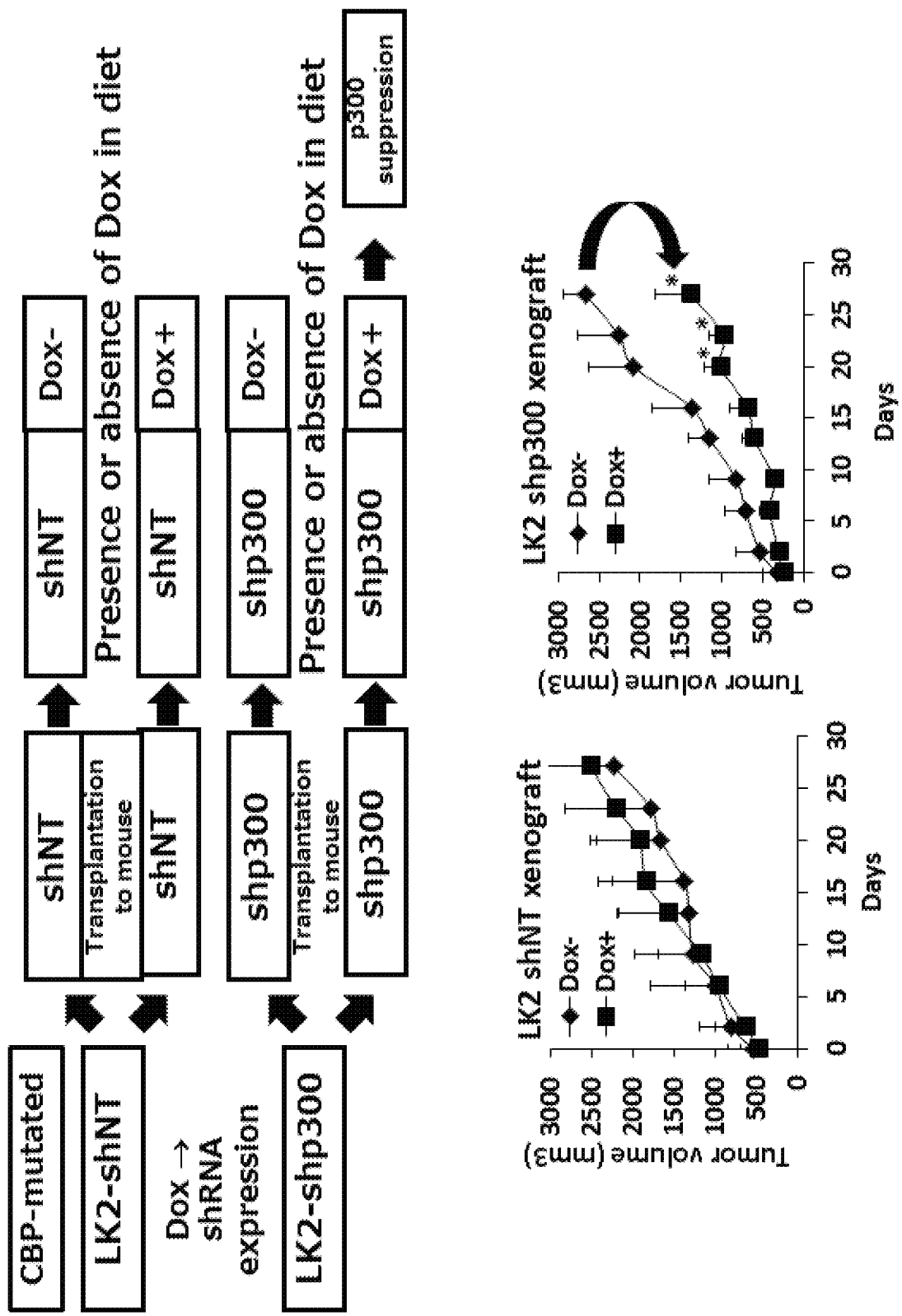
FIG. 6 is a diagram showing the effect of suppression of p300 expression in mice in which a cancer cell line having CBP mutations was transplanted. The upper diagram shows the outline of the experiment. The lower graphs show results of assaying tumor growth in mice in which control cancer cells (left) or cancer cells whose p300 expression was suppressed by the action of Dox (right) were transplanted.

CBP-mutated LK2 cells were used as in vivo preclinical validation models. Cells expressing non-targeting shRNA or shp300 were prepared using a tetracycline-inducible shRNA expression system and subcutaneously transplanted to nude mice. After transplanted tumor size reached 200 mm$^3$ or larger, doxycycline was administered to the mice to induce RNAi. Tumor growth was measured over time. As shown in FIG. 6, the growth of the LK2 shp300 xenograft was significantly suppressed in the mice treated with. Dox, whereas the growth of the LK2 shNT xenograft was not significantly suppressed. This supports the relationship of synthetic lethality between CBP and p300 found in vivo.

(5) Influence of Knockdown of Various HATs on Cell Survival Rate

Figure 8:
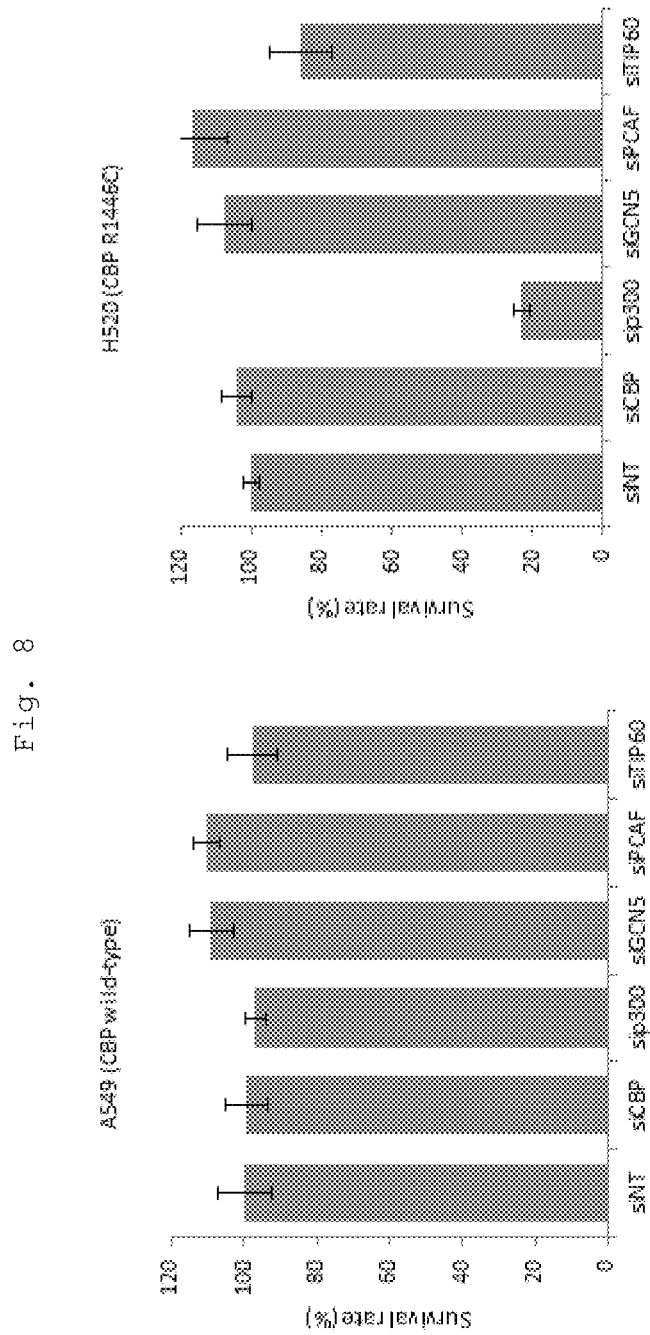
FIG. 8 is a diagram showing the effect of suppression of expression of various histone acetyltransferases (HATs) on A549 cells (CBP-proficient) and H520 cells (CBP-mutated). The ordinate depicts cell survival rates (colony formation rates).

The influence of knockdown of various HATs in A549 cells (CBP-proficient) and H520 cells (CBP-mutated) on their cell survival rates was observed. The influence of knockdown of various HATs on the cell survival rate was not observed in the A549 cells, whereas the knockdown of p300 in the H520 cells was confirmed to significantly reduce the cell survival rate (FIG. 8).

(6) Influence of Knockdown of p300 on c-Myc Expression

Change in c-Myc protein expression caused by p300 knockdown in various cells was observed.

Figure 9:
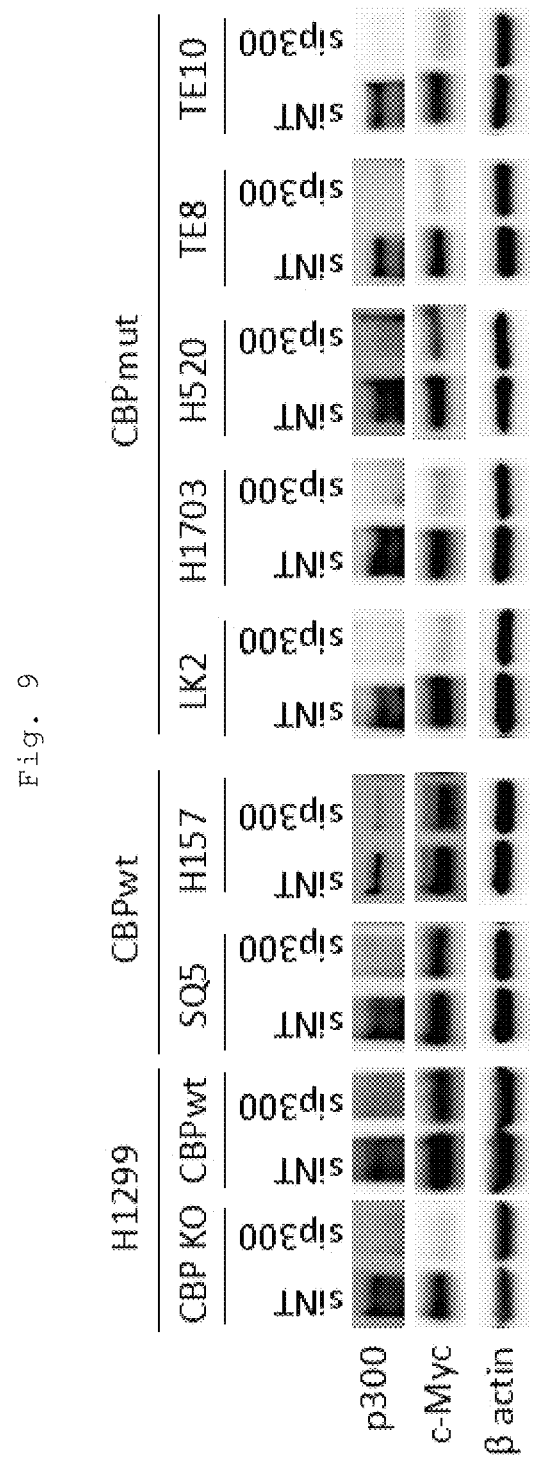
FIG. 9 is a diagram showing change in c-Myc expression level caused by suppression of p300 expression in various CBP-proficient cell lines and CBP-mutated cell lines.
Figure 10:
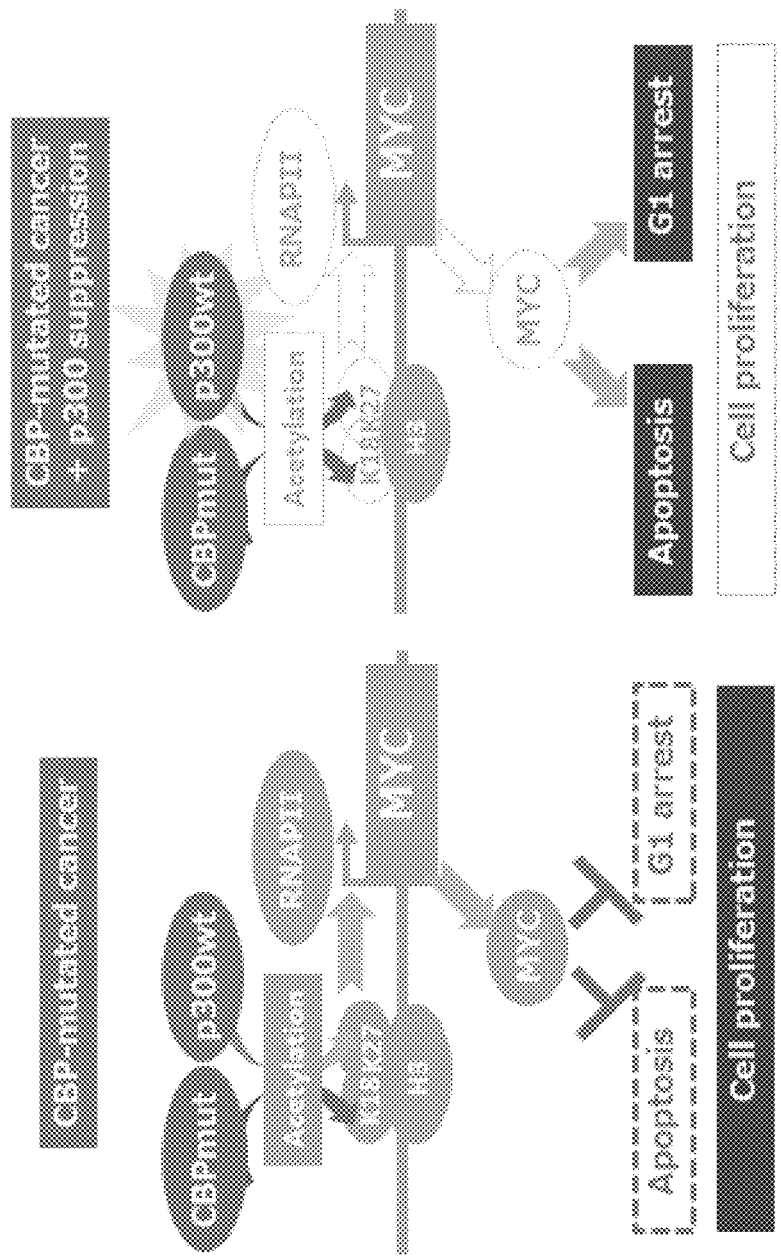
FIG. 10 is a diagram schematically showing the mechanism underlying suppression of c-Myc expression and suppression of cell growth by functional suppression of p300 in CBP-mutated cells.

Change in c-Myc protein expression by p300 knockdown was not observed in CBP-proficient H1299 cells, SQ5 cells, and H157 cells, whereas the p300 knockdown was confirmed to significantly decrease c-Myc protein expression in CBP-mutated LK2 cells, H1703 cells, H520 cells, TE8 cells, and TE10 cells, and CBP-knockout H1299 cells (FIG. 9).

Reduction in c-Myc expression was observed in the cells having functional suppression of both CBP and p300, indicating that c-Myc may be used as a marker for confirming the effect of a p300 inhibitor on cells found to have functional suppression of CBP.

INDUSTRIAL APPLICABILITY

The present invention provides a therapeutic strategy for specifically targeting cancer cells having functional suppression of CBP. In the present invention, it has been found that CBP and p300 are in the relationship of synthetic lethality, and treatment inhibiting p300 is a promising approach for the treatment of cancer having functional suppression of CBP. It has also been revealed that this therapeutic strategy achieves efficient treatment based on companion diagnostics because a p300 inhibitor can be administered to a cancer patient selected with functional suppression of CBP as an index. Thus, the present invention can have a great contribution to the medical field, particularly, the field of cancer treatment.

The invention claimed is:

1. A method for improving the response rate of the treatment of cancer, comprising using a biological sample derived from a cancer patient, detecting the presence of a CBP mutation contained in the biological sample, determining the patient is responsive to the treatment of cancer with a compound inhibiting p300, and treating the patient by a method consisting of administrating to the patient an amount of a compound inhibiting p300 and a pharmaceutically acceptable carrier effective to suppress the growth of cancer cells, wherein the mutation is a homozygous CBP deletion, a nonsense mutation, or one of the mutations Asn83Thr, Ser893Leu, Arg1446Cys, Trp1472Cys, Asn2175Ser, Glu1835Stop, Asn2111Ser, Leu551Ile, Gly1411Glu, or Ala2044Gly.

2. A method for improving the response rate of the treatment of cancer, comprising using a biological sample derived from a cancer patient, detecting the presence of a CBP mutation in the biological sample, selecting the patient as the candidate for the treatment of cancer with a compound inhibiting p300, and treating the patient by a method consisting of administrating to the patient an amount of a compound inhibiting p300 and a pharmaceutically acceptable carrier effective to suppress the growth of cancer cells, wherein the mutation is a homozygous CBP deletion, a nonsense mutation, or one of the mutations Asn83Thr, Ser893Leu, Arg1446Cys, Trp1472Cys, Asn2175Ser, Glu1835Stop, Asn2111Ser, Leu551Ile, Gly1411Glu, or Ala2044Gly.

3. A method for treating cancer having functional suppression of CBP, comprising using a biological sample derived from a cancer patient, detecting the presence of functional suppression of CBP contained in the biological sample, and treating the patient by a method consisting of administering to the patient an amount of a compound inhibiting p300 and a pharmaceutically acceptable carrier effective to suppress the growth of cancer cells, and suppressing the growth of the cancer cells to the patient.

4. The method of claim 1, wherein detecting the presence of a CBP mutation contained in the biological sample comprises contacting the biological sample with a reagent comprising any of the following molecules (a) to (c) as an active ingredient:
(a) an oligonucleotide primer specifically binding to the CBP gene,
(b) an oligonucleotide probe specifically binding to the CBP gene, and
(c) an antibody specifically binding to the CBP protein.

5. The method of claim 2, wherein detecting the presence of a CBP mutation contained in the biological sample comprises contacting the biological sample with a reagent comprising any of the following molecules (a) to (c) as an active ingredient:
(a) an oligonucleotide primer specifically binding to the CBP gene,
(b) an oligonucleotide probe specifically binding to the CBP gene, and
(c) an antibody specifically binding to the CBP protein.

6. The method of claim 3, wherein detecting the presence of functional suppression of CBP contained in the biological sample comprises contacting the biological sample with a reagent comprising any of the following molecules (a) to (c) as an active ingredient:
(a) an oligonucleotide primer specifically binding to the CBP gene,
(b) an oligonucleotide probe specifically binding to the CBP gene, and
(c) an antibody specifically binding to the CBP protein.

7. The method of claim 3, wherein detecting the presence of functional suppression of CBP contained in the biological sample comprises detecting the presence of a CBP mutation contained in the biological sample, wherein the mutation is a homozygous CBP deletion, a nonsense mutation, or one of the mutations Asn83Thr, Ser893Leu, Arg1446Cys, Trp1472Cys, Asn2175Ser, Glu1835Stop, Asn2111Ser, Leu551Ile, Gly1411Glu, or Ala2044Gly.

8. The method of claim 3, wherein the cancer having functional suppression of CBP is lung cancer, bladder cancer, lymphoma, or adenoid cystic cancer.

9. A method for treating a cancer patient, wherein the patient has been determined to have functional suppression of CBP, comprising treating the patient by a method consisting of administering to the patient an amount of a compound inhibiting p300 and a pharmaceutically acceptable carrier effective to suppress the growth of cancer cells, and suppressing the growth of the cancer cells.

10. The method of claim 9, wherein the presence of functional suppression of CBP is determined by using a biological sample derived from the patient, contacting the biological sample with a reagent comprising any of the following molecules (a) to (c) as an active ingredient:
(a) an oligonucleotide primer specifically binding to the CBP gene,
(b) an oligonucleotide probe specifically binding to the CBP gene, and
(c) an antibody specifically binding to the CBP, and
detecting the presence of functional suppression of CBP in the biological sample.

11. The method of claim 9, wherein the presence of functional suppression of CBP is determined by detecting the presence of a CBP mutation contained in a biological sample derived from the patient, wherein the mutation is a homozygous CBP deletion, a nonsense mutation, or one of the mutations Asn83Thr, Ser893Leu, Arg1446Cys, Trp1472Cys, Asn2175Ser, Glu1835Stop, Asn2111 Ser, Leu551Ile, Gly1411Glu, or Ala2044Gly.

12. The method of claim 9, wherein the patient is affected by lung cancer, bladder cancer, lymphoma, or adenoid cystic cancer.

* * * * *